United States Patent
Fine et al.

(10) Patent No.: US 11,120,889 B2
(45) Date of Patent: Sep. 14, 2021

(54) METHOD FOR SYNTHESIZING A NUCLEASE WITH REDUCED OFF-SITE CLEAVAGE

(71) Applicant: Georgia Tech Research Corporation, Atlanta, GA (US)

(72) Inventors: Eli Fine, Atlanta, GA (US); Thomas J. Cradick, Atlanta, GA (US); Yanni Lin, Atlanta, GA (US); Gang Bao, Mabelton, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 921 days.

(21) Appl. No.: 14/399,837

(22) PCT Filed: Mar. 15, 2013

(86) PCT No.: PCT/US2013/032658
§ 371 (c)(1),
(2) Date: Nov. 7, 2014

(87) PCT Pub. No.: WO2013/169398
PCT Pub. Date: Nov. 14, 2013

(65) Prior Publication Data
US 2015/0132821 A1 May 14, 2015

Related U.S. Application Data

(60) Provisional application No. 61/644,754, filed on May 9, 2012, provisional application No. 61/644,743, filed on May 9, 2012.

(51) Int. Cl.
*G16B 20/00* (2019.01)
*G16B 30/00* (2019.01)
*C12N 9/22* (2006.01)

(52) U.S. Cl.
CPC .............. *G16B 20/00* (2019.02); *C12N 9/22* (2013.01); *G16B 30/00* (2019.02)

(58) Field of Classification Search
None
See application file for complete search history.

(56) References Cited

U.S. PATENT DOCUMENTS

2011/0145940 A1    6/2011    Voytas

OTHER PUBLICATIONS

Honisch et al. (PNAS; Jun. 19, 2007; vol. 104; No. 25, pp. 10649-10654) (Year: 2007).*
Nilsson et al. (Annu Rev Biophys Biomol Struct. 2005; 34: 91-118). (Year: 2005).*
Cradick et al. (BMC Bioinformatics 2011, 12:152, pp. 1-9) (Year: 2011).*
Gupta et al. (Nucleic Acids Research, 2011, vol. 39, No. 1 381-392) (Year: 2011).*
Carroll et al. (Genetics, 2011, vol. 188, 773-782) (Year: 2011).*
Beerli, et al., "Engineering polydactyl zinc-finger transcription factors", Nature Biotechnol., 20:135-41(2002).
Boch, et al., "Breaking the Code of DNA Binding Specificity of TAL-Type III Effectors", Science, 36:1509-12 (2009).
Cermak, et al., "Efficient design and assembly of custom TALEN and other TAL effector-based constructs for DNA targeting", Nucl. Acids Res.,39(12): 1-11 (2011).
Choo, et al., "Advances in zinc finger engineering", Curr. Opin. Struct. Biol. 10:411-6 (2000).
Christian, et al., "Targeting DNA double-strand breaks with TAL effector nucleases", Genetics 186:757-61(2010).
Cradick, et al., "ZFN-site searches genomes for zinc finger nuclease target sites and off-target sites", BMC Bioinformatics, 12(1):152 (2011).
Doyle, et al., "TAL Effector-Nucleotide Targeter (TALE-NT) 2.0: tools for TAL effector design and target prediction", Nucleic Acid Res., 1-6 (2012).
Gabriel, et al., "An unbiased genome-wide analysis of zinc-finger nuclease specificity", Nat Biotech, 29:816-23 (2011).
Gupta, et al., "Zinc finger protein-dependent and -independent contributions to the in vito off-target activity of zinc finger nucleases", Nucleic Acids Res., 39(1) 381-92 (2011).
Hockemeyer, et al.,"Genetic engineering of human pluripotent cells using TALE nucleases", Nat. Biotech., 29:731-4 (2011).
Huang, et al., "Heritable gene targeting in zebrafish using customized TALENs", Nat. Biotech. 29:699-700 (2011).
Isalan, et al., "A rapid, generally applicable method to engineer zinc fingers illustrated by targeting the HIV-1 promoter", Nature Biotechnol. 19:656-60 (2001).
Lei, et al., "Efficient targeted gene disruption in Xenopus embryos using engineered transcription activator-like: effector nucleases (TALENs)", PNAS, 109:17484-9 (2012).
Li, et al., "TAL nucleases (TALNs): hybrid proteins composed of TAL effectors and FokI DNA-cleavage domain", Nucleic Acids Res., 39:359-72 (2011).
Li, et al., "Rapid and highly efficient construction of TALE-based transcriptional regulators and nucleases for genome modification", Plant Mol Biol., 78:407-16 (2012).

(Continued)

*Primary Examiner* — Pablo S Whaley
(74) *Attorney, Agent, or Firm* — Smith Gambrell & Russell

(57) ABSTRACT

Endonucleases play an essential role in genetic engineering and molecular biology. A major barrier to the clinical adoption of nucleases and engineered nucleases remain the overall lack of specificity and activity. Off-site cleavage, cleavage at loci other than the target loci, typically occurs resulting in mutations, unexpected gene-knockouts, or translocations. Provided herein are systems and methods for identifying the off-site cleavage loci and predicting the activity of engineered endonucleases for a given genome. It is expected that these tools and methods will be useful for designing nucleases and other related DNA binding domains (e.g. TAL effectors) for genomic therapy and engineering.

3 Claims, 19 Drawing Sheets
Specification includes a Sequence Listing.

(56) References Cited

OTHER PUBLICATIONS

Miller, et al., "A TALE nuclease architecture for efficient genome editing", Nature Biotechnol., 29:143-8 (2011).
Moscou, et al., "A Simple Cipher Governs DNA Recognition by TAL Effectors", Science, 326:1501 (2009).
Neff, et al., "Mojo Hand, a TALEN design tool for genome editing applications", BMC Bioinformatics, 14:1-7 (2013).
Pabo, et al., "Design and selection of novel Cys2His2 zinc finger proteins", Ann. Rev. Biochem., 70:313-40 (2001).
Pattanayak, et al., "Revealing off-target cleavage specificities of zinc-finger nucleases by in vitro selection", Nat. Meth., 8:765-70 (2011).
Reyon, et al., "ZFNGenome: A comprehensive resource for locating zinc finger nuclease target sites in model organisms", BMC Genomics, 12(83):1-9 (2011).
Reyon, et al., "FLASH assembly of TALENs for high-throughput genome editing", Nat Biotechnol., 30:460-465 (2012).
Sander, et al., "Predicting success of oligomerized pool engineering (OPEN) for zinc finger target site sequences", BMC Bioinformatics, 11(543):1-11 (2010).
Segal, et al., "Custom DNA-binding proteins come of age: polydactyl zinc-finger proteins", Curr. Opin. Biotechnol., 12:632-7 (2001).
Tesson, et al., "Knockout rats generated by embryo microinjection of TALENs", Nat. Biotech., 29:695-6 (2011).
Watanabe, et al., "Non-transgenic genome modifications in a hemimetabolous insect using zinc-finger and TAL effector nucleases", Nat. Comm., 3(1017):1-8 (2012).
Zschemisch, et al., "Zinc-finger nuclease mediated disruption of Rag1 in the LEW/Ztm rat", BMC Immunology, 13(60):1-13 (2012).

\* cited by examiner

Search Type    ⊙ TALEN Pair
               ○ Single TAL Effector
               ○ Score an individual TAL binding site Require 5'T ☐
Minimum Spacer Length [14]
Maximum Spacer Length [19]
Minimum TAL Repeat Array Length [15]
Maximum TAL Repeat Array Length [25]
Display [100] Top TALEN sites Display Advanced Settings ☐

Enter a DNA sequence

```
CATCTATTGCTTACATTTGCTTCTGACACAACTGTGTTCACTAGCAACCTCAAACAGACACC
ATGGTGCACCTGACTCCTG[T]GGAGAAGTCTGCCGTTACTGCCCTGTGGGGCAAGGTGAAC
GTGGATGAAGTTGGTGGTGAGGCCCTGGGCAGGTTGGTATCAAGGTTACAAGACAGGTTTAA
GGAGACCAATAGAAACTGGGCATGTGGAGACAGAGAAGACTCTTGGGTTTCTGATAGGCACT
GACTCTCTCTGCCTATTGGTCTATTTTCCCACCCTTAGGCTGCTGGTGGTCTACCCTTGGAC
```

☑ Mask redundant sites
☐ Override the 1500 base pair limit?
☐ Process the entirety of the sequence instead of just the top 50% of the TALENs?

*FIG. 12*

| Starting Index | Left TALEN Sequence | Right TALEN Sequence | Left TALEN Size | Spacer Size | Right TALEN Size | Left TALEN Score | Right TALEN Score | Composite Score | Restriction Enzyme Name |
|---|---|---|---|---|---|---|---|---|---|
| -13 | T-GCACCTGACTCCTGTGGAG | T-CCACGTTCACCTTGCCCCACAG | 19 | 18 | 22 | 27.76 | 32.76 | 48.97 | N/A |
| -64 | T-TTGCTTCTGACACAACTGT | T-GCACCATGGGTGTCTGTTT | 19 | 16 | 18 | 25.63 | 27.52 | 46.23 | BfaI |
| 174 | T-CTGCCTATTGGTCTAT | T-GGGTCCAAGGGTAGACCACCAG | 16 | 18 | 22 | 38.24 | 15.51 | 45.49 | N/A |

FIG. 13

METHOD FOR SYNTHESIZING A NUCLEASE WITH REDUCED OFF-SITE CLEAVAGE

CROSS-REFERENCE TO RELATED APPLICATIONS

This application is a 371 application of International Application No. PCT/US2013/032658, filed Mar. 15, 2013, which claims priority to and the benefit of U.S. Provisional Applications U.S. Ser. No. 61/644,743 and U.S. Ser. No. 61/644,754 filed May 9, 2012.

STATEMENT REGARDING FEDERALLY SPONSORED RESEARCH

This invention was made with Government Support Under Contract Number EY018244 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 16, 2013, is named GTRC6047-6058_SL.txt and is 317,458 bytes in size.

FIELD OF THE INVENTION

This invention is generally in the field of bioinformatics, in particular for systems and methods for improving nuclease specificity and activity.

BACKGROUND OF THE INVENTION

Molecular biology has clearly benefited from the ability to controllably and selectively alter a particular genotype and observe the resulting phenotype. As the ability to precisely alter and rewrite a particular genotype progresses, the ability to target specific gene mutations, to create chromosomal rearrangements, to insert gene labels, to insert domains or full coding regions, or otherwise edit a genome will continue to contribute to exciting advances in molecular genetics.

Endonucleases play an important role in genetic engineering and molecular biology. When a double strand DNA cleavage occurs in cells, the damaged region of the DNA is repaired by the cell's repair system. It is possible to harness the cell's repair system which can be used to mutate, edit or insert new genetic information into the DNA strand. Various attempts have been made to create novel engineered endonucleases capable of recognizing and cleaving specific DNA sequences. Current engineered endonucleases typically consist of zinc finger nucleases (ZFNs) and transcription activator-like effector nucleases (TALENs).

A major barrier to the clinical adoption of nucleases and engineered nucleases remains the overall lack of specificity and activity. Cleavage of DNA by the nuclease at sites other than the target site occur resulting in mutations, unexpected gene-knockouts, or translocations that have detrimental effects. Nucleases that are highly active and specific for a single locus within a given genome and thereby have reduced off-target cleavage of DNA are needed.

Various attempts have been made to create novel engineered endonucleases capable of recognizing and cleaving specific DNA sequences. Current engineered endonucleases typically consist of zinc finger nucleases (ZFNs) and transcription activator-like effector nucleases (TALENs), although RNA-guided nuclease systems based on Clustered Regularly Interspaced Short Palindromic Repeats (CRISPR) associated genes are a promising new technology. ZFNs and TALENs are fusion proteins containing a sequence-specific binding domain fused to a non-specific cleavage domain. The efficiency of genome editing in cells has been shown to be greatly increased by specific DNA cleavage with ZFNs or TALENs, which have been used to create new model organisms [Huang, P. et al., (2011) Nat. Biotech., 29:699-700; Lei, Y. et al., (2012) PNAS, 109:17484-17489; Zschemisch, N.-H. et al., (2012) BMC Immunology, 13; Watanabe, T. et al., (2012) Nat. Comm., 3; Tesson, L. et al., (2011) Nat. Biotech., 29:695-696], correct disease-causing mutations [Sebastiano, V. et al., (2011) STEM CELLS, 29:1717-1726], and genetically engineer stem cells [Hockemeyer, D. et al., (2011) Nat. Biotech., 29:731-734]. However, both ZFNs and TALENs have been shown to have off-target cleavage activity [Tesson, L. et al., (2011) Nat. Biotech., 29:695-696; Gupta, A. et al., (2011) Nucleic Acids Res., 39:381-392; Hockemeyer, D. et al., (2011)Nat. Biotech., 29:731-734; Pattanayak, V, et al., (2011) Nat. Meth., 8:765-770; Gabriel, R. et al., (2011) Nat. Biotech., 29:816-823]. This off-target cleavage could lead to genomic instability, chromosomal rearrangement, and disruption of the function of other genes or sequences To ensure specificity and safety of nuclease-based genome editing, it is vitally important to identify the locations and frequency of off-target cleavage to reduce these adverse events.

While it is possible to identify ZFN or TALEN off-target sites experimentally, practically this is a daunting task because the entire genome needs to be searched and the number of potential cleavage sites to assay is often extremely large. Previous published attempts to identify off-target sites entirely in-silico based on bioinformatics-based search methods have failed to locate any off-target cleavage site. See for example Huang, P. et al., (2011) Nat. Biotech., 29:699-700; Lei, Y. et al., (2012) PNAS, 109: 17484-17489; Zschemisch, N.-H. et al., (2012) BMC Immunology, 13; Watanabe, T. et al., (2012) Nat. Comm., 3. These disappointing results have led to the belief by some in the field that estimating off-target cleavage activity based on sequence homology would not be fruitful. See for example Gabriel, R. et al., (2011) Nat Biotech, 29:816-823. In contrast, efforts using experimental methods to characterize the specificity of nucleases have successfully identified off-target cleavage sites for ZFNs and TALENs. See for example Tesson, L. et al., (2011) Nat. Biotech., 29:695-696; Gupta, A. et al., (2011) Nucleic Acids Res., 39:381-392; Hockemeyer, D. et al., (2011) Nat. Biotech., 29:731-734; Pattanayak, V, et al., (2011) Nat. Meth., 8:765-770; Gabriel, R. et al., (2011) Nat. Biotech., 29:816-823. However, these methods, including SELEX, bacterial one-hybrid, in vitro cleavage, or IDLV LAM-PCR, are very time consuming, costly, and/or technically challenging, which have severely limited the number of labs undertaking these experiments and the number of nucleases characterized.

Another major obstacle in the design of enhanced nucleases is predicting nuclease activity. For example, recent evaluation of TALEN design guidelines using hetero-dimeric TALEN pairs revealed that the activities of the TALEN pairs varied markedly; however, no significant correlation between guideline violations and TALEN activities was found. [Reyon, D. et al., (2012) Nat Biotechnol: 30:460-465] The use of existing design tools that are based on simple design criteria often gives a large number (hundreds to thousands) of potential nuclease target sites within a gene region with activities varying over a wide range.

Existing tools for guiding the identification of off-target sites or for predicting nuclease activity are limited and lack the capabilities of the methods and tools provided herein. Two online tools have recently emerged to aid in searching genomes for sites with homology to ZFN and TALEN target sites, but they lack important features. ZFN-Site returns a list of all sites in a genome with two or fewer mismatches in each nuclease half-site, but it does not provide any ranking of the likelihood of off-site targeting and the limitations are insufficient for 4-finger ZFNs, which have been shown to cleave with as many as 5 mismatches in a half-site. To search off-target sites, TALE-NT returns a list of sites in a genome with sequences in each half-site similar to the bases preferred by the RVDs in each TALEN, but no overall ranking is assigned to the full bipartite sites to identify the likelihood of targeting. To aid the design of TALENs, TALE-NT and other similar online search tools filter a DNA sequence of interest by specifying ranges of the repeat array length, spacer length, and if certain guidelines need to be applied, but no score or ranking is assigned to the output target sites to indicate the likelihood of obtaining highly active TALENsoff-target activity. Importantly, neither of these online tools has yet to have been reported to aid the identification of any nuclease off-target cleavage events. Traditional tools such as BLAST or e-PCR are also non-optimal. Electronic PCR only allows up to two mismatches in each half-site, similar to ZFN-Site searches. BLAST uses a seed-based search which makes searching over different spacers difficult and does not perform an exhaustive search of the genome and thus may miss potential homologous sites.

There is a need for easy, rapid, and scalable methods to predict nuclease off-target sites and nuclease activities.

It is therefore an object of the invention to provide tools and methods for designing engineered nucleases that are both highly specific and highly active.

It is a further object of this invention to provide tools and methods for identifying the off-site target loci for a given nuclease.

It is a further object of this invention to provide tools and methods for identifying amplicons for the off-target genomic regions and primers for generating these amplicons.

It is a further object of this invention to provide tools and methods for predicting the intracellular activity of an engineered nuclease.

It is a further object of this invention to provide tools and methods for reliably ranking both the off-target cleavage loci and the intracellular activities of engineered nucleases.

It is a further object of this invention to provide the above tools in a user-friendly graphical user interface.

It is a further object of this invention to provide novel engineered nucleases or DNA binding domain developed using the tools and methods provided herein.

SUMMARY OF THE INVENTION

Provided herein are systems and methods to predict off-target cleavage sites of nucleases, to predict nuclease cleavage activity, and to generally aid in the design of nucleases or DNA binding domains. Nucleases designed using the disclosed tools are also provided. The designed nucleases or DNA binding domains include, but are not limited to zinc-finger nucleases, transcription activator-like effector nucleases (TALENs), transcription activator-like (TAL) effectors, or clustered regularly interspaced short palindromic repeats (CRISPR).

A first embodiment provides a computer-implemented method of detecting target and off-target sites and providing a ranking that correlates with the likelihood for off-target cleavage by an engineered nuclease.

A further embodiment provides a computer-implemented method of generating lists of nucleases or DNA binding domains targeting an input genomic region ranked by nuclease cleavage activity or DNA binding activity.

In some embodiments the computer-implemented methods represent advances over previous methods by providing numerical scorings of activity or the likelihood of off-site cleavage. The numerical scorings can be provided in some embodiments as a ranked list, ranking the likelihood of cleavage or binding at a given site or ranking the predicted activity of several engineered nucleases. In some embodiments the ranking provided correlates with the experimentally observed values, thereby providing useful design tools.

Some embodiments provide a system including a computer server containing at least i) a storage means to store sequence data for one or more genomes, and ii) a processor operative to receive as input information descriptive of the target site of an engineered nuclease or a DNA sequence to be targeted and to generate a ranked list of off-target cleavage sites or to generate a ranked list of nucleases or DNA binding domains having activity by one or more methods described herein. The computer server can be operably connected to and accessible on a computer network, for example an intranet or the internet. In some embodiments the input search query is provided to the apparatus through one or more graphical user interfaces (GUIs).

Still other embodiments provide methods and tools that can be used in combination with one or more biochemical assays to drive the design of new nucleases or DNA binding domains. Engineered nucleases are also provided that have been designed using the tools and methods described herein.

BRIEF DESCRIPTION OF THE DRAWINGS

FIG. 10 discloses SEQ ID NOS 359-363, respectively, in order of appearance.

FIG. 12 is a schematic of a graphical user interface (GUI) for receiving input parameters for a predicted TALEN activity search. The GUI contains radio buttons, check boxes, and text boxes for entering the search criteria. FIG. 12 discloses SEQ ID NO: 364.

FIG. 13 is a schematic of a tabular output that can be obtained from a predicted TALEN activity search. The output describes the starting location, the left (SEQ ID NOS 365-367, respectively, in order of appearance) and right (SEQ ID NOS 368-370, respectively, in order of appearance) TALEN target sequences, TALEN and spacer lengths, as well as the left and right half-site scores, the composite score, and the identity of available restriction enzyme site located in the spacer.

FIG. 19A compares the predicted activity for seven engineered TALEN pairs targeting five human cancer genes. FIG. 19B compares the predicted activity for six engineered TALEN pairs targeting CXADR, CFTR, and AAVS1 genes.

DETAILED DESCRIPTION OF THE INVENTION

I. Systems and Methods

Figure 4:
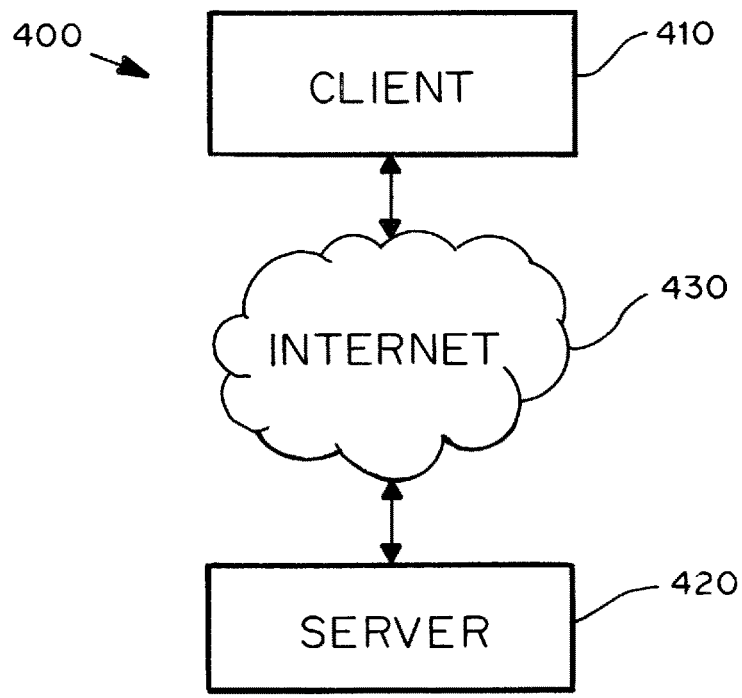
FIG. 4 is a block diagram of a preferred network-based implementation containing a computer server and one or more client computers in communication over a network.

The systems and methods provided herein are generally useful for predicting the location of off-target cleavage sites, for predicting the nuclease cleavage activity or for the design of engineered nucleases or DNA binding domains. In certain embodiments the methods are implemented on a computer server accessible over one or more computer networks. FIG. 4 is a block diagram of a preferred network-based implementation (400) wherein a client computer system (410) is in communication with a server computer system (420) via a network (430), i.e. the Internet or in some cases a private network or a local intranet. One or both of the connections to the network may be wireless. In a preferred embodiment the server is in communication with a multitude of clients over the network, preferably a heterogeneous multitude of clients including personal computers and other computer servers as well as hand-held devices such as smartphones or tablet computers. In some embodiments the server computer is in communication, i.e. is able to receive an input query from or direct output results to, one or more laboratory automation systems, i.e. one or more automated laboratory systems or automation robotics that automate biochemical assays, PCR amplification, or synthesis of PCR primers. See for example automated systems available from Beckman Coulter.

Figure 5:
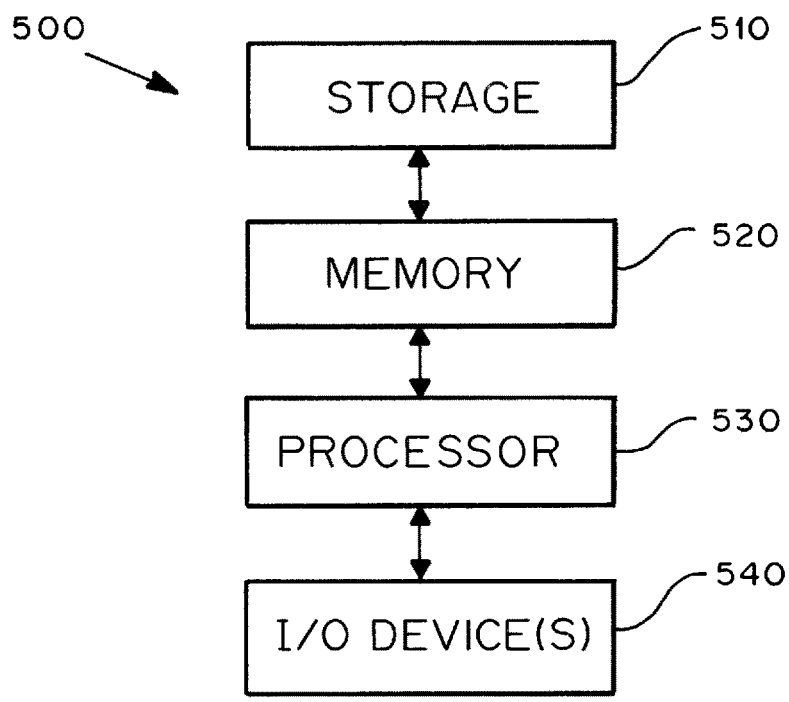
FIG. 5 is a block diagram of a computer server containing I/O device(s), a processor, memory, and storage.

The computer server where the methods are implemented may in principle be any computing system or architecture capable of performing the computations and storing the necessary data. The exact specifications of such a system will change with the growth and pace of technology, so the exemplary computer systems and components described herein should not be seen as limiting. FIG. 5 is a block diagram of the basic components of an exemplary computer server (500) on which the methods may be implemented. The systems will typically contain storage space (510), memory (520), one or more processors (530), and one or more input/output devices (540). It is to be appreciated that the term "processor" as used herein is intended to include any processing device, such as, for example, one that includes a CPU (central processing unit). The term "memory" as used herein is intended to include memory associated with a processor or CPU, such as, for example, RAM, ROM, etc. In addition, the term "input/output devices" or "I/O devices" as used herein is intended to include, for example, one or more input devices, e.g., keyboard, for making queries and/or inputting data to the processing unit, and/or one or more output devices, e.g., a display and/or printer, for presenting query results and/or other results associated with the processing unit. An I/O device might also be a connection to the network where queries are received from and results are directed to one or more client computers. It is also to be understood that the term "processor" may refer to more than one processing device. Other processing devices, either on a computer cluster or in a multi-processor computer server, may share the elements associated with the processing device. Accordingly, software components including instructions or code for performing the methodologies of the invention, as described herein, may be stored in one or more of the associated memory or storage devices (e.g., ROM, fixed or removable memory) and, when ready to be utilized, loaded in part or in whole into memory (e.g., into RAM) and executed by a CPU. The storage may be further utilized for storing program codes, databases of genomic sequences, etc. The storage can be any suitable form of computer storage including traditional hard-disk drives, solid-state drives, or ultrafast disk arrays. In some embodiments the storage includes network-attached storage that may be operatively connected to multiple similar computer servers that comprise a computing cluster.

Figure 6:
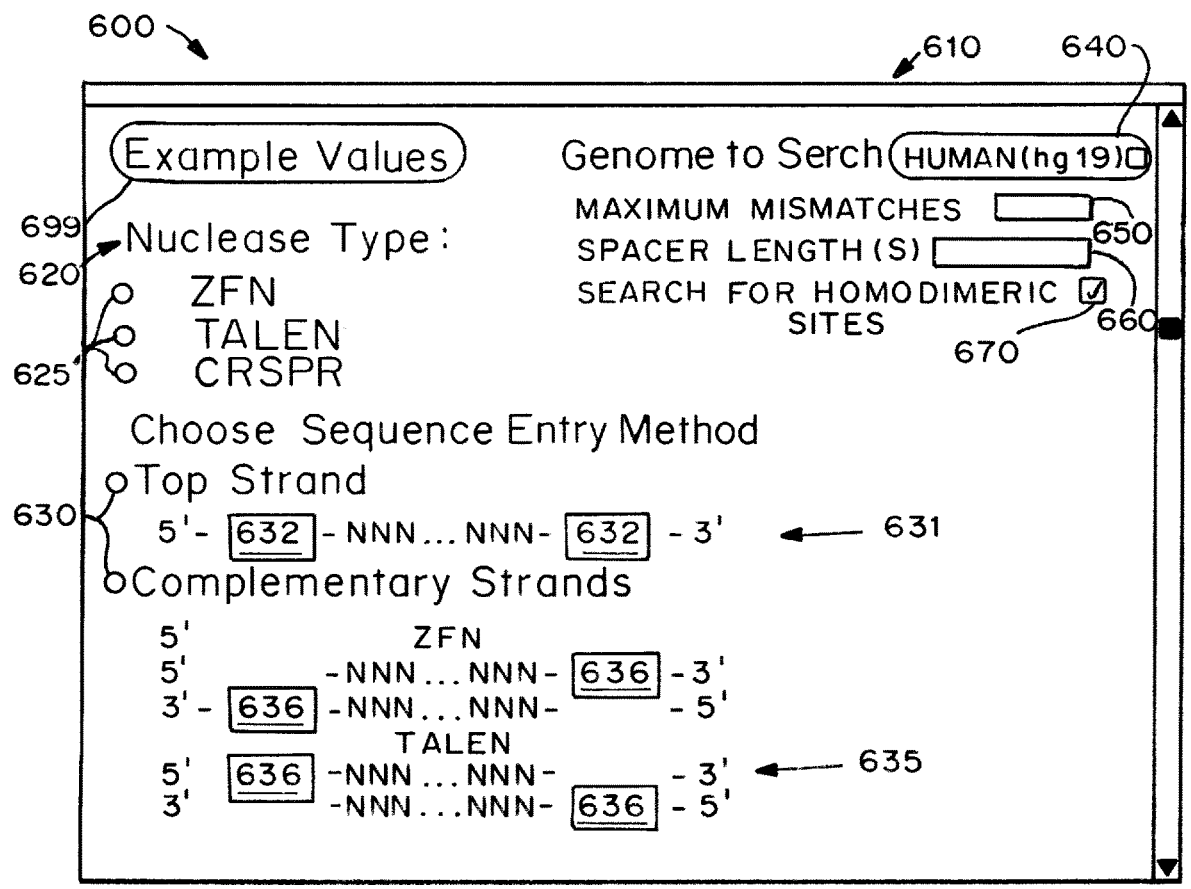
FIG. 6 is a schematic of a graphical user interface (GUI) for receiving input parameters for a computer-implemented off-target site search method. The GUI is displayed in a web browser and contains check boxes, drop-down lists, radio buttons, and text boxes for inputting search parameters and an example button for generating an example query.

In a preferred set of embodiments the computer server receives input submitted through a graphical user interface (GUI). The GUI may be presented on an attached monitor or display and may accept input through a touch screen, attached mouse or pointing device, or from an attached keyboard. In some embodiments the GUI will be communicated across a network using an accepted standard to be rendered on a monitor or display attached to a client computer and capable of accepting input from one or more input devices attached to the client computer. FIG. 6 depicts some of the components that may be found in an exemplary GUI (600) for inputting parameters for off-target site searches capable of being rendered in a standard web browser window (610) on the client computer. The GUI contains a nuclease selection region (620) where the user selects the type of nuclease being input. In this exemplary system the nuclease is indicated by clicking, touching, or selecting one of the radio buttons (625). The GUI contains additional radio buttons for choosing the method of sequence entry (630), a first sequence entry region (631) for entering the target sequence of the top/positive DNA strand with text boxes (632) for entry of the sequence, and a second sequence entry region (635) for entering the sequence for both the top and bottom target sequences with text boxes (636) for entry of the sequences. The sequence will generally be entered using a combination of characters selected from the allowable characters and dependent upon the implementation may be limited to characters for the standard nucleotides, or may include non-standard nucleotides. The character set is described in more detail in the notation section below. The GUI contains a drop-down list (640) for selecting which of the available genomes to search, a text box for entering the maximum number of mismatches (650), a text box for entering the spacer length(s) (660), and a check box (670) for selecting if homodimeric sites should be included in the search. The maximum number of mismatches will in some embodiments be the maximum number of mismatches per half site, in others will be the total across both sites, or in some embodiments will be either of the two options depending upon additional input (i.e. an additional check box). The spacer length in some embodiments may be entered as individual numeric values, as a list of numeric values, or as a range of numeric values. For example, the input strings "1,2,3", "1-3", "1,2-3", or "1-2,3" would in some cases all be accepted inputs and would generate all possible spacer lengths of 1, 2, or 3 base pairs. The GUI will in some embodiments have an example button (699) that, when selected by the user populates all of the input fields with default values. The option selected by the example values may in some embodiments coincide to an example described in detail in a tutorial, manual, or help section. The GUI will in some embodiments contain all or only some of the elements described above. The GUI may contain any graphical user input element or combination thereof including one or more menu bars, text boxes, buttons, hyperlinks, drop-down lists, list boxes, combo boxes, check boxes, radio buttons, cycle buttons, data grids, or tabs.

A. Systems and Methods for Predicting Off-Target Cleavage

Figure 7:
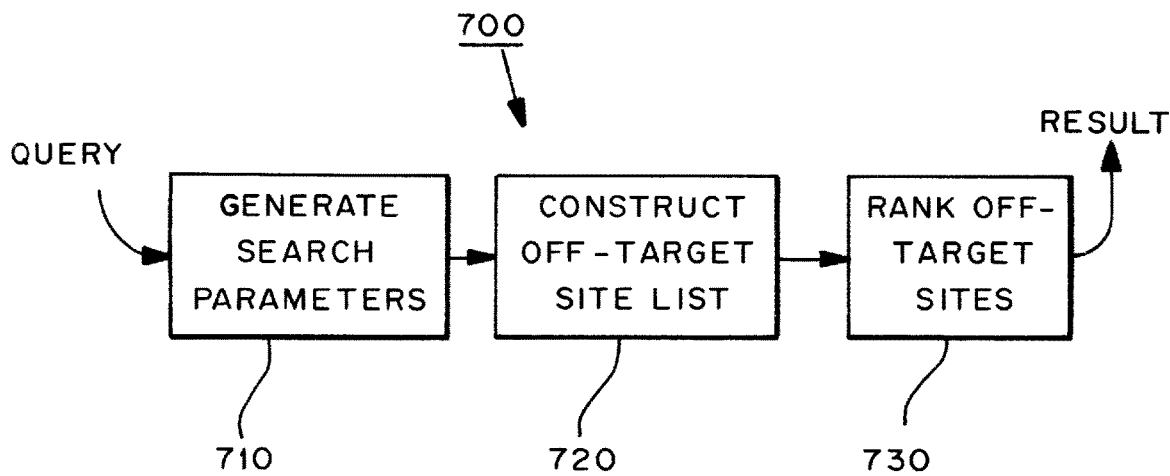
FIG. 7 is a flow chart of an exemplary method for generating a ranked list of off-target sites that could be implemented on a computer. A user query is used to generate search parameters used by the algorithm to construct a list of off-target cleavage sites. The off-target sites are ranked by their predicted off-target cleavage activity and output as results in a ranked list.

Systems and methods described herein for predicting off-target cleavage sites generally involve generating search criteria derived from the input criteria, generating a list of off-target sites, and directing the list of off-target sites as output to the user. The input criteria will generally include information regarding the target sequence, the linker distance, allowed mismatches, genome to be searched, etc. In preferred embodiments the output is provided in the form of a ranked-list wherein each of the target sites is assigned a numerical value, "score", that correlates with the likelihood of off-target cleavage at that site. FIG. 7 presents a flow chart of an exemplary off-target site prediction method (700) that generates search parameters (710) based upon an input query, constructs a list of off-target sites (720) based upon the search parameters, and ranks (730) the off-target sites in the list before outputting the results.

One embodiment provides a computer-implemented method for identifying off-target cleavage locations of a nuclease by scanning complete genomic sequence data for the off-target cleavage locations of the nuclease based on parameters selected from the group consisting of type of nuclease, genomic target sequence, organismal genome, number of mismatches or minimal level of homology between the target sequence and the organismal genome, to return off-target cleavage locations in the genome; assigning a score to the returned off-target cleavage locations indicative of the predictive likelihood of off-target cleavage and ranking the off-target cleavage locations based on the score. The nuclease can contain a first half-site and a second half-site, and the score can be based on an energy compensation model taking both the first half-site and the second half-site into account.

The score can be weighted based on one or more of factors selected from the group consisting of empirically derived weighting factors, the number of guanine residues in the target sequence, the type of genomic region annotated for each target site according to Exon>Promoter & Regulatory>Intron>Intergenic, and chromosome location. For example, the score can be a homology score based on the number of mismatches in the first half-site and the second half-site and the maximum number of mismatches allowed per half-site.

When the nuclease is a zinc finger nuclease, the score can be based on the homology between the genomic target sequence and the organismal genome and the number of conserved guanine residues. When the nuclease is a transcription activator-like effector nuclease, the score can be based on the homology between the genomic target sequence and the organismal genome and repeat variable di-residues. The nuclease can use a guide RNA strand, such as the CRISPR, and/or CAS9 systems.

The method can include returning polymerase chain reaction primer sequences for amplification of the ranked off-site cleavage locations;
returning a full nucleic acid sequence of an amplicon for detecting induced mutations; and
designating the off-target cleavage location as being in an exon, intron, promoter or regulatory, or intergenic region. In addition, the method can return hyperlinks to internet resources on the genomic region of the off-target cleavage location.

Constructing the Off-Target Site List

The off-target site lists can be constructed for instance using existing homology search algorithms such as FASTA or BLAST. The FASTA algorithm is described in W. R. Pearson, and D. J. Lipman (1988) *Proc. Natl. Acad. Sci.*, 85:2444-2448 and D. J. Lipman, and W. R. Pearson (1989) *Science*, 227:1435-1441. The BLAST algorithm is described in S. Altschul, et al. (1990) *J. Mol. Biology*, 215:403-410. While FASTA and BLAST can be used to construct a list of homologous off-target sites, these are not the preferred approaches. Firstly, neither of these approaches exhaustively searches the genome and therefore the off-target site list will typically be incomplete. Secondly, conducting off-target site searches with FASTA or BLAST requires separate searches be performed for each possible spacer length adding to the computational expense.

Figure 8:
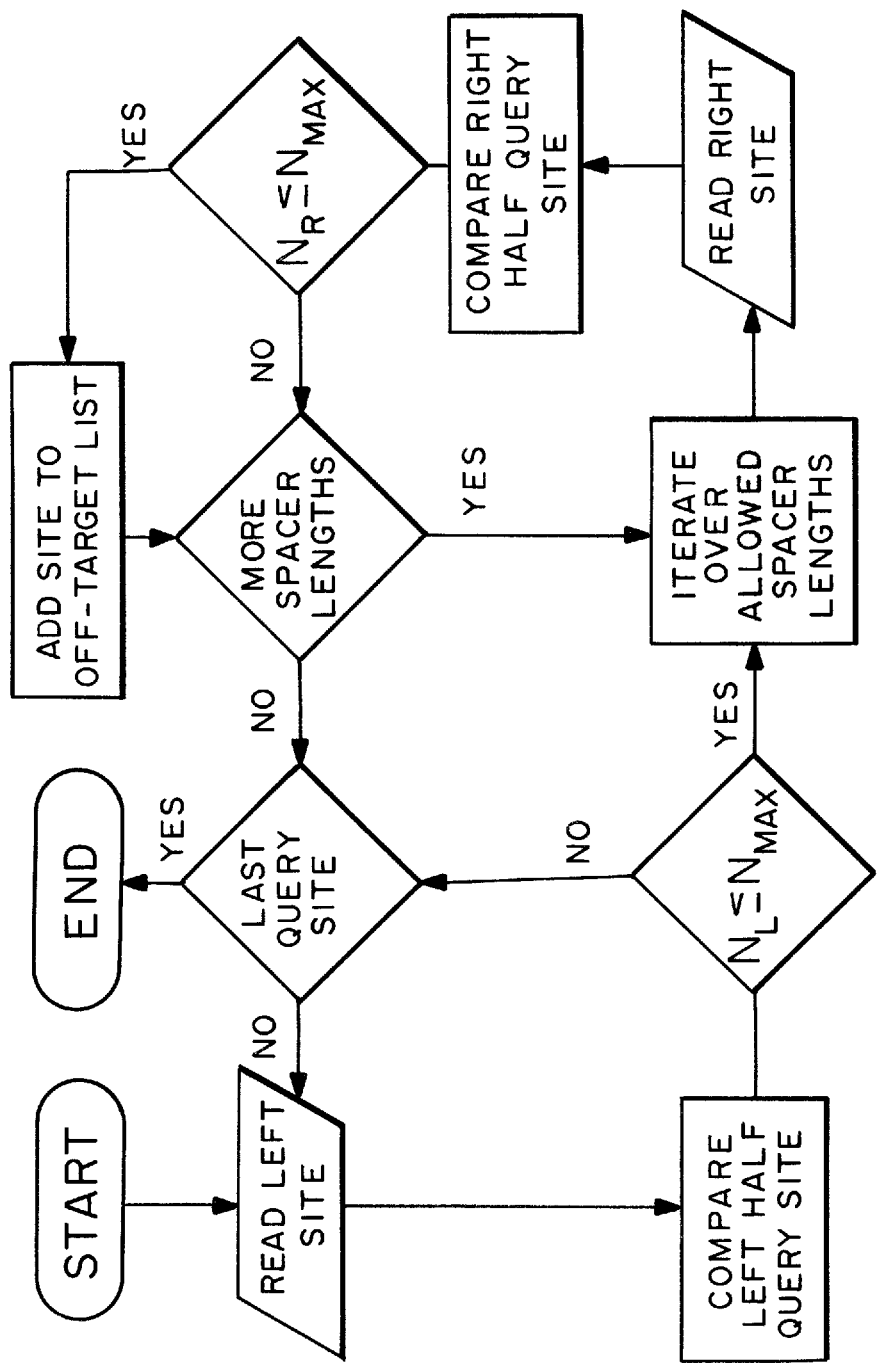
FIG. 8 is a flow chart for an exemplary algorithm containing multiple loop structures that performs an exhaustive search of off-target sites within a genome. The algorithm loops over all possible left half-sites. For left-half sites having an acceptable number of mismatches, the algorithm loops over allowed spacer lengths looking for right half-sites having acceptable number of mismatches.

In certain embodiments the method for constructing the off-target site list exhaustively searches for sites by moving the query mask iteratively across the sequence of an entire genome. To optimize search time, the sequence containing the length of the 5' binding site is first examined to determine if the number of mismatches does not exceed the query maximum. If that requirement is met, the sequences comprising potential 3' binding sites (separated by allowed spacer lengths) are examined. In some embodiments the algorithm only compares right half target sites that are within allowed spacer length from a left half target site, preferably only after checking that the number of mismatches in the left half target sight satisfies the search criteria. FIG. 8 depicts a flow chart demonstrating an example algorithm for constructing the off-target site list. The algorithm depicted starts by reading a left site and comparing to the left half query site (the left half target site). If the number of mismatches in the left half is not less than the maximum number of mismatches per half site, then the algorithm checks if this was the last sight, and either ends or reads the next left site. If the number of mismatches is less than the maximum number of mismatches per half site, the algorithm proceeds to check for right half target sites by iterating over the allowed spacer lengths, reading a right site, and comparing to the right half query site (right half target site). If the number of mismatches on the right is less than the maximum number of mismatches per half site, the site is added to the off-target site list, otherwise the algorithm checks if there are additional spacer lengths or additional sites. The algorithm can be performed in parallel of different processors, for example on 4, 8, 12, or 16 processors. In some embodiments the tasks are distributed across multiple computer servers comprising a computer cluster.

Ranking the Off-Target Sites

Although online tools exist to help search genomes for cleavage sites with homology to nuclease target sites, none of them ranks the potential off-target sites or has succeeded in aiding the identification of any off-target cleavage sites. Embodiments of the disclosed methods assign a score to off-target sites and rank them according to the predicted likelihood of off-target cleavage. In principle any scoring function may be employed to rank the off-target sites that give a reliable agreement with observed off-target cleavage activity. The scoring function for off-target cleavage may in some cases be an empirical function derived from experimental results on off-target cleavage sites.

Exemplary scoring functions are based on both sequence homology and nuclease-DNA binding preferences, such as conserved G's for ZFNs and RVDs (Repeat Variable Di-residues) for TALENs. See Gupta et al. (2011), *Nucleic Acids Res.*, 39:381-392; Pattanayak et al. (2011), *Nat. Meth.* 8:765-770; and Doyle et al. (2012), *Nucleic Acid Res.* A 'Homology' algorithm can be employed to rank the off-target sites. For example, a homology score can be based on the number of mismatches in the left and right half-site respectively, and the maximum number of mismatches allowed per half-site. A representative scoring formula is:

$$SCORE_H = (N_{MAX} + 1 - N_L)^2 + (N_{MAX} + 1 - N_R)^2 \quad (1)$$

where $N_L$ and $N_R$ are the number of mismatches in the left and right half sites respectively and $N_{MAX}$ is the maximum number of mismatches per half site. A higher score indicates a more likely off-target site. The squared factor is an attempt to capture the "energy compensation" effects observed in previous work. See Pattanayak et al. (2011), *Nat. Meth.* 8:765-770.

Other scoring functions can be based on nuclease-DNA binding preferences and can include weighting a homology score based on empirically derived weighting factors. Ranking ZFN off-target sites by counting the number of guanine residues—the "G's"—is particularly useful because many ZFNs, especially those using canonical frameworks, bind to guanosine residues more strongly than other nucleic acids. The Conserved G's ranking system adds a weighting factor to the homology score based on the number of guanosine residues in the intended target sequence (G) and total, the number of guanosine residues matching the target sequence at potential off-target sites ($G_{conserved}$). An exemplary "Conserved G" score is:

$$SCORE_G = SCORE_H * \left(\frac{G_{conserved}}{G_{total}} * 10\right)^\alpha \quad (2)$$

where α can be optimized to provide agreements to available experimental off-target sites.

The repeat variable di-residue (RVD) ranking system is intended for ranking TALEN off-target sites. Given $RVD_{L\ min}$, and $RVD_{R\ min}$ as the scores for the left and right TALs binding to their intended target sites, and $RVD_L$ and $RVD_R$ as the scores for the TALs binding to a potential off-target sequence:

$$SCORE_{RVD} = \left(\frac{RVD_L}{RVD_{Lmin}}\right)^{0.5} + \left(\frac{RVD_R}{RVD_{Rmin}}\right)^{0.5} \quad (3)$$

A lower score indicates a more likely off-target site. The square root factor is an attempt to capture the "energy compensation" effects observed for ZFNs in previous work.

In some cases, if the calculated score for two sites is the same, these sites are further ranked for example by the type of genomic region annotated for each site: i.e. Exon>Promoter>Intron>Intergenic. A final ranking by chromosome location can also be employed to ensure consistency in the ranking order in cases where none of the other criteria differentiate between sites.

Figure 9:
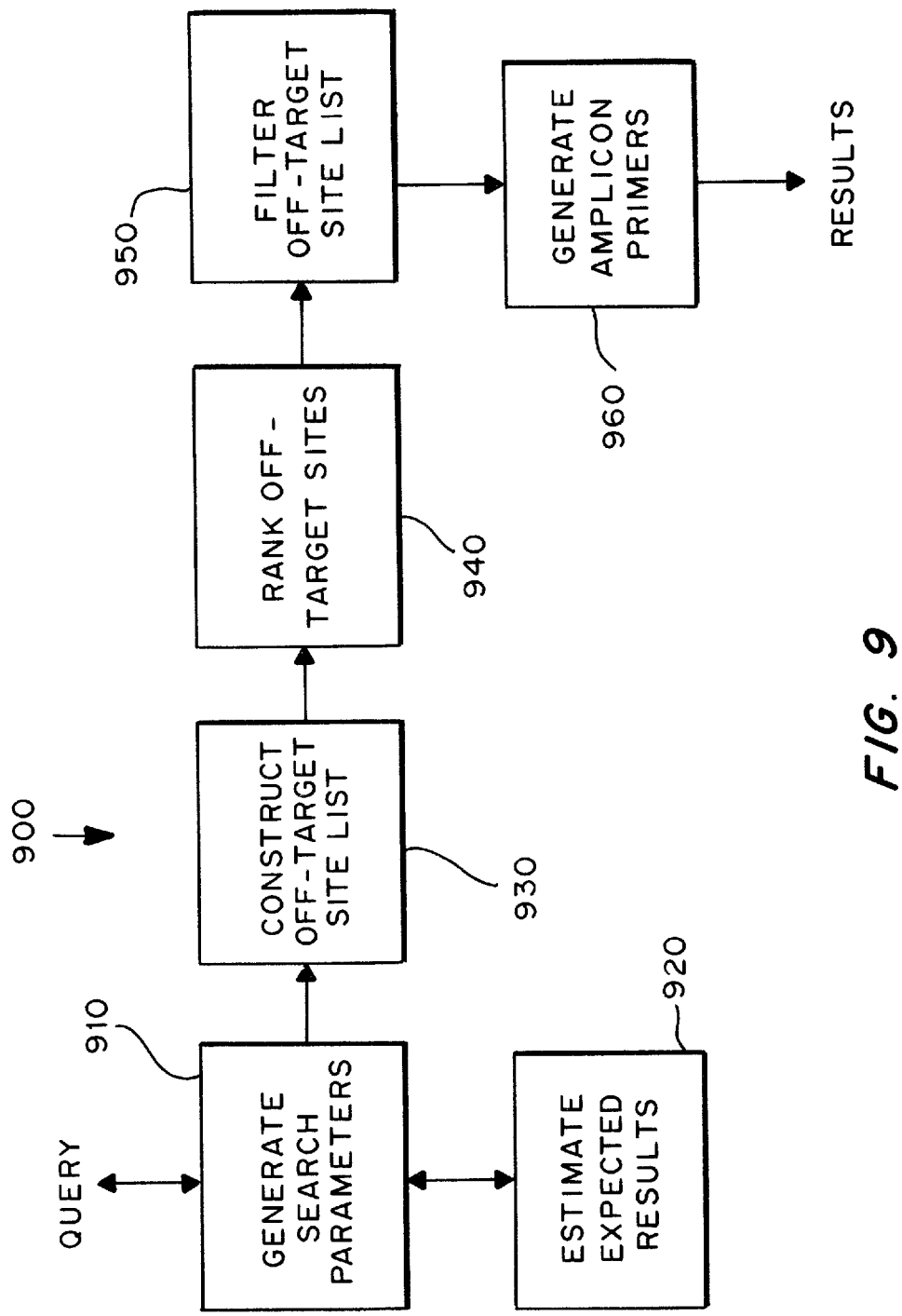
FIG. 9 is a flow chart of an exemplary method amenable to computer implementation that can be used for generating a ranked list of off-target sites including estimating the number of hits, filtering the list, and generating amplicon primers for PCR amplification.

While the ability to generate a ranked list of off-target sites provides many advantages over other available tools and method for off-site prediction, in other disclosed methods provide additional capabilities that further assist in the design of nucleases with high specificity. For example, the method identifies primer pairs useful for PCR amplification of the target regions and activity assays. In some cases the methods provide estimates for the number of off-target sites that will be identified by a given query. FIG. 9 depicts a flow chart for one such exemplary method (900) for generating off-target sites. A query is obtained and search parameters are generated (910), as estimate of the number of expected results is provided (920). The query may then be updated with a revised query, wherein a revised estimate is subsequently generated of the number of expected results. This process can be completed to obtain the desirable number of expected results. The query is then used to construct an off-target site list (930) using methods provided herein. The results in the off-target site list are ranked (940) and then filtered by specified selection criteria (950). The filtered list of off-target sites is then used to generate primer pairs (960) for generating amplicons. The filtered list of off-target sites and primer pairs is then output as results.

Identify Primer Pairs

An automated primer pair design is sometimes included to design primers appropriate for off-target validation assays, matching user input criteria. This greatly simplifies the standard method for primer design that requires iterative steps of primer design and verification of the resulting fragment sizes. In addition to speeding the primer design throughput, an automated design process allows the primers to be custom designed for the downstream assays or sequencing, and to be matched for high-throughput, full-plate PCR amplification.

To optimize amplicons for different sequencing platforms, the primer pair design will sometimes provide for specifying the minimum distance from the edge of the amplicon to the nuclease site. The recommended parameters will in some cases include a separation distance between cleavage bands that is greater than 0, 20, 40, 60, 80, 100, 120, 140, 160, 180, or 200 base pairs. In some embodiments primer pairs are chosen such that the minimum separation between uncleaved and cleaved products is greater than 50, 75, 100, 125, 150, 175, or 200 base pairs. The primers may be optimally chosen for a variety of sequencing assays. In one example, for SMRT sequencing, the recommended parameters are: Minimum Distance Between Cleavage Bands of 0 base pairs, Minimum Separation Between Uncleaved and Cleaved Products of 125 base pairs. In another example, for surveyor assays, the primer design parameters can be specified to ensure that the nuclease site is placed in an optimal position within the amplicon to yield cleavage bands that can be easily distinguished on gels from the parental band and each other. In a particular embodiment, for resolution on a 2% agarose gel, the recommended parameters may be: Minimum Distance Between Cleavage Bands of 100 base pairs, Minimum Separation Between Uncleaved and Cleaved Products of 150 base pairs.

The primer pair design process implemented will in some cases use the following steps and considerations to yield primer pairs suitable for high-throughput PCR. In some embodiments the primer design process may take into account the potential secondary structure that could arise of the 3' end of a primer folding back; may take into account estimated physical properties including the temperature or length; may define targets for the content of specific bases in the primer; and may check to ensure for primers that are not self complementary.

Outlined below is an example primer design process that may be employed in certain preferred embodiments.

Primer Design Process

Each possible position in the sequence 5' of the nuclease binding sites is considered as a possible 5' base for a primer (in some cases allowing for a user-specified minimum distance between the edge of the amplicon and the nuclease site).

For a given 5' starting position, a first number of bases in the 3' direction are taken as an initial sequence for the primer. The first number of bases may be any integer number of bases, but in some preferred embodiments the first number of bases chosen will be 15, 16, 17, 18, 19, or 20 bases. Then the following design loop begins:

LOOP:
1) Check for potential secondary structure that could result from the 3' end folding back.

Check that the sequence of the primer up to the $4^{th}$ most 3' base does not contain any exact matches to the reverse complement of the three most 3' bases.

Example

Potential Primer Sequence: 5'-ACATTGAGGCAC-TACTTG-3' (SEQ ID NO: 30)

Check that the sequence CAA does not appear in ACAT-TGAGGCACTA (SEQ ID NO: 31)

If there is a match, lengthen the primer by one base in the 3' direction and repeat the loop.

2) Check the predicted melting temperature of the primer and GC content.

% GC—the percentage (not fraction) of G and C residues in the sequence i.e. 33 not 0.33

If the % GC content falls outside a specified range then lengthen the primer by one base in the 3' direction and repeat the loop. In some embodiments the specified range may be greater than 25, 30, 31, 32, 33, 34, 35, or 40% and less than 55, 60, 61, 62, 63, 64, 65, 70, or 75%.

The melting temperature can be approximated by a number of methods. In one embodiment it is approximated by the empirical relation below, where the % GC is the percentage of G and C residues and the length is the primer length in units of the number of nucleotides.

$$T_m = 56.7 + 0.44668 * \% \, GC - \left(\frac{479.7}{\text{Length}}\right) \quad (4)$$

If the predicted melting temperature falls outside of certain specified values, then lengthen the primer by one base in the 3' direction and repeat the loop. In preferred embodiments the predicted melting temperature is desirably less than 70, 65, 60, 59, 58, 57, 56, 55, 50 degrees when using the empirical formula above.

3) If the primer is longer than a specified maximum primer length, i.e. 30 base pairs, then exit the loop unsuccessfully—no primer for this position. In some cases the maximum primer length may be 20, 30, 35, 40, 50, 60, or 70 base pairs.

4) Check the primer sequence for high self-complementarity.

Ensure that all base pair sequences in the primer are not a perfect match to anywhere in the reverse complement sequence of the primer.

If any match is found, then exit the loop unsuccessfully—no primer for this position.

5) If all requirements are met, then exit the loop successfully and record the primer for this position.

END LOOP

After attempts to generate primers for all forward positions and all reverse positions are complete, pairs may then be made with each forward pair to each possible reverse pair. This list of pairs can then be pruned in some cases to remove any that would result in products where the distances between nuclease sites and the ends of the amplicon fall outside of some specified ranges. This list may further pruned to remove primer pairs that are somehow undesirable, i.e. could potentially form primer dimers as defined by having the final 3' bases of one primer match the reverse complement of the final 3' bases of the other primer.

The primer pairs may then be sorted by some selection criteria depending upon the application, for example how close the melting temperature is to a specified target melting temperature. Primer pairs may also be sorted and/or filtered by providing a preference, for instance for shorter amplicon lengths, or may be sorted alphabetically or any other acceptable manner. If no primer pairs are found acceptable under a specified set of criteria, the algorithm may selectively relax constraints in some embodiments to generate a minimum number of primer pairs.

Estimating Off-Target Sites

Some embodiments provide an estimate of the number of expected off-target site based upon the search criteria, for example to provide the user with a guide for selecting appropriate search parameters or to prohibit queries that would generate such a large number of hits to be too time or resource intensive.

Using the Off-Site Prediction Methods

Figure 10:
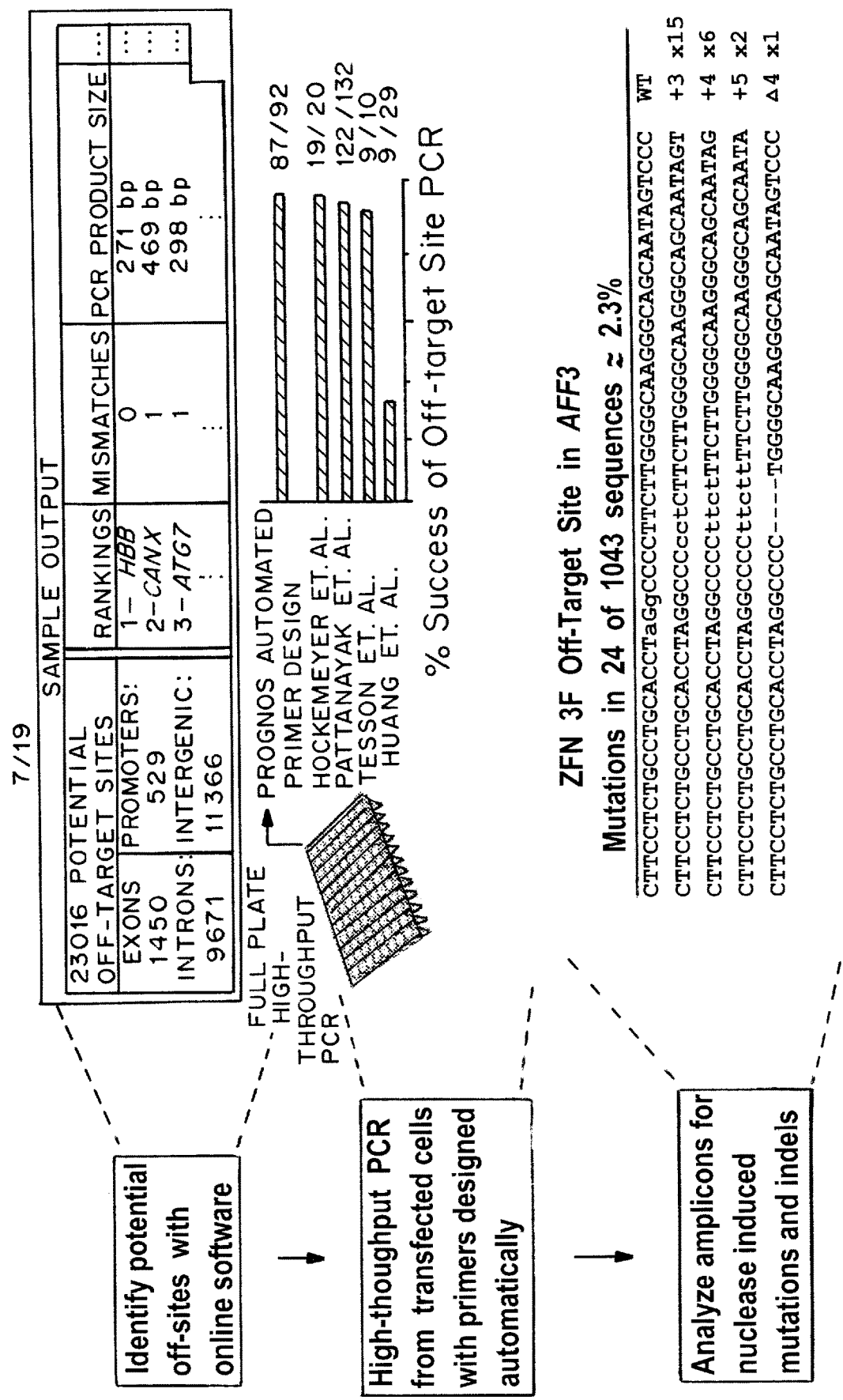
FIG. 10 is a flow chart illustrating how the off-target site detection methods can be employed in combination with experimental assays to greatly accelerate the discovery and testing of new nucleases. The off-target sites identified by the method are output along with the PCR primers designed for those sites. High-throughput PCR from cells transfected with the design primers results in amplification of regions of interest with a high success rate. The amplicons are analysed for nuclease induced mutations and indels indicative of off-target activity.
Figure 11:
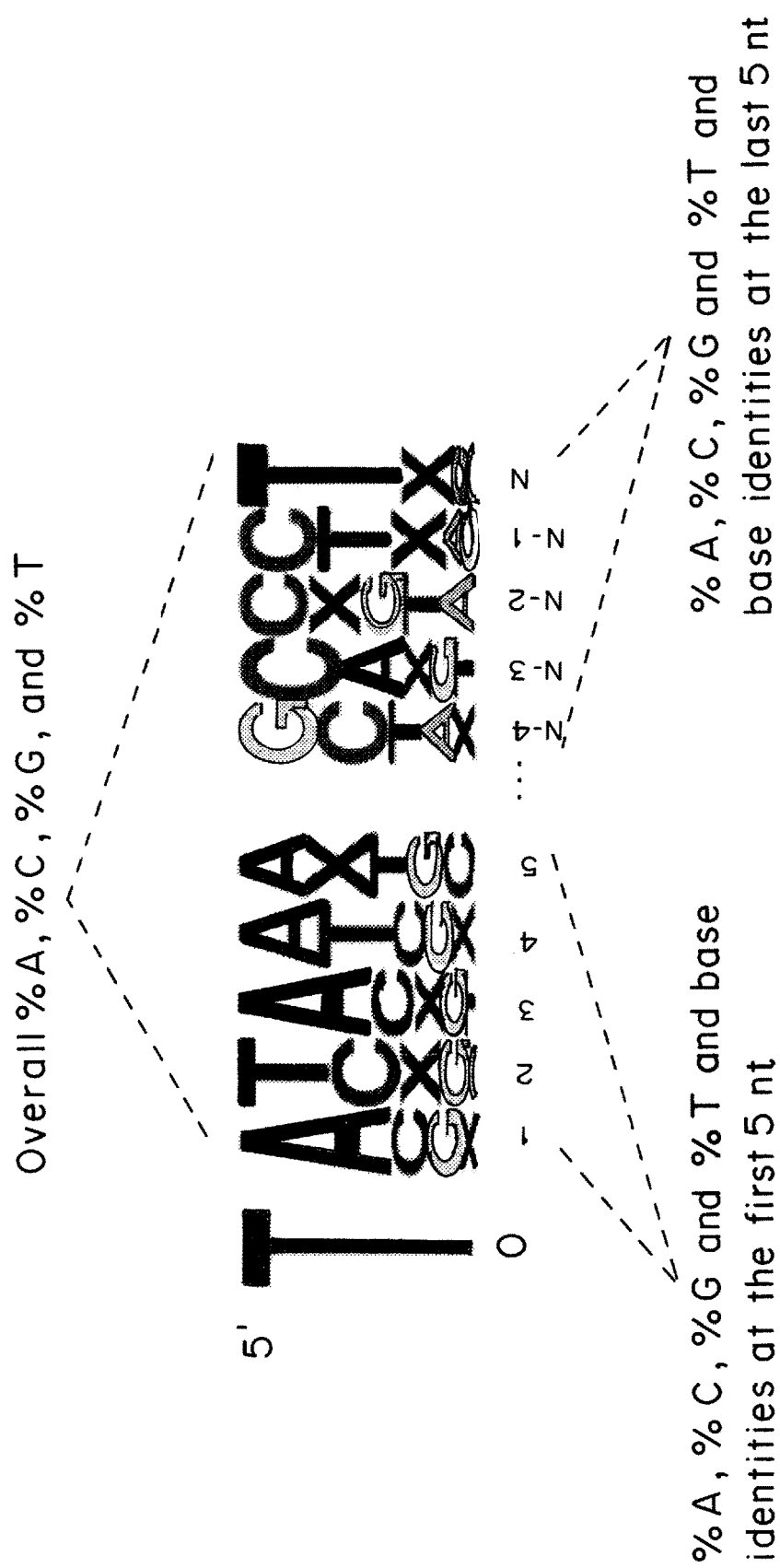
FIG. 11 is a representation of some of the parameters for TALEN design including the identity of specific nucleotides, their percentages, and the length.

The methods for off-target site prediction aid in the design of improved nucleases that have more specific cleavage sites. In some embodiments the methods complement or guide experimental investigations. FIG. 10 depicts an exemplary process where the off-site detection method or an apparatus for off-site detection is first used to identify off-target sites and primer pairs; the primer pairs are used in a high throughput PCR amplification to generate the amplicons; and the amplicons are assayed for nuclease induced mutations or indels. Investigating off-target sites in multiples of 8 will in some cases make the process more amenable to standard high-throughput equipment such as multi-channel pipettes and 96-well plates.

B. Systems and Methods for Predicting Nuclease Activity

A method is provided for identifying nuclease target sites or DNA binding sites with high activity and the corresponding nucleases or DNA binding domains. The method is based upon a scoring function for predicting nuclease activity or DNA binding domain. In some embodiments the scoring function is derived empirically or by incorporating various design rules. In some cases the scoring function is derived to predict activities for a specific type of nuclease, or in some cases for a few limited classes of nucleases or DNA binding domains. In some embodiments the scoring function derived for one class of nucleases can still be applied to predict the activities of other related classes and related DNA binding domains. The method is based on the sum of scores corresponding to different design considerations. Therefore, the method is flexible and will be able to incorporate more design variables into the function as more information about the factors affecting a given nuclease activity becomes available. In addition, the method is flexible and can be re-applied to an enlarged training set of data once more experimental data become available. In some embodiments a range of different scoring functions is provided with some applying generally and others optimal for a specific class of nucleases or DNA binding domains. For example, in some embodiments a scoring function is provided that can generally predict activities for TALENs, while additional scoring functions are provided that are optimized individually for predicting activities of NH, NK, and NN TALENs, TALENs with different N-terminal and C-terminal architectures, and TAL effectors.

The scoring function will contain a number of variables. In some cases, more than 40, 50, 60, 70, 80, 90, or more than 100 variables are included in the scoring function. The scoring function in some cases contains an optimized set of dummy variables and continuous variables. Dummy variables are used to describe for example base identities of certain nucleotides in the monomer target sequence, whereas cubic functions may be used to characterize the effect of changes in other variables, including the length of the target sequence, the overall percentages of a specific nucleotide in the target sequence, or the maximum numbers of consecutive nucleotide in a given target sequence. For composite nucleases, i.e. for a TALEN pair the composite score is a combination of the monomer scores, or in some cases is a function of the monomer scores.

The scoring function is developed based on monomer nuclease activity, for example that was quantified using a cellular SSA assay. Nucleases with similar activity levels in cleaving plasmid targets may have different levels of activity when targeting endogenous gene sequences, most likely due to different target accessibilities controlled by genomic context and the methylation state of endogenous genes. Therefore, the rate of endogenous gene modification is difficult to predict. Since it may not be feasible to fully model all the effects of genomic context, the scoring function will typically provide an ordered list of the top target sites in a gene segment to help obtain intrinsically active nucleases despite genomic context.

Recent publications have shown that TAL effectors containing NN and NH RVDs have activities that are often higher than those with an NK RVD. See for example Christian et al. (2010), *Genetics* 186:757-761 and Li et al. (2010), *Nucleic Acids Res.* 39:359-372. However, they also showed that NN RVD in TAL effectors was less specific compared to NK NN-TALENs have a higher level of off-target cleavage activity than NK-TALENs As papers on NH-TALEs have been published only recently, the specificity and activity of NH-TALENs has not been well established. The method is described based upon NK-TALENs since they tend to have higher specificity, but with lower activity than NN-TALENs.

To develop a scoring function for TALEN activity, a scoring function is defined to approximate the activity at a given monomer target. An exemplary scoring function, S, is defined as a sum of seven terms:

$$S = S_{POS} + S_N + S_{PER} + S_{PER,F5} + S_{PER,L5} + S_{CONS} + C_0 \quad (5)$$

although in some cases a greater or fewer number of terms could be used. In Equation 5, $C_o$ is a constant, and $$S_{POS} = F(d_1) + F(d_2) + F(d_3) + F(d_4) + F(d_5) + F(d_{N-4}) + F(d_{N-3}) + F(d_{N-2}) + F(d_{N-1}) + F(d_N) \quad (6)$$

represents the effects of each nucleotide at the first five and last five positions of the target sequence (e.g., the impact of having a C as the first nucleotide in the target sequence). In other embodiments or for other types of nucleases it may be necessary to take into account a greater or fewer number of nucleotides in the target sequence. For example, the scoring function will in some cases take into account the first and last 3, 4, 5, 6, 7, 8, 9, or 10 nucleotides in a given target sequence, where the contribution at each nucleotide can be given by a formula according to:

$$F(d_i) = \beta_{1,A} \cdot d_{i,A} + \beta_{i,C} \cdot d_{i,C} + \beta_{i,G} \cdot d_{i,G} + \beta_{i,T} \cdot d_{i,T} \quad (7)$$

The dummy variable $d_{i,x}$ is either 1 (if the nucleotide at the position i is x) or 0 (otherwise). Positions are numbered starting from the first nucleotide after the 5'-T. In the equation, N denotes the total number of nucleotides in the sequence. For example, $d_N$ corresponds to the last nucleotide at the 3' end of the sequence. Parameters ($\beta$) associated with the variables (d) are optimized according to a training set of data.

$$S_N = Q(N), \quad (8)$$

represents the effect of the length of target sequence (N);

$$S_{PER} = Q(\% A) + Q(\% C) + Q(\% G) + Q(\% T), \quad (9)$$

represents the effect of the overall base composition (percentages of A, C, G, T);

$$S_{PER,F5} = Q(\% A_{F5}) + Q(\% C_{F5}) + Q(\% G_{F5}) + Q(\% T_{F5}) \quad (10)$$

represents the effect of the base composition of the first five nucleotides (% $A_{F5}$, % $C_{F5}$, % $G_{F5}$, and % $T_{F5}$);

$$S_{PER,L5} = Q(\% A_{L5}) + Q(\% C_{L5}) + Q(\% G_{L5}) + Q(\% T_{L5}) \quad (11)$$

represents the effect of the base composition of the last five nucleotides (% $A_{L5}$, % $C_{L5}$, % $G_{L5}$, and % $T_{L5}$);

$$S_{CONS} = Q(A_{CONS}) + Q(G_{CONS}) \quad (12)$$

represents the effect of the maximum numbers of consecutive A's ($A_{CONS}$) and consecutive G's ($G_{CONS}$).

In equations (10-14), Q(x) is a cubic function defined as $Q(x) = ax^3 + bx^2 + cx + d$ where the values of a, b, c are all optimized to reproduce the activity data in the training set, along with the constant $C_0$ in equation 5.

Cubic functions were chosen since a third-degree polynomial has the flexibility to approximate various curves, including linear, parabola, exponential, and asymmetric concave curves. Higher order polynomials may be used in some embodiments.

In the functions defined above for TALEN activities, there are a total of 55 variables and 86 parameters. To fully demonstrate the above algorithm for TALEN activity, 116 NK-TALENs were individually tested for their monomer SSA activity in cultured cells. The experimental results were used to determine the parameters by minimizing the total squared differences between computed scores and measured SSA activities of the training set (116 TALENs), which allows the scoring function to best predict cellular SSA activity of newly designed TALENs. The parameters of the algorithm were optimized using the Generalized Reduced Gradient non-linear optimization algorithm, although other optimization methods could be used.

The methods provided herein can be used to create a ranked list of high-activity nuclease target sites or DNA binding domains such as those in TAL effectors. For the example TALEN systems, tools do not exist that can rank predicted TALEN activity. The TALE-NT tool identifies all TALEN pairs that meet the following three criteria without further discrimination/ranking: (1) a T or C precedes the 5' end of each target half-site; (2) a spacer range (15~20); (3) a range for repeat array length (15~20). As shown in the study by Reyon et al., TALENs that meet all these criteria have activities (measured as NHEJ-mediated mutagenesis) varying over a wide range, from zero to 55.8%. See Reyon et al, (2012), *Nat. Biotech.* 30:465-465. Designing TALENs solely based on these criteria may not lead to high cleavage activity, since there is no sufficient guidance in selecting target sites.

TALE-NT typically provides hundreds of potential target sites that meet the design criteria without further discrimination. In contrast, the TALEN scoring function described above (Equation 5) provides a ranked list of target sites with scores that correlate with the activity, allowing researchers to choose the top-ranked TALENs for testing.

C. Experimental Methods

The methods provided herein will in some cases completely replace the need for experimentally screening nuclease off-target sites or nuclease activities, allowing for the design of engineered nucleases in a completely in-silico manner. In some cases the tools provided herein will serve as an essential first step in the design process by screening and selecting only the few potential nucleases that are predicted to have high activities and limited off-site targeting. This will allow for far less experimental time and resources being applied to preparing and testing nucleases that do not have the desired features.

In some cases the methods provided herein for predicting off-target sites and nuclease activities will be used without the need for experimental data. In some cases the methods provided herein for predicting off-target sites and nuclease activities will be parameterized to correlate with experimentally determined values. In some embodiments the methods provided herein for predicting off-target sites and nuclease activities will be used to screen candidate nucleases wherein a much smaller subset are subsequently tested experimentally.

The methods of predicting off-target sites and nuclease activities can be used in combination with experimental methods for measuring cleavage activity or identifying off-target active sites of a nuclease. In some embodiments this includes using the results from one or more experiments to guide the search for off-target sites or nucleases with high activity. An exemplary embodiment includes experimentally determining the binding preference of a nuclease, and subsequently using this binding preference to guide the off-target site searching method. Some of these experimental methods are described below.

The methods of predicting off-target sites and nuclease activities can be used in combination with experimental methods for measuring cleavage activity or identifying off-target active sites of a nuclease. In some embodiments this includes using the results from one or more experiments to guide the search for off-target site or nucleases with high activity. An exemplary embodiment includes experimentally determining the binding preference of a nuclease, and subsequently using this binding preference to guide the off-target site searching method. Some of these experimental methods are described below.

The experimental methods can include any method capable of measuring the cleavage activity or identifying off-target active sites of a nuclease. Non-limiting exemplary experimental methods are described below. Other potentially suitable experimental methods could include those described in U.S. Pat. No. 5,554,502 to Mitsuhashi et al., U.S. patent application publication number US 2010/0323906 by Chen et al., or U.S. Pat. No. 6,787,304 to Han et al.

SELEX

Systematic Evolution of Ligands by Exponential Enrichment (SELEX) is a widespread technique for determining the DNA binding preference of a target ligand, including ZFNs or TALENs, through the use of a semi-randomized library of DNA sequences. Typically, the nuclease is genetically tagged with an affinity molecule such as hemagglutinin (HA) and then expressed in vitro. The nuclease protein is then incubated with a semi-randomized library of DNA fragments (biased towards the expected target sequence of the nuclease). Then the nuclease is captured with an antibody and any unbound fragments of DNA are washed away. The captured fragments of DNA are then PCR amplified and the process is repeated using these PCR amplicons instead of the randomized library. After a number of rounds of selection, the bound fragments of DNA are sequenced to determine the frequencies at each position for each nucleotide. Once a frequency matrix has been generated for each nuclease, the genome is searched to find sites that score highly in the frequency matrix of each nuclease at sites separated by allowed spacing distances. In summary, SELEX reveals the DNA binding preferences of the individual nuclease monomers in vitro.

In Vitro Cleavage

In this technique, oligonucleotides comprising a semi-randomized library of full-length nuclease target sites (left half-site, spacer, and right half-site) are incubated with nuclease protein. Targets that are cleaved by the nucleases are recovered, amplified, and sequenced. The genome is then searched to locate any sites that match sequences that were cleaved in vitro3. In summary, in vitro cleavage reveals the sequences that the pair of nucleases can cleave in vitro.

Bacterial One-Hybrid

In bacterial one-hybrid (B1H), a semi-randomized library of nuclease monomer binding sites is cloned upstream of a reporter gene in a plasmid5. The DNA binding domain of the nuclease is fused to a polymerase domain that can activate the reporter gene if bound to the target upstream of the start site. The plasmid encoding the reporter target and the plasmid encoding the DNA binding domain polymerase fusion are co-transformed into bacteria. The activity of the reporter gene is then measured and the binding site of the reporter plasmid in that transformation is sequenced. These different sequences are compiled to create a frequency matrix of the different nucleotides at each position in the nuclease binding site. Once a frequency matrix has been generated for each nuclease, the genome is searched to find sites that score highly in the frequency matrix of each nuclease at sites separated by allowed spacing distances. In summary, B1H reveals the DNA binding preferences of the individual monomers in bacterial cells.

IDLV LAM-PCR

Integrase-Deficient Lentiviral Vector Linear Amplification Mediated Polymerase Chain Reaction (IDLV LAM-PCR) is a more unbiased, genomewide technique to locate sites of nuclease cleavage as opposed to the other methods of characterization which use sequence libraries4. This technique centers on the ability of IDLVs to enter the genome ONLY at sites where a double strand break has been induced, because they lack the integrase that typically facilitates non-specific integration into the genome. If co-transfected with nucleases, the IDLV will integrate into the genome of the host cell only at sites where a double strand break is created by the nucleases. The LAM-PCR technique can then create an amplicon with one end inside the IDLV vector and one end spanning a stretch of surrounding genomic sequence. These amplicons can then be sequenced and the integration site mapped to a region of the genome. The surrounding sequence can then be scanned for probable sites with homology to the nuclease target sites that may be the site of nuclease off-target cleavage. In summary, IDLV LAM-PCR reveals sites in the genome that the nuclease pair cleaves in cells.

SMRT Sequencing

Figure 15:
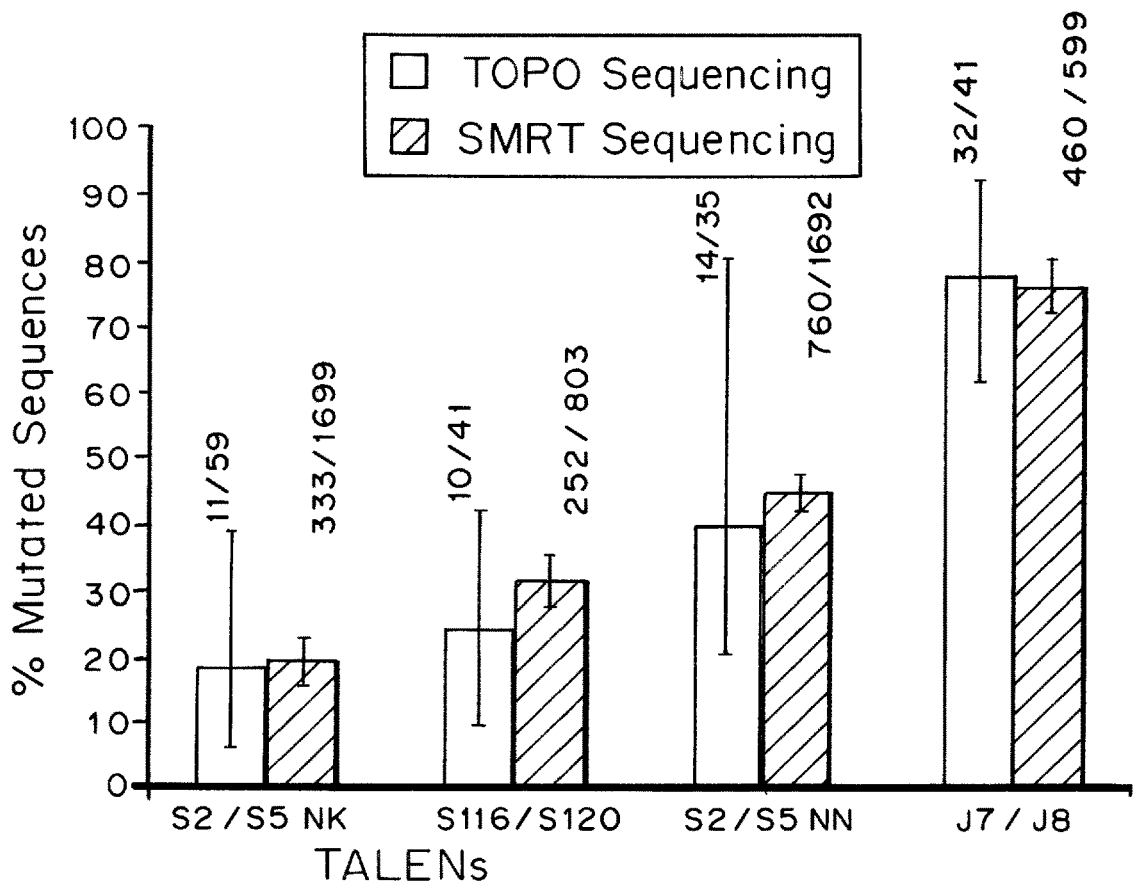
FIG. 15 is a comparison of TOPO and single molecule real-time (SMRT) Sequencing for detecting the rate of nuclease induced mutations in cells. The target sites of four TALENs were analyzed using both SMRT sequencing and standard sequencing of TOPO-cloned plasmids. S2/S5 NN and S2/S5 KK are the TALENS designed targeting beta-globin. S116/5120 and J7/J8 are the TALENS from Lin et al.
Figure 16:
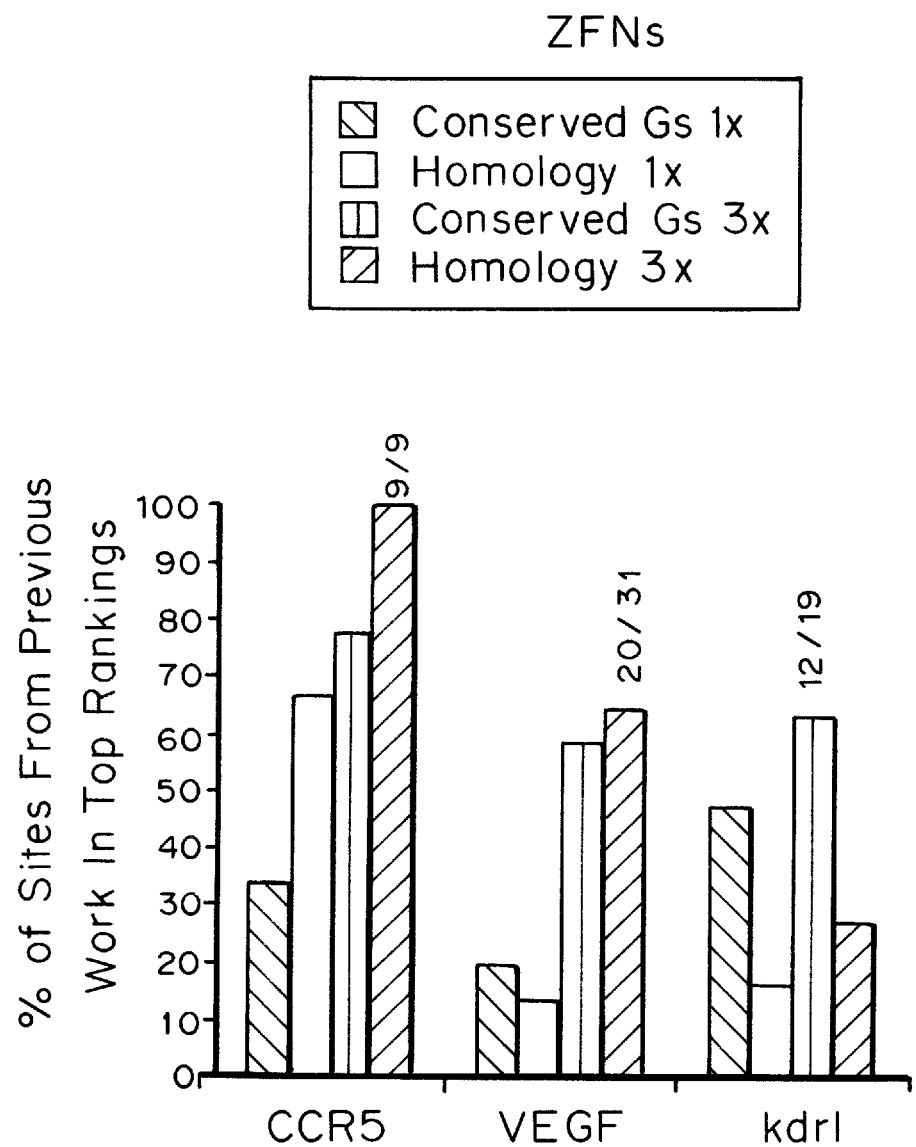
FIG. 16 is a bar graph showing the number of number of sites with previously reported off-target activity for ZFNs that were in the list of the top ranked sites using the homology and Conserved G scorings. The 1× corresponds the searching only the same number of sites as were reported, and 3× corresponds to searching three times as many sites.

Single Molecule Real-Time (SMRT) sequencing can be used to analyze the off-target sites of newly constructed nucleases. SMRT allows long read lengths and reasonable sensitivity to determine nuclease activity and specificity at a lower cost than other deep sequencing platforms. The accuracy of SMRT sequencing based analysis of nuclease cleavage was established by the good agreement between SMRT sequencing results and the results from standard sequencing of TOPO-cloned products. FIG. 15 compares rates of nuclease induced mutations target site of four TALENs using both SMRT sequencing and standard Sanger sequencing of TOPO-cloned plasmids. SMRT sequencing produced very similar results to TOPO cloning over a range of mutation rates from ~20% to ~76%. Error bars are 90% confidence intervals. S2/S5 NK and S2/S5 NN are the TALENs targeting beta-globin described below. S116/S120 and J7/J8 are NK-TALENs targeting beta-globin and CDH1, respectively.

ZFNs predominately induced 3, 4, and 5 bp insertions or deletions, with a few large deletions. In contrast, TALENs induced mutations over a much broader range, centered around 5 bp to 20 bp deletions, possibly due to the flexibility of the +63 C-terminal TAL domain.

There are three main processing steps of the raw SMRT sequencing reads to detect nuclease-induced non-homologous end joining (NHEJ). First, because many amplicons are pooled into a single SMRT sequencing cell, sequencing reads must be mapped to the amplicon from which they were generated. Second, because the processivity of the polymerase used in SMRT sequencing is a stochastic factor, the quality of the sequencing reads ranges over a distribution. However, for detecting the small insertions and deletions characteristic of NHEJ, sequencing artifacts that would yield false positives should be eliminated. Therefore, the sequencing reads will in some cases be filtered to obtain only the higher quality sequencing reads. Third, the high quality sequencing reads need to be analyzed to determine if they show mutations consistent with nuclease-induced NHEJ.

In some cases a sequencing processing pipeline can be used. It can be based in Perl or any acceptable programming language depending upon the platform. An outline of an exemplary sequencing pipeline is presented below.

Sequence Mapping
1) Create a BLAST database of all expected amplicons obtained from the reference genome.
2) BLAST each consensus SMRT sequencing read against the BLAST database.
   a. BLAST Parameters: gapopen 2, gapextend 1, reward 1, penalty −1
3) Remove from further processing any reads that failed to make a significant BLAST alignment to any sequence in the database.

Pairwise Alignment
1) Use the Needleman-Wunsch algorithm to align each sequence read with the expected amplicon to which it was mapped.
   a. Needle Parameters: gapopen 10, gapextend 1
2) If the alignment of the sequencing read extends more than 65 bp past the end of the reference sequence, remove it from further processing.

Sequence Quality Filtering
1) Calculate the average Phred score of each consensus SMRT read from the FASTQ data.
2) Remove from further processing any reads that have an average Phred score lower than 40.
3) Scan the region of the pairwise alignment extending 100 bp out from the edge of the nuclease binding sites for indels.
   a. indel—a stretch of deleted, inserted, or mismatched bases in the sequencing read relative to the reference sequence.
4) If an indel is found that does not overlap the nuclease target site, add the square of its length to a running total "errorCount".
   a. nuclease target site—the region encompassing the binding site of the left nuclease, the spacer region, and the right nuclease in the reference sequence.
   b. Example—an indel of length 4 that did not overlap the nuclease target site would add $4^2=16$ to "errorCount".
5) If "errorCount" divided by the length of the scanned sequence is greater than 0.005, remove that sequencing read from further processing.

Identifying Events of Non-Homologous End Joining (NHEJ)
1) Scan the pairwise alignment extending 100 bp out from the edge of the nuclease binding site for indels.
2) Check if the observed indel overlaps the spacer region in the reference sequence.
3) If the indel overlaps the spacer and is of length 5 or greater, classify as NHEJ.
4) If the indel overlaps the spacer and is of length 3 or 4:
   a. If the indel is composed entirely of a deletion, classify as NHEJ.
   b. If the indel is composed entirely of a tandem repeat of the flanking sequence, classify as NHEJ.
5) Manually verify suspected NHEJ events by hand to confirm true cases of NHEJ.

II. Engineered Nucleases

Engineered nucleases that target specific DNA sequences with reduced off-site cleavage are provided. The nuclease can be a fusion protein that contains a cleavage domain and a DNA binding domain (also referred to as a recognition domain). The cleavage domain in some nucleases can be a cleavage half-domain, such as the Fok I cleavage half-domain, therefore requiring two nucleases to bind for cleavage. In other cases a single nuclease may be all that is required for cleavage to occur, and such nucleases may consist of a single cleavage domain and a single binding domain. By separating the recognition and cleavage components, the design of new nucleases is greatly simplified. Many nucleases have these components together. Exemplary nucleases described herein include the zinc finger nucleases (ZFNs), the transcription activator-like effector nucleases (TALENs), the clustered regularly interspaced short palindromic repeats (CRISPR) nucleases, and the meganucleases.

A. The Non-Specific Cleavage Domain

The engineered nucleases described herein (e.g., ZFNs, TALENs, etc.) include a cleavage domain or a cleavage half-domain. The cleavage half-domain is a functional half of a cleavage domain that can "dimerize" or form a dimer when two nucleases bind with the proper orientation. The cleavage domain portion of the fusion proteins can in principle be obtained from any endonuclease or exonuclease. Exemplary endonucleases from which a cleavage domain can be derived include, but are not limited to, restriction endonucleases and homing endonucleases. See, for examples Belfort et al. (1997) Nucleic Acids Res. 25:3379-3388. Many enzymes that are capable of cleaving DNA are known (e.g., Sl Nuclease; mung bean nuclease; pancreatic DNase I; micrococcal nuclease; yeast HO endonuclease). Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc, Natl. Acad.

Sci. USA 89:4275-4279; Li et al. (1993) Proc. Natl. Acad. Sci. USA 90:2764-2768; Kim et al. (1994a) Proc. Natl Acad, Sci. USA 91:883-887; Kim et al. (1994b) J. Biol. Chem. 269:31,978-31,982. One or more of these enzymes (or enzymatically functional fragments thereof) can be used as a source of cleavage domains and cleavage half-domains. In other embodiments the cleavage domain or cleavage half domain can be a variant of a wild type cleavage domain or cleavage half domain. Such variant cleavage domains or half domains may contain 1, 2, 3, 4, 5, 6, or more mutations. In some embodiments the cleavage half domain is the wild type FokI cleavage half domain. In some embodiments the cleavage half domains are mutant FoId cleavage domains containing one or more substitutions to prevent homodimerization. Engineered cleavage half domains that minimize or prevent homodimerization are described for example in U.S. Patent Publication Nos. 2005/0064474 and 2006/0188987, incorporated herein by reference in their entireties.

A cleavage half-domain can be derived from any nuclease or portion thereof that requires dimerization for cleavage activity. In certain preferred embodiments the tools and methods disclosed herein are useful for the design of nucleases of this type, i.e. for predicting the specificity and activity of nucleases that contain cleavage half domains that must dimerize to cleave DNA. In general, two complementary fusion proteins are required for cleavage if the fusion proteins comprise cleavage half-domains. Alternatively, in some embodiments a single protein comprising two cleavage half-domains can be used. The two cleavage half-domains can be derived from the same endonuclease (or functional fragments thereof), or each cleavage half-domain can be derived from a different endonuclease (or functional fragments thereof). A cleavage domain or cleavage half-domain can be any portion of a protein that retains cleavage activity, or that retains the ability to dimerize to form a functional cleavage domain.

In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage. In certain embodiments fusion proteins target a single-stranded cleavage in a double-stranded section of DNA. Fusion proteins of this type are sometimes referred to as nickases, and can in some embodiments be preferred to limit undesired mutations. In some cases a nickase is created by blocking or limiting the activity of one half of a fusion half-domain dimer.

Exemplary Type IIS restriction enzymes are described in International Publication WO 07/014275, incorporated herein in its entirety. Additional restriction enzymes also contain separable binding and cleavage domains. See, for example, Roberts et al. (2003) Nucleic Acids Res. 31:418-420. In certain embodiments, the cleavage domain comprises one or more engineered cleavage half-domain (also referred to as dimerization domain mutants) that minimize or prevent homodimerization, as described, for example, in U.S. Patent Publication Nos. 2005/0064474, 2006/0188987, and 2008/0131962. In certain embodiments the cleave half domain is a mutant of the wild type Fok I cleavage half domain. In some embodiments the cleavage half domain is a wild type Foki I mutant where one or more amino acid residues at positions 446, 447, 479, 483, 484, 486, 487, 490, 491, 496, 498, 499, 500, 531, 534, 537, and 538 is substituted. See, e.g., Example 1 of WO 07/139898. Numbering of amino acid residues in the Fok I protein is according to Wah et al., (1998) *Proc Natl Acad Sci USA* 95:10564-10569. In some embodiments the cleavage half domains are modified to include nuclear or other localization signals, peptide tags, or other binding domains.

B. Zinc Finger Nucleases

Figure 1A:
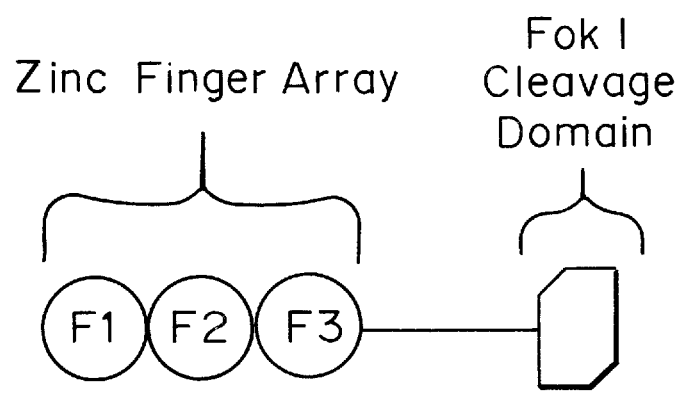
FIG. 1A is a schematic of a 3-finger ZFN. Each of the Zinc fingers is designed to bind a specific 3-bp sequence, and each ZFN will contain typically 3-6 Zinc fingers providing recognition for a 9-18 bp target site. The most common cleavage domain is the FokI cleavage half domain.
Figure 1B:
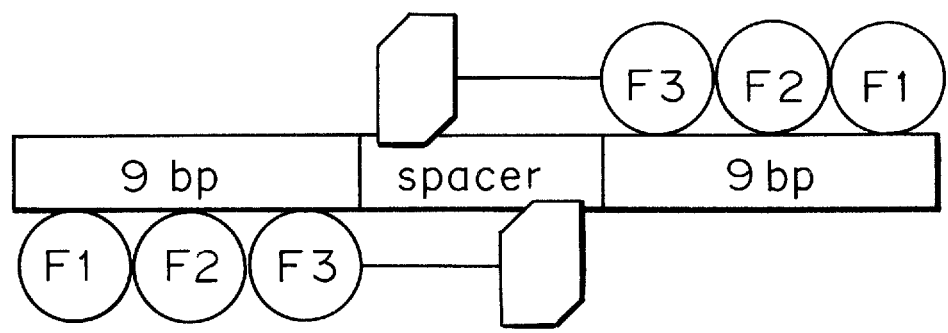
FIG. 1B is a schematic of a dimer of two 3-finger ZFNs bound to the target site. Complementary left and right ZFN pairs bind oriented for dimerization of the Fok I cleavage half domains.

Zinc finger nucleases (ZFNs) consist of a DNA-binding domain, derived from zinc-finger proteins, linked to a cleavage domain. The most common cleavage domain is Fok I. This is depicted in FIG. 1A. The DNA-binding domain, which can be designed (in principle) to target any genomic location of interest, is a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe(sometimes Tyr)-(5 amino acids)-Leu-(2 amino acids)-His-(3 amino acids)-His (SEQ ID NO: 32). By linking together multiple fingers (the number varies: three to six fingers have been used per monomer in published studies), ZFN pairs can be designed to bind to genomic sequences 18-36 nucleotides long. When two ZFN monomers bind (See FIG. 1B), in inverse orientation, with an optimal spacing, generally 5-7 nucleotides, the resulting dimeric nuclease cleaves the DNA between the binding sites.

Another type of zinc finger that binds zinc between 2 pairs of cysteines has been found in a range of DNA binding proteins. The general structure of this type of zinc finger is: Cys-(2 amino acids)-Cys-(13 amino acids)-Cys-(2 amino acids)-Cys (SEQ ID NO: 33). This is called a $Cys_2 Cys_2$ zinc finger. It is found in a group of proteins known as the steroid receptor superfamily, each of which has 2 $Cys_2Cys_2$ zinc fingers.

The DNA-binding domain of a ZFN may be composed of two to six zinc fingers. Each zinc finger motif is typically considered to recognize and bind to a three-base pair sequence and as such, a protein including more zinc fingers targets a longer sequence and therefore may have a greater specificity and affinity to the target site. Zinc finger binding domains can be "engineered" to bind to a predetermined nucleotide sequence. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416. Consequently, zinc finger binding domains can be engineered to have a novel binding specificity, compared to a naturally-occurring zinc finger protein. Engineering methods include, but are not limited to, rational design and various types of empirical selection methods. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Patent Application Publication Nos. 2002/0165356; 2004/0197892; 2007/0154989; 2007/0213269; and International Patent Application Publication Nos. WO 98/53059 and WO 2003/016496, all of which are incorporate by reference in their entireties.

C. Transcription Activator-Like Effector Nucleases

Figure 2:
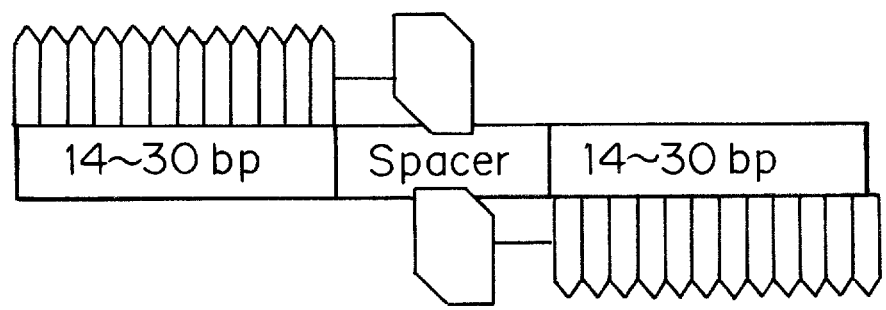
FIG. 2 is a schematic of a generic TALEN. The protein is a fusion of a transcription activator-like effector DNA binding domain to a DNA cleavage domain, such as the Fold cleavage domain. The binding domain contains a highly conserved repeat sequence consisting of 33-34 amino acids. The $12^{th}$ and $13^{th}$ amino acids in the repeat sequence are referred to as the repeat variable diresidues (RVDs) and have been observed to correlate with site recognition.
Figure 3:
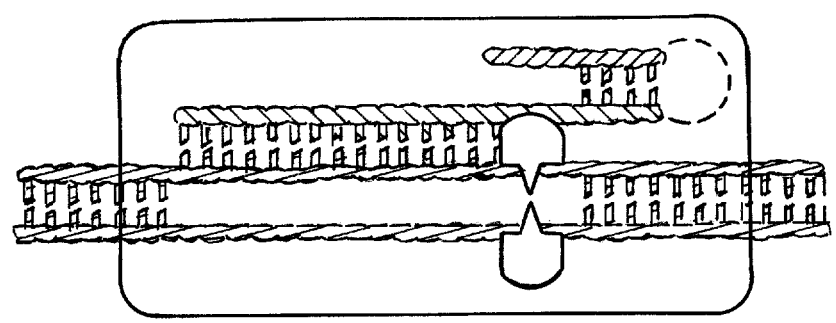
FIG. 3 is a schematic of a clustered regularly interspaced short palindromic repeats (CRISPR)nuclease bound to the target site. Unlike the ZFN and TALEN fusion proteins described above, the CRISPR nucleases recognition site is a CRISPR RNA guide strand segment.

Transcription activator-like effector nucleases (TALENs) have an overall architecture similar to that of ZFNs, with the main difference that the DNA-binding domain comes from TAL effector proteins, transcription factors from plant pathogenic bacteria (FIG. 2). The DNA-binding domain of a TALEN is a tandem array of amino acid repeats, each about 34 residues long. The repeats are very similar to each other; typically they differ principally primarily at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. The monomeric and dimeric TALENs disclosed herein will typically comprised more than 10, more than 14, more than 20, or more than 24 repeats.

Methods of engineering TAL to bind to specific nucleic acids are described in Cermak, et al., Nucl. Acids Res. (2011) 1-11. US Patent Publication No. 2011/0145940, which is incorporated by reference in its entirety, discloses TAL effectors and methods of using them to modify DNA. Miller et al. (Miller et al. (2011) Nature Biotechnol 29:143) reported making TALENs for site-specific nuclease architecture by linking TAL truncation variants to the catalytic domain of FokI nuclease. The resulting TALENs were shown to induce gene modification in immortalized human cells. General design principles for TALE binding domains can be found, for instance in WO 2011/072246.

Although TALENs seem to be much easier to design and appear less cytotoxic than ZFNs, there still remain concerns about off-target effects. The three previously reported cases of TALEN off-target sites shared only 78%, 74%, and 72% sequence homology to the intended target site. See Tesson et al. (2011), *Nature Biotech.* 29:695-696 and Hockemeyer et al. (2002), *Nature Biotech.* 29:731-734. Given the abundance of sites in a genome that share that level of homology with a TALEN target site, these findings strongly reinforce the need to interrogate these types of genomic loci for possible off-target cleavage. The lack of discrimination of NN RVDs between guanosine and adenosine is a major concern. TALENs using the +63 C-terminal truncation have been shown to cleave over a wide range of spacers. This makes design of TALENs easier and increases the number of potential sequences that can be targeted, but it also increases the number of potential regions of the genome that could be cleaved through off-target activity.

D. Linkers

There are numerous strategies for creating the fusion proteins described above. These will typically involve joining the DNA binding domain to the cleavage domain or half domain by an operable linker. For instance in typical ZFN with a FokI cleavage domain cleavage is obtained when the zinc finger proteins bind to target sites separated by approximately 5-6 base pairs. A linker, typically a flexible linker rich in glycine and serine, is used to join each zinc finger binding domain to the cleavage domain See, e.g., U.S. Patent Publication No. 2005/0064474 and PCT Application WO 07/139898. In some embodiments the engineered nuclease may use modified linkers, linkers that are longer or shorter, more or less rigid, etc. than those conventionally employed for created ZFN or TALEN fusion proteins. The linker may form a stable alpha helix linker. See, e.g., Yan et al. (2007) Biochemistry 46:8517-24 and Merutka and Stellwagen (1991) Biochemistry 30:4245-8. Although the methods described herein are flexible to describe nucleases having a range of linkers, in some embodiments the linkers will be preferentially less than 50 base pairs, less than 30 base pairs, less than 20 base pairs, less than 15 base pairs, or less than 10 base pairs in length.

IV. Definitions

A "cleavage half-domain" is a polypeptide sequence that, in conjunction with a second polypeptide (either identical or different) forms a complex having cleavage activity (preferably double-strand cleavage activity). The terms "first and second cleavage half-domains;" "+ and − cleavage half-domains" and "left and right cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication No. 20050064474; and WO 2007/13989, incorporated herein by reference in their entireties.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule, a malfunctioning version of a normally-functioning endogenous molecule or an ortholog (functioning version of endogenous molecule from a different species).

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general and unless otherwise specified, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

The terms "cleavage" or "cleaving" of nucleic acids, as used herein, refer to the breakage of the covalent backbone of a nucleic acid molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments cleavage refers to the double-stranded cleavage between nucleic acids within a double-stranded DNA or RNA chain.

The term "genome", as used herein, refers to the nuclear DNA of an organism. The term "genomic DNA" as used herein refers to deoxyribonucleic acids that are obtained from the nucleus of an organism. The terms "genome" and "genomic DNA" encompass genetic material that may have undergone amplification, purification, or fragmentation. In some cases, genomic DNA encompasses nucleic acids isolated from a single cell, or a small number of cells. The "genome" in the sample that is of interest in a study may encompass the entirety of the genetic material from an organism, or it may encompass only a selected fraction thereof: for example, a genome may encompass one chromosome from an organism with a plurality of chromosomes.

The terms "genomic region" or "genomic segment", as used interchangeably herein, denote a contiguous length of nucleotides in a genome of an organism. A genomic region may be of a length as small as a few kb (e.g., at least 5 kb, at least 10 kb or at least 20 kb), up to an entire chromosome or more.

The terms "genome-wide" and "whole genome", as used interchangeably herein, refer generally to the entire genome of a cell or population of cells. The terms "genome-wide" and "whole genome" will generally encompass a complete DNA sequence of all of an organisms DNA (chromosomal, mitochondrial, etc.). Alternatively, the terms "genome-wide" or "whole genome" may refer to most or nearly all of the genome. For example, the terms "genome-wide" or "whole genome" may exclude a few portions of the genome that are difficult to sequence, do not differ among cells or cell types, are not represented on a whole genome array, or raise some other issue or difficulty that prompts exclusion of such portions of the genome. In some embodiments the genome is considered complete if more than 90%, more than 95%, more than 99%, or more than 99.9% of the base pairs have been sequenced. Broadly the genome can refer to any organism for which a portion of the genome has been sequenced. In some embodiments the whole genome is the human genome, the rat genome, the mouse genome, the Zebrafish genome, the *Arabidopsis* genome, the yeast genome, the *D. melanogaster* genome, the *C. elegans* genome, the dog genome, the cow genome, the ape genome, or the pig genome.

The term "endonuclease", as used herein, refers to any wild-type or variant enzyme capable of catalyzing the hydrolysis (cleavage) of bonds between nucleic acids within a DNA or RNA molecule, preferably a DNA molecule. Non-limiting examples of endonucleases include type II restriction endonucleases such as FokI, HhaI, HindIII, NotI, BbvCI, EcoRI, BglIII, and AlwI. Endonucleases comprise also rare-cutting endonucleases when having typically a polynucleotide recognition site of about 12-45 basepairs (bp) in length, more preferably of 14-45 bp. Rare-cutting endonucleases induce DNA double-strand breaks (DSBs) at a defined locus. Rare-cutting endonucleases can for example be a homing endonuclease, a chimeric Zinc-Finger nuclease (ZFN) resulting from the fusion of engineered zinc-finger domains with the catalytic domain of a restriction enzyme such as FokI or a chemical endonuclease The term "exonuclease", as used herein, refers to any wild type or variant enzyme capable of removing nucleic acids from the terminus of a DNA or RNA molecule, preferably a DNA molecule. Non-limiting examples of exonucleases include exonuclease I, exonuclease II, exonuclease III, exonuclease IV, exonuclease V, exonuclease VI, exonuclease VII, exonuclease VII, Xrn1, and Rat1.

In some cases an enzyme is capable of functioning both as an endonuclease and an exonuclease. The term nuclease generally encompasses both endonucleases and exonucleases, however in some embodiments the terms "nuclease" and "endonuclease" are used interchangeably herein to refer to endonucleases, i.e. to refer to enzyme that catalyze bond cleavage within a DNA or RNA molecule.

A "zinc finger DNA binding protein" (or binding domain) is a protein, or a domain within a larger protein, that binds DNA in a sequence-specific manner through one or more zinc fingers. The term zinc finger DNA binding protein is often abbreviated as zinc finger protein or ZFP.

In some cases nucleotide sequences are providing using character representations recommended by the International Union of Pure and Applied Chemistry (IUPAC) or a subset thereof. In some embodiments the set {A, C, G, T, U} for adenosine, cytidine, guanosine, thymidine, and uridine respectively. In some embodiments the set {A, C, G, T, U, I, X, Ψ} for adenosine, cytidine, guanosine, thymidine, uridine, inosine, uridine, xanthosine, pseudouridine respectively. In some embodiments the set of characters is {A, C, G, T, U, I, X, Ψ, R, Y, N} for adenosine, cytidine, guanosine, thymidine, uridine, inosine, uridine, xanthosine, pseudouridine, unspecified purine, unspecified pyrimidine, and unspecified nucleotide respectively.

EXAMPLES

Example 1

Identification of Off-Site Nuclease Cleavage

Materials and Methods
Off-Target Search and Ranking

An exhaustive off-target site searching algorithm based upon the algorithm described above was implemented in Strawberry Perl 5.12 on a Windows computer. The methods were implemented with a user friendly online interface similar to the GUI described above and depicted in FIG. 6.

Two ranking algorithms for TALENs based on homology and RVD respectively, and two ranking algorithms for ZFNs based on homology and conserved G's, respectively were each implemented in the off-target site search for ranking the off-target sites. The "5TC" versions of the algorithms requires that each TALEN binding site be preceded by a 5' thymidine or cytidine since this was the case for all previously reported TAL binding sites. In the homology-based method, the maximum number of mismatches allowed per nuclease half-site is calculated as already described in Equation 1 above. A higher homology score indicates a more likely off-target site. Ranking ZFN off-target sites by counting the number of guanine residues is accomplished by adding a weighting factor to the homology score as described in Equation 2 above. A higher score indicates a more likely off-target site. The weighting factor of 2.5 was developed here by optimizing the number of previously published off-target sites identified in the top rankings. The repeat variable di-residue (RVD) ranking system is implemented as described in Equation 3 above based upon observed TAL affinities. A lower score indicates a more likely off-target site. In all the cases, if the calculated score for two sites is the same, these sites are further ranked by the type of genomic region annotated for each site: Exon>Promoter>Intron>Intergenic. A final ranking by chromosome location is employed to ensure consistency in the ranking order.

Cell Cultures

HEK-293T cells were cultured under standard conditions (37 C, 5% CO2) in Dulbecco's Modified Eagle's Medium (Sigma Aldrich) supplemented with 10% FBS. Plates were coated with 0.1% gelatin prior to plating cells and passaging was performed with 0.25% Trypsin-EDTA. For TALENs, $2*10^5$ cells/well were seeded in 6-well plates 24 hours prior to transfection with FuGene HD (Promega). 3.3 ug of each nuclease plasmid along with 80 ng of an eGFP plasmid were transfected with 19.8 uL of FuGene reagent. Media was changed 24 and 48 hours after transfection. 72 hours after transfection, cells were trypsinized and had their genomic DNA extracted using the DNEasy Kit (Qiagen). A small fraction of the cells were analyzed with the Accuri C6 flow cytometer to determine transfection efficiency by GFP fluorescence. For ZFNs, $8*10^4$ cells/well were seeded in 24-well plates and 100 ng of each ZFN was transfected using 3.4 uL of FuGene HD along with 10 ng of eGFP and 340 ng of a Mock vector containing Fold but no DNA binding domain. 72 hours after transfection, cells were harvested and the genomic DNA was extracted using 100 uL of QuickExtract (EpiCentre). Mock transfections were performed similarly to the TALEN transfections except that 6.6 ug of the Mock FokI vector was transfected instead of TALEN plasmid.

PCR Amplification of Genomic Regions

The primers designed by the off-target site search methods were ordered from Eurofins-MWG-Operon and used in a high-throughput manner to amplify genomic regions of interest in a single plate PCR reaction. Each 25 uL reaction contained 0.5 units of AccuPrime Taq DNA Polymerase High Fidelity (Invitrogen) in AccuPrime Buffer 2 along with 150 ng of genomic DNA or 0.5 uL of QuickExtract, 0.2 uM of each primer, and 5% DMSO. A touchdown PCR reaction was found to yield the highest rate of specific amplification. Following an initial 2 minute denaturing at 94 C, 15 cycles of touchdown were performed by lowering the annealing temperature 0.5 C per cycle from 63.5 C to 56 C (94 C for 30 seconds, anneal for 30 seconds, extend at 68 C for 1:30). After the touchdown, an additional 29 cycles of amplification were performed with the annealing temperature at 56 C before a final extension at 68 C for 10 minutes. Reactions were cleaned up using MagBind EZ-Pure (Omega), quantified using a Take3 Plate and SynergyH4 Reader (Biotek) and normalized to 10 ng/uL.

High Throughput Sequencing

High-Throughput Sequencing. Amplicons from each transfection were pooled in roughly equimolar ratios and sent for SMRT sequence according to the manufacturer's protocol (Pacific Biosciences). Sequencing reads were aligned and processed using the SMRT sequencing pipeline as described above. This pipeline can be easily implemented on a Windows machine.

Results

Figure 17:
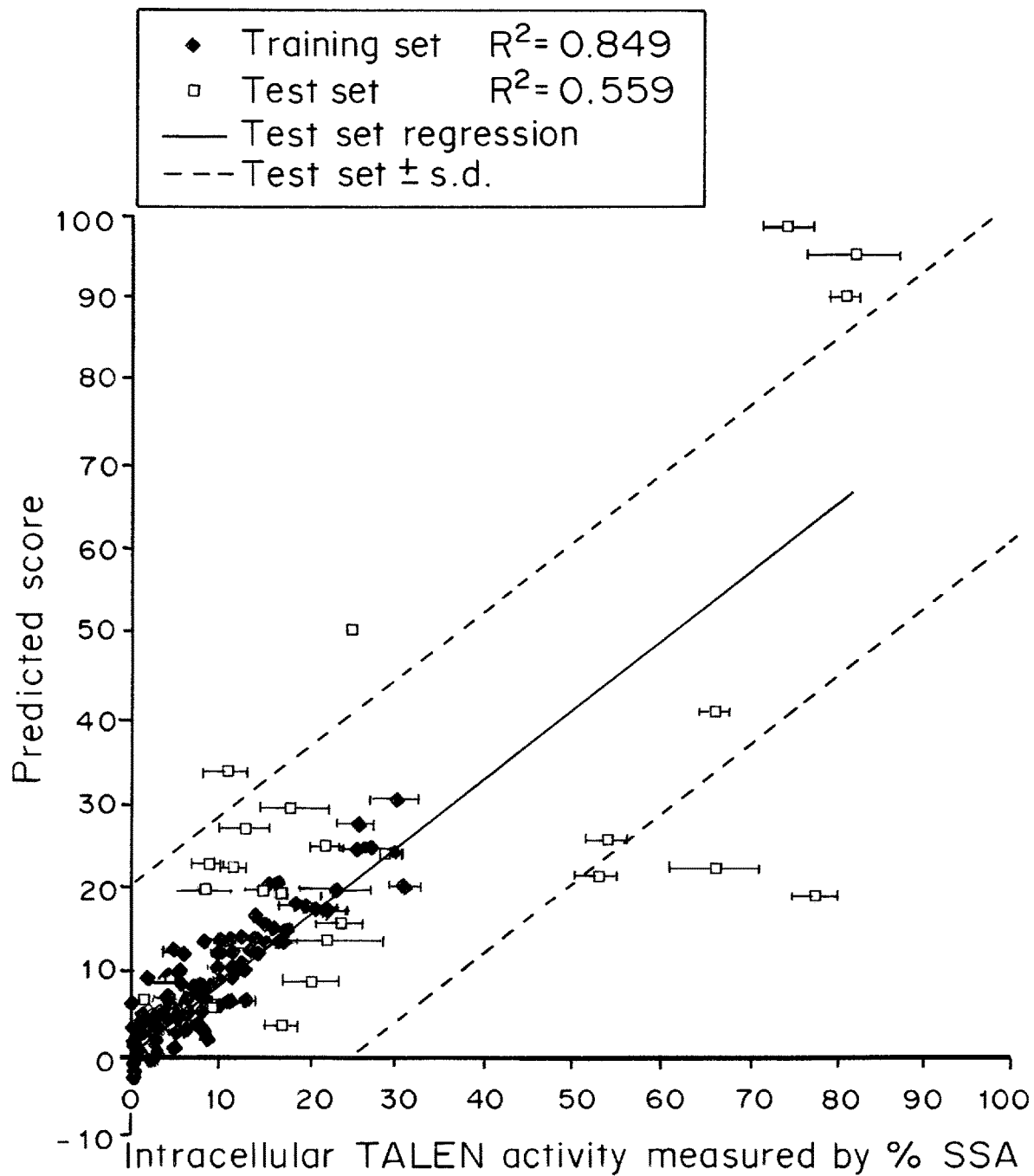
FIG. 17 is a plot of the predicted TALEN nuclease activity as a function of the intracellular activity measured by SSA activity assay for the training set of 116 TALENs used to determine the parameters and the test set of 26 additional TALENs used for validation.

To validate the off-target site ranking algorithms, the predictions with off-target sites of ZFN and TALEN pairs identified by others were compared experimental characterization methods. The top-ranked cleavage sites with the same number (1×) of sites as that interrogated using in vitro characterization were considered first, and it was found that the off-target search and ranking was able to locate 33±21% (mean±std) of the off-target sites previously discovered for ZFNs targeting CCR5, VEGF, and kdrl. Since off-target predictions using the method can be scaled up readily, the off-target sites identified when the number of top-ranked sites considered was tripled (3×) were also compared, and it was found that method could identify 65±24% of the off-target sites previously confirmed experimentally. FIG. 17 depicts the number of previously observed off-target sites that fall within the top fractions of the ranked off-target sites when ranking 1× and 3× the sites characterized in vitro for ZFNs. A rigorous analysis of ranking TALEN off-target sites is difficult, since only three such sites have been experimentally identified to date, excluding sites in closely related genes such as CCR5/CCR213. Nevertheless, it was found that the Homology-5TC and RVD-5TC algorithms could predict several off-target sites confirmed previously for TALEN pairs targeting the AAVS1 and IgM loci.

The results and rankings for all sites is reported in Tables 1-3 for the ZFNs and Tables 4 and 5 for the TALENs.

Comparison of the off-target site predictions with previous results is limited by off-target sites validated experimentally, which may not be comprehensive for a given nuclease pair. The only pair of nuclease having its off-target sites analyzed using two independent methods is a ZFN pair targeting CCR5 (in vitro cleavage9 and IDLV10), with a total of 12 hetero-dimeric off-target cleavage sites identified. A comparison between predictions using Homology and Conserved G's algorithms with these 12 sites shows that the methods was able to predict 10 of the 12 sites. The implemented method provides ranked-lists of potential cleavage sites that can be used to guide experimental evaluation of nuclease off-target activity.

The method was implemented to output PCR primers to amplify the potential off-target sites for further interrogation in a high-throughput manner, a unique feature not present in other online search tools. Automated design of PCR primers can significantly aid the experimental validation of off-target sites, since an initial examination of cleavage by a single pair of nucleases typically requires at least 40 primers and an in-depth investigation of nuclease off-target effects may require >250 primers. PCR amplification is an essential step in examining a potential off-target site; however the success rates amplifying off-target loci varied from 31%1 to 95% in previous PCR assays. In contrast, the off-target search and primer design algorithms implemented here designed primers that had a success rate of 95% (87 of 92 primers designed were successful.

Since Gabriel et al. did not rank their predicted off-target sites, their rankings are marked here as N/A. Sites with observed off-target activity are listed in the order of the amount of NHEJ at the site quantified by Pattanayak et al. In the half-sites, mismatches to the intended target sequence are shown in lower case. In the rankings, sites that did not match the search criteria are listed as "N/A" and sites are highlighted if they fall within certain fractions of the top rankings relative to how many sites were investigated in the paper by Pattanayak et al.:

Homology 1X$^a$, Homology 3X$^b$, Conserved G's 1X$^c$, Conserved G's 3X$^d$

TABLE 1

Comparison of off-target analysis of CCR5 ZFNs to rankings

Search Parameters
Target Site: GTCATCCTCATC...NNNN...AAACTGCAAAAG
(SEQ ID NO: 34)
Allowed Spacings: 5,6
Maximum Mismatches per half-site: 3
Allow Homodimers? No
ZFN or TALEN: ZFN
Genome: hg19

Pattanayak et al. Publication
Experimental Characterization Method:
In vitro cleavage
Total Potential Off-target Sites
Searched: 36
Number of Off-target Sites with
Observed Activity: 9
1X Comparison Ranking Cut-off: 37
3X Comparison Ranking Cut-off: 109

| Closest Gene | Genomic Coordinates | (+) half-site | Spacer | (-) half-site | SEQ ID NO: | Ranking by Pattanayak et al. | Activity Observed? | Three Homology | Three Conserved G's | Four Homology | Four Conserved G's | Five Homology | Five Conserved G's |
|---|---|---|---|---|---|---|---|---|---|---|---|---|---|
| CCR5 | chr3:46414544 | GTCATC CTCATC | ctgat | AAACTG CAAAAG | 35 | 1 | X | 1 | 1 | 1 | 1 | 1 | 1 |
| CCR2 | chr3:46399205 | GTCgTC CTCATC | ttaat | AAACTG CAAAAa | 36 | 2 | X | 2$^a$ | 5$^c$ | 2$^a$ | 5$^c$ | 2$^a$ | 11$^c$ |
| TACR3 | chr4:104555726 | GTCATC tTCATC | agcat | AAACTG tAAAgt | 37 | 11 | X | 17$^a$ | 193 | 31$^a$ | 1971 | 79$^b$ | 3638 |
| WBSCR17 | chr7:70919318 | CTgTTc CAGTTT | tagttt | GcTGAG GATaAC | 38 | 25 | X | 60$^b$ | 51$^d$ | 78$^b$ | 253 | 122 | 385 |
| KCNB2 | chr8:73736816 | aTgtTC CTCATC | tcccg | AAACTG CAAAtG | 39 | 15 | X | 29$^a$ | 33$^c$ | 43$^b$ | 109$^d$ | 91$^b$ | 369 |
| BTBD10 | chr11:13485162 | GTttTC CTCATC | aaagc | AAACTG CAAAAt | 40 | 3 | X | 3$^a$ | 45$^d$ | 18$^a$ | 359 | 3$^a$ | 2404 |
| PSAT1 | chr9:81394380 | CTTTTG CAGTcT | gtaggt | GtTGAG GtTGAC | 41 | 21 | X | 8$^a$ | 4$^c$ | 23$^a$ | 4$^c$ | 8$^a$ | 4$^c$ |
| CEP112 | chr17:64193967 | gTTTTG CAGTTc | ctttt | GATGAG GATGAC | 42 | 9 | X | 7$^a$ | 46$^d$ | 22$^a$ | 360 | 7$^a$ | 2405 |
| MIR206 | chr6:52006356 | GTCcTg CTCAgC | aaaag | AAACTG aAAAAG | 43 | 14 | X | 42$^b$ | 40$^d$ | 57$^b$ | 116 | 104$^b$ | 376 |

TABLE 1-continued

Comparison of off-target analysis of CCR5 ZFNs to rankings

| | | | | | | | | | | | | |
|---|---|---|---|---|---|---|---|---|---|---|---|---|
| CSMD1 | chr8:4878478 | CTTTTc ggtag CAGTTT | cATcAG GAaGAC | 44 | 16 | X | 40[b] | 203 | 55[b] | 1977 | 102[b] | 3644 |
| LYZL1 | chr10:29564346 | aTTagc tctct CAGTTT | GATGAG GATGAC | 45 | 4 | | N/A | N/A | 14[a] | 28[c] | 20[a] | 107[d] |
| SLC4A8 | chr12:51900386 | CTTTTG tataga CAtTTT | GATGAG GATtta | 46 | 5 | | 25[a] | 32[c] | 39[b] | 108[d] | 87 | 368 |
| SYT10 | chr12:33593166 | GTCATC gaagaa CcaATC | AAACTG aAAAAG | 47 | 6 | | 4[a] | 16[c] | 19[a] | 29[c] | 11270 | 103[d] |
| DGKK | chrX:50133221 | cTCATC catgc CTCATC | AcAaTG CAAAAG | 48 | 7 | | 6[a] | 3[c] | 21[a] | 3[c] | 6[a] | 3[c] |
| GALNT13 | chr2:154859418 | CTTcTG cccat CtGTTT | GATGAG GATGAC | 49 | 8 | | 5[a] | 2[c] | 20[a] | 2[c] | 5[a] | 2[c] |
| MIR891A | chrX:145467761 | CcTTTG tattg ttcTTT | GATGAG GATGAC | 50 | 10 | | N/A | N/A | 13[a] | 27[c] | 19[a] | 106[d] |
| PIWIL2 | chr8:22135725 | GTCATC cataa CTCATa | AAACTG CcttAG | 51 | 12 | | 21[a] | 29[c] | 36[a] | 105[d] | 83 | 365 |
| RORB | chr9:77004531 | aTCATC catcc CTCATC | AAtgTt CAAAAG | 52 | 13 | | 47[b] | 43[d] | 62[b] | 119 | 109 | 379 |
| FREM1 | chr9:14941072 | tTTTTG ttcat CAGTTT | GATGtG GATGtt | 53 | 17 | | 37[a] | 37[c] | 52[b] | 113 | 99 | 373 |
| PCDH9 | chr13:66639257 | aTCtTC acagg CTCATt | AAAaTG tAAtAG | 54 | 18 | | 3192 | 1534 | 8804 | 4351 | 10166 | 7214 |
| CUBN | chr10:17004843 | GgCtTC cacgg CTgAcC | AAACTG tAAAtG | 55 | 19 | | N/A | N/A | 1844 | 2477 | 3206 | 3848 |
| NID1 | chr1:236178204 | GTtTTg tcaat CaCATt | tAACTG CAAAAG | 56 | 20 | | N/A | N/A | N/A | N/A | 738 | 59486 |
| WWOX | chr16:78627805 | CTTTaG gagttg CAaTTg | GAgGAG GATGAC | 57 | 22 | | 46[b] | 12[c] | 46[b] | 12[c] | 93 | 18[c] |
| AMBRA1 | chr11:46466224 | GTCtTC tgcaca CTCcTC | tcACTG CAAAAG | 58 | 23 | | 57[b] | 19[c] | 72[b] | 18[c] | 119 | 24[c] |
| LPPR4 | chr1:99684028 | CTTaTG gctgat CAGaTT | GATGAG tATcAC | 59 | 24 | | 92[b] | 216 | 107[b] | 2193 | 154 | 3657 |
| ITSN1 | chr21:35176340 | aTTTTG acaaat CAGTTa | GATGAG cATGAg | 60 | 26 | | 55[b] | 206 | 70[b] | 2183 | 117 | 3647 |
| OR13C9 | chr9:107417578 | GcCAgt atggtg CTCAgC | AAACTG CAAAAG | 61 | 27 | | N/A | N/A | 11[a] | 25[c] | 17[a] | 104[d] |
| TOM1L1 | chr17:52574142 | cTCATt atgaaa CTgtTC | AAACTG CAAAAG | 62 | 28 | | N/A | N/A | 15[a] | 356 | 21[a] | 2412 |
| FAM169B | chr15:98897429 | GaagTC ccgaag CTCATC | AAACTG aAAgAG | 63 | 29 | | 708 | 414 | 1022 | 1966 | 2384 | 2612 |
| ZNF462 | chr9:109645037 | CaTTTG tatgtg CgGTTT | aAaGAG GAaGAC | 64 | 30 | | 126 | 230 | 440 | 1782 | 1802 | 2428 |
| SLCO4C1 | chr5:101085745 | aTaATC tgttta CTttTC | AAACaG CAAAAG | 65 | 31 | | N/A | N/A | 227 | 2230 | 274 | 6434 |
| SKAP1 | chr17:46553811 | CTTTTt ccatgt CAGTTT | aATttG GATGtC | 66 | 32 | | N/A | N/A | 326 | 2263 | 373 | 6467 |
| SDK1 | chr7:3480406 | GTCtTg cacctc CTgtTg | AAACTG CAAAAG | 67 | 33 | | N/A | N/A | N/A | N/A | 35[a] | 15170 |
| SPTB | chr14:65260119 | GTCATC gccctg CgCATC | gAACTG gAAAAa | 68 | 34 | | 13[c] | 27[c] | 28[a] | 103[d] | 75[b] | 363 |
| MBL2 | chr10:54598723 | CTTTTc tagttt CtGTTT | GtTGAG GATGAt | 69 | 35 | | 83[b] | 24[c] | 98[b] | 23[c] | 145 | 29[c] |

TABLE 1-continued

Comparison of off-target analysis of CCR5 ZFNs to rankings

| | | | | | | | | | | | | | |
|---|---|---|---|---|---|---|---|---|---|---|---|---|---|
| FAM190A | chr4:92103828 | GgaATg CcCATC | accaca | AAACTG CAAAAG | 70 | 36 | N/A | N/A | 9$^a$ | 354 | 15$^a$ | 2410 |
| CCDC112 | chr5:114680243 | GTttTg CTCcTg | tacttc | AAACTG CAAAAG | 71 | 37 | N/A | N/A | N/A | N/A | 47$^b$ | 15175 |
| CCR5 | chr3:46414544 | GTCATC CTCATC | ctgat | AAACTG CAAAAG | 72 | N/A | X | 1 | 1 | 1 | 1 | 1 | 1 |
| CCR2 | chr3:46399205 | GTCgTC CTCATC | ttaat | AAACTG CAAAAa | 73 | N/A | X | 2$^a$ | 5$^c$ | 2$^a$ | 5$^c$ | 2$^a$ | 11$^c$ |
| KRR1 | chr12:75963450 | CaTTTc CAGTTT | aaaga | GATGAG GAgGcC | 74 | N/A | X | 87$^b$ | 25$^c$ | 102$^b$ | 24$^c$ | 149 | 30$^c$ |
| KDM2A | chr11:66963780 | CTaTTa CAGTTT | taaga | GATGAG Gtctca | 75 | N/A | X | N/A | N/A | N/A | N/A | 17133 | 8523 |
| ZCCHC14 | chr16:87499212 | CTgTTa CAGTTT | aaaga | GAgGAG Gcctct | 76 | N/A | X | N/A | N/A | N/A | N/A | N/A | N/A |

To validate the ranking algorithms, the rankings were compared with previous off-target investigations of different ZFNs and TALENs. There was substantial overlap between the sites ranked highly by and the sites with observed off-target activity in the previous publications. In the half-sites, mismatches to the intended target sequence are shown in lower case. Due to the large number of off-target sites investigated, only the sites with observed activity are shown. The order of the sites is sorted by the amount of NHEJ observed by Pattanayak et al. In the Rankings, sites that did not match the search criteria are listed as "N/A" and sites are highlighted if they fall within certain fractions of the top rankings relative to how many sites were investigated in the original publication:

Homology 1X$^a$,Homology 3X$^b$,Conserved G's 1X$^c$,Conserved G's 3X$^d$

TABLE 2

Comparison of off-target analysis of VEGF ZFNs to Rankings

| Search Parameters for | Pattanayak et al. Publication |
|---|---|
| Target Site: AGCAGCGTC...NNNN...GAGTGAGGA | Experimental Characterization Method: |
| (SEQ ID NO: 77) | In vitro cleavage |
| Allowed Spacings: 5,6 | Total Potential Off-target Sites Searched: 96 |
| Maximum Mismatches per half-site: 2 | Number of Off-target Sites with Observed Activity: 31 |
| Allow Homodimers? No | 1X Comparison Ranking Cut-off: 97 |
| ZFN or TALEN: ZFN | 3X Comparison Ranking Cut-off: 289 |
| Genome: hg19 | |

| Closest Gene | Genomic Coordinates | (+) half-site | Spacer | (-) half-site | SEQ ID NO: | Ranking by Pattanayak et al. | Activity Observed? | Algorithm Rankings with various Maximum Mismatches per Half-site Two | |
|---|---|---|---|---|---|---|---|---|---|
| | | | | | | | | Homology | Conserved G's |
| VEGFA | chr6:43737415 | AGCAGCGTC | ttcga | GAGTGAGGA | 78 | 1 | X | 1 | 1 |
| MIR548I1 | chr3:125488072 | AGCAGtGTC | aggctg | GtGTGAGGA | 79 | 33 | X | 178$^b$ | 170$^d$ |
| TRH | chr3:129719205 | TCCTCACaC | cagcct | GACaCTGCT | 80 | 30 | X | 181$^b$ | 171$^d$ |
| OPN5 | chr6:47783456 | cCCTCACTC | agtaca | GACttTGCT | 81 | 73 | X | 1196 | 992 |
| PDX1 | chr13:28501187 | aCCTCACTC | ccagge | GtCGCTGCT | 82 | 23 | X | 199$^b$ | 41$^c$ |

TABLE 2-continued

Comparison of off-target analysis of VEGF ZFNs to Rankings

| | | | | | | | | | |
|---|---|---|---|---|---|---|---|---|---|
| WISP3 | chr6:112314783 | AGCAtCGTC | tgaagt | GAGTGAGGc | 83 | 37 | X | 173[b] | 33[c] |
| GBF1 | chr10:104083999 | TtCTCACaC | actatg | GACGtTGCT | 84 | 66 | X | 517 | 728 |
| SLC47A1 | chr17:19493916 | AGCAttGTC | tcatgt | GAGTGAGGt | 85 | 87 | X | 1975 | 1283 |
| HAUS5 | chr19:36108957 | cCOICcOIC | cccta | GACGCTGCT | 86 | 9 | X | 31[a] | 11[c] |
| CDH11 | chr16:64045802 | cCCTCACTC | atgtga | tACGCTGCT | 87 | 24 | X | 218[b] | 193[d] |
| MIR1324 | chr3:75626697 | TCCTCACaC | cagcct | GACaCTGCT | 88 | 31 | X | 234[b] | 202[d] |
| IFLTD1 | chr12:25833299 | cCCTCACTC | ccagga | GAaGCTGCT | 89 | 28 | X | 198[b] | 40[c] |
| MTX2 | chr2:177134202 | gCCTCACTg | cagcc | GcCGCTGCT | 90 | 69 | X | 291 | 620 |
| PDE9A | chr21:44109014 | AGCAcCGTC | coect | DAGTGAGGc | 91 | 68 | X | 1158 | 976 |
| SLITRK1 | chr13:83141139 | gCCTCACTC | agccct | GACcCTGCT | 92 | 29 | X | 241[b] | 208[d] |
| HRASLS | chr3:192969431 | cCCTCACTC | cttgg | GACcaTGCT | 93 | 86 | X | 876 | 865 |
| KRTAP5-11 | chr11:71353236 | AGCAGtGTC | aggctg | GtGTGAGGA | 94 | 34 | X | 227[b] | 197[d] |
| SIK3 | chr11:116787174 | gCCTCACTC | tttttt | GACatTGCT | 95 | 78 | X | 580 | 758 |
| SBF2 | chr11:9927635 | TCCTCACcC | ccttag | GACaCTGCT | 96 | 35 | X | 171[b] | 168[d] |
| TRPC2 | chr11:3599723 | TCCTCACaC | cagcct | GACaCTGCT | 97 | 32 | X | 205[b] | 184[d] |
| LOC550643 | chrX:56814185 | AGCAGaGTC | agactt | GAGTGAGGt | 98 | 18 | X | 160[b] | 161[d] |
| HEATR8-TTC4 | chr1:55109307 | AGCAGaGTC | tctga | GAGTGAGGc | 99 | 19 | X | 159[b] | 160[d] |
| C9orf62 | chr9:138175678 | TttTCACTC | tttca | GACGCTGCT | 100 | 12 | X | 92[a] | 574 |
| SARDH | chr9:136602418 | tGCAGCGgC | gtaggg | GAGTGAGGA | 101 | 62 | X | 17[a] | 8[c] |
| MICAL3 | chr22:18338914 | AGCAtCGTC | ttctgt | GAGTGAGtA | 102 | 38 | X | 143[b] | 151[d] |
| LSAMP-AS3 | chr3:117112188 | AGCAtaGTC | taggcc | GAGTGAGGc | 103 | 85 | X | 1634 | 1161 |
| LOC157381 | chr8:125913398 | AGCAttGTC | tcctg | GAGTGAGGg | 104 | 88 | X | 1681 | 1175 |
| DMRTB1 | chr1:53948080 | TCCTCACTg | aatat | GACGtTGCT | 105 | 15 | X | 211[b] | 186[d] |
| LINC00570 | chr2:11511744 | AGaAaCGTC | gtggag | GAGTGAGGg | 106 | 72 | X | 1621 | 1155 |
| PLXNA4 | chr7:131853168 | AGCAcgGTC | atgat | GAGTGAGGc | 107 | 80 | X | 270[b] | 610 |
| PTK2B | chr8:27284038 | AGCAGCGTC | tccctt | GAGTGAtGg | 108 | 11 | X | 25[a] | 65[c] |
| ETV1 | chr7:13360335 | TtCTCACTC | actcag | GACaCTtCT | 109 | 79 | X | 1741 | 3565 |

To validate the ranking algorithms, the rankings were compared with previous off-target investigations of different ZFNs and TALENs. There was substantial overlap between the sites ranked highly by and the sites with observed off-target activity in the previous publications. Gupta et al. did not rank their predicted off-target sites so they are listed as "N/A". Due to the large number of off-target sites investigated, only the sites with observed activity are shown. In the half-sites, mismatches to the intended target sequence are shown in lower case. In the rankings, sites that did not match the search criteria are listed as "N/A" and sites are highlighted if they fall within certain fractions of the top rankings relative to how many sites were investigated in the paper by Gupta et al.:

TABLE 3

Comparison of off-target analysis of kdrl ZFNs to Rankings.

Search Parameters
Target Site: TCCCACCAA...NNNN...GAAGGTGTG
(SEQ ID NO: 110)
Allowed Spacings: 5,6
Maximum Mismatches per half-site: 3
Allow Homodimers? No
ZFN or TALEN: ZFN
Genome: danRer7

Gupta et al. Publication
Experimental Characterization Method:
Bacterial 1-hybrid
Total Potential Off-target Sites Searched: 144
Number of Off-target Sites with Observed Activity: 19
1X Comparison Ranking Cut-off: 145
3X Comparison Ranking Cut-off: 433

| Closest Gene | Genomic Coordinates | (+) half-site | Spacer | (−) half-site | SEQ ID NO: | Ranking by Gupta et al. | Activity Observed | Two Homology | Two Conserved G's | Three Homology | Three Conserved G's |
|---|---|---|---|---|---|---|---|---|---|---|---|
| kdrl | chr14:33887254 | TCCCACCAA | catgct | GAAGGTGTG | 111 | N/A | X | 1 | 1 | 1 | 1 |
| kif18a | chr7:33480733 | CACACCggC | aggact | cgGGTGGGA | 112 | N/A | X | 688 | 71$^c$ | 859 | 100$^c$ |
| adar | chr16:25865799 | CACACCaTC | ctacct | TTGGTGGGt | 113 | N/A | X | 49$^a$ | 7$^c$ | 49$^a$ | 7$^c$ |
| sgcg | chr15:22065892 | TCCCcCCAc | gtctgt | GAAGGTGTG | 114 | N/A | X | 18$^a$ | 4$^c$ | 18$^a$ | 4$^c$ |
| trim2a | chr1:24258837 | cCCgACCAg | attgt | GAAGGTGTG | 115 | N/A | X | N/A | N/A | 155$^b$ | 64$^c$ |
| N/A | Zv9_NA675:292209 | aCCCACCgA | gatac | GcgGGTGTG | 116 | N/A | X | 5136 | 1068 | 12271 | 510 |
| odf3b | chr18:7076612 | TCCCtCCAA | catcac | GAgGGTGgG | 117 | N/A | X | 117 | 51 | 288$^b$ | 80$^c$ |
| tmpoa | chr4:15926498 | CACACCggC | agact | gcGGcGGGA | 118 | N/A | X | N/A | N/A | 15721 | 5542 |
| cyb561 | chr3:23069061 | CACACCcaC | aaaag | aTGGTGGGt | 119 | N/A | X | 4453 | 1060 | 11587 | 502 |
| hk2 | chr5:15562194 | CtCACCaTC | acttcc | TgGGTGGGA | 120 | N/A | X | 423$^b$ | 64$^c$ | 594 | 93$^c$ |
| sc:d0284 | chr1:57642177 | ttCACCaTC | accgct | ccGGTGGGA | 121 | N/A | X | N/A | N/A | 38905 | 12800 |
| mboat1 | chr16:7752061 | TCCCgCCAA | caaat | GAcGGaGTG | 122 | N/A | X | 990 | 74$^c$ | 1161 | 103$^c$ |
| sox6 | chr7:28400961 | CgCACCgcC | agacat | aTGGTGGGA | 123 | N/A | X | N/A | N/A | 5099 | 152 |
| wu:fc88b07 | chr2:49357853 | TCCCcCCtg | ccatga | GgAGGTGTG | 124 | N/A | X | N/A | N/A | 7062 | 167 |
| kal1a | chr1:31442407 | aCCCACCcA | ctact | GAgGGTGaG | 125 | N/A | X | 5369 | 1069 | 12503 | 511 |
| stxbp1b | chr5:30608533 | CACACCTcC | aatta | gaGGcGGGA | 126 | N/A | X | N/A | N/A | 5310 | 154 |
| adcyap1b | chr2:31013814 | TCCCtCCct | aagggt | GAtGGgGTG | 127 | N/A | X | N/A | N/A | 70540 | 5697 |
| lpar2a | chr3:53742053 | aCCCACCAA | aatgca | GctGGTGTG | 128 | N/A | X | 912 | 72$^c$ | 1083 | 101$^c$ |
| ctnna2 | chr1:43417395 | TtCCACCAA | gtatca | GAAGGTGTa | 129 | N/A | X | 36$^a$ | 75$^c$ | 36$^a$ | 117$^c$ |
| myo5aa | chr18:37375434 | TCCCACCAg | gatatc cgggttac | GcAGGTGTG | 130 | N/A | X | N/A | N/A | N/A | N/A |

To validate the ranking algorithms, the rankings were compared with previous off-target investigations of different ZFNs and TALENs. There was substantial overlap between the sites ranked highly by and the sites with observed off-target activity in the previous publications. In the half-sites, mismatches to the intended target sequence are shown in lower case. The allowed spacing distances in the search match the spacing distances allowed in the original publication. In the rankings, sites that did not match the search criteria are listed as "N/A" and sites are highlighted if they fall within certain fractions of the top rankings relative to how many sites were investigated in the original publication:

Homology 1X$^a$, Homology 3X$^b$, RVDs 1X$^c$, RVDs 3X$^f$

TABLE 4

Comparison of off-target analysis of the IgM TALENs to rankings.

Search Parameters
Target Site:
TCCTGCCCAGCTCCAT...NNNN...ACCAGAACACACTGA
(SEQ ID NO: 131)
Allowed Spacings: 12-24
Maximum Mismatches per half-site: 5
Allow Homodimers? No
ZFN or TALEN: TALEN
Genome: rn4

Tesson et al. Publication
Experimental Characterization Method: SELEX
Total Potential Off-target Sites Searched: 10
Number of Off-target Sites with Observed Activity: 1
1X Comparison Ranking Cut-off: 11
3X Comparison Ranking Cut-off: 31

| Closest Gene | Genomic Coordinates | (+) half-site | Spacer Length (-) half-site | SEQ ID NO: | Ranking by Tesson et al. | Activity Observed? | Algorithm Rankings with various Maximum Mismatches per Half-Site | | | | | | | | | | | | | | |
|---|---|---|---|---|---|---|---|---|---|---|---|---|---|---|---|---|---|---|---|---|---|
| | | | | | | | Five | | | | Six | | | | Seven | | | | | | |
| | | | | | | | Homology? | Homology 5TC | RVDs | RVDs-5TC | RVDs-Homology | Homology | Homology 5TC | RVDs | RVDs-5TC | RVDs-Homology | Homology | Homology 5TC | RVDs | RVDs-5TC | |
| Adam6 | chr6: 138444138 | TCAGTGTTGTTCTGGT | 17 ATGGAGCTGGGCAGGA | 132 | 1 | 1 | 1 | 1 | 1 | 1 | 1 | 1 | 1 | 1 | 1 | 1 | 1 | 1 | 1 | 1 | |
| RGD1309079 | chr8: 99182623 | TCAaTtTCTaCTGTt | 12 tTGGAGCTGGtCAGGA | 133 | 2 | X | 42 | 34 | 25$^f$ | 12$^f$ | 49 | 40 | 54 | 22$^f$ | 81 | 35 | 79 | 35 | |
| Tssc1 | chr6: 46986828 | TCCTGCCCAGaTCCT | 17 tCCAGcACAAtATTGA | 134 | 3 | | 6$^a$ | 5 | 21$^f$ | 10$^e$ | 13$^b$ | 11$^a$ | 44 | 18$^f$ | 14$^b$ | 29$^b$ | 64 | 29$^f$ | |
| Rnf4 | chr14: 82098808 | cCCTCCCCAGCTCCCT | 19 ACatGAtCAACAtTcA | 135 | 4 | | 197 | 151 | 31$^f$ | 17$^f$ | 325 | 234 | 64 | 28$^f$ | 907 | 42 | 92 | 42 | |
| Pdcd11 | chr14: 252428805 | gCAGacTTGTTCTGGT | 16 AgGGAtCTGGGgAGGA | 136 | 5 | | 9$^a$ | N/A | 7$^e$ | N/A | 16$^b$ | N/A | 8$^e$ | N/A | 24$^b$ | N/A | 8$^e$ | N/A | |
| Esrrg | chr13: 104232554 | TCAATGTTGgTTaacT | 14 ATGGAtTGGGCAGGA | 137 | 6 | | N/A | N/A | N/A | N/A | 58 | 45 | 36 | 14$^f$ | 140 | 22$^b$ | 50 | 22$^f$ | |
| Sorcs1 | chr1: 256616339 | TCCTGCCAtCTCCAT | 14 gCaAtAaCAtaAaTGA | 138 | 7 | | N/A | N/A | N/A | N/A | 6$^a$ | 6$^a$ | 89 | 36 | 7$^a$ | 52 | 133 | 52 | |
| RGD1561065 | chrX: 40774024 | gCAtTGaTGTaCTGtT | 24 AgcGAGTGGGgAGGA | 139 | 8 | | 2726 | 331 | N/A | 4531 | N/A | N/A | 765 | N/A | 11684 | N/A | 1246 | N/A | |
| RGD1559903 | chr20: 16461090 | gCAGTGTTGTTCTGtT | 16 AgaGAGTGGGatGGA | 140 | 9 | | 31$^b$ | 47 | N/A | 38 | N/A | N/A | 100 | N/A | 70 | N/A | 150 | N/A | |
| Gng7 | chr7: 10221799 | TCAcTGTTcaTCTtaT | 23 AcGGAGCTGGGCAGGg | 141 | 10 | | 14$^b$ | 11$^a$ | 6$^e$ | 4$^e$ | 21$^b$ | 17$^b$ | 7$^e$ | 5$^e$ | 53 | 5$^a$ | 7$^e$ | 5$^e$ | |

TABLE 4-continued

Comparison of off-target analysis of the IgM TALENs to rankings.

| | | | | | | | | | | |
|---|---|---|---|---|---|---|---|---|---|---|
| Mfap1a | chr3: 108471540 | TCCTGCCCcGcaCCAT | 12 | caCAGAACActgaTGt | 142 | 11 | N/A | N/A | N/A | N/A | N/A | N/A | 450 | N/A | 1222 | N/A |

To validate the ranking algorithms, the rankings were compared with previous off-target investigations of different ZFNs and TALENs. There was substantial overlap between the sites ranked highly and the sites with observed off-target activity in the previous publications. In the half-sites, mismatches to the intended target sequence are shown in lower case. The allowed spacing distances in the search match the spacing distances allowed in the original publication. In the rankings, sites that did not match the search criteria are listed as "N/A" and sites are highlighted if they fall within certain fractions of the top rankings relative to how many sites were investigated in the original publication:

TABLE 5

Comparison of off-target analysis of AAVS1 TALENs to rankings

Search Parameters
Target Site: TTTTCTGTCACCAATCCT...NNNN...ACTGTGGGTGGAGGGGA (SEQ ID NO: 143)
SELEX (SEQ ID NO: 143)
Allowed Spacings: 11-26
Maximum Mismatches per half-site: 5
Allow Homodimers? No
ZFN or TALEN: TALEN
Genome: hg19

Hockemeyer et al. Publication
Experimental Characterization Method:
Total Potential Off-target Sites Searched: 20
Number of Off-target Sites with Observed
Activity: 2
1X Comparison Ranking Cut-off: 21
3X Comparison Ranking Cut-off: 61

| Closest Gene | Genomic Coordinates | (+) half-site | Spacer Length | (−) half-site | SEQ ID NO: | Ranking by Hockemeyer et al. | Activity Observed? | Algorithm Rankings with various Maximum Mismatches per Half-Site | | | | | | | | | | | | | |
|---|---|---|---|---|---|---|---|---|---|---|---|---|---|---|---|---|---|---|---|---|---|
| | | | | | | | | Five | | | | Six | | | | Seven | | | | | |
| | | | | | | | | Homology-5TC | RVDs | RVDs-5TC | RVDs-Homology | Homology-5TC | RVDs | RVDs-5TC | RVDs-Homology | Homology-5TC | RVDs | RVDs-5TC | RVDs-Homology |
| PPP1R12C | chr19: 55627107 | TTTTCTGTCA CCAATCCT | 15 | ACTGTGGGT GGAGGGGA | 144 | 1 | X | 1 | 1 | 1 | 1 | 1 | 1 | 1 | 1 | 1 | 1 | 1 | 1 |
| SMAD3 | chr15: 67305690 | TtCCacCCAg CCCtCAGT | 13 | AGGAtGGGTG gCtGgAAA | 145 | 11 | X | 66 | 94 | 54$^f$ | 114 | 86 | 400 | 180 | 287 | 224 | 694 | 277 |
| ODZ2 | chr5: 165831362 | TTTTCTaTaA CtcATatT | 24 | tttTtGGGGT GGAGGGGg | 146 | 15 | X | N/A | N/A | N/A | 320 | 232 | 9$^e$ | 5$^e$ | 493 | 370 | 10$^e$ | 5$^e$ |
| AVPR1B | chr1: 206211379 | gggTaaGTCA CtcAaCCT | 26 | AtGTGTGGGT GGgGGGGA | 147 | 2 | | N/A | N/A | N/A | N/A | N/A | N/A | N/A | N/A | N/A | N/A | N/A |
| DMD | chrX: 31479738 | TcTTCcaTCA CtAATtCT | 23 | AtgGTaGGGT GGAGGGtA | 148 | 3 | | 28$^b$ | 11$^e$ | 6$^e$ | 76 | 58$^b$ | 28$^b$ | 17$^e$ | 249 | 196 | 40$^f$ | 19$^e$ |
| STPG1 | chr1: 24697473 | TCCCCaCCAC aCCACAaT | 11 | AGaAactGTG ACAGAAtA | 149 | 4 | | 5$^a$ | 8$^e$ | 4$^e$ | 5$^a$ | 5 | 21$^e$ | 14$^e$ | 17$^a$ | 14$^e$ | 24$^f$ | 14$^e$ |
| PHLPP1 | chr18: 60653603 | TaTTCTGTCA CtATTCCT | 17 | ACgatGGGGc GtgGGGg | 150 | 5 | N/A | N/A | N/A | N/A | 49$^b$ | 38$^b$ | 225 | 97 | 161 | 47$^b$ | 208 | 61$^f$ |
| CPN1 | chr10: 101836509 | TCCCtcCCAC CCCACcta | 11 | AGGATTGGgG gCAGgAct | 151 | 6 | | 80 | 43$^b$ | N/A | 467 | N/A | 130 | N/A | 640 | N/A | 195 | N/A |
| RPS6KA2 | chr6: 167286955 | ccgTCaGTCA CCcCTCCT | 14 | ACaGTGGGGT GGAGtGGg | 152 | 7 | N/A | N/A | N/A | N/A | 42$^b$ | 31$^b$ | 6 | 3 | 54$^b$ | 40$^b$ | 6$^e$ | 3$^e$ |
| HEG1 | chr3: 124702672 | TCCCtTCCAC CtACCaa | 18 | AGGgTTGGgt ACAGAAcA | 153 | 8 | | 17$^a$ | 13 | 34$^f$ | 18$^e$ | 65 | 48$^b$ | 96 | 46$^f$ | 238 | 186 | 144 | 59$^f$ |

TABLE 5-continued

Comparison of off-target analysis of AAVS1 TALENs to rankings

| | | | | | | | | | | | | | | | |
|---|---|---|---|---|---|---|---|---|---|---|---|---|---|---|---|
| AK8 | chr9: 135721617 | TaTcCaGaCA CCcAcCCT | 17 | tgTGTGGGGT GGAtGGGg | 154 | 9 | N/A | N/A | N/A | N/A | 160 | 117 | 12$^e$ | 8$^e$ | 19275 | 255 | 8$^e$ | 333 |
| SHANK3 | chr22: 51139503 | ctCCCcCCAC CCCcCAaa | 18 | tGGAgTGGgG ACAGAAAA | 155 | 10 | N/A | N/A | N/A | N/A | 25$^b$ | 18$^a$ | 4$^e$ | 2$^e$ | 37$^b$ | 27$^b$ | 4$^e$ | 2$^e$ |
| ARHGAP10 | chr4: 148942810 | TtCCCaCCAC CCCACAac | 17 | AtGAcaGaTG ACAGtAAA | 156 | 12 | 21$^a$ | 17 | 52$^f$ | 29$^f$ | 69 | 52$^b$ | 165 | 77 | 242 | 190 | 250 | 103 |
| FOXP1 | chr3: 70995951 | TgCCCCcCAC CCCAgAGT | 157 | AttATaaGaG ACAGAAAA | 20 | 13 | 6$^a$ | 6 | 98 | 58$^f$ | 6$^a$ | 6$^a$ | 415 | 188 | 18$^a$ | 15$^a$ | 713 | 287 |
| CLIC5 | chr6: 45952065 | agTaCTGTCA CCtgTgCT | 158 | AtgtTGGGGT GGAaGGGA | 15 | 14 | N/A | N/A | N/A | N/A | 218 | N/A | 307 | N/A | 391 | N/A | 494 | N/A |
| CCDC64 | chr12: 120531853 | TgtTCaGcCA CCCcaCCT | 159 | ACCacCGGGT GGAGGGGA | 16 | 16 | N/A | N/A | N/A | N/A | N/A | N/A | N/A | N/A | 14499 | 52$^b$ | 1519 | 70 |
| STAMBP | chr2: 74063520 | TCCCCTCCAC CCCgtgGT | 160 | AGGtggGGTG gCtGAccA | 16 | 17 | N/A | N/A | N/A | N/A | 3585 | 2366 | 376 | 168 | 137 | 106 | 3801 | 1520 |
| PVRL3 | chr3: 110893535 | TgTTCcaTCg CCAcTgCT | 161 | ttTGgGGGGT GGgGGgtg | 16 | 18 | N/A | N/A | N/A | N/A | 3862 | 2543 | 100 | 49$^f$ | 17282 | 10354 | 17284 | 17283 |
| GPR19 | chr12: 12838164 | caTCCcaTCA CCCATCCT | 162 | tttTttTtGGT GGgGGGGA | 25 | 19 | N/A | N/A | N/A | N/A | N/A | N/A | N/A | N/A | 17360 | 10531 | 150 | 64 |
| MLLT1 | chr19: 6213604 | aggaCTGTCc CTgcTCCT | 163 | ACTGTGGGGT GttGAGGg | 16 | 20 | N/A | N/A | N/A | N/A | N/A | N/A | 143 | 65 | N/A | N/A | N/A | N/A |
| FAM157B | chr9: 141119480 | caCCCCcCAC CCCcCAca | 164 | tGGAgTGtTG AtAGtAtA | 15 | 21 | N/A | N/A | N/A | N/A | 4032 | 2635 | N/A | N/A | 17530 | 10623 | 215 | 87 |

Prediction of Off-Site Cleavage Loci for Tnikb TALEN in Zebrafish Genome

Huang et al looked for off-target cleavage resulting from injecting Zebrafish embryos with mRNA coding for a pair of TALEN that target the tnikb gene. See Huang et al. (2011) *Nat. Biotech.* 29:699-700. This study used an unpublished algorithm to identify potential off-target sites in the Zebrafish genome. Their search identified 29 possible off-target sites, 9 of which they were able to amplify from the genome for further analysis. Using the methods implemented here to search the Zebrafish genome with the same TALEN half-sites and settings (4 mismatches allowed per half-site, spacing from 13 to 19 base pairs), returned the TALEN target site as well as every one of the off-target sites on the list of Huang et al.

Prediction of Off-Site Cleavage Loci for ZFN in Human Genome

To further validate the off-target search and rankings, the results were compared to an intensive, unbiased in vitro selection strategy to identify sequences that the ZFN pair would cleave and an in-house search program identified sites in the human genome matching the top 36 of those sequences. The off-target site search and ranking was able to locate all of those genomic loci when using similar search parameters (4 mismatches allowed per half-site, 5 or 6 bp spacing). Of the 36 sites examined, all sites showing off-site cleavage in culture were ranked in the top 80 sites in the ranked list.

Using the Method to Identify Off-Target Sites in New ZFNs and TALENS

We designed TALENs and ZFNs targeting the beta-globin gene near the A-T mutation that causes sickle-cell anemia, expressed them in HEK-293T cells, and analyzed the top-ranked off-target sites.

A new 3-finger ZFN pair (3F ZFN) was designed having a left ZFN with a sequence identity:

```
                                                            (SEQ ID NO: 1)
MDYKDHDGDY KDHDIDYKDD DDKPKKKRKV PFACDICGRK FARTDTLRDH TKIHTGEKPF  60

QCRICMRNFS QSSSLVRHIR THTGEKPFAC DICGRKFAQS GDLTRHQRTH GSQLVKSELE 120

EKKSELRHKL KYVPHEYIEL IEIARNSTQD RILEMKVMEF FMKVYGYRGK HLGGSRKPDG 180

AIYTVGSPID YGVIVDTKAY SGGYNLPIGQ ADEMQRYVEE NQTRNKHINP NEWWKVYPSS 240

VTEFKFLFVS GHFKGNYKAQ LTRLNHITNC NGAVLSVEEL LIGGEMIKAG TLTLEEVRRK 300

FNNGEIN                                                          307
``` and a right ZFN with a sequence identity:

```
                                                            (SEQ ID NO: 2)
MDYKDHDGDY KDHDIDYKDD DDKPKKKRKV PFACDICGRK FARSDHLTNH TKIHTGEKPF  60

QCRICMRNFS QSGDLTRHIR THTGEKPFAC DICGRKFARS DHLSRHQRTH GSQLVKSELE 120

EKKSELRHKL KYVPHEYIEL IEIARNSTQD RILEMKVMEF FMKVYGYRGK HLGGSRKPDG 180

AIYTVGSPID YGVIVDTKAY SGGYNLPIGQ ADEMQRYVEE NQTRNKHINP NEWWKVYPSS 240

VTEFKFLFVS GHFKGNYKAQ LTRLNHITNC NGAVLSVEEL LIGGEMIKAG TLTLEEVRRK 300

FNNCEINF.                                                        308
```

The Zinc Finger helices are underlined for clarity.

A new 4-finger ZFN pair (4F ZFN) was designed having a left ZN with a sequence identity

```
                                                            (SEQ ID NO: 3)
MDYKDHDGDY KDHDIDYKDD DDKPKKKRKV PFQCRICMRN FSQSGSLTRH IRTHTGEKPF  60

ACDICGRKFA RTDTLRDHTK IHTGGEKPFQ CRICMRNFSQ SSSLVRHIRT HTGEKPFACD 120

ICGRKFAQSG DLTRHQRTHG SQLVKSELEE KKSELRHKLK YVPHEYIELI EIARNSTQDR 180

ILEMKVMEFF MKVYGYRGKH LGGSRKPDGA IYTVGSPIDY GVIVDTKAYS GGYNLPIGQA 240

DEMQRYVEEN QTRNKHINPN EWWKVYPSSV TEFKFLFVSG HFKGNYKAQL TRLNHITNCN 300

GAVLSVEELL IGGEMIKAGT LTLEEVRRKF NNGEINF                         337
``` and a right ZFN with a sequence identity

```
                                                            (SEQ ID NO: 4)
MDYKDHDGDY KDHDIDYKDD DDKPKKKRKV PFQCRICMRN FSQSGHLASH IRTHTGEKPF  60
```

```
                                                  -continued
ACDICGRKFA RSDHLTNHTK IHTGGGSEKP FQCRICMRNF SQSGDLTRHI RTHTGEKPFA 120

CDICGRKFAR SDHLSRHQRT HGSQLVKSEL EEKKSELRHK LKYVPHEYIE LIEIARNSTQ 180

DRILEMKVME FFMKVYGYRG KHLGGSRKPD GAIYTVGSPI DYGVIVDTKA YSGGYNLPIG 240

QADEMQRYVE ENQTRNKHIN PNEWWKVYPS SVTEFKFLFV SGHFKGNYKA QLTRLNHITN 300

CNGAVLSVEE LLIGGEMIKA GTLTLEEVRR KFNNGEINF.                    339
```

The Zinc Finger helices are underlined for clarity

A new NK TALEN (S1 NK) targeting the beta-globin gene was designed having the TALEN identity

```
                                                          (SEQ ID NO: 5)
MDYKDHDGDY KDHDIDYKDD DDKMAPKKKR KVGIHRGVPM VDLRTLGYSQ QQQEKIKPKV  60

RSTVAQHHEA LVGHGFTHAH IVALSQHPAA LGTVAVKYQD MIAALPEATH EAIVGVGKQW 120

SGAAALEALL TVAGELRGPP LQLDTGQLLK IAKRGGVTAV EAVHAWRNAL TGAPLNLTPD 180

QVVAIASNKG GKQALETVQR LLPVLCQDHG LTPDQVVAIA SNKGGKQALE TVQRLLPVLC 240

QDHGLTPDQV VAIASNGGGK QALETVQRLL PVLCQDHGLT PDQVVAIASN KGGKQALETV 300

QRLLPVLCQD HGLTPDQVVA IASHDGGKQA LETVQRLLPV LCQDHGLTPD QVVAIASNIG 360

GKQALETVQR LLPVLCQDHG LTPDQVVAIA SHDGGKQALE TVQRLLPVLC QDHGLTPDQV 420

VAIASHDGGK QALETVQRLL PVLCQDHGLT PDQVVAIASN GGGKQALETV QRLLPVLCQD 480

HGLTPDQVVA IASNKGGKQA LETVQRLLPV LCQDHGLTPD QVVAIASNIG GKQALETVQR 540

LLPVLCQDHG LTPDQVVAIA SHDGGKQALE TVQRLLPVLC QDHGLTPDQV VAIASNGGGK 600

QALETVQRLL PVLCQDHGLT PDQVVAIASH DGGKQALETV QRLLPVLCQD HGLTPDQVVA 660

IASHDGGKQA LETVQRLLPV LCQDHGLTPD QVVAIASNGG GKQALESIVA QLSRPDPALA 720

ALTNDHLVAL ACLGGRPALD AVKKGLPHAP ALIKRTNRRI PERTSHRVAG SQLVKSELEE 780

KKSELRHKLK YVPHEYIELI EIARNSTQDR ILEMKVMEFF MKVYGYRGKH LGGSRKPDGA 840

IYTVGSPIDY GVIVDTKAYS GGYNLPIGQA DEMQRYVEEN QTRNKHINPN EWWKVYPSSV 900

TEFKFLFVSG HFKGNYKAQL TRLNHITNCN GAVLSVEELL IGGEMIKAGT LTLEEVRRKF 960

NNGEINF.                                                      967
```

The RVDs are underlined for clarity.

A new NK TALEN (S2 NK) targeting the beta-globin gene was designed having the TALEN identity

```
                                                          (SEQ ID NO: 6)
MDYKDHDGDY KDHDIDYKDD DDKMAPKKKR KVGIHRGVPM VDLRTLGYSQ QQQEKIKPKV  60

RSTVAQHHEA LVGHGFTHAH IVALSQHPAA LGTVAVKYQD MIAALPEATH EAIVGVGKQW 120

SGAAALEALL TVAGELRGPP LQLDTGQLLK IAKRGGVTAV EAVHAWRNAL TGAPLNLTPD 180

QVVAIASNKG GKQALETVQR LLPVLCQDHG LTPDQVVAIA SHDGGKQALE TVQRLLPVLC 240

QDHGLTPDQV VAIASNIGGK QALETVQRLL PVLCQDHGLT PDQVVAIASH DGGKQALETV 300

QRLLPVLCQD HGLTPDQVVA IASHDGGKQA LETVQRLLPV LCQDHGLTPD QVVAIASNGG 360

GKQALETVQR LLPVLCQDHG LTPDQVVAIA SNKGGKQALE TVQRLLPVLC QDHGLTPDQV 420

VAIASNIGGK QALETVQRLL PVLCQDHGLT PDQVVAIASH DGGKQALETV QRLLPVLCQD 480

HGLTPDQVVA IASNGGGKQA LETVQRLLPV LCQDHGLTPD QVVAIASHDG GKQALETVQR 540

LLPVLCQDHG LTPDQVVAIA SHDGGKQALE TVQRLLPVLC QDHGLTPDQV VAIASNGGGK 600

QALETVQRLL PVLCQDHGLT PDQVVAIASN KGGKQALETV QRLLPVLCQD HGLTPDQVVA 660
```

-continued

```
IASNGGGKQA LESIVAQLSR PDPALAALTN DHLVALACLG GRPALDAVKK GLPHAPALIK  720

RTNRRIPERT SHRVAGSQLV KSELEEKKSE LRHKLKYVPH EYIELIEIAR NSTQDRILEM  780

KVMEFFMKVY GYRGKHLGGS RKPDGAIYTV GSPIDYGVIV DTKAYSGGYN LPIGQADEMQ  840

RYVEENQTRN KHINPNEWWK VYPSSVTEFK FLFVSGHFKG NYKAQLTRLN HITNCNGAVL  900

SVEELLIGGE MIKAGTLTLE EVRRKFNNGE INF.                             933
```

The RVDs are underlined for clarity.
A new NN TALEN pair (S1 NN) targeting the beta-globin gene was designed having the TALEN identity

```
                                                         (SEQ ID NO: 7)
MDYKDHDGDY KDHDIDYKDD DDKMAPKKKR KVGIHRGVPM VDLRTLGYSQ QQQEKIKPKV   60

RSTVAQHHEA LVGHGFTHAH IVALSQHPAA LGTVAVKYQD MIAALPEATH EAIVGVGKQW  120

SGAAALEALL TVAGELRGPP LQLDTGQLLK IAKRGGVTAV EAVHAWRNAL TGAPLNLTPD  180

QVVAIASNNG GKQALETVQR LLPVLCQDHG LTPDQVVAIA SNNGGKQALE TVQRLLPVLC  240

QDHGLTPDQV VAIASNGGGK QALETVQRLL PVLCQDHGLT PDQVVAIASN NGGKQALETV  300

QRLLPVLCQD HGLTPDQVVA IASHDGGKQA LETVQRLLPV LCQDHGLTPD QVVAIASNIG  360

GKQALETVQR LLPVLCQDHG LTPDQVVAIA SHDGGKQALE TVQRLLPVLC QDHGLTPDQV  420

VAIASHDGGK QALETVQRLL PVLCQDHGLT PDQVVAIASN GGGKQALETV QRLLPVLCQD  480

HGLTPDQVVA IASNNGGKQA LETVQRLLPV LCQDHGLTPD QVVAIASNIG GKQALETVQR  540

LLPVLCQDHG LTPDQVVAIA SHDGGKQALE TVQRLLPVLC QDHGLTPDQV VAIASNGGGK  600

QALETVQRLL PVLCQDHGLT PDQVVAIASH DGGKQALETV QRLLPVLCQD HGLTPDQVVA  660

IASHDGGKQA LETVQRLLPV LCQDHGLTPD QVVAIASNGG GKQALESIVA QLSRPDPALA  720

ALTNDHLVAL ACLGGRPALD AVKKGLPHAP ALIKRTNRRI PERTSHRVAG SQLVKSELEE  780

KKSELRHKLK YVPHEYIELI EIARNSTQDR ILEMKVMEFF MKVYGYRGKH LGGSRKPDGA  840

IYTVGSPIDY GVIVDTKAYS GGYNLPIGQA DEMQRYVEEN QTRNKHINPN EWWKVYPSSV  900

TEFKFLFVSG HFKGNYKAQL TRLNHITNCN GAVLSVEELL IGGEMIKAGT LTLEEVRRKF  960

NNGEINF.                                                          967
```

The RVDs are underlined for clarity.
A new NN TALEN pair (S2 NN) targeting the beta-globin gene was designed having the TALEN identity

```
                                                         (SEQ ID NO: 8)
MDYKDHDGDY KDHDIDYKDD DDKMAPKKKR KVGIHRGVPM VDLRTLGYSQ QQQEKIKPKV  60

RSTVAQHHEA LVGHGFTHAH IVALSQHPAA LGTVAVKYQD MIAALPEATH EAIVGVGKQW 120

SGAAALEALL TVAGELRGPP LQLDTGQLLK IAKRGGVTAV EAVHAWRNAL TGAPLNLTPD 180

QVVAIASNNG GKQALETVQR LLPVLCQDHG LTPDQVVAIA SHDGGKQALE TVQRLLPVLC 240

QDHGLTPDQV VAIASNIGGK QALETVQRLL PVLCQDHGLT PDQVVAIASH DGGKQALETV 300

QRLLPVLCQD HGLTPDQVVA IASHDGGKQA LETVQRLLPV LCQDHGLTPD QVVAIASNGG 360

GKQALETVQR LLPVLCQDHG LTPDQVVAIA SNNGGKQALE TVQRLLPVLC QDHGLTPDQV 420

VAIASNIGGK QALETVQRLL PVLCQDHGLT PDQVVAIASH DGGKQALETV QRLLPVLCQD 480

HGLTPDQVVA IASNGGGKQA LETVQRLLPV LCQDHGLTPD QVVAIASHDG GKQALETVQR 540

LLPVLCQDHG LTPDQVVAIA SHDGGKQALE TVQRLLPVLC QDHGLTPDQV VAIASNGGGK 600
```

```
QALETVQRLL PVLCQDHGLT PDQVVAIASN NGGKQALETV QRLLPVLCQD HGLTPDQVVA  660
IASNGGGKQA LESIVAQLSR PDPALAALTN DHLVALACLG GRPALDAVKK GLPHAPALIK  720
RTNRRIPERT SHRVAGSQLV KSELEEKKSE LRHKLKYVPH EYIELIEIAR NSTQDRILEM  780
KVMEFFMKVY GYRGKHLGGS RKPDGAIYTV GSPIDYGVIV DTKAYSGGYN LPIGQADEMQ  840
AYVEENQTAN KHINPNEWWK VYPSSVTEFK FLFVSGHFKG NYKAQLTRLN HITNCNGAVL  900
SVEELLIGGE MIKAGTLTLE EVRRKFNNGE INF.                              933
```

The RVDs are underlined for clarity.

A new NK TALEN pair (S5 NK) targeting the beta-globin gene was designed having the TALEN identity:

```
                                                      (SEQ ID NO: 9)
MDYKDHDGDY KDHDIDYKDD DDKMAPKKKR KVGIHAGVPM VDLATLGYSQ QQQEKIKPKV   60
ASTVAQHHEA LVGHGFTHAH IVALSQHPAA LGTVAVKYQD MIAALPEATH EAIVGVGKQW  120
SGAAALEALL TVAGELAGPP LQLDTGQLLK IAKAGGVTAV EAVHAWANAL TGAPLNLTPD  180
QVVAIASHDG GKQALETVQA LLPVLCQDHG LTPDQVVAIA SNIGGKQALE TVQALLPVLC  240
QDHGLTPDQV VAIASHDGGK QALETVQALL PVLCQDHGLT PDQVVAIASH DGGKQALETV  300
QALLPVLCQD HGLTPDQVVA IASNGGGKQA LETVQALLPV LCQDHGLTPD QVVAIASNGG  360
GKQALETVQA LLPVLCQDHG LTPDQVVAIA SNKGGKQALE TVQALLPVLC QDHGLTPDQV  420
VAIASHDGGK QALETVQALL PVLCQDHGLT PDQVVAIASH DGGKQALETV QALLPVLCQD  480
HGLTPDQVVA IASHDGGKQA LETVQALLPV LCQDHGLTPD QVVAIASHDG GKQALETVQA  540
LLPVLCQDHG LTPDQVVAIA SNIGGKQALE TVQALLPVLC QDHGLTPDQV VAIASHDGGK  600
QALETVQALL PVLCQDHGLT PDQVVAIASN IGGKQALETV QALLPVLCQD HGLTPDQVVA  660
IASNKGGKQA LETVQALLPV LCQDHGLTPD QVVAIASNKG GKQALETVQA LLPVLCQDHG  720
LTPDQVVAIA SNKGGKQALE TVQALLPVLC QDHGLTPDQV VAIASHDGGK QALETVQALL  780
PVLCQDHGLT PDQVVAIASN IGGKQALETV QALLPVLCQD HGLTPDQVVA IASNKGGKQA  840
LETVQALLPV LCQDHGLTPD QVVAIASNGG GKQALESIVA QLSAPDPALA ALTNDHLVAL  900
ACLGGAPALD AVKKGLPHAP ALIKATNRAI PEATSHAVAG SQLVKSELEE KKSELAHKLK  960
YVPHEYIELI EIARNSTQDR ILEMKVMEFF MKVYGYAGKH LGGSAKPDGA IYTVGSPIDY 1020
GVIVDTKAYS GGYNLPIGQA DEMQAYVEEN QTRNKHINPN EWWKVYPSSV TEFKFLFVSG 1080
HFKGNYKAQL TRLNHITNCN GAVLSVEELL IGGEMIKAGT LTLEEVRRKF NNGEINF.   1137
```

The RVDs are underlined for clarity.

A new NK TALEN pair (S7 NK) targeting the beta-globin gene was designed having the TALEN identity:

```
                                                     (SEQ ID NO: 10)
MDYKDHDGDY KDHDIDYKDD DDKMAPKKKR KVGIHRGVPM VDLRTLGYSQ QQQEKIKPKV   60
RSTVAQHHEA LVGHGFTHAH IVALSQHPAA LGTVAVKYQD MIAALPEATH EAIVGVGKQW  120
SGAAALEALL TVAGELRGPP LQLDTGQLLK IAKRGGVTAV EAVHAWRNAL TGAPLNLTPD  180
QVVAIASHDG GKQALETVQR LLPVLCQDHG LTPDQVVAIA SNIGGKQALE TVQRLLPVLC  240
QDHGLTPDQV VAIASHDGGK QALETVQRLL PVLCQDHGLT PDQVVAIASH DGGKQALETV  300
QRLLPVLCQD HGLTPDQVVA IASNGGGKQA LETVQRLLPV LCQDHGLTPD QVVAIASNGG  360
GKQALETVQR LLPVLCQDHG LTPDQVVAIA SNKGGKQALE TVQRLLPVLC QDHGLTPDQV  420
VAIASHDGGK QALETVQRLL PVLCQDHGLT PDQVVAIASH DGGKQALETV QRLLPVLCQD  480
```

```
HGLTPDQVVA IASHDGGKQA LETVQRLLPV LCQDHGLTPD QVVAIASHDG GKQALETVQR    540

LLPVLCQDHG LTPDQVVAIA SNIGGKQALE TVQRLLPVLC QDHGLTPDQV VAIASHDGGK    600

QALETVQRLL PVLCQDHGLT PDQVVAIASN IGGKQALETV QRLLPVLCQD HGLTPDQVVA    660

IASNKGGKQA LETVQRLLPV LCQDHGLTPD QVVAIASNKG GKQALETVQR LLPVLCQDHG    720

LTPDQVVAIA SNKGGKQALE TVQRLLPVLC QDHGLTPDQV VAIASHDGGK QALETVQRLL    780

PVLCQDHGLT PDQVVAIASN IGGKQALETV QRLLPVLCQD HGLTPDQVVA IASNKGGKQA    840

LETVQRLLPV LCQDHGLTPD QVVAIASNGG GKQALETVQR LLPVLCQDHG LTPDQVVAIA    900

SNIGGKQALE TVQRLLPVLC QDHGLTPDQV VAIASNIGGK QALETVQRLL PVLCQDHGLT    960

PDQVVAIASH DGGKQALESI VAQLSRPDPA LAALTNDHLV ALACLGGRPA LDAVKKGLPH   1020

APALIKRTNR RIPERTSHRV AGSQLVKSEL EEKKSELRHK LKYVPHEYIE LIEIARNSTQ   1080

DRILEMKVME FFMKVYGYRG KHLGGSRKPD GAIYTVGSPI DYGVIVDTKA YSGGYNLPIG   1140

QADEMQRYVE ENQTRNKHIN PNEWWKVYPS SVTEFKFLFV SGHFKGNYKA QLTRLNHITN   1200

CNGAVLSVEE LLIGGEMIKA GTLTLEEVRR KFNNGEINF.                        1239
```

The RVDs are underlined for clarity.

A new NK TALEN pair (S5 NN) targeting the beta-globin gene was designed having the TALEN identity:

```
                                                      (SEQ ID NO: 11)
MDYKDHDGDY KDHDIDYKDD DDKMAPKKKR KVGIHRGVPM VDLRTLGYSQ QQQEKIKPKV     60

RSTVAQHHEA LVGHGFTHAH IVALSQHPAA LGTVAVKYQD MIAALPEATH EAIVGVGKQW    120

SGAAALEALL TVAGELRGPP LQLDTGQLLK IAKRGGVTAV EAVHAWRNAL TGAPLNLTPD    180

QVVAIASHDG GKQALETVQR LLPVLCQDHG LTPDQVVAIA SNIGGKQALE TVQRLLPVLC    240

QDHGLTPDQV VAIASHDGGK QALETVQRLL PVLCQDHGLT PDQVVAIASH DGGKQALETV    300

QRLLPVLCQD HGLTPDQVVA IASNGGGKQA LETVQRLLPV LCQDHGLTPD QVVAIASNGG    360

GKQALETVQA LLPVLCQDHG LTPDQVVAIA SNNGGKQALE TVQALLPVLC QDHGLTPDQV    420

VAIASHDGGK QALETVQALL PVLCQDHGLT PDQVVAIASH DGGKQALETV QALLPVLCQD    480

HGLTPDQVVA IASHDGGKQA LETVQALLPV LCQDHGLTPD QVVAIASHDG GKQALETVQA    540

LLPVLCQDHG LTPDQVVAIA SNIGGKQALE TVQALLPVLC QDHGLTPDQV VAIASHDGGK    600

QALETVQALL PVLCQDHGLT PDQVVAIASN IGGKQALETV QALLPVLCQD HGLTPDQVVA    660

IASNNGGKQA LETVQALLPV LCQDHGLTPD QVVAIASNNC GKQALETVQR LLPVLCQDHC    720

LTPDQVVAIA SNNGGKQALE TVQALLPVLC QDHGLTPDQV VAIASHDGGK QALETVQRLL    780

PVLCQDHGLT PDQVVAIASN IGGKQALETV QALLPVLCQD HGLTPDQVVA IASNNGGKQA    840

LETVQRLLPV LCQDHGLTPD QVVAIASNGG GKQALESIVA QLSAPDPALA ALTNDHLVAL    900

ACLGGRPALD AVKKGLPHAP ALIKRTNRRI PEATSHRVAG SQLVKSELEE KKSELRHKLK    960

YVPHEYIELI EIARNSTQDR ILEMKVMEFF MKVYGYRGKH LGGSRKPDGA IYTVGSPIDY   1020

GVIVDTKAYS GGYNLPIGQA DEMQRYVEEN QTRNKHINPN EWWKVYPSSV TEFKFLFVSG   1080

HFKGNYKAQL TRLNHITNCN GAVLSVEELL IGGEMIKAGT LTLEEVRRKF NNGEINF.    1137
```

The RVDs are underlined for clarity.

A new NK TALEN pair (S7 NN) targeting the beta-globin gene was designed having the TALEN identity:

(SEQ ID NO: 12)

```
MDYKDHDGDY KDHDIDYKDD DDKMAPKKKR KVGIHRGVPM VDLRTLGYSQ QQQEKIKPKV   60
RSTVAQHHEA LVGHGFTHAH IVALSQHPAA LGTVAVKYQD MIAALPEATH EAIVGVGKQW  120
SGAAALEALL TVAGELRGPP LQLDTGQLLK IAKRGGVTAV EAVHAWRNAL TGAPLNLTPD  180
QVVAIASHDG GKQALETVQR LLPVLCQDHG LTPDQVVAIA SNIGGKQALE TVQRLLPVLC  240
QDHGLTPDQV VAIASHDGGK QALETVQRLL PVLCQDHGLT PDQVVAIASH DGGKQALETV  300
QRLLPVLCQD HGLTPDQVVA IASNGGGKQA LETVQRLLPV LCQDHGLTPD QVVAIASNGG  360
GKQALETVQR LLPVLCQDHG LTPDQVVAIA SNNGGKQALE TVQRLLPVLC QDHGLTPDQV  420
VAIASHDGGK QALETVQRLL PVLCQDHGLT PDQVVAIASH DGGKQALETV QRLLPVLCQD  480
HGLTPDQVVA IASHDGGKQA LETVQRLLPV LCQDHGLTPD QVVAIASHDG GKQALETVQR  540
LLPVLCQDHG LTPDQVVAIA SNIGGKQALE TVQRLLPVLC QDHGLTPDQV VAIASHDGGK  600
QALETVQRLL PVLCQDHGLT PDQVVAIASN IGGKQALETV QRLLPVLCQD HGLTPDQVVA  660
IASNNGGKQA LETVQRLLPV LCQDHGLTPD QVVAIASNNG GKQALETVQR LLPVLCQDHG  720
LTPDQVVAIA SNNGGKQALE TVQRLLPVLC QDHGLTPDQV VAIASHDGGK QALETVQRLL  780
PVLCQDHGLT PDQVVAIASN IGGKQALETV QRLLPVLCQD HGLTPDQVVA IASNNGGKQA  840
LETVQRLLPV LCQDHGLTPD QVVAIASNGG GKQALETVQR LLPVLCQDHG LTPDQVVAIA  900
SNIGGKQALE TVQRLLPVLC QDHGLTPDQV VAIASNIGGK QALETVQRLL PVLCQDHGLT  960
PDQVVAIASH DGGKQALESI VAQLSRPDPA LAALTNDHLV ALACLGGRPA LDAVKKGLPH 1020
APALIKRTNR RIPERTSHRV AGSQLVKSEL EEKKSELRHK LKYVPHEYIE LIEIARNSTQ 1080
DRILEMKVME FFMKVYGYRG KHLGGSRKPD GAIYTVGSPI DYGVIVDTKA YSGGYNLPIG 1140
QADEMQRYVE ENQTRNKHIN PNEWWKVYPS SVTEFKFLFV SGHFKGNYKA QLTRLNHITN 1200
CNGAVLSVEE LLIGGEMIKA GTLTLEEVRR KFNNGEINF.                      1239
```

The RVDs are underlined for clarity

The plasmid that codes for SEQ ID NO: 1 has an identity (SEQ ID NO: 13)

```
GACGGATCGGGAGATCTCCCGATCCCCTATGGTGCACTCTCAGTACAATCTGCTCTGATGCCGCATAGTTAAGCCAG
TATCTGCTCCCTGCTTGTGTGTTGGAGGTCGCTGAGTAGTGCGCGAGCAAAATTTAAGCTACAACAAGGCAAGGCTT
GACCGACAATTGCATGAAGAATCTGCTTAGGGTTAGGCGTTTTGCGCTGCTTCGCGATGTACGGGCCAGATATACGC
GTTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTG
ACGTCAATGGGAGTTTGTTTTGGCACCAAAATCAACGGGACTTTCCAAAATGTCGTAACAACTCCGCCCCATTGACG
CAAATGGGCGGTAGGCGTGTACGGTGGGAGGTCTATATAAGCAGAGCTCTCTGGCTAACTAGAGAACCCACTGCTTA
CTGGCTTATCGAAATTAATACGACTCACTATAGGGAGACCCAAGCTGGCTAGCACCATGGACTACAAAGACCATGAC
GGTGATTATAAAGATCATGACATCGATTACAAGGATGACGATGACAAGCCAAAAAAGAAGCGAAAGGTACCTTTTGC
CTGCGACATCTGCGGCCGCAAGTTCGCCCGGACTGACACCCTGAGGGATCACACCAAAATCCACACTGGAGAGAAGC
```

-continued

```
CCTTCCAGTGCAGAATCTGCATGCGCAACTTTAGCCAGAGCTCCTCTCTGGTGAGGCACATTAGAACACACACCGGC
GAAAAGCCCTTCGCTTGTGATATCTGTGGTCGTAAATTTGCCCAGAGCGGGGACCTGACAAGACACCAGCGCACTCA
TGGATCCCAGCTGGTGAAGAGCGAGCTGGAGGAGAAGAAGTCCGAGCTGCGGCACAAGCTGAAGTACGTGCCCCACG
AGTACATCGAGCTGATCGAGATCGCCAGGAACAGCACCCAGGACCGCATCCTGGAGATGAAGGTGATGGAGTTCTTC
ATGAAGGTGTACGGCTACAGGGGAAAGCACCTGGGCGGAAGCAGAAAGCCTGACGGCGCCATCTATACAGTGGGCAG
CCCCATCGATTACGGCGTGATCGTGGACACAAAGGCCTACAGCGGCGGCTACAATCTGCCTATCGGCCAGGCCGACG
AGATGCAGAGATACGTGGAGGAGAACCAGACCCGGAATAAGCACATCAACCCCAACGAGTGGTGGAAGGTGTACCCT
AGCAGCGTGACCGAGTTCAAGTTCCTGTTCGTGAGCGGCCACTTCAAGGGCAACTACAAGGCCCAGCTGACCAGGCT
GAACCACATCACCAACTGCAATGGCGCCGTGCTGAGCGTGGAGGAGCTGCTGATCGGCGGCGAGATGATCAAAGCCG
GCACCCTGACACTGGAGGAGGTGCGGCGCAAGTTCAACAACGGCGAGATCAACTTCTGATAACTCGAGCGGCCGCCA
CTGTGCTGGATAAACCGCTGATCAGCCTCGACTGTGCCTTCTAGTTGCCAGCCATCTGTTGTTTGCCCCTCCCCCGT
GCCTTCCTTGACCCTGGAAGGTGCCACTCCCACTGTCCTTTCCTAATAAAATGAGGAAATTGCATCGCATTGTCTGA
GTAGGTGTCATTCTATTCTGGGGGGTGGGGTGGGGCAGGACAGCAAGGGGGAGGATTGGGAAGACAATAGCAGGCAT
GCTGGGGATGCGGTGGGCTCTATGGCTTCTGAGGCGGAAAGAACCAGCTGGGGCTCTAGGGGGTATCCCCACGCGCC
CTGTAGCGGCGCATTAAGCGCGGCGGGTGTGGTGGTTACGCGCAGCGTGACCGCTACACTTGCCAGCGCCCTAGCGC
CCGCTCCTTTCGCTTTCTTCCCTTCCTTTCTCGCCACGTTCGCCGGCTTTCCCCGTCAAGCTCTAAATCGGGGCTC
CCTTTAGGGTTCCGATTTAGTGCTTTACGGCACCTCGACCCCAAAAAACTTGATTAGGGTGATGGTTCACGTAGTGG
GCCATCGCCCTGATAGACGGTTTTTCGCCCTTTGACGTTGGAGTCCACGTTCTTTAATAGTGGACTCTTGTTCCAAA
CTGGAACAACACTCAACCCTATCTCGGTCTATTCTTTTGATTTATAAGGGATTTTGCCGATTTCGGCCTATTGGTTA
AAAAATGAGCTGATTTAACAAAAATTTAACGCGAATTAATTCTGTGGAATGTGTGTCAGTTAGGGTGTGGAAAGTCC
CCAGGCTCCCCAGCAGGCAGAAGTATGCAAAGCATGCATCTCAATTAGTCAGCAACCAGGTGTGGAAAGTCCCCAGG
CTCCCCAGCAGGCAGAAGTATGCAAAGCATGCATCTCAATTAGTCAGCAACCATAGTCCCGCCCCTAACTCCGCCCA
TCCCGCCCCTAACTCCGCCCAGTTCCGCCCATTCTCCGCCCCATGGCTGACTAATTTTTTTTATTTATGCAGAGGCC
GAGGCCGCCTCTGCCTCTGAGCTATTCCAGAAGTAGTGAGGAGGCTTTTTTGGAGGCCTAGGCTTTTGCAAAAAGCT
CCCGGGAGCTTGTATATCCATTTTCGGATCTGATCAAGAGACAGGATGAGGATCGTTTCGCATGATTGAACAAGATG
GATTGCACGCAGGTTCTCCGGCCGCTTGGGTGGAGAGGCTATTCGGCTATGACTGGGCACAACAGACAATCGGCTGC
TCTGATGCCGCCGTGTTCCGGCTGTCAGCGCAGGGGCGCCCGGTTCTTTTTGTCAAGACCGACCTGTCCGGTGCCCT
GAATGAACTGCAGGACGAGGCAGCGCGGCTATCGTGGCTGGCCACGACGGGCGTTCCTTGCGCAGCTGTGCTCGACG
TTGTCACTGAAGCGGGAAGGGACTGGCTGCTATTGGGCGAAGTGCCGGGGCAGGATCTCCTGTCATCTCACCTTGCT
CCTGCCGAGAAAGTATCCATCATGGCTGATGCAATGCGGCGGCTGCATACGCTTGATCCGGCTACCTGCCCATTCGA
CCACCAAGCGAAACATCGCATCGAGCGAGCACGTACTCGGATGGAAGCCGGTCTTGTCGATCAGGATGATCTGGACG
AAGAGCATCAGGGGCTCGCGCCAGCCGAACTGTTCGCCAGGCTCAAGGCGCGCATGCCCGACGGCGAGGATCTCGTC
GTGACCCATGGCGATGCCTGCTTGCCGAATATCATGGTGGAAAATGGCCGCTTTTCTGGATTCATCGACTGTGGCCG
GCTGGGTGTGGCGGACCGCTATCAGGACATAGCGTTGGCTACCCGTGATATTGCTGAAGAGCTTGGCGGCGAATGGG
CTGACCGCTTCCTCGTGCTTTACGGTATCGCCGCTCCCGATTCGCAGCGCATCGCCTTCTATCGCCTTCTTGACGAG
TTCTTCTGAGCGGGACTCTGGGGTTCGAAATGACCGACCAAGCGACGCCCAACCTGCCATCACGAGATTTCGATTCC
ACCGCCGCCTTCTATGAAAGGTTGGGCTTCGGAATCGTTTTCCGGGACGCCGGCTGGATGATCCTCCAGCGCGGGGA
TCTCATGCTGGAGTTCTTCGCCCACCCCAACTTGTTTATTGCAGCTTATAATGGTTACAAATAAAGCAATAGCATCA
CAAATTTCACAAATAAAGCATTTTTTTCACTGCATTCTAGTTGTGGTTTGTCCAAACTCATCAATGTATCTTATCAT
GTCTGTATACCGTCGACCTCTAGCTAGAGCTTGGCGTAATCATGGTCATAGCTGTTTCCTGTGTGAAATTGTTATCC
GCTCACAATTCCACACAACATACGAGCCGGAAGCATAAAGTGTAAAGCCTGGGGTGCCTAATGAGTGAGCTAACTCA
```

-continued

```
CATTAATTGCGTTGCGCTCACTGCCCGCTTTCCAGTCGGGAAACCTGTCGTGCCAGCTGCATTAATGAATCGGCCAA

CGCGCGGGGAGAGGCGGTTTGCGTATTGGGCGCTCTTCCGCTTCCTCGCTCACTGACTCGCTGCGCTCGGTCGTTCG

GCTGCGGCGAGCGGTATCAGCTCACTCAAAGGCGGTAATACGGTTATCCACAGAATCAGGGGATAACGCAGGAAAGA

ACATGTGAGCAAAAGGCCAGCAAAAGGCCAGGAACCGTAAAAAGGCCGCGTTGCTGGCGTTTTTCCATAGGCTCCGC

CCCCCTGACGAGCATCACAAAAATCGACGCTCAAGTCAGAGGTGGCGAAACCCGACAGGACTATAAAGATACCAGGC

GTTTCCCCCTGGAAGCTCCCTCGTGCGCTCTCCTGTTCCGACCCTGCCGCTTACCGGATACCTGTCCGCCTTTCTCC

CTTCGGGAAGCGTGGCGCTTTCTCATAGCTCACGCTGTAGGTATCTCAGTTCGGTGTAGGTCGTTCGCTCCAAGCTG

GGCTGTGTGCACGAACCCCCCGTTCAGCCCGACCGCTGCGCCTTATCCGGTAACTATCGTCTTGAGTCCAACCCGGT

AAGACACGACTTATCGCCACTGGCAGCAGCCACTGGTAACAGGATTAGCAGAGCGAGGTATGTAGGCGGTGCTACAG

AGTTCTTGAAGTGGTGGCCTAACTACGGCTACACTAGAAGAACAGTATTTGGTATCTGCGCTCTGCTGAAGCCAGTT

ACCTTCGGAAAAAGAGTTGGTAGCTCTTGATCCGGCAAACAAACCACCGCTGGTAGCGGTTTTTTTGTTTGCAAGCA

GCAGATTACGCGCAGAAAAAAAGGATCTCAAGAAGATCCTTTGATCTTTTCTACGGGGTCTGACGCTCAGTGGAACG

AAAACTCACGTTAAGGGATTTTGGTCATGAGATTATCAAAAAGGATCTTCACCTAGATCCTTTTAAATTAAAAATGA

AGTTTTAAATCAATCTAAAGTATATATGAGTAAACTTGGTCTGACAGTTACCAATGCTTAATCAGTGAGGCACCTAT

CTCAGCGATCTGTCTATTTCGTTCATCCATAGTTGCCTGACTCCCCGTCGTGTAGATAACTACGATACGGGAGGGCT

TACCATCTGGCCCCAGTGCTGCAATGATACCGCGAGACCCACGCTCACCGGCTCCAGATTTATCAGCAATAAACCAG

CCAGCCGGAAGGGCCGAGCGCAGAAGTGGTCCTGCAACTTTATCCGCCTCCATCCAGTCTATTAATTGTTGCCGGGA

AGCTAGAGTAAGTAGTTCGCCAGTTAATAGTTTGCGCAACGTTGTTGCCATTGCTACAGGCATCGTGGTGTCACGCT

CGTCGTTTGGTATGGCTTCATTCAGCTCCGGTTCCCAACGATCAAGGCGAGTTACATGATCCCCCATGTTGTGCAAA

AAAGCGGTTAGCTCCTTCGGTCCTCCGATCGTTGTCAGAAGTAAGTTGGCCGCAGTGTTATCACTCATGGTTATGGC

AGCACTGCATAATTCTCTTACTGTCATGCCATCCGTAAGATGCTTTTCTGTGACTGGTGAGTACTCAACCAAGTCAT

TCTGAGAATAGTGTATGCGGCGACCGAGTTGCTCTTGCCCGGCGTCAATACGGGATAATACCGCGCCACATAGCAGA

ACTTTAAAAGTGCTCATCATTGGAAAACGTTCTTCGGGGCGAAAACTCTCAAGGATCTTACCGCTGTTGAGATCCAG

TTCGATGTAACCCACTCGTGCACCCAACTGATCTTCAGCATCTTTTACTTTCACCAGCGTTTCTGGGTGAGCAAAA

CAGGAAGGCAAAATGCCGCAAAAAAGGGAATAAGGGCGACACGGAAATGTTGAATACTCATACTCTTCCTTTTTCAA

TATTATTGAAGCATTTATCAGGGTTATTGTCTCATGAGCGGATACATATTTGAATGTATTTAGAAAAATAAACAAAT

AGGGGTTCCGCGCACATTTCCCCGAAAAGTGCCACCTGACGTC.
```

The plasmid that codes for SEQ ID NO: 2 has an identity (SEQ ID NO: 14)
```
GACGGATCGGGAGATCTCCCGATCCCCTATGGTGCACTCTCAGTACAATCTGCTCTGATGCCGCATAGTTAAGCCAG

TATCTGCTCCCTGCTTGTGTGTTGGAGGTCGCTGAGTAGTGCGCGAGCAAAATTTAAGCTACAACAAGGCAAGGCTT

GACCGACAATTGCATGAAGAATCTGCTTAGGGTTAGGCGTTTTGCGCTGCTTCGCGATGTACGGGCCAGATATACGC

GTTGACATTGATTATTGACTAGTTATTAATAGTAATCAATTACGGGGTCATTAGTTCATAGCCCATATATGGAGTTC

CGCGTTACATAACTTACGGTAAATGGCCCGCCTGGCTGACCGCCCAACGACCCCCGCCCATTGACGTCAATAATGAC

GTATGTTCCCATAGTAACGCCAATAGGGACTTTCCATTGACGTCAATGGGTGGAGTATTTACGGTAAACTGCCCACT

TGGCAGTACATCAAGTGTATCATATGCCAAGTACGCCCCCTATTGACGTCAATGACGGTAAATGGCCCGCCTGGCAT

TATGCCCAGTACATGACCTTATGGGACTTTCCTACTTGGCAGTACATCTACGTATTAGTCATCGCTATTACCATGGT

GATGCGGTTTTGGCAGTACATCAATGGGCGTGGATAGCGGTTTGACTCACGGGGATTTCCAAGTCTCCACCCCATTG

ACGTCAATGGGAGTTTGTTTTGGCACCAAAATCAACGGGACTTTCCAAAATGTCGTAACAACTCCGCCCCATTGACG

CAAATGGGCGGTAGGCGTGTACGGTGGGAGGTCTATATAAGCAGAGCTCTCTGGCTAACTAGAGAACCCACTGCTTA
```

-continued

```
CTGGCTTATCGAAATTAATACGACTCACTATAGGGAGACCCAAGCTGGCTAGCACCATGGACTACAAAGACCATGAC

GGTGATTATAAAGATCATGACATCGATTACAAGGATGACGATGACAAGCAAAAAAGAAGCGAAAGGTACCTTTTGC

CTGCGACATCTGCGGCCGCAAGTTCGCCAGAAGCGACCACCTGACCAACCACACCAAAATCCACACTGGAGAGAAGC

CCTTCCAGTGCAGAATCTGCATGCGCAACTTTAGCCAGAGCGGCGACCTGACCAGACACATTAGAACACACACCGGC

GAAAAGCCCTTCGCTTGTGATATCTGTGGTCGTAAATTTGCCAGAAGCGACCACCTGAGCAGACACCAGCGCACTCA

TGGATCCCAGCTGGTGAAGAGCGAGCTGGAGGAGAAGAAGTCCGAGCTGCGGCACAAGCTGAAGTACGTGCCCCACG

AGTACATCGAGCTGATCGAGATCGCCAGGAACAGCACCCAGGACCGCATCCTGGAGATGAAGGTGATGGAGTTCTTC

ATGAAGGTGTACGGCTACAGGGGAAAGCACCTGGGCGGAAGCAGAAAGCCTGACGGCGCCATCTATACAGTGGGCAG

CCCCATCGATTACGGCGTGATCGTGGACACAAAGGCCTACAGCGGCGGCTACAATCTGCCTATCGGCCAGGCCGACG

AGATGCAGAGATACGTGGAGGAGAACCAGACCCGGAATAAGCACATCAACCCCAACGAGTGGTGGAAGGTGTACCCT

AGCAGCGTGACCGAGTTCAAGTTCCTGTTCGTGAGCGGCCACTTCAAGGGCAACTACAAGGCCCAGCTGACCAGGCT

GAACCACATCACCAACTGCAATGGCGCCGTGCTGAGCGTGGAGGAGCTGCTGATCGGCGGCGAGATGATCAAAGCCG

GCACCCTGACACTGGAGGAGGTGCGGCGCAAGTTCAACAACGGCGAGATCAACTTCTGATAACTCGAGCGGCCGCCA

CTGTGCTGGATAAACCGCTGATCAGCCTCGACTGTGCCTTCTAGTTGCCAGCCATCTGTTGTTTGCCCCTCCCCCGT

GCCTTCCTTGACCCTGGAAGGTGCCACTCCCACTGTCCTTTCCTAATAAAATGAGGAAATTGCATCGCATTGTCTGA

GTAGGTGTCATTCTATTCTGGGGGGTGGGGTGGGGCAGGACAGCAAGGGGGAGGATTGGGAAGACAATAGCAGGCAT

GCTGGGGATGCGGTGGGCTCTATGGCTTCTGAGGCGGAAAGAACCAGCTGGGGCTCTAGGGGGTATCCCCACGCGCC

CTGTAGCGGCGCATTAAGCGCGGCGGGTGTGGTGGTTACGCGCAGCGTGACCGCTACACTTGCCAGCGCCCTAGCGC

CCGCTCCTTTCGCTTTCTTCCCTTCCTTTCTCGCCACGTTCGCCGGCTTTCCCCGTCAAGCTCTAAATCGGGGGCTC

CCTTTAGGGTTCCGATTTAGTGCTTTACGGCACCTCGACCCCAAAAAACTTGATTAGGGTGATGGTTCACGTAGTGG

GCCATCGCCCTGATAGACGGTTTTTCGCCCTTTGACGTTGGAGTCCACGTTCTTTAATAGTGGACTCTTGTTCCAAA

CTGGAACAACACTCAACCCTATCTCGGTCTATTCTTTTGATTTATAAGGGATTTTGCCGATTTCGGCCTATTGGTTA

AAAAATGAGCTGATTTAACAAAAATTTAACGCGAATTAATTCTGTGGAATGTGTGTCAGTTAGGGTGTGGAAAGTCC

CCAGGCTCCCCAGCAGGCAGAAGTATGCAAAGCATGCATCTCAATTAGTCAGCAACCAGGTGTGGAAAGTCCCCAGG

CTCCCCAGCAGGCAGAAGTATGCAAAGCATGCATCTCAATTAGTCAGCAACCATAGTCCCGCCCCTAACTCCGCCCA

TCCCGCCCCTAACTCCGCCCAGTTCCGCCCATTCTCCGCCCCATGGCTGACTAATTTTTTTATTTATGCAGAGGCC

GAGGCCGCCTCTGCCTCTGAGCTATTCCAGAAGTAGTGAGGAGGCTTTTTTGGAGGCCTAGGCTTTTGCAAAAAGCT

CCCGGGAGCTTGTATATCCATTTTCGGATCTGATCAAGAGACAGGATGAGGATCGTTTCGCATGATTGAACAAGATG

GATTGCACGCAGGTTCTCCGGCCGCTTGGGTGGAGAGGCTATTCGGCTATGACTGGGCACAACAGACAATCGGCTGC

TCTGATGCCGCCGTGTTCCGGCTGTCAGCGCAGGGGCGCCCGGTTCTTTTTGTCAAGACCGACCTGTCCGGTGCCCT

GAATGAACTGCAGGACGAGGCAGCGCGGCTATCGTGGCTGGCCACGACGGGCGTTCCTTGCGCAGCTGTGCTCGACG

TTGTCACTGAAGCGGGAAGGGACTGGCTGCTATTGGGCGAAGTGCCGGGGCAGGATCTCCTGTCATCTCACCTTGCT

CCTGCCGAGAAAGTATCCATCATGGCTGATGCAATGCGGCGGCTGCATACGCTTGATCCGGCTACCTGCCCATTCGA

CCACCAAGCGAAACATCGCATCGAGCGAGCACGTACTCGGATGGAAGCCGGTCTTGTCGATCAGGATGATCTGGACG

AAGAGCATCAGGGGCTCGCGCCAGCCGAACTGTTCGCCAGGCTCAAGGCGCGCATGCCCGACGGCGAGGATCTCGTC

GTGACCCATGGCGATGCCTGCTTGCCGAATATCATGGTGGAAAATGGCCGCTTTTCTGGATTCATCGACTGTGGCCG

GCTGGGTGTGGCGGACCGCTATCAGGACATAGCGTTGGCTACCCGTGATATTGCTGAAGAGCTTGGCGGCGAATGGG

CTGACCGCTTCCTCGTGCTTTACGGTATCGCCGCTCCCGATTCGCAGCGCATCGCCTTCTATCGCCTTCTTGACGAG

TTCTTCTGAGCGGGACTCTGGGGTTCGAAATGACCGACCAAGCGACGCCCAACCTGCCATCACGAGATTTCGATTCC

ACCGCCGCCTTCTATGAAAGGTTGGGCTTCGGAATCGTTTTCCGGGACGCCGGCTGGATGATCCTCCAGCGCGGGGA
```

-continued

```
TCTCATGCTGGAGTTCTTCGCCCACCCCAACTTGTTTATTGCAGCTTATAATGGTTACAAATAAAGCAATAGCATCA

CAAATTTCACAAATAAAGCATTTTTTTCACTGCATTCTAGTTGTGGTTTGTCCAAACTCATCAATGTATCTTATCAT

GTCTGTATACCGTCGACCTCTAGCTAGAGCTTGGCGTAATCATGGTCATAGCTGTTTCCTGTGTGAAATTGTTATCC

GCTCACAATTCCACACAACATACGAGCCGGAAGCATAAAGTGTAAAGCCTGGGGTGCCTAATGAGTGAGCTAACTCA

CATTAATTGCGTTGCGCTCACTGCCCGCTTTCCAGTCGGGAAACCTGTCGTGCCAGCTGCATTAATGAATCGGCCAA

CGCGCGGGGAGAGGCGGTTTGCGTATTGGGCGCTCTTCCGCTTCCTCGCTCACTGACTCGCTGCGCTCGGTCGTTCG

GCTGCGGCGAGCGGTATCAGCTCACTCAAAGGCGGTAATACGGTTATCCACAGAATCAGGGGATAACGCAGGAAAGA

ACATGTGAGCAAAAGGCCAGCAAAAGGCCAGGAACCGTAAAAAGGCCGCGTTGCTGGCGTTTTTCCATAGGCTCCGC

CCCCCTGACGAGCATCACAAAAATCGACGCTCAAGTCAGAGGTGGCGAAACCCGACAGGACTATAAAGATACCAGGC

GTTTCCCCCTGGAAGCTCCCTCGTGCGCTCTCCTGTTCCGACCCTGCCGCTTACCGGATACCTGTCCGCCTTTCTCC

CTTCGGGAAGCGTGGCGCTTTCTCATAGCTCACGCTGTAGGTATCTCAGTTCGGTGTAGGTCGTTCGCTCCAAGCTG

GGCTGTGTGCACGAACCCCCCGTTCAGCCCGACCGCTGCGCCTTATCCGGTAACTATCGTCTTGAGTCCAACCCGGT

AAGACACGACTTATCGCCACTGGCAGCAGCCACTGGTAACAGGATTAGCAGAGCGAGGTATGTAGGCGGTGCTACAG

AGTTCTTGAAGTGGTGGCCTAACTACGGCTACACTAGAAGAACAGTATTTGGTATCTGCGCTCTGCTGAAGCCAGTT

ACCTTCGGAAAAAGAGTTGGTAGCTCTTGATCCGGCAAACAAACCACCGCTGGTAGCGGTTTTTTTGTTTGCAAGCA

GCAGATTACGCGCAGAAAAAAAGGATCTCAAGAAGATCCTTTGATCTTTTCTACGGGGTCTGACGCTCAGTGGAACG

AAAACTCACGTTAAGGGATTTTGGTCATGAGATTATCAAAAAGGATCTTCACCTAGATCCTTTTAAATTAAAAATGA

AGTTTTAAATCAATCTAAAGTATATATGAGTAAACTTGGTCTGACAGTTACCAATGCTTAATCAGTGAGGCACCTAT

CTCAGCGATCTGTCTATTTCGTTCATCCATAGTTGCCTGACTCCCCGTCGTGTAGATAACTACGATACGGGAGGGCT

TACCATCTGGCCCCAGTGCTGCAATGATACCGCGAGACCCACGCTCACCGGCTCCAGATTTATCAGCAATAAACCAG

CCAGCCGGAAGGGCCGAGCGCAGAAGTGGTCCTGCAACTTTATCCGCCTCCATCCAGTCTATTAATTGTTGCCGGGA

AGCTAGAGTAAGTAGTTCGCCAGTTAATAGTTTGCGCAACGTTGTTGCCATTGCTACAGGCATCGTGGTGTCACGCT

CGTCGTTTGGTATGGCTTCATTCAGCTCCGGTTCCCAACGATCAAGGCGAGTTACATGATCCCCCATGTTGTGCAAA

AAAGCGGTTAGCTCCTTCGGTCCTCCGATCGTTGTCAGAAGTAAGTTGGCCGCAGTGTTATCACTCATGGTTATGGC

AGCACTGCATAATTCTCTTACTGTCATGCCATCCGTAAGATGCTTTTCTGTGACTGGTGAGTACTCAACCAAGTCAT

TCTGAGAATAGTGTATGCGGCGACCGAGTTGCTCTTGCCCGGCGTCAATACGGGATAATACCGCGCCACATAGCAGA

ACTTTAAAAGTGCTCATCATTGGAAAACGTTCTTCGGGGCGAAAACTCTCAAGGATCTTACCGCTGTTGAGATCCAG

TTCGATGTAACCCACTCGTGCACCCAACTGATCTTCAGCATCTTTTACTTTCACCAGCGTTTCTGGGTGAGCAAAAA

CAGGAAGGCAAAATGCCGCAAAAAAGGGAATAAGGGCGACACGGAAATGTTGAATACTCATACTCTTCCTTTTTCAA

TATTATTGAAGCATTTATCAGGGTTATTGTCTCATGAGCGGATACATATTTGAATGTATTTAGAAAAATAAACAAAT

AGGGGTTCCGCGCACATTTCCCCGAAAAGTGCCACCTGACGTC.
```

The plasmid that codes for SEQ ID NO: 3 has an identity

```
                                                        (SEQ ID NO: 15)
GACGGATCGGGAGATCTCCCGATCCCCTATGGTGCACTCTCAGTACAATCTGCTCTGATGCCGCATAGTTAAGCCAG

TATCTGCTCCCTGCTTGTGTGTTGGAGGTCGCTGAGTAGTGCGCGAGCAAAATTTAAGCTACAACAAGGCAAGGCTT

GACCGACAATTGCATGAAGAATCTGCTTAGGGTTAGGCGTTTTGCGCTGCTTCGCGATGTACGGGCCAGATATACGC

GTTGACATTGATTATTGACTAGTTATTAATAGTAATCAATTACGGGGTCATTAGTTCATAGCCCATATATGGAGTTC

CGCGTTACATAACTTACGGTAAATGGCCCGCCTGGCTGACCGCCCAACGACCCCCGCCCATTGACGTCAATAATGAC

GTATGTTCCCATAGTAACGCCAATAGGGACTTTCCATTGACGTCAATGGGTGGAGTATTTACGGTAAACTGCCCACT

TGGCAGTACATCAAGTGTATCATATGCCAAGTACGCCCCCTATTGACGTCAATGACGGTAAATGGCCCGCCTGGCAT
```

-continued

```
TATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTG
ACGTCAATGGGAGTTTGTTTTGGCACCAAAATCAACGGGACTTTCCAAAATGTCGTAACAACTCCGCCCCATTGACG
CAAATGGGCGGTAGGCGTGTACGGTGGGAGGTCTATATAAGCAGAGCTCTCTGGCTAACTAGAGAACCCACTGCTTA
CTGGCTTATCGAAATTAATACGACTCACTATAGGGAGACCCAAGCTGGCTAGCACCATGGACTACAAAGACCATGAC
GGTGATTATAAAGATCATGACATCGATTACAAGGATGACGATGACAAGCCAAAAAAGAAGCGAAAGGTACCATTCCA
GTGCCGCATTTGTATGCGCAATTTCAGCCAGAGTGGAAGTCTGACCCGGCATATCCGTACCCACACCGGTGAGAAAC
CTTTTGCCTGCGACATCTGCGGCCGCAAGTTCGCCCGGACTGACACCCTGAGGGATCACACCAAAATCCACACTGGA
GGCGAGAAGCCCTTCCAGTGCAGAATCTGCATGCGCAACTTTAGCCAGAGCTCCTCTCTGGTGAGGCACATTAGAAC
ACACACCGGCGAAAAGCCCTTCGCTTGTGATATCTGTGGTCGTAAATTTGCCCAGAGCGGGGACCTGACAAGACACC
AGCGCACTCATGGATCCCAGCTGGTGAAGAGCGAGCTGGAGGAGAAGAAGTCCGAGCTGCGGCACAAGCTGAAGTAC
GTGCCCCACGAGTACATCGAGCTGATCGAGATCGCCAGGAACAGCACCCAGGACCGCATCCTGGAGATGAAGGTGAT
GGAGTTCTTCATGAAGGTGTACGGCTACAGGGGAAAGCACCTGGGCGGAAGCAGAAAGCCTGACGGCGCCATCTATA
CAGTGGGCAGCCCCATCGATTACGGCGTGATCGTGGACACAAAGGCCTACAGCGGCGGCTACAATCTGCCTATCGGC
CAGGCCGACGAGATGCAGAGATACGTGGAGGAGAACCAGACCCGGAATAAGCACATCAACCCCAACGAGTGGTGGAA
GGTGTACCCTAGCAGCGTGACCGAGTTCAAGTTCCTGTTCGTGAGCGGCCACTTCAAGGGCAACTACAAGGCCCAGC
TGACCAGGCTGAACCACATCACCAACTGCAATGGCGCCGTGCTGAGCGTGGAGGAGCTGCTGATCGGCGGCGAGATG
ATCAAAGCCGGCACCCTGACACTGGAGGAGGTGCGGCGCAAGTTCAACAACGGCGAGATCAACTTCTGATAACTCGA
GCGGCCGCCACTGTGCTGGATAAACCGCTGATCAGCCTCGACTGTGCCTTCTAGTTGCCAGCCATCTGTTGTTTGCC
CCTCCCCCGTGCCTTCCTTGACCCTGGAAGGTGCCACTCCCACTGTCCTTTCCTAATAAAATGAGGAAATTGCATCG
CATTGTCTGAGTAGGTGTCATTCTATTCTGGGGGGTGGGGTGGGCAGGACAGCAAGGGGGAGGATTGGGAAGACAA
TAGCAGGCATGCTGGGGATGCGGTGGGCTCTATGGCTTCTGAGGCGGAAAGAACCAGCTGGGGCTCTAGGGGGTATC
CCCACGCGCCCTGTAGCGGCGCATTAAGCGCGGCGGGTGTGGTGGTTACGCGCAGCGTGACCGCTACACTTGCCAGC
GCCCTAGCGCCCGCTCCTTTCGCTTTCTTCCCTTCCTTTCTCGCCACGTTCGCCGGCTTTCCCCGTCAAGCTCTAAA
TCGGGGGCTCCCTTTAGGGTTCCGATTTAGTGCTTTACGGCACCTCGACCCCAAAAAACTTGATTAGGGTGATGGTT
CACGTAGTGGGCCATCGCCCTGATAGACGGTTTTTCGCCCTTTGACGTTGGAGTCCACGTTCTTTAATAGTGGACTC
TTGTTCCAAACTGGAACAACACTCAACCCTATCTCGGTCTATTCTTTTGATTTATAAGGGATTTTGCCGATTTCGGC
CTATTGGTTAAAAAATGAGCTGATTTAACAAAAATTTAACGCGAATTAATTCTGTGGAATGTGTGTCAGTTAGGGTG
TGGAAAGTCCCCAGGCTCCCCAGCAGGCAGAAGTATGCAAAGCATGCATCTCAATTAGTCAGCAACCAGGTGTGGAA
AGTCCCCAGGCTCCCCAGCAGGCAGAAGTATGCAAAGCATGCATCTCAATTAGTCAGCAACCATAGTCCCGCCCCTA
ACTCCGCCCATCCCGCCCCTAACTCCGCCCAGTTCCGCCCATTCTCCGCCCCATGGCTGACTAATTTTTTTATTTA
TGCAGAGGCCGAGGCCGCCTCTGCCTCTGAGCTATTCCAGAAGTAGTGAGGAGGCTTTTTTGGAGGCCTAGGCTTTT
GCAAAAAGCTCCCGGGAGCTTGTATATCCATTTTCGGATCTGATCAAGAGACAGGATGAGGATCGTTTCGCATGATT
GAACAAGATGGATTGCACGCAGGTTCTCCGGCCGCTTGGGTGGAGAGGCTATTCGGCTATGACTGGGCACAACAGAC
AATCGGCTGCTCTGATGCCGCCGTGTTCCGGCTGTCAGCGCAGGGGCGCCCGGTTCTTTTTGTCAAGACCGACCTGT
CCGGTGCCCTGAATGAACTGCAGGACGAGGCAGCGCGGCTATCGTGGCTGGCCACGACGGGCGTTCCTTGCGCAGCT
GTGCTCGACGTTGTCACTGAAGCGGGAAGGGACTGGCTGCTATTGGGCGAAGTGCCGGGGCAGGATCTCCTGTCATC
TCACCTTGCTCCTGCCGAGAAAGTATCCATCATGGCTGATGCAATGCGGCGGCTGCATACGCTTGATCCGGCTACCT
GCCCATTCGACCACCAAGCGAAACATCGCATCGAGCGAGCACGTACTCGGATGGAAGCCGGTCTTGTCGATCAGGAT
GATCTGGACGAAGAGCATCAGGGGCTCGCGCCAGCCGAACTGTTCGCCAGGCTCAAGGCGCGCATGCCCGACGGCGA
GGATCTCGTCGTGACCCATGGCGATGCCTGCTTGCCGAATATCATGGTGGAAAATGGCCGCTTTTCTGGATTCATCG
```

-continued

```
ACTGTGGCCGGCTGGGTGTGGCGGACCGCTATCAGGACATAGCGTTGGCTACCCGTGATATTGCTGAAGAGCTTGGC
GGCGAATGGGCTGACCGCTTCCTCGTGCTTTACGGTATCGCCGCTCCCGATTCGCAGCGCATCGCCTTCTATCGCCT
TCTTGACGAGTTCTTCTGAGCGGGACTCTGGGGTTCGAAATGACCGACCAAGCGACGCCCAACCTGCCATCACGAGA
TTTCGATTCCACCGCCGCCTTCTATGAAAGGTTGGGCTTCGGAATCGTTTTCCGGGACGCCGGCTGGATGATCCTCC
AGCGCGGGATCTCATGCTGGAGTTCTTCGCCCACCCCAACTTGTTTATTGCAGCTTATAATGGTTACAAATAAAGC
AATAGCATCACAAATTTCACAAATAAAGCATTTTTTTCACTGCATTCTAGTTGTGGTTTGTCCAAACTCATCAATGT
ATCTTATCATGTCTGTATACCGTCGACCTCTAGCTAGAGCTTGGCGTAATCATGGTCATAGCTGTTTCCTGTGTGAA
ATTGTTATCCGCTCACAATTCCACACAACATACGAGCCGGAAGCATAAAGTGTAAAGCCTGGGGTGCCTAATGAGTG
AGCTAACTCACATTAATTGCGTTGCGCTCACTGCCCGCTTTCCAGTCGGGAAACCTGTCGTGCCAGCTGCATTAATG
AATCGGCCAACGCGCGGGGAGAGGCGGTTTGCGTATTGGGCGCTCTTCCGCTTCCTCGCTCACTGACTCGCTGCGCT
CGGTCGTTCGGCTGCGGCGAGCGGTATCAGCTCACTCAAAGGCGGTAATACGGTTATCCACAGAATCAGGGGATAAC
GCAGGAAAGAACATGTGAGCAAAAGGCCAGCAAAAGGCCAGGAACCGTAAAAAGGCCGCGTTGCTGGCGTTTTTCCA
TAGGCTCCGCCCCCCTGACGAGCATCACAAAAATCGACGCTCAAGTCAGAGGTGGCGAAACCCGACAGGACTATAAA
GATACCAGGCGTTTCCCCCTGGAAGCTCCCTCGTGCGCTCTCCTGTTCCGACCCTGCCGCTTACCGGATACCTGTCC
GCCTTTCTCCCTTCGGGAAGCGTGGCGCTTTCTCATAGCTCACGCTGTAGGTATCTCAGTTCGGTGTAGGTCGTTCG
CTCCAAGCTGGGCTGTGTGCACGAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGATTAGCAGAGCGAGGTATGTAGGC
GGTGCTACAGAGTTCTTGAAGTGGTGGCCTAACTACGGCTACACTAGAAGAACAGTATTTGGTATCTGCGCTCTGCT
GAAGCCAGTTACCTTCGGAAAAAGAGTTGGTAGCTCTTGATCCGGCAAACAAACCACCGCTGGTAGCGGTTTTTTTG
TTTGCAAGCAGCAGATTACGCGCAGAAAAAAAGGATCTCAAGAAGATCCTTTGATCTTTTCTACGGGGTCTGACGCT
CAGTGGAACGAAAACTCACGTTAAGGGATTTTGGTCATGAGATTATCAAAAAGGATCTTCACCTAGATCCTTTTAAA
TTAAAAATGAAGTTTTAAATCAATCTAAAGTATATATGAGTAAACTTGGTCTGACAGTTACCAATGCTTAATCAGTG
AGGCACCTATCTCAGCGATCTGTCTATTTCGTTCATCCATAGTTGCCTGACTCCCCGTCGTGTAGATAACTACGATA
CGGGAGGGCTTACCATCTGGCCCCAGTGCTGCAATGATACCGCGAGACCCACGCTCACCGGCTCCAGATTTATCAGC
AATAAACCAGCCAGCCGGAAGGGCCGAGCGCAGAAGTGGTCCTGCAACTTTATCCGCCTCCATCCAGTCTATTAATT
GTTGCCGGGAAGCTAGAGTAAGTAGTTCGCCAGTTAATAGTTTGCGCAACGTTGTTGCCATTGCTACAGGCATCGTG
GTGTCACGCTCGTCGTTTGGTATGGCTTCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAAGTAAGTTGGCCGCAGTGTTATCACTCA
TGGTTATGGCAGCACTGCATAATTCTCTTACTGTCATGCCATCCGTAAGATGCTTTTCTGTGACTGGTGAGTACTCA
ACCAAGTCATTCTGAGAATAGTGTATGCGGCGACCGAGTTGCTCTTGCCCGGCGTCAATACGGGATAATACCGCGCC
ACATAGCAGAACTTTAAAAGTGCTCATCATTGGAAAACGTTCTTCGGGGCGAAAACTCTCAAGGATCTTACCGCTGT
TGAGATCCAGTTCGATGTAACCCACTCGTGCACCCAACTGATCTTCAGCATCTTTTACTTTCACCAGCGTTTCTGGG
TGAGCAAAAACAGGAAGGCAAAATGCCGCAAAAAAGGGAATAAGGGCGACACGGAAATGTTGAATACTCATACTCTT
CCTTTTTCAATATTATTGAAGCATTTATCAGGGTTATTGTCTCATGAGCGGATACATATTTGAATGTATTTAGAAAA
ATAAACAAATAGGGGTTCCGCGCACATTTCCCCGAAAAGTGCCACCTGACGTC.
```

The plasmid that codes for SEQ ID NO: 4 has an identity (SEQ ID NO: 16)
```
GACGGATCGGGAGATCTCCCGATCCCCTATGGTGCACTCTCAGTACAATCTGCTCTGATGCCGCATAGTTAAGCCAG
TATCTGCTCCCTGCTTGTGTGTTGGAGGTCGCTGAGTAGTGCGCGAGCAAAATTTAAGCTACAACAAGGCAAGGCTT
GACCGACAATTGCATGAAGAATCTGCTTAGGGTTAGGCGTTTTGCGCTGCTTCGCGATGTACGGGCCAGATATACGC
```

-continued

```
GTTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTG
ACGTCAATGGGAGTTTGTTTTGGCACCAAAATCAACGGGACTTTCCAAAATGTCGTAACAACTCCGCCCCATTGACG
CAAATGGGCGGTAGGCGTGTACGGTGGGAGGTCTATATAAGCAGAGCTCTCTGGCTAACTAGAGAACCCACTGCTTA
CTGGCTTATCGAAATTAATACGACTCACTATAGGGAGACCCAAGCTGGCTAGCACCATGGACTACAAAGACCATGAC
GGTGATTATAAAGATCATGACATCGATTACAAGGATGACGATGACAAGCCAAAAAAGAAGCGAAAGGTACCATTCCA
GTGCCGCATTTGTATGCGCAATTTCAGCCAGAGCGGCCACCTGGCCAGCCATATCCGTACCCACACCGGTGAGAAAC
CTTTTGCCTGCGACATCTGCGGCCGCAAGTTCGCCAGAAGCGACCACCTGACCAACCACACCAAAATCCACACTGGA
GGCGGATCTGAGAAGCCCTTCCAGTGCAGAATCTGCATGCGCAACTTTAGCCAGAGCGGCGACCTGACCAGACACAT
TAGAACACACACCGGCGAAAAGCCCTTCGCTTGTGATATCTGTGGTCGTAAATTTGCCAGAAGCGACCACCTGAGCA
GACACCAGCGCACTCATGGATCCCAGCTGGTGAAGAGCGAGCTGGAGGAGAAGAAGTCCGAGCTGCGGCACAAGCTG
AAGTACGTGCCCCACGAGTACATCGAGCTGATCGAGATCGCCAGGAACAGCACCCAGGACCGCATCCTGGAGATGAA
GGTGATGGAGTTCTTCATGAAGGTGTACGGCTACAGGGGAAAGCACCTGGGCGGAAGCAGAAAGCCTGACGGCGCCA
TCTATACAGTGGGCAGCCCCATCGATTACGGCGTGATCGTGGACACAAAGGCCTACAGCGGCGGCTACAATCTGCCT
ATCGGCCAGGCCGACGAGATGCAGAGATACGTGGAGGAGAACCAGACCCGGAATAAGCACATCAACCCCAACGAGTG
GTGGAAGGTGTACCCTAGCAGCGTGACCGAGTTCAAGTTCCTGTTCGTGAGCGGCCACTTCAAGGGCAACTACAAGG
CCCAGCTGACCAGGCTGAACCACATCACCAACTGCAATGGCGCCGTGCTGAGCGTGGAGGAGCTGCTGATCGGCGGC
GAGATGATCAAAGCCGGCACCCTGACACTGGAGGAGGTGCGGCGCAAGTTCAACAACGGCGAGATCAACTTCTGATA
ACTCGAGCGGCCGCCACTGTGCTGGATAAACCGCTGATCAGCCTCGACTGTGCCTTCTAGTTGCCAGCCATCTGTTG
TTTGCCCCTCCCCCGTGCCTTCCTTGACCCTGGAAGGTGCCACTCCCACTGTCCTTTCCTAATAAAATGAGGAAATT
GCATCGCATTGTCTGAGTAGGTGTCATTCTATTCTGGGGGGTGGGGTGGGGCAGGACAGCAAGGGGGAGGATTGGGA
AGACAATAGCAGGCATGCTGGGGATGCGGTGGGCTCTATGGCTTCTGAGGCGGAAAGAACCAGCTGGGGCTCTAGGG
GGTATCCCCACGCGCCCTGTAGCGGCGCATTAAGCGCGGCGGGTGTGGTGGTTACGCGCAGCGTGACCGCTACACTT
GCCAGCGCCCTAGCGCCCGCTCCTTTCGCTTTCTTCCCTTCCTTTCTCGCCACGTTCGCCGGCTTTCCCCGTCAAGC
TCTAAATCGGGGGCTCCCTTTAGGGTTCCGATTTAGTGCTTTACGGCACCTCGACCCCAAAAAACTTGATTAGGGTG
ATGGTTCACGTAGTGGGCCATCGCCCTGATAGACGGTTTTTCGCCCTTTGACGTTGGAGTCCACGTTCTTTAATAGT
GGACTCTTGTTCCAAACTGGAACAACACTCAACCCTATCTCGGTCTATTCTTTTGATTTATAAGGGATTTTGCCGAT
TTCGGCCTATTGGTTAAAAAATGAGCTGATTTAACAAAAATTTAACGCGAATTAATTCTGTGGAATGTGTGTCAGTT
AGGGTGTGGAAAGTCCCCAGGCTCCCCAGCAGGCAGAAGTATGCAAAGCATGCATCTCAATTAGTCAGCAACCAGGT
GTGGAAAGTCCCCAGGCTCCCCAGCAGGCAGAAGTATGCAAAGCATGCATCTCAATTAGTCAGCAACCATAGTCCCG
CCCCTAACTCCGCCCATCCCGCCCCTAACTCCGCCCAGTTCCGCCCATTCTCCGCCCCATGGCTGACTAATTTTTTT
TATTTATGCAGAGGCCGAGGCCGCCTCTGCCTCTGAGCTATTCCAGAAGTAGTGAGGAGGCTTTTTTGGAGGCCTAG
GCTTTTGCAAAAAGCTCCCGGGAGCTTGTATATCCATTTTCGGATCTGATCAAGAGACAGGATGAGGATCGTTTCGC
ATGATTGAACAAGATGGATTGCACGCAGGTTCTCCGGCCGCTTGGGTGGAGAGGCTATTCGGCTATGACTGGGCACA
ACAGACAATCGGCTGCTCTGATGCCGCCGTGTTCCGGCTGTCAGCGCAGGGGCGCCCGGTTCTTTTTGTCAAGACCG
ACCTGTCCGGTGCCCTGAATGAACTGCAGGACGAGGCAGCGCGGCTATCGTGGCTGGCCACGACGGGCGTTCCTTGC
```

-continued

```
GCAGCTGTGCTCGACGTTGTCACTGAAGCGGGAAGGGACTGGCTGCTATTGGGCGAAGTGCCGGGGCAGGATCTCCT
GTCATCTCACCTTGCTCCTGCCGAGAAAGTATCCATCATGGCTGATGCAATGCGGCGGCTGCATACGCTTGATCCGG
CTACCTGCCCATTCGACCACCAAGCGAAACATCGCATCGAGCGAGCACGTACTCGGATGGAAGCCGGTCTTGTCGAT
CAGGATGATCTGGACGAAGAGCATCAGGGGCTCGCGCCAGCCGAACTGTTCGCCAGGCTCAAGGCGCGCATGCCCGA
CGGCGAGGATCTCGTCGTGACCCATGGCGATGCCTGCTTGCCGAATATCATGGTGGAAAATGGCCGCTTTTCTGGAT
TCATCGACTGTGGCCGGCTGGGTGTGGCGGACCGCTATCAGGACATAGCGTTGGCTACCCGTGATATTGCTGAAGAG
CTTGGCGGCGAATGGGCTGACCGCTTCCTCGTGCTTTACGGTATCGCCGCTCCCGATTCGCAGCGCATCGCCTTCTA
TCGCCTTCTTGACGAGTTCTTCTGAGCGGACTCTGGGGTTCGAAATGACCGACCAAGCGACGCCCAACCTGCCATC
ACGAGATTTCGATTCCACCGCCGCCTTCTATGAAAGGTTGGGCTTCGGAATCGTTTTCCGGGACGCCGGCTGGATGA
TCCTCCAGCGCGGGGATCTCATGCTGGAGTTCTTCGCCCACCCCAACTTGTTTATTGCAGCTTATAATGGTTACAAA
TAAAGCAATAGCATCACAAATTTCACAAATAAAGCATTTTTTTCACTGCATTCTAGTTGTGGTTTGTCCAAACTCAT
CAATGTATCTTATCATGTCTGTATACCGTCGACCTCTAGCTAGAGCTTGGCGTAATCATGGTCATAGCTGTTTCCTG
TGTGAAATTGTTATCCGCTCACAATTCCACACAACATACGAGCCGGAAGCATAAAGTGTAAAGCCTGGGGTGCCTAA
TGAGTGAGCTAACTCACATTAATTGCGTTGCGCTCACTGCCCGCTTTCCAGTCGGGAAACCTGTCGTGCCAGCTGCA
TTAATGAATCGGCCAACGCGCGGGGAGAGGCGGTTTGCGTATTGGGCGCTCTTCCGCTTCCTCGCTCACTGACTCGC
TGCGCTCGGTCGTTCGGCTGCGGCGAGCGGTATCAGCTCACTCAAAGGCGGTAATACGGTTATCCACAGAATCAGGG
GATAACGCAGGAAAGAACATGTGAGCAAAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACCGCTGCGCCTTATCCGGTAACTATCGTC
TTGAGTCCAACCCGGTAAGACACGACTTATCGCCACTGGCAGCAGCCACTGGTAACAGGATTAGCAGAGCGAGGTAT
GTAGGCGGTGCTACAGAGTTCTTGAAGTGGTGGCCTAACTACGGCTACACTAGAAGAACAGTATTTGGTATCTGCGC
TCTGCTGAAGCCAGTTACCTTCGGAAAAAGAGTTGGTAGCTCTTGATCCGGCAAACAAACCACCGCTGGTAGCGGTT
TTTTTGTTTGCAAGCAGCAGATTACGCGCAGAAAAAAAGGATCTCAAGAAGATCCTTTGATCTTTTCTACGGGGTCT
GACGCTCAGTGGAACGAAAACTCACGTTAAGGGATTTTGGTCATGAGATTATCAAAAAGGATCTTCACCTAGATCCT
TTTAAATTAAAAATGAAGTTTTAAATCAATCTAAAGTATATATGAGTAAACTTGGTCTGACAGTTACCAATGCTTAA
TCAGTGAGGCACCTATCTCAGCGATCTGTCTATTTCGTTCATCCATAGTTGCCTGACTCCCCGTCGTGTAGATAACT
ACGATACGGGAGGGCTTACCATCTGGCCCCAGTGCTGCAATGATACCGCGAGACCCACGCTCACCGGCTCCAGATTT
ATCAGCAATAAACCAGCCAGCCGGAAGGGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTCCCAACGATCAAGGCGAGTTACATGATC
CCCCATGTTGTGCAAAAAAGCGGTTAGCTCCTTCGGTCCTCCGATCGTTGTCAGAAGTAAGTTGGCCGCAGTGTTAT
CACTCATGGTTATGGCAGCACTGCATAATTCTCTTACTGTCATGCCATCCGTAAGATGCTTTTCTGTGACTGGTGAG
TACTCAACCAAGTCATTCTGAGAATAGTGTATGCGGCGACCGAGTTGCTCTTGCCCGGCGTCAATACGGGATAATAC
CGCGCCACATAGCAGAACTTTAAAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGCATCTTTTACTTTCACCAGCGTT
TCTGGGTGAGCAAAAACAGGAAGGCAAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCGGATACATATTTGAATGTATTT
AGAAAAATAAACAAATAGGGGTTCCGCGCACATTTCCCCGAAAAGTGCCACCTGACGTC.
```

The plasmid that codes for SEQ ID NO: 5 has an identity (SEQ ID NO: 17)
```
GTTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTG
ACGTCAATGGGAGTTTGTTTTGGCACCAAAATCAACGGGACTTTCCAAAATGTCGTAACAACTCCGCCCCATTGACG
CAAATGGGCGGTAGGCGTGTACGGTGGGAGGTCTATATAAGCAGAGCTCTCTGGCTAACTAGAGAACCCACTGCTTA
CTGGCTTATCGAAATTAATACGACTCACTATAGGGAGACCCAAGCTGGCTAGCGCCACCATGGACTACAAAGACCAT
GACGGTGATTATAAAGATCATGACATCGATTACAAGGATGACGATGACAAGATGGCCCCAAGAAGAAGAGGAAGGT
GGGCATTCACCGCGGGGTACCTATGGTGGACTTGAGGACACTCGGTTATTCGCAACAGCAACAGGAGAAAATCAAGC
CTAAGGTCAGGAGCACCGTCGCGCAACACCACGAGGCGCTTGTGGGCATGGCTTCACTCATGCGCATATTGTCGCG
CTTTCACAGCACCCTGCGGCGCTTGGGACGGTGGCTGTCAAATACCAAGATATGATTGCGGCCCTGCCCGAAGCCAC
GCACGAGGCAATTGTAGGGGTCGGTAAACAGTGGTCGGGAGCGCGAGCACTTGAGGCGCTGCTGACTGTGGCGGGTG
AGCTTAGGGGGCCTCCGCTCCAGCTCGACACCGGGCAGCTGCTGAAGATCGCGAAGAGAGGGGGAGTAACAGCGGTA
GAGGCAGTGCACGCCTGGCGCAATGCGCTCACCGGTGCCCCCCTGAACCTGACCCCGGACCAAGTGGTGGCTATCGC
CAGCAACAAGGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAAGGGCGGCAAGCAAGCGCTCGAAACGGTGCAGCGGCTGTTGCCG
GTGCTGTGCCAGGACCATGGCCTGACCCCGGACCAAGTGGTGGCTATCGCCAGCAACGGTGGCGGCAAGCAAGCGCT
CGAAACGGTGCAGCGGCTGTTGCCGGTGCTGTGCCAGGACCATGGCCTGACCCCGGACCAAGTGGTGGCTATCGCCA
GCAACAAGGGCGGCAAGCAAGCGCTCGAAACGGTGCAGCGGCTGTTGCCGGTGCTGTGCCAGGACCATGGCCTGACT
CCGGACCAAGTGGTGGCTATCGCCAGCCACGATGGCGGCAAGCAAGCGCTCGAAACGGTGCAGCGGCTGTTGCCGGT
GCTGTGCCAGGACCATGGCCTGACCCCGGACCAAGTGGTGGCTATCGCCAGCAACATTGGCGGCAAGCAAGCGCTCG
AAACGGTGCAGCGGCTGTTGCCGGTGCTGTGCCAGGACCATGGCCTGACTCCGGACCAAGTGGTGGCTATCGCCAGC
CACGATGGCGGCAAGCAAGCGCTCGAAACGGTGCAGCGGCTGTTGCCGGTGCTGTGCCAGGACCATGGCCTGACTCC
GGACCAAGTGGTGGCTATCGCCAGCCACGATGGCGGCAAGCAAGCGCTCGAAACGGTGCAGCGGCTGTTGCCGGTGC
TGTGCCAGGACCATGGCCTGACCCCGGACCAAGTGGTGGCTATCGCCAGCAACGGTGGCGGCAAGCAAGCGCTCGAA
ACGGTGCAGCGGCTGTTGCCGGTGCTGTGCCAGGACCATGGCCTGACCCCGGACCAAGTGGTGGCTATCGCCAGCAA
CAAGGGCGGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCCGGTGCTG
TGCCAGGACCATGGCCTGACTCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCCAGCAACG
GTGGCGGCAAGCAAGCGCTCGAAACGGTGCAGCGGCTGTTGCCGGTGCTGTGCCAGGACCATGGCCTGACTCCGGAC
CAAGTGGTGGCTATCGCCAGCCACGATGGCGGCAAGCAAGCGCTCGAAACGGTGCAGCGGCTGTTGCCGGTGCTGTG
CCAGGACCATGGCCTGACTCCGGACCAAGTGGTGGCTATCGCCAGCCACGATGGCGGCAAGCAAGCGCTCGAAACGG
TGCAGCGGCTGTTGCCGGTGCTGTGCCAGGACCATGGCCTGACCCCGGACCAAGTGGTGGCTATCGCCAGCAACGGT
GGCGGCAAGCAAGCGCTCGAAAGCATTGTGGCCCAGCTGAGCCGGCCTGATCCGGCGTTGGCCGCGTTGACCAACGA
CCATCTGGTGGCGTTGGCATGTCTTGGTGGACGACCCGCGCTCGATGCAGTCAAAAAGGGTCTGCCTCATGCTCCCG
CATTGATCAAAAGAACCAACCGGCGGATTCCCGAGAGAACTTCCCATCGAGTCGCGGGATCCCAGCTGGTGAAGAGC
```

-continued

```
GAGCTGGAGGAGAAGAAGTCCGAGCTGCGGCACAAGCTGAAGTACGTGCCCCACGAGTACATCGAGCTGATCGAGAT
CGCCAGGAACAGCACCCAGGACCGCATCCTGGAGATGAAGGTGATGGAGTTCTTCATGAAGGTGTACGGCTACAGGG
GAAAGCACCTGGGCGGAAGCAGAAAGCCTGACGGCGCCATCTATACAGTGGGCAGCCCCATCGATTACGGCGTGATC
GTGGACACAAAGGCCTACAGCGGCGGCTACAATCTGCCTATCGGCCAGGCCGACGAGATGCAGAGATACGTGGAGGA
GAACCAGACCCGGAATAAGCACATCAACCCCAACGAGTGGTGGAAGGTGTACCCTAGCAGCGTGACCGAGTTCAAGT
TCCTGTTCGTGAGCGGCCACTTCAAGGGCAACTACAAGGCCCAGCTGACCAGGCTGAACCACATCACCAACTGCAAT
GGCGCCGTGCTGAGCGTGGAGGAGCTGCTGATCGGCGGCGAGATGATCAAAGCCGGCACCCTGACACTGGAGGAGGT
GCGGCGCAAGTTCAACAACGGCGAGATCAACTTCTGATAACTTAAGTTTAAACCGCTGATCAGCCTCGACTGTGCCT
TCTAGTTGCCAGCCATCTGTTGTTTGCCCCTCCCCCGTGCCTTCCTTGACCCTGGAAGGTGCCACTCCCACTGTCCT
TTCCTAATAAAATGAGGAAATTGCATCGCATTGTCTGAGTAGGTGTCATTCTATTCTGGGGGGTGGGGTGGGGCAGG
ACAGCAAGGGGGAGGATTGGGAAGACAATAGCAGGCATGCTGGGGATGCGGTGGGCTCTATGGCTTCTGAGGCGGAA
AGAACCAGCTGGGGCTCTAGGGGGTATCCCCACGCGCCCTGTAGCGGCGCATTAAGCGCGGCGGGTGTGGTGGTTAC
GCGCAGCGTGACCGCTACACTTGCCAGCGCCCTAGCGCCCGCTCCTTTCGCTTTCTTCCCTTCCTTTCTCGCCACGT
TCGCCGGCTTTCCCCGTCAAGCTCTAAATCGGGGGCTCCCTTTAGGGTTCCGATTTAGTGCTTTACGGCACCTCGAC
CCCAAAAAACTTGATTAGGGTGATGGTTCACGTAGTGGGCCATCGCCCTGATAGACGGTTTTTCGCCCTTTGACGTT
GGAGTCCACGTTCTTTAATAGTGGACTCTTGTTCCAAACTGGAACAACACTCAACCCTATCTCGGTCTATTCTTTTG
ATTTATAAGGGATTTTGCCGATTTCGGCCTATTGGTTAAAAAATGAGCTGATTTAACAAAAATTTAACGCGAATTAA
TTCTGTGGAATGTGTGTCAGTTAGGGTGTGGAAAGTCCCCAGGCTCCCCAGCAGGCAGAAGTATGCAAAGCATGCAT
CTCAATTAGTCAGCAACCAGGTGTGGAAAGTCCCCAGGCTCCCCAGCAGGCAGAAGTATGCAAAGCATGCATCTCAA
TTAGTCAGCAACCATAGTCCCGCCCCTAACTCCGCCCATCCCGCCCCTAACTCCGCCCAGTTCCGCCCATTCTCCGC
CCCATGGCTGACTAATTTTTTTTATTTATGCAGAGGCCGAGGCCGCCTCTGCCTCTGAGCTATTCCAGAAGTAGTGA
GGAGGCTTTTTTGGAGGCCTAGGCTTTTGCAAAAAGCTCCCGGGAGCTTGTATATCCATTTTCGGATCTGATCAAGA
GACAGGATGAGGATCGTTTCGCATGATTGAACAAGATGGATTGCACGCAGGTTCTCCGGCCGCTTGGGTGGAGAGGC
TATTCGGCTATGACTGGGCACAACAGACAATCGGCTGCTCTGATGCCGCCGTGTTCCGGCTGTCAGCGCAGGGGCGC
CCGGTTCTTTTTGTCAAGACCGACCTGTCCGGTGCCCTGAATGAACTGCAGGACGAGGCAGCGCGGCTATCGTGGCT
GGCCACGACGGGCGTTCCTTGCGCAGCTGTGCTCGACGTTGTCACTGAAGCGGGAAGGGACTGGCTGCTATTGGGCG
AAGTGCCGGGGCAGGATCTCCTGTCATCTCACCTTGCTCCTGCCGAGAAAGTATCCATCATGGCTGATGCAATGCGG
CGGCTGCATACGCTTGATCCGGCTACCTGCCCATTCGACCACCAAGCGAAACATCGCATCGAGCGAGCACGTACTCG
GATGGAAGCCGGTCTTGTCGATCAGGATGATCTGGACGAAGAGCATCAGGGGCTCGCGCCAGCCGAACTGTTCGCCA
GGCTCAAGGCGCGCATGCCCGACGGCGAGGATCTCGTCGTGACCCATGGCGATGCCTGCTTGCCGAATATCATGGTG
GAAAATGGCCGCTTTTCTGGATTCATCGACTGTGGCCGGCTGGGTGTGGCGGACCGCTATCAGGACATAGCGTTGGC
TACCCGTGATATTGCTGAAGAGCTTGGCGGCGAATGGGCTGACCGCTTCCTCGTGCTTTACGGTATCGCCGCTCCCG
ATTCGCAGCGCATCGCCTTCTATCGCCTTCTTGACGAGTTCTTCTGAGCGGGACTCTGGGGTTCGAAATGACCGACC
AAGCGACGCCCAACCTGCCATCACGAGATTTCGATTCCACCGCCGCCTTCTATGAAAGGTTGGGCTTCGGAATCGTT
TTCCGGGACGCCGGCTGGATGATCCTCCAGCGCGGGGATCTCATGCTGGAGTTCTTCGCCCACCCCAACTTGTTTAT
TGCAGCTTATAATGGTTACAAATAAAGCAATAGCATCACAAATTTCACAAATAAAGCATTTTTTTCACTGCATTCTA
GTTGTGGTTTGTCCAAACTCATCAATGTATCTTATCATGTCTGTATACCGTCGACCTCTAGCTAGAGCTTGGCGTAA
TCATGGTCATAGCTGTTTCCTGTGTGAAATTGTTATCCGCTCACAATTCCACACAACATACGAGCCGGAAGCATAAA
GTGTAAAGCCTGGGGTGCCTAATGAGTGAGCTAACTCACATTAATTGCGTTGCGCTCACTGCCCGCTTTCCAGTCGG
GAAACCTGTCGTGCCAGCTGCATTAATGAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGCGGTATCAGCTCACTCAAAGGCGGTAAT
```

-continued

```
ACGGTTATCCACAGAATCAGGGGATAACGCAGGAAAGAACATGTGAGCAAAAGGCCAGCAAAAGGCCAGGAACCGTA

AAAAGGCCGCGTTGCTGGCGTTTTTCCATAGGCTCCGCCCCCCTGACGAGCATCACAAAAATCGACGCTCAAGTCAG

AGGTGGCGAAACCCGACAGGACTATAAAGATACCAGGCGTTTCCCCCTGGAAGCTCCCTCGTGCGCTCTCCTGTTCC

GACCCTGCCGCTTACCGGATACCTGTCCGCCTTTCTCCCTTCGGGAAGCGTGGCGCTTTCTCATAGCTCACGCTGTA

GGTATCTCAGTTCGGTGTAGGTCGTTCGCTCCAAGCTGGGCTGTGTGCACGAACCCCCCGTTCAGCCCGACCGCTGC

GCCTTATCCGGTAACTATCGTCTTGAGTCCAACCCGGTAAGACACGACTTATCGCCACTGGCAGCAGCCACTGGTAA

CAGGATTAGCAGAGCGAGGTATGTAGGCGGTGCTACAGAGTTCTTGAAGTGGTGGCCTAACTACGGCTACACTAGAA

GAACAGTATTTGGTATCTGCGCTCTGCTGAAGCCAGTTACCTTCGGAAAAAGAGTTGGTAGCTCTTGATCCGGCAAA

CAAACCACCGCTGGTAGCGGTTTTTTTGTTTGCAAGCAGCAGATTACGCGCAGAAAAAAAGGATCTCAAGAAGATCC

TTTGATCTTTTCTACGGGGTCTGACGCTCAGTGGAACGAAAACTCACGTTAAGGGATTTTGGTCATGAGATTATCAA

AAAGGATCTTCACCTAGATCCTTTTAAATTAAAAATGAAGTTTTAAATCAATCTAAAGTATATATGAGTAAACTTGG

TCTGACAGTTACCAATGCTTAATCAGTGAGGCACCTATCTCAGCGATCTGTCTATTTCGTTCATCCATAGTTGCCTG

ACTCCCCGTCGTGTAGATAACTACGATACGGGAGGGCTTACCATCTGGCCCCAGTGCTGCAATGATACCGCGAGACC

CACGCTCACCGGCTCCAGATTTATCAGCAATAAACCAGCCAGCCGGAAGGGCCGAGCGCAGAAGTGGTCCTGCAACT

TTATCCGCCTCCATCCAGTCTATTAATTGTTGCCGGGAAGCTAGAGTAAGTAGTTCGCCAGTTAATAGTTTGCGCAA

CGTTGTTGCCATTGCTACAGGCATCGTGGTGTCACGCTCGTCGTTTGGTATGGCTTCATTCAGCTCCGGTTCCCAAC

GATCAAGGCGAGTTACATGATCCCCCATGTTGTGCAAAAAAGCGGTTAGCTCCTTCGGTCCTCCGATCGTTGTCAGA

AGTAAGTTGGCCGCAGTGTTATCACTCATGGTTATGGCAGCACTGCATAATTCTCTTACTGTCATGCCATCCGTAAG

ATGCTTTTCTGTGACTGGTGAGTACTCAACCAAGTCATTCTGAGAATAGTGTATGCGGCGACCGAGTTGCTCTTGCC

CGGCGTCAATACGGGATAATACCGCGCCACATAGCAGAACTTTAAAAGTGCTCATCATTGGAAAACGTTCTTCGGGG

CGAAAACTCTCAAGGATCTTACCGCTGTTGAGATCCAGTTCGATGTAACCCACTCGTGCACCCAACTGATCTTCAGC

ATCTTTTACTTTCACCAGCGTTTCTGGGTGAGCAAAAACAGGAAGGCAAAATGCCGCAAAAAAGGGAATAAGGGCGA

CACGGAAATGTTGAATACTCATACTCTTCCTTTTTCAATATTATTGAAGCATTTATCAGGGTTATTGTCTCATGAGC

GGATACATATTTGAATGTATTTAGAAAAATAAACAAATAGGGGTTCCGCGCACATTTCCCCGAAAAGTGCCACCTGA

CGTCGACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGGCAAG

GCTTGACCGACAATTGCATGAAGAATCTGCTTAGGGTTAGGCGTTTTGCGCTGCTTCGCGATGTACGGGCCAGATAT

ACGC.
```

The plasmid that codes for SEQ ID NO: 6 has an identity (SEQ ID NO: 18)
```
GTTGACATTGATTATTGACTAGTTATTAATAGTAATCAATTACGGGGTCATTAGTTCATAGCCCATATATGGAGTTC

CGCGTTACATAACTTACGGTAAATGGCCCGCCTGGCTGACCGCCCAACGACCCCCGCCCATTGACGTCAATAATGAC

GTATGTTCCCATAGTAACGCCAATAGGGACTTTCCATTGACGTCAATGGGTGGAGTATTTACGGTAAACTGCCCACT

TGGCAGTACATCAAGTGTATCATATGCCAAGTACGCCCCCTATTGACGTCAATGACGGTAAATGGCCCGCCTGGCAT

TATGCCCAGTACATGACCTTATGGGACTTTCCTACTTGGCAGTACATCTACGTATTAGTCATCGCTATTACCATGGT

GATGCGGTTTTGGCAGTACATCAATGGGCGTGGATAGCGGTTTGACTCACGGGGATTTCCAAGTCTCCACCCCATTG

ACGTCAATGGGAGTTTGTTTTGGCACCAAAATCAACGGGACTTTCCAAAATGTCGTAACAACTCCGCCCCATTGACG

CAAATGGGCGGTAGGCGTGTACGGTGGGAGGTCTATATAAGCAGAGCTCTCTGGCTAACTAGAGAACCCACTGCTTA

CTGGCTTATCGAAATTAATACGACTCACTATAGGGAGACCCAAGCTGGCTAGCGCCACCATGGACTACAAAGACCAT

GACGGTGATTATAAAGATCATGACATCGATTACAAGGATGACGATGACAAGATGGCCCCCAAGAAGAAGAGGAAGGT
```

-continued

```
GGGCATTCACCGCGGGGTACCTATGGTGGACTTGAGGACACTCGGTTATTCGCAACAGCAACAGGAGAAAATCAAGC
CTAAGGTCAGGAGCACCGTCGCGCAACACCACGAGGCGCTTGTGGGCATGGCTTCACTCATGCGCATATTGTCGCG
CTTTCACAGCACCCTGCGGCGCTTGGGACGGTGGCTGTCAAATACCAAGATATGATTGCGGCCCTGCCCGAAGCCAC
GCACGAGGCAATTGTAGGGGTCGGTAAACAGTGGTCGGGAGCGCGAGCACTTGAGGCGCTGCTGACTGTGGCGGGTG
AGCTTAGGGGGCCTCCGCTCCAGCTCGACACCGGGCAGCTGCTGAAGATCGCGAAGAGAGGGGGAGTAACAGCGGTA
GAGGCAGTGCACGCCTGGCGCAATGCGCTCACCGGTGCCCCCCTGAACCTGACCCCGGACCAAGTGGTGGCTATCGC
CAGCAACAAGGGCGGCAAGCAAGCGCTCGAAACGGTGCAGCGGCTGTTGCCGGTGCTGTGCCAGGACCATGGCCTGA
CTCCGGACCAAGTGGTGGCTATCGCCAGCCACGATGGCGGCAAGCAAGCGCTCGAAACGGTGCAGCGGCTGTTGCCG
GTGCTGTGCCAGGACCATGGCCTGACCCCGGACCAAGTGGTGGCTATCGCCAGCAACATTGGCGGCAAGCAAGCGCT
CGAAACGGTGCAGCGGCTGTTGCCGGTGCTGTGCCAGGACCATGGCCTGACTCCGGACCAAGTGGTGGCTATCGCCA
GCCACGATGGCGGCAAGCAAGCGCTCGAAACGGTGCAGCGGCTGTTGCCGGTGCTGTGCCAGGACCATGGCCTGACT
CCGGACCAAGTGGTGGCTATCGCCAGCCACGATGGCGGCAAGCAAGCGCTCGAAACGGTGCAGCGGCTGTTGCCGGT
GCTGTGCCAGGACCATGGCCTGACCCCGGACCAAGTGGTGGCTATCGCCAGCAACGGTGGCGGCAAGCAAGCGCTCG
AAACGGTGCAGCGGCTGTTGCCGGTGCTGTGCCAGGACCATGGCCTGACCCCGGACCAAGTGGTGGCTATCGCCAGC
AACAAGGGCGGCAAGCAAGCGCTCGAAACGGTGCAGCGGCTGTTGCCGGTGCTGTGCCAGGACCATGGCCTGACCCC
GGACCAAGTGGTGGCTATCGCCAGCAACATTGGCGGCAAGCAAGCGCTCGAAACGGTGCAGCGGCTGTTGCCGGTGC
TGTGCCAGGACCATGGCCTGACTCCGGACCAAGTGGTGGCTATCGCCAGCCACGATGGCGGCAAGCAAGCGCTCGAA
ACGGTGCAGCGGCTGTTGCCGGTGCTGTGCCAGGACCATGGCCTGACCCCGGACCAAGTGGTGGCTATCGCCAGCAA
CGGTGGCGGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCCGGTGCTG
TGCCAGGACCATGGCCTGACTCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCCAGCAACG
GTGGCGGCAAGCAAGCGCTCGAAACGGTGCAGCGGCTGTTGCCGGTGCTGTGCCAGGACCATGGCCTGACCCCGGAC
CAAGTGGTGGCTATCGCCAGCAACAAGGGCGGCAAGCAAGCGCTCGAAACGGTGCAGCGGCTGTTGCCGGTGCTGTG
CCAGGACCATGGCCTGACCCCGGACCAAGTGGTGGCTATCGCCAGCAACGGTGGCGGCAAGCAAGCGCTCGAAAGCA
TTGTGGCCCAGCTGAGCCGGCCTGATCCGGCGTTGGCCGCGTTGACCAACGACCATCTGGTGGCGTTGGCATGTCTT
GGTGGACGACCCGCGCTCGATGCAGTCAAAAAGGGTCTGCCTCATGCTCCCGCATTGATCAAAAGAACCAACCGGCG
GATTCCCGAGAGAACTTCCCATCGAGTCGCGGGATCCCAGCTGGTGAAGAGCGAGCTGGAGGAGAAGAAGTCCGAGC
TGCGGCACAAGCTGAAGTACGTGCCCCACGAGTACATCGAGCTGATCGAGATCGCCAGGAACAGCACCCAGGACCGC
ATCCTGGAGATGAAGGTGATGGAGTTCTTCATGAAGGTGTACGGCTACAGGGGAAAGCACCTGGGCGGAAGCAGAAA
GCCTGACGGCGCCATCTATACAGTGGGCAGCCCCATCGATTACGGCGTGATCGTGGACACAAAGGCCTACAGCGGCG
GCTACAATCTGCCTATCGGCCAGGCCGACGAGATGCAGAGATACGTGGAGGAGAACCAGACCCGGAATAAGCACATC
AACCCCAACGAGTGGTGGAAGGTGTACCCTAGCAGCGTGACCGAGTTCAAGTTCCTGTTCGTGAGCGGCCACTTCAA
GGGCAACTACAAGGCCCAGCTGACCAGGCTGAACCACATCACCAACTGCAATGGCGCCGTGCTGAGCGTGGAGGAGC
TGCTGATCGGCGGCGAGATGATCAAAGCCGGCACCCTGACACTGGAGGAGGTGCGGCGCAAGTTCAACAACGGCGAG
ATCAACTTCTGATAACTTAAGTTTAAACCGCTGATCAGCCTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATAAAATGAGGAAATTGCA
TCGCATTGTCTGAGTAGGTGTCATTCTATTCTGGGGGGTGGGTGGGCAGGACAGCAAGGGGGAGGATTGGGAAGA
CAATAGCAGGCATGCTGGGGATGCGGTGGGCTCTATGGCTTCTGAGGCGGAAAGAACCAGCTGGGGCTCTAGGGGGT
ATCCCCACGCGCCCTGTAGCGGCGCATTAAGCGCGGCGGGTGTGGTGGTTACGCGCAGCGTGACCGCTACACTTGCC
```

-continued

```
AGCGCCCTAGCGCCCGCTCCTTTCGCTTTCTTCCCTTCCTTTCTCGCCACGTTCGCCGGCTTTCCCCGTCAAGCTCT
AAATCGGGGGCTCCCTTTAGGGTTCCGATTTAGTGCTTTACGGCACCTCGACCCCAAAAAACTTGATTAGGGTGATG
GTTCACGTAGTGGGCCATCGCCCTGATAGACGGTTTTTCGCCCTTTGACGTTGGAGTCCACGTTCTTTAATAGTGGA
CTCTTGTTCCAAACTGGAACAACACTCAACCCTATCTCGGTCTATTCTTTTGATTTATAAGGGATTTTGCCGATTTC
GGCCTATTGGTTAAAAAATGAGCTGATTTAACAAAAATTTAACGCGAATTAATTCTGTGGAATGTGTGTCAGTTAGG
GTGTGGAAAGTCCCCAGGCTCCCCAGCAGGCAGAAGTATGCAAAGCATGCATCTCAATTAGTCAGCAACCAGGTGTG
GAAAGTCCCCAGGCTCCCCAGCAGGCAGAAGTATGCAAAGCATGCATCTCAATTAGTCAGCAACCATAGTCCCGCCC
CTAACTCCGCCCATCCCGCCCCTAACTCCGCCCAGTTCCGCCCATTCTCCGCCCCATGGCTGACTAATTTTTTTTAT
TTATGCAGAGGCCGAGGCCGCCTCTGCCTCTGAGCTATTCCAGAAGTAGTGAGGAGGCTTTTTTGGAGGCCTAGGCT
TTTGCAAAAAGCTCCCGGGAGCTTGTATATCCATTTTCGGATCTGATCAAGAGACAGGATGAGGATCGTTTCGCATG
ATTGAACAAGATGGATTGCACGCAGGTTCTCCGGCCGCTTGGGTGGAGAGGCTATTCGGCTATGACTGGGCACAACA
GACAATCGGCTGCTCTGATGCCGCCGTGTTCCGGCTGTCAGCGCAGGGGCGCCCGGTTCTTTTTGTCAAGACCGACC
TGTCCGGTGCCCTGAATGAACTGCAGGACGAGGCAGCGCGGCTATCGTGGCTGGCCACGACGGGCGTTCCTTGCGCA
GCTGTGCTCGACGTTGTCACTGAAGCGGGAAGGGACTGGCTGCTATTGGGCGAAGTGCCGGGGCAGGATCTCCTGTC
ATCTCACCTTGCTCCTGCCGAGAAAGTATCCATCATGGCTGATGCAATGCGGCGGCTGCATACGCTTGATCCGGCTA
CCTGCCCATTCGACCACCAAGCGAAACATCGCATCGAGCGAGCACGTACTCGGATGGAAGCCGGTCTTGTCGATCAG
GATGATCTGGACGAAGAGCATCAGGGGCTCGCGCCAGCCGAACTGTTCGCCAGGCTCAAGGCGCGCATGCCCGACGG
CGAGGATCTCGTCGTGACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGATATTGCTGAAGAGCTT
GGCGGCGAATGGGCTGACCGCTTCCTCGTGCTTTACGGTATCGCCGCTCCCGATTCGCAGCGCATCGCCTTCTATCG
CCTTCTTGACGAGTTCTTCTGAGCGGGACTCTGGGGTTCGAAATGACCGACCAAGCGACGCCCAACCTGCCATCACG
AGATTTCGATTCCACCGCCGCCTTCTATGAAAGGTTGGGCTTCGGAATCGTTTTCCGGGACGCCGGCTGGATGATCC
TCCAGCGCGGGGATCTCATGCTGGAGTTCTTCGCCCACCCCAACTTGTTTATTGCAGCTTATAATGGTTACAAATAA
AGCAATAGCATCACAAATTTCACAAATAAAGCATTTTTTTCACTGCATTCTAGTTGTGGTTTGTCCAAACTCATCAA
TGTATCTTATCATGTCTGTATACCGTCGACCTCTAGCTAGAGCTTGGCGTAATCATGGTCATAGCTGTTTCCTGTGT
GAAATTGTTATCCGCTCACAATTCCACACAACATACGAGCCGGAAGCATAAAGTGTAAAGCCTGGGGTGCCTAATGA
GTGAGCTAACTCACATTAATTGCGTTGCGCTCACTGCCCGCTTTCCAGTCGGGAAACCTGTCGTGCCAGCTGCATTA
ATGAATCGGCCAACGCGCGGGGAGAGGCGGTTTGCGTATTGGGCGCTCTTCCGCTTCCTCGCTCACTGACTCGCTGC
GCTCGGTCGTTCGGCTGCGGCGAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGCGTTGCTGGCGTTTTT
CCATAGGCTCCGCCCCCCTGACGAGCATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCATAGCTCACGCTGTAGGTATCTCAGTTCGGTGTAGGTCGT
TCGCTCCAAGCTGGGCTGTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGAACAGTATTTGGTATCTGCGCTCT
GCTGAAGCCAGTTACCTTCGGAAAAAGAGTTGGTAGCTCTTGATCCGGCAAACAAACCACCGCTGGTAGCGGTTTTT
TTGTTTGCAAGCAGCAGATTACGCGCAGAAAAAAAGGATCTCAAGAAGATCCTTTGATCTTTTCTACGGGGTCTGAC
GCTCAGTGGAACGAAAACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTTACCAATGCTTAATCA
GTGAGGCACCTATCTCAGCGATCTGTCTATTTCGTTCATCCATAGTTGCCTGACTCCCCGTCGTGTAGATAACTACG
```

-continued

```
ATACGGGAGGGCTTACCATCTGGCCCCAGTGCTGCAATGATACCGCGAGACCCACGCTCACCGGCTCCAGATTTATC
AGCAATAAACCAGCCAGCCGGAAGGGCCGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCAGAAGTAAGTTGGCCGCAGTGTTATCAC
TCATGGTTATGGCAGCACTGCATAATTCTCTTACTGTCATGCCATCCGTAAGATGCTTTTCTGTGACTGGTGAGTAC
TCAACCAAGTCATTCTGAGAATAGTGTATGCGGCGACCGAGTTGCTCTTGCCCGGCGTCAATACGGGATAATACCGC
GCCACATAGCAGAACTTTAAAAGTGCTCATCATTGGAAAACGTTCTTCGGGGCGAAAACTCTCAAGGATCTTACCGC
TGTTGAGATCCAGTTCGATGTAACCCACTCGTGCACCCAACTGATCTTCAGCATCTTTTACTTTCACCAGCGTTTCT
GGGTGAGCAAAAACAGGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATACATATTTGAATGTATTTAGA
AAAATAAACAAATAGGGGTTCCGCGCACATTTCCCCGAAAAGTGCCACCTGACGTCGACGGATCGGGAGATCTCCCG
ATCCCCTATGGTGCACTCTCAGTACAATCTGCTCTGATGCCGCATAGTTAAGCCAGTATCTGCTCCCTGCTTGTGTG
TTGGAGGTCGCTGAGTAGTGCGCGAGCAAAATTTAAGCTACAACAAGGCAAGGCTTGACCGACAATTGCATGAAGAA
TCTGCTTAGGGTTAGGCGTTTTGCGCTGCTTCGCGATGTACGGGCCAGATATACGC.
```

The plasmid that codes for SEQ ID NO: 7 has an identity (SEQ ID NO: 19)
```
GTTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTG
ACGTCAATGGGAGTTTGTTTTGGCACCAAAATCAACGGGACTTTCCAAAATGTCGTAACAACTCCGCCCCATTGACG
CAAATGGGCGGTAGGCGTGTACGGTGGGAGGTCTATATAAGCAGAGCTCTCTGGCTAACTAGAGAACCCACTGCTTA
CTGGCTTATCGAAATTAATACGACTCACTATAGGGAGACCCAAGCTGGCTAGCGCCACCATGGACTACAAAGACCAT
GACGGTGATTATAAAGATCATGACATCGATTACAAGGATGACGATGACAAGATGGCCCCCAAGAAGAAGAGGAAGGT
GGGCATTCACCGCGGGGTACCTATGGTGGACTTGAGGACACTCGGTTATTCGCAACAGCAACAGGAGAAAATCAAGC
CTAAGGTCAGGAGCACCGTCGCGCAACACCACGAGGCGCTTGTGGGGCATGGCTTCACTCATGCGCATATTGTCGCG
CTTTCACAGCACCCTGCGGCGCTTGGGACGGTGGCTGTCAAATACCAAGATATGATTGCGGCCCTGCCCGAAGCCAC
GCACGAGGCAATTGTAGGGGTCGGTAAACAGTGGTCGGGAGCGCGAGCACTTGAGGCGCTGCTGACTGTGGCGGGTG
AGCTTAGGGGGCCTCCGCTCCAGCTCGACACCGGGCAGCTGCTGAAGATCGCGAAGAGAGGGGGAGTAACAGCGGTA
GAGGCAGTGCACGCCTGGCGCAATGCGCTCACCGGTGCCCCCCTGAACCTGACCCCGGACCAAGTGGTGGCTATCGC
CAGCAACAATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACAATGGCGGCAAGCAAGCGCTCGAAACGGTGCAGCGGCTGTTGCCG
GTGCTGTGCCAGGACCATGGCCTGACCCCGGACCAAGTGGTGGCTATCGCCAGCAACGGTGGCGGCAAGCAAGCGCT
CGAAACGGTGCAGCGGCTGTTGCCGGTGCTGTGCCAGGACCATGGCCTGACCCCGGACCAAGTGGTGGCTATCGCCA
GCAACAATGGCGGCAAGCAAGCGCTCGAAACGGTGCAGCGGCTGTTGCCGGTGCTGTGCCAGGACCATGGCCTGACT
CCGGACCAAGTGGTGGCTATCGCCAGCCACGATGGCGGCAAGCAAGCGCTCGAAACGGTGCAGCGGCTGTTGCCGGT
GCTGTGCCAGGACCATGGCCTGACCCCGGACCAAGTGGTGGCTATCGCCAGCAACATTGGCGGCAAGCAAGCGCTCG
```

```
AAACGGTGCAGCGGCTGTTGCCGGTGCTGTGCCAGGACCATGGCCTGACTCCGGACCAAGTGGTGGCTATCGCCAGC
CACGATGGCGGCAAGCAAGCGCTCGAAACGGTGCAGCGGCTGTTGCCGGTGCTGTGCCAGGACCATGGCCTGACTCC
GGACCAAGTGGTGGCTATCGCCAGCCACGATGGCGGCAAGCAAGCGCTCGAAACGGTGCAGCGGCTGTTGCCGGTGC
TGTGCCAGGACCATGGCCTGACCCCGGACCAAGTGGTGGCTATCGCCAGCAACGGTGGCGGCAAGCAAGCGCTCGAA
ACGGTGCAGCGGCTGTTGCCGGTGCTGTGCCAGGACCATGGCCTGACCCCGGACCAAGTGGTGGCTATCGCCAGCAA
CAATGGCGGCAAGCAAGCGCTCGAAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGGTGCAGCGGCTGTTGCCGGTGCTG
TGCCAGGACCATGGCCTGACTCCGGACCAAGTGGTGGCTATCGCCAGCCACGATGGCGGCAAGCAAGCGCTCGAAAC
GGTGCAGCGGCTGTTGCCGGTGCTGTGCCAGGACCATGGCCTGACCCCGGACCAAGTGGTGGCTATCGCCAGCAACG
GTGGCGGCAAGCAAGCGCTCGAAACGGTGCAGCGGCTGTTGCCGGTGCTGTGCCAGGACCATGGCCTGACTCCGGAC
CAAGTGGTGGCTATCGCCAGCCACGATGGCGGCAAGCAAGCGCTCGAAACGGTGCAGCGGCTGTTGCCGGTGCTGTG
CCAGGACCATGGCCTGACTCCGGACCAAGTGGTGGCTATCGCCAGCCACGATGGCGGCAAGCAAGCGCTCGAAACGG
TGCAGCGGCTGTTGCCGGTGCTGTGCCAGGACCATGGCCTGACCCCGGACCAAGTGGTGGCTATCGCCAGCAACGGT
GGCGGCAAGCAAGCGCTCGAAAGCATTGTGGCCCAGCTGAGCCGGCCTGATCCGGCGTTGGCCGCGTTGACCAACGA
CCATCTGGTGGCGTTGGCATGTCTTGGTGGACGACCCGCGCTCGATGCAGTCAAAAAGGGTCTGCCTCATGCTCCCG
CATTGATCAAAAGAACCAACCGGCGGATTCCCGAGAGAACTTCCCATCGAGTCGCGGGATCCCAGCTGGTGAAGAGC
GAGCTGGAGGAGAAGAAGTCCGAGCTGCGGCACAAGCTGAAGTACGTGCCCCACGAGTACATCGAGCTGATCGAGAT
CGCCAGGAACAGCACCCAGGACCGCATCCTGGAGATGAAGGTGATGGAGTTCTTCATGAAGGTGTACGGCTACAGGG
GAAAGCACCTGGGCGGAAGCAGAAAGCCTGACGGCGCCATCTATACAGTGGGCAGCCCCATCGATTACGGCGTGATC
GTGGACACAAAGGCCTACAGCGGCGGCTACAATCTGCCTATCGGCCAGGCCGACGAGATGCAGAGATACGTGGAGGA
GAACCAGACCCGGAATAAGCACATCAACCCCAACGAGTGGTGGAAGGTGTACCCTAGCAGCGTGACCGAGTTCAAGT
TCCTGTTCGTGAGCGGCCACTTCAAGGGCAACTACAAGGCCCAGCTGACCAGGCTGAACCACATCACCAACTGCAAT
GGCGCCGTGCTGAGCGTGGAGGAGCTGCTGATCGGCGGCGAGATGATCAAAGCCGGCACCCTGACACTGGAGGAGGT
GCGGCGCAAGTTCAACAACGGCGAGATCAACTTCTGATAACTTAAGTTTAAACCGCTGATCAGCCTCGACTGTGCCT
TCTAGTTGCCAGCCATCTGTTGTTTGCCCCTCCCCCGTGCCTTCCTTGACCCTGGAAGGTGCCACTCCCACTGTCCT
TTCCTAATAAAATGAGGAAATTGCATCGCATTGTCTGAGTAGGTGTCATTCTATTCTGGGGGGTGGGGTGGGGCAGG
ACAGCAAGGGGGAGGATTGGGAAGACAATAGCAGGCATGCTGGGGATGCGGTGGGCTCTATGGCTTCTGAGGCGGAA
AGAACCAGCTGGGGCTCTAGGGGGTATCCCCACGCGCCCTGTAGCGGCGCATTAAGCGCGGCGGGTGTGGTGGTTAC
GCGCAGCGTGACCGCTACACTTGCCAGCGCCCTAGCGCCCGCTCCTTTCGCTTTCTTCCCTTCCTTTCTCGCCACGT
TCGCCGGCTTTCCCCGTCAAGCTCTAAATCGGGGGCTCCCTTTAGGGTTCCGATTTAGTGCTTTACGGCACCTCGAC
CCCAAAAAACTTGATTAGGGTGATGGTTCACGTAGTGGGCCATCGCCCTGATAGACGGTTTTTCGCCCTTTGACGTT
GGAGTCCACGTTCTTTAATAGTGGACTCTTGTTCCAAACTGGAACAACACTCAACCCTATCTCGGTCTATTCTTTTG
ATTTATAAGGGATTTTGCCGATTTCGGCCTATTGGTTAAAAAATGAGCTGATTTAACAAAAATTTAACGCGAATTAA
TTCTGTGGAATGTGTGTCAGTTAGGGTGTGGAAAGTCCCCAGGCTCCCCAGCAGGCAGAAGTATGCAAAGCATGCAT
CTCAATTAGTCAGCAACCAGGTGTGGAAAGTCCCCAGGCTCCCCAGCAGGCAGAAGTATGCAAAGCATGCATCTCAA
TTAGTCAGCAACCATAGTCCCGCCCCTAACTCCGCCCATCCCGCCCCTAACTCCGCCCAGTTCCGCCCATTCTCCGC
CCCATGGCTGACTAATTTTTTTTATTTATGCAGAGGCCGAGGCCGCCTCTGCCTCTGAGCTATTCCAGAAGTAGTGA
GGAGGCTTTTTTGGAGGCCTAGGCTTTTGCAAAAAGCTCCCGGGAGCTTGTATATCCATTTTCGGATCTGATCAAGA
GACAGGATGAGGATCGTTTCGCATGATTGAACAAGATGGATTGCACGCAGGTTCTCCGGCCGCTTGGGTGGAGAGGC
TATTCGGCTATGACTGGGCACAACAGACAATCGGCTGCTCTGATGCCGCCGTGTTCCGGCTGTCAGCGCAGGGGCGC
```

-continued

CCGGTTCTTTTTGTCAAGACCGACCTGTCCGGTGCCCTGAATGAACTGCAGGACGAGGCAGCGCGGCTATCGTGGCT

GGCCACGACGGGCGTTCCTTGCGCAGCTGTGCTCGACGTTGTCACTGAAGCGGGAAGGGACTGGCTGCTATTGGGCG

AAGTGCCGGGGCAGGATCTCCTGTCATCTCACCTTGCTCCTGCCGAGAAAGTATCCATCATGGCTGATGCAATGCGG

CGGCTGCATACGCTTGATCCGGCTACCTGCCCATTCGACCACCAAGCGAAACATCGCATCGAGCGAGCACGTACTCG

GATGGAAGCCGGTCTTGTCGATCAGGATGATCTGGACGAAGAGCATCAGGGGCTCGCGCCAGCCGAACTGTTCGCCA

GGCTCAAGGCGCGCATGCCCGACGGCGAGGATCTCGTCGTGACCCATGGCGATGCCTGCTTGCCGAATATCATGGTG

GAAAATGGCCGCTTTTCTGGATTCATCGACTGTGGCCGGCTGGGTGTGGCGGACCGCTATCAGGACATAGCGTTGGC

TACCCGTGATATTGCTGAAGAGCTTGGCGGCGAATGGGCTGACCGCTTCCTCGTGCTTTACGGTATCGCCGCTCCCG

ATTCGCAGCGCATCGCCTTCTATCGCCTTCTTGACGAGTTCTTCTGAGCGGGACTCTGGGGTTCGAAATGACCGACC

AAGCGACGCCCAACCTGCCATCACGAGATTTCGATTCCACCGCCGCCTTCTATGAAAGGTTGGGCTTCGGAATCGTT

TTCCGGGACGCCGGCTGGATGATCCTCCAGCGCGGGGATCTCATGCTGGAGTTCTTCGCCCACCCCAACTTGTTTAT

TGCAGCTTATAATGGTTACAAATAAAGCAATAGCATCACAAATTTCACAAATAAAGCATTTTTTTCACTGCATTCTA

GTTGTGGTTTGTCCAAACTCATCAATGTATCTTATCATGTCTGTATACCGTCGACCTCTAGCTAGAGCTTGGCGTAA

TCATGGTCATAGCTGTTTCCTGTGTGAAATTGTTATCCGCTCACAATTCCACACAACATACGAGCCGGAAGCATAAA

GTGTAAAGCCTGGGGTGCCTAATGAGTGAGCTAACTCACATTAATTGCGTTGCGCTCACTGCCCGCTTTCCAGTCGG

GAAACCTGTCGTGCCAGCTGCATTAATGAATCGGCCAACGCGCGGGGAGAGGCGGTTTGCGTATTGGGCGCTCTTCC

GCTTCCTCGCTCACTGACTCGCTGCGCTCGGTCGTTCGGCTGCGGCGAGCGGTATCAGCTCACTCAAAGGCGGTAAT

ACGGTTATCCACAGAATCAGGGGATAACGCAGGAAAGAACATGTGAGCAAAAGGCCAGCAAAAGGCCAGGAACCGTA

AAAAGGCCGCGTTGCTGGCGTTTTTCCATAGGCTCCGCCCCCCTGACGAGCATCACAAAAATCGACGCTCAAGTCAG

AGGTGGCGAAACCCGACAGGACTATAAAGATACCAGGCGTTTCCCCCTGGAAGCTCCCTCGTGCGCTCTCCTGTTCC

GACCCTGCCGCTTACCGGATACCTGTCCGCCTTTCTCCCTTCGGGAAGCGTGGCGCTTTCTCATAGCTCACGCTGTA

GGTATCTCAGTTCGGTGTAGGTCGTTCGCTCCAAGCTGGGCTGTGTGCACGAACCCCCCGTTCAGCCCGACCGCTGC

GCCTTATCCGGTAACTATCGTCTTGAGTCCAACCCGGTAAGACACGACTTATCGCCACTGGCAGCAGCCACTGGTAA

CAGGATTAGCAGAGCGAGGTATGTAGGCGGTGCTACAGAGTTCTTGAAGTGGTGGCCTAACTACGGCTACACTAGAA

GAACAGTATTTGGTATCTGCGCTCTGCTGAAGCCAGTTACCTTCGGAAAAAGAGTTGGTAGCTCTTGATCCGGCAAA

CAAACCACCGCTGGTAGCGGTTTTTTTGTTTGCAAGCAGCAGATTACGCGCAGAAAAAAAGGATCTCAAGAAGATCC

TTTGATCTTTTCTACGGGGTCTGACGCTCAGTGGAACGAAAACTCACGTTAAGGGATTTTGGTCATGAGATTATCAA

AAAGGATCTTCACCTAGATCCTTTTAAATTAAAAATGAAGTTTTAAATCAATCTAAAGTATATATGAGTAAACTTGG

TCTGACAGTTACCAATGCTTAATCAGTGAGGCACCTATCTCAGCGATCTGTCTATTTCGTTCATCCATAGTTGCCTG

ACTCCCCGTCGTGTAGATAACTACGATACGGGAGGGCTTACCATCTGGCCCCAGTGCTGCAATGATACCGCGAGACC

CACGCTCACCGGCTCCAGATTTATCAGCAATAAACCAGCCAGCCGGAAGGGCCGAGCGCAGAAGTGGTCCTGCAACT

TTATCCGCCTCCATCCAGTCTATTAATTGTTGCCGGGAAGCTAGAGTAAGTAGTTCGCCAGTTAATAGTTTGCGCAA

CGTTGTTGCCATTGCTACAGGCATCGTGGTGTCACGCTCGTCGTTTGGTATGGCTTCATTCAGCTCCGGTTCCCAAC

GATCAAGGCGAGTTACATGATCCCCCATGTTGTGCAAAAAAGCGGTTAGCTCCTTCGGTCCTCCGATCGTTGTCAGA

AGTAAGTTGGCCGCAGTGTTATCACTCATGGTTATGGCAGCACTGCATAATTCTCTTACTGTCATGCCATCCGTAAG

ATGCTTTTCTGTGACTGGTGAGTACTCAACCAAGTCATTCTGAGAATAGTGTATGCGGCGACCGAGTTGCTCTTGCC

CGGCGTCAATACGGGATAATACCGCGCCACATAGCAGAACTTTAAAAGTGCTCATCATTGGAAAACGTTCTTCGGGG

CGAAAACTCTCAAGGATCTTACCGCTGTTGAGATCCAGTTCGATGTAACCCACTCGTGCACCCAACTGATCTTCAGC

ATCTTTTACTTTCACCAGCGTTTCTGGGTGAGCAAAAACAGGAAGGCAAAATGCCGCAAAAAAGGGAATAAGGGCGA

CACGGAAATGTTGAATACTCATACTCTTCCTTTTTCAATATTATTGAAGCATTTATCAGGGTTATTGTCTCATGAGC

GGATACATATTTGAATGTATTTAGAAAAATAAACAAATAGGGGTTCCGCGCACATTTCCCCGAAAAGTGCCACCTGA

-continued

CGTCGACGGATCGGGAGATCTCCCGATCCCCTATGGTGCACTCTCAGTACAATCTGCTCTGATGCCGCATAGTTAAG

CCAGTATCTGCTCCCTGCTTGTGTGTTGGAGGTCGCTGAGTAGTGCGCGAGCAAAATTTAAGCTACAACAAGGCAAG

GCTTGACCGACAATTGCATGAAGAATCTGCTTAGGGTTAGGCGTTTTGCGCTGCTTCGCGATGTACGGGCCAGATAT

ACGC.

The plasmid that codes for SEQ ID NO: 8 has an identity (SEQ ID NO: 20)
GTTGACATTGATTATTGACTAGTTATTAATAGTAATCAATTACGGGGTCATTAGTTCATAGCCCATATATGGAGTTC

CGCGTTACATAACTTACGGTAAATGGCCCGCCTGGCTGACCGCCCAACGACCCCCGCCCATTGACGTCAATAATGAC

GTATGTTCCCATAGTAACGCCAATAGGGACTTTCCATTGACGTCAATGGGTGGAGTATTTACGGTAAACTGCCCACT

TGGCAGTACATCAAGTGTATCATATGCCAAGTACGCCCCCTATTGACGTCAATGACGGTAAATGGCCCGCCTGGCAT

TATGCCCAGTACATGACCTTATGGGACTTTCCTACTTGGCAGTACATCTACGTATTAGTCATCGCTATTACCATGGT

GATGCGGTTTTGGCAGTACATCAATGGGCGTGGATAGCGGTTTGACTCACGGGGATTTCCAAGTCTCCACCCCATTG

ACGTCAATGGGAGTTTGTTTTGGCACCAAAATCAACGGGACTTTCCAAAATGTCGTAACAACTCCGCCCCATTGACG

CAAATGGGCGGTAGGCGTGTACGGTGGGAGGTCTATATAAGCAGAGCTCTCTGGCTAACTAGAGAACCCACTGCTTA

CTGGCTTATCGAAATTAATACGACTCACTATAGGGAGACCCAAGCTGGCTAGCGCCACCATGGACTACAAAGACCAT

GACGGTGATTATAAAGATCATGACATCGATTACAAGGATGACGATGACAAGATGGCCCCCAAGAAGAAGAGGAAGGT

GGGCATTCACCGCGGGGTACCTATGGTGGACTTGAGGACACTCGGTTATTCGCAACAGCAACAGGAGAAAATCAAGC

CTAAGGTCAGGAGCACCGTCGCGCAACACCACGAGGCGCTTGTGGGGCATGGCTTCACTCATGCGCATATTGTCGCG

CTTTCACAGCACCCTGCGGCGCTTGGGACGGTGGCTGTCAAATACCAAGATATGATTGCGGCCCTGCCCGAAGCCAC

GCACGAGGCAATTGTAGGGGTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAGAGGGGGAGTAACAGCGGTA

GAGGCAGTGCACGCCTGGCGCAATGCGCTCACCGGTGCCCCCCTGAACCTGACCCCGGACCAAGTGGTGGCTATCGC

CAGCAACAATGGCGGCAAGCAAGCGCTCGAAACGGTGCAGCGGCTGTTGCCGGTGCTGTGCCAGGACCATGGCCTGA

CTCCGGACCAAGTGGTGGCTATCGCCAGCCACGATGGCGGCAAGCAAGCGCTCGAAACGGTGCAGCGGCTGTTGCCG

GTGCTGTGCCAGGACCATGGCCTGACCCCGGACCAAGTGGTGGCTATCGCCAGCAACATTGGCGGCAAGCAAGCGCT

CGAAACGGTGCAGCGGCTGTTGCCGGTGCTGTGCCAGGACCATGGCCTGACTCCGGACCAAGTGGTGGCTATCGCCA

GCCACGATGGCGGCAAGCAAGCGCTCGAAACGGTGCAGCGGCTGTTGCCGGTGCTGTGCCAGGACCATGGCCTGACT

CCGGACCAAGTGGTGGCTATCGCCAGCCACGATGGCGGCAAGCAAGCGCTCGAAACGGTGCAGCGGCTGTTGCCGGT

GCTGTGCCAGGACCATGGCCTGACCCCGGACCAAGTGGTGGCTATCGCCAGCAACGGTGGCGGCAAGCAAGCGCTCG

AAACGGTGCAGCGGCTGTTGCCGGTGCTGTGCCAGGACCATGGCCTGACCCCGGACCAAGTGGTGGCTATCGCCAGC

AACAATGGCGGCAAGCAAGCGCTCGAAACGGTGCAGCGGCTGTTGCCGGTGCTGTGCCAGGACCATGGCCTGACCCC

GGACCAAGTGGTGGCTATCGCCAGCAACATTGGCGGCAAGCAAGCGCTCGAAACGGTGCAGCGGCTGTTGCCGGTGC

TGTGCCAGGACCATGGCCTGACTCCGGACCAAGTGGTGGCTATCGCCAGCCACGATGGCGGCAAGCAAGCGCTCGAA

ACGGTGCAGCGGCTGTTGCCGGTGCTGTGCCAGGACCATGGCCTGACCCCGGACCAAGTGGTGGCTATCGCCAGCAA

CGGTGGCGGCAAGCAAGCGCTCGAAACGGTGCAGCGGCTGTTGCCGGTGCTGTGCCAGGACCATGGCCTGACCCCGG

ACCAAGTGGTGGCTATCGCCAGCCACGATGGCGGCAAGCAAGCGCTCGAAACGGTGCAGCGGCTGTTGCCGGTGCTG

TGCCAGGACCATGGCCTGACTCCGGACCAAGTGGTGGCTATCGCCAGCCACGATGGCGGCAAGCAAGCGCTCGAAAC

GGTGCAGCGGCTGTTGCCGGTGCTGTGCCAGGACCATGGCCTGACCCCGGACCAAGTGGTGGCTATCGCCAGCAACG

GTGGCGGCAAGCAAGCGCTCGAAACGGTGCAGCGGCTGTTGCCGGTGCTGTGCCAGGACCATGGCCTGACCCCGGAC

CAAGTGGTGGCTATCGCCAGCAACAATGGCGGCAAGCAAGCGCTCGAAACGGTGCAGCGGCTGTTGCCGGTGCTGTG

-continued

```
CCAGGACCATGGCCTGACCCCGGACCAAGTGGTGGCTATCGCCAGCAACGGTGGCGGCAAGCAAGCGCTCGAAAGCA
TTGTGGCCCAGCTGAGCCGGCCTGATCCGGCGTTGGCCGCGTTGACCAACGACCATCTGGTGGCGTTGGCATGTCTT
GGTGGACGACCCGCGCTCGATGCAGTCAAAAAGGGTCTGCCTCATGCTCCCGCATTGATCAAAAGAACCAACCGGCG
GATTCCCGAGAGAACTTCCCATCGAGTCGCGGGATCCCAGCTGGTGAAGAGCGAGCTGGAGGAGAAGAAGTCCGAGC
TGCGGCACAAGCTGAAGTACGTGCCCCACGAGTACATCGAGCTGATCGAGATCGCCAGGAACAGCACCCAGGACCGC
ATCCTGGAGATGAAGGTGATGGAGTTCTTCATGAAGGTGTACGGCTACAGGGGAAAGCACCTGGGCGGAAGCAGAAA
GCCTGACGGCGCCATCTATACAGTGGGCAGCCCCATCGATTACGGCGTGATCGTGGACACAAAGGCCTACAGCGGCG
GCTACAATCTGCCTATCGGCCAGGCCGACGAGATGCAGAGATACGTGGAGGAGAACCAGACCCGGAATAAGCACATC
AACCCCAACGAGTGGTGGAAGGTGTACCCTAGCAGCGTGACCGAGTTCAAGTTCCTGTTCGTGAGCGGCCACTTCAA
GGGCAACTACAAGGCCCAGCTGACCAGGCTGAACCACATCACCAACTGCAATGGCGCCGTGCTGAGCGTGGAGGAGC
TGCTGATCGGCGGCGAGATGATCAAAGCCGGCACCCTGACACTGGAGGAGGTGCGGCGCAAGTTCAACAACGGCGAG
ATCAACTTCTGATAACTTAAGTTTAAACCGCTGATCAGCCTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATAAAATGAGGAAATTGCA
TCGCATTGTCTGAGTAGGTGTCATTCTATTCTGGGGGGTGGGGTGGGGCAGGACAGCAAGGGGGAGGATTGGGAAGA
CAATAGCAGGCATGCTGGGGATGCGGTGGGCTCTATGGCTTCTGAGGCGGAAAGAACCAGCTGGGGCTCTAGGGGGT
ATCCCCACGCGCCCTGTAGCGGCGCATTAAGCGCGGCGGGTGTGGTGGTTACGCGCAGCGTGACCGCTACACTTGCC
AGCGCCCTAGCGCCCGCTCCTTTCGCTTTCTTCCCTTCCTTTCTCGCCACGTTCGCCGGCTTTCCCCGTCAAGCTCT
AAATCGGGGGCTCCCTTTAGGGTTCCGATTTAGTGCTTTACGGCACCTCGACCCCAAAAAACTTGATTAGGGTGATG
GTTCACGTAGTGGGCCATCGCCCTGATAGACGGTTTTTCGCCCTTTGACGTTGGAGTCCACGTTCTTTAATAGTGGA
CTCTTGTTCCAAACTGGAACAACACTCAACCCTATCTCGGTCTATTCTTTTGATTTATAAGGGATTTTGCCGATTTC
GGCCTATTGGTTAAAAAATGAGCTGATTTAACAAAAATTTAACGCGAATTAATTCTGTGGAATGTGTGTCAGTTAGG
GTGTGGAAAGTCCCCAGGCTCCCCAGCAGGCAGAAGTATGCAAAGCATGCATCTCAATTAGTCAGCAACCAGGTGTG
GAAAGTCCCCAGGCTCCCCAGCAGGCAGAAGTATGCAAAGCATGCATCTCAATTAGTCAGCAACCATAGTCCCGCCC
CTAACTCCGCCCATCCCGCCCCTAACTCCGCCCAGTTCCGCCCATTCTCCGCCCCATGGCTGACTAATTTTTTTTAT
TTATGCAGAGGCCGAGGCCGCCTCTGCCTCTGAGCTATTCCAGAAGTAGTGAGGAGGCTTTTTTGGAGGCCTAGGCT
TTTGCAAAAAGCTCCCGGGAGCTTGTATATCCATTTTCGGATCTGATCAAGAGACAGGATGAGGATCGTTTCGCATG
ATTGAACAAGATGGATTGCACGCAGGTTCTCCGGCCGCTTGGGTGGAGAGGCTATTCGGCTATGACTGGGCACAACA
GACAATCGGCTGCTCTGATGCCGCCGTGTTCCGGCTGTCAGCGCAGGGGCGCCCGGTTCTTTTTGTCAAGACCGACC
TGTCCGGTGCCCTGAATGAACTGCAGGACGAGGCAGCGCGGCTATCGTGGCTGGCCACGACGGGCGTTCCTTGCGCA
GCTGTGCTCGACGTTGTCACTGAAGCGGGAAGGGACTGGCTGCTATTGGGCGAAGTGCCGGGGCAGGATCTCCTGTC
ATCTCACCTTGCTCCTGCCGAGAAAGTATCCATCATGGCTGATGCAATGCGGCGGCTGCATACGCTTGATCCGGCTA
CCTGCCCATTCGACCACCAAGCGAAACATCGCATCGAGCGAGCACGTACTCGGATGGAAGCCGGTCTTGTCGATCAG
GATGATCTGGACGAAGAGCATCAGGGGCTCGCGCCAGCCGAACTGTTCGCCAGGCTCAAGGCGCGCATGCCCGACGG
CGAGGATCTCGTCGTGACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGATATTGCTGAAGAGCTT
GGCGGCGAATGGGCTGACCGCTTCCTCGTGCTTTACGGTATCGCCGCTCCCGATTCGCAGCGCATCGCCTTCTATCG
CCTTCTTGACGAGTTCTTCTGAGCGGGACTCTGGGGTTCGAAATGACCGACCAAGCGACGCCCAACCTGCCATCACG
AGATTTCGATTCCACCGCCGCCTTCTATGAAAGGTTGGGCTTCGGAATCGTTTTCCGGGACGCCGGCTGGATGATCC
TCCAGCGCGGGGATCTCATGCTGGAGTTCTTCGCCCACCCCAACTTGTTTATTGCAGCTTATAATGGTTACAAATAA
AGCAATAGCATCACAAATTTCACAAATAAAGCATTTTTTTCACTGCATTCTAGTTGTGGTTTGTCCAAACTCATCAA
```

-continued

```
TGTATCTTATCATGTCTGTATACCGTCGACCTCTAGCTAGAGCTTGGCGTAATCATGGTCATAGCTGTTTCCTGTGT
GAAATTGTTATCCGCTCACAATTCCACACAACATACGAGCCGGAAGCATAAAGTGTAAAGCCTGGGGTGCCTAATGA
GTGAGCTAACTCACATTAATTGCGTTGCGCTCACTGCCCGCTTTCCAGTCGGGAAACCTGTCGTGCCAGCTGCATTA
ATGAATCGGCCAACGCGCGGGGAGAGGCGGTTTGCGTATTGGGCGCTCTTCCGCTTCCTCGCTCACTGACTCGCTGC
GCTCGGTCGTTCGGCTGCGGCGAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGCGTTGCTGGCGTTTTT
CCATAGGCTCCGCCCCCCTGACGAGCATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCATAGCTCACGCTGTAGGTATCTCAGTTCGGTGTAGGTCGT
TCGCTCCAAGCTGGGCTGTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGAACAGTATTTGGTATCTGCGCTCT
GCTGAAGCCAGTTACCTTCGGAAAAAGAGTTGGTAGCTCTTGATCCGGCAAACAAACCACCGCTGGTAGCGGTTTTT
TTGTTTGCAAGCAGCAGATTACGCGCAGAAAAAAAGGATCTCAAGAAGATCCTTTGATCTTTTCTACGGGGTCTGAC
GCTCAGTGGAACGAAAACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTTACCAATGCTTAATCA
GTGAGGCACCTATCTCAGCGATCTGTCTATTTCGTTCATCCATAGTTGCCTGACTCCCCGTCGTGTAGATAACTACG
ATACGGGAGGGCTTACCATCTGGCCCCAGTGCTGCAATGATACCGCGAGACCCACGCTCACCGGCTCCAGATTTATC
AGCAATAAACCAGCCAGCCGGAAGGGCCGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCAGAAGTAAGTTGGCCGCAGTGTTATCAC
TCATGGTTATGGCAGCACTGCATAATTCTCTTACTGTCATGCCATCCGTAAGATGCTTTTCTGTGACTGGTGAGTAC
TCAACCAAGTCATTCTGAGAATAGTGTATGCGGCGACCGAGTTGCTCTTGCCCGGCGTCAATACGGGATAATACCGC
GCCACATAGCAGAACTTTAAAAGTGCTCATCATTGGAAAACGTTCTTCGGGGCGAAAACTCTCAAGGATCTTACCGC
TGTTGAGATCCAGTTCGATGTAACCCACTCGTGCACCCAACTGATCTTCAGCATCTTTTACTTTCACCAGCGTTTCT
GGGTGAGCAAAAACAGGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATACATATTTGAATGTATTTAGA
AAAATAAACAAATAGGGGTTCCGCGCACATTTCCCCGAAAAGTGCCACCTGACGTCGACGGATCGGGAGATCTCCCG
ATCCCCTATGGTGCACTCTCAGTACAATCTGCTCTGATGCCGCATAGTTAAGCCAGTATCTGCTCCCTGCTTGTGTG
TTGGAGGTCGCTGAGTAGTGCGCGAGCAAAATTTAAGCTACAACAAGGCAAGGCTTGACCGACAATTGCATGAAGAA
TCTGCTTAGGGTTAGGCGTTTTGCGCTGCTTCGCGATGTACGGGCCAGATATACGC.
```

The plasmid that codes for SEQ ID NO: 9 has an identity (SEQ ID NO: 21)
```
GTTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTG
```

-continued

```
ACGTCAATGGGAGTTTGTTTTGGCACCAAAATCAACGGGACTTTCCAAAATGTCGTAACAACTCCGCCCCATTGACG
CAAATGGGCGGTAGGCGTGTACGGTGGGAGGTCTATATAAGCAGAGCTCTCTGGCTAACTAGAGAACCCACTGCTTA
CTGGCTTATCGAAATTAATACGACTCACTATAGGGAGACCCAAGCTGGCTAGCGCCACCATGGACTACAAAGACCAT
GACGGTGATTATAAAGATCATGACATCGATTACAAGGATGACGATGACAAGATGGCCCCAAGAAGAAGAGGAAGGT
GGGCATTCACCGCGGGGTACCTATGGTGGACTTGAGGACACTCGGTTATTCGCAACAGCAACAGGAGAAAATCAAGC
CTAAGGTCAGGAGCACCGTCGCGCAACACCACGAGGCGCTTGTGGGGCATGGCTTCACTCATGCGCATATTGTCGCG
CTTTCACAGCACCCTGCGGCGCTTGGGACGGTGGCTGTCAAATACCAAGATATGATTGCGGCCCTGCCCGAAGCCAC
GCACGAGGCAATTGTAGGGGTCGGTAAACAGTGGTCGGGAGCGCGAGCACTTGAGGCGCTGCTGACTGTGGCGGGTG
AGCTTAGGGGGCCTCCGCTCCAGCTCGACACCGGGCAGCTGCTGAAGATCGCGAAGAGAGGGGGAGTAACAGCGGTA
GAGGCAGTGCACGCCTGGCGCAATGCGCTCACCGGTGCCCCCCTGAACCTGACCCCGGACCAAGTGGTGGCTATCGC
CAGCCACGATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACATTGGCGGCAAGCAAGCGCTCGAAACGGTGCAGCGGCTGTTGCCG
GTGCTGTGCCAGGACCATGGCCTGACTCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACTCCGGACCAAGTGGTGGCTATCGCCA
GCCACGATGGCGGCAAGCAAGCGCTCGAAACGGTGCAGCGGCTGTTGCCGGTGCTGTGCCAGGACCATGGCCTGACC
CCGGACCAAGTGGTGGCTATCGCCAGCAACGGTGGCGGCAAGCAAGCGCTCGAAACGGTGCAGCGGCTGTTGCCGGT
GCTGTGCCAGGACCATGGCCTGACCCCGGACCAAGTGGTGGCTATCGCCAGCAACGGTGGCGGCAAGCAAGCGCTCG
AAACGGTGCAGCGGCTGTTGCCGGTGCTGTGCCAGGACCATGGCCTGACCCCGGACCAAGTGGTGGCTATCGCCAGC
AACAAGGGCGGCAAGCAAGCGCTCGAAACGGTGCAGCGGCTGTTGCCGGTGCTGTGCCAGGACCATGGCCTGACTCC
GGACCAAGTGGTGGCTATCGCCAGCCACGATGGCGGCAAGCAAGCGCTCGAAACGGTGCAGCGGCTGTTGCCGGTGC
TGTGCCAGGACCATGGCCTGACTCCGGACCAAGTGGTGGCTATCGCCAGCCACGATGGCGGCAAGCAAGCGCTCGAA
ACGGTGCAGCGGCTGTTGCCGGTGCTGTGCCAGGACCATGGCCTGACTCCGGACCAAGTGGTGGCTATCGCCAGCCA
CGATGGCGGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCCGGTGCTG
TGCCAGGACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACTCCGGACCAAGTGGTGGCTATCGCCAGCCACG
ATGGCGGCAAGCAAGCGCTCGAAACGGTGCAGCGGCTGTTGCCGGTGCTGTGCCAGGACCATGGCCTGACCCCGGAC
CAAGTGGTGGCTATCGCCAGCAACATTGGCGGCAAGCAAGCGCTCGAAACGGTGCAGCGGCTGTTGCCGGTGCTGTG
CCAGGACCATGGCCTGACCCCGGACCAAGTGGTGGCTATCGCCAGCAACAAGGGCGGCAAGCAAGCGCTCGAAACGG
TGCAGCGGCTGTTGCCGGTGCTGTGCCAGGACCATGGCCTGACCCCGGACCAAGTGGTGGCTATCGCCAGCAACAAG
GGCGGCAAGCAAGCGCTCGAAACGGTGCAGCGGCTGTTGCCGGTGCTGTGCCAGGACCATGGCCTGACCCCGGACCA
AGTGGTGGCTATCGCCAGCAACAAGGGCGGCAAGCAAGCGCTCGAAACGGTGCAGCGGCTGTTGCCGGTGCTGTGCC
AGGACCATGGCCTGACTCCGGACCAAGTGGTGGCTATCGCCAGCCACGATGGCGGCAAGCAAGCGCTCGAAACGGTG
CAGCGGCTGTTGCCGGTGCTGTGCCAGGACCATGGCCTGACCCCGGACCAAGTGGTGGCTATCGCCAGCAACATTGG
CGGCAAGCAAGCGCTCGAAACGGTGCAGCGGCTGTTGCCGGTGCTGTGCCAGGACCATGGCCTGACCCCGGACCAAG
TGGTGGCTATCGCCAGCAACAAGGGCGGCAAGCAAGCGCTCGAAACGGTGCAGCGGCTGTTGCCGGTGCTGTGCCAG
GACCATGGCCTGACCCCGGACCAAGTGGTGGCTATCGCCAGCAACGGTGGCGGCAAGCAAGCGCTCGAAAGCATTGT
GGCCCAGCTGAGCCGGCCTGATCCGGCGTTGGCCGCGTTGACCAACGACCATCTGGTGGCGTTGGCATGTCTTGGTG
GACGACCCGCGCTCGATGCAGTCAAAAAGGGTCTGCCTCATGCTCCCGCATTGATCAAAAGAACCAACCGGCGGATT
CCCGAGAGAACTTCCCATCGAGTCGCGGGATCCCAGCTGGTGAAGAGCGAGCTGGAGGAGAAGAAGTCCGAGCTGCG
GCACAAGCTGAAGTACGTGCCCCACGAGTACATCGAGCTGATCGAGATCGCCAGGAACAGCACCCAGGACCGCATCC
```

-continued

```
TGGAGATGAAGGTGATGGAGTTCTTCATGAAGGTGTACGGCTACAGGGGAAAGCACCTGGGCGGAAGCAGAAAGCCT
GACGGCGCCATCTATACAGTGGGCAGCCCCATCGATTACGGCGTGATCGTGGACACAAAGGCCTACAGCGGCGGCTA
CAATCTGCCTATCGGCCAGGCCGACGAGATGCAGAGATACGTGGAGGAGAACCAGACCCGGAATAAGCACATCAACC
CCAACGAGTGGTGGAAGGTGTACCCTAGCAGCGTGACCGAGTTCAAGTTCCTGTTCGTGAGCGGCCACTTCAAGGGC
AACTACAAGGCCCAGCTGACCAGGCTGAACCACATCACCAACTGCAATGGCGCCGTGCTGAGCGTGGAGGAGCTGCT
GATCGGCGGCGAGATGATCAAAGCCGGCACCCTGACACTGGAGGAGGTGCGGCGCAAGTTCAACAACGGCGAGATCA
ACTTCTGATAACTTAAGTTTAAACCGCTGATCAGCCTCGACTGTGCCTTCTAGTTGCCAGCCATCTGTTGTTTGCCC
CTCCCCCGTGCCTTCCTTGACCCTGGAAGGTGCCACTCCCACTGTCCTTTCCTAATAAAATGAGGAAATTGCATCGC
ATTGTCTGAGTAGGTGTCATTCTATTCTGGGGGGTGGGGTGGGGCAGGACAGCAAGGGGGAGGATTGGGAAGACAAT
AGCAGGCATGCTGGGGATGCGGTGGGCTCTATGGCTTCTGAGGCGGAAAGAACCAGCTGGGGCTCTAGGGGGTATCC
CCACGCGCCCTGTAGCGGCGCATTAAGCGCGGCGGGTGTGGTGGTTACGCGCAGCGTGACCGCTACACTTGCCAGCG
CCCTAGCGCCCGCTCCTTTCGCTTTCTTCCCTTCCTTTCTCGCCACGTTCGCCGGCTTTCCCCGTCAAGCTCTAAAT
CGGGGGCTCCCTTTAGGGTTCCGATTTAGTGCTTTACGGCACCTCGACCCCAAAAAACTTGATTAGGGTGATGGTTC
ACGTAGTGGGCCATCGCCCTGATAGACGGTTTTTCGCCCTTTGACGTTGGAGTCCACGTTCTTTAATAGTGGACTCT
TGTTCCAAACTGGAACAACACTCAACCCTATCTCGGTCTATTCTTTTGATTTATAAGGGATTTTGCCGATTTCGGCC
TATTGGTTAAAAAATGAGCTGATTTAACAAAAATTTAACGCGAATTAATTCTGTGGAATGTGTGTCAGTTAGGGTGT
GGAAAGTCCCCAGGCTCCCCAGCAGGCAGAAGTATGCAAAGCATGCATCTCAATTAGTCAGCAACCAGGTGTGGAAA
GTCCCCAGGCTCCCCAGCAGGCAGAAGTATGCAAAGCATGCATCTCAATTAGTCAGCAACCATAGTCCCGCCCCTAA
CTCCGCCCATCCCGCCCCTAACTCCGCCCAGTTCCGCCCATTCTCCGCCCCATGGCTGACTAATTTTTTTTATTTAT
GCAGAGGCCGAGGCCGCCTCTGCCTCTGAGCTATTCCAGAAGTAGTGAGGAGGCTTTTTTGGAGGCCTAGGCTTTTG
CAAAAAGCTCCCGGGAGCTTGTATATCCATTTTCGGATCTGATCAAGAGACAGGATGAGGATCGTTTCGCATGATTG
AACAAGATGGATTGCACGCAGGTTCTCCGGCCGCTTGGGTGGAGAGGCTATTCGGCTATGACTGGGCACAACAGACA
ATCGGCTGCTCTGATGCCGCCGTGTTCCGGCTGTCAGCGCAGGGGCGCCCGGTTCTTTTTGTCAAGACCGACCTGTC
CGGTGCCCTGAATGAACTGCAGGACGAGGCAGCGCGGCTATCGTGGCTGGCCACGACGGGCGTTCCTTGCGCAGCTG
TGCTCGACGTTGTCACTGAAGCGGGAAGGGACTGGCTGCTATTGGGCGAAGTGCCGGGGCAGGATCTCCTGTCATCT
CACCTTGCTCCTGCCGAGAAAGTATCCATCATGGCTGATGCAATGCGGCGGCTGCATACGCTTGATCCGGCTACCTG
CCCATTCGACCACCAAGCGAAACATCGCATCGAGCGAGCACGTACTCGGATGGAAGCCGGTCTTGTCGATCAGGATG
ATCTGGACGAAGAGCATCAGGGGCTCGCGCCAGCCGAACTGTTCGCCAGGCTCAAGGCGCGCATGCCCGACGGCGAG
GATCTCGTCGTGACCCATGGCGATGCCTGCTTGCCGAATATCATGGTGGAAAATGGCCGCTTTTCTGGATTCATCGA
CTGTGGCCGGCTGGGTGTGGCGGACCGCTATCAGGACATAGCGTTGGCTACCCGTGATATTGCTGAAGAGCTTGGCG
GCGAATGGGCTGACCGCTTCCTCGTGCTTTACGGTATCGCCGCTCCCGATTCGCAGCGCATCGCCTTCTATCGCCTT
CTTGACGAGTTCTTCTGAGCGGGACTCTGGGGTTCGAAATGACCGACCAAGCGACGCCCAACCTGCCATCACGAGAT
TTCGATTCCACCGCCGCCTTCTATGAAAGGTTGGGCTTCGGAATCGTTTTCCGGGACGCCGGCTGGATGATCCTCCA
GCGCGGGGATCTCATGCTGGAGTTCTTCGCCCACCCCAACTTGTTTATTGCAGCTTATAATGGTTACAAATAAAGCA
ATAGCATCACAAATTTCACAAATAAAGCATTTTTTTCACTGCATTCTAGTTGTGGTTTGTCCAAACTCATCAATGTA
TCTTATCATGTCTGTATACCGTCGACCTCTAGCTAGAGCTTGGCGTAATCATGGTCATAGCTGTTTCCTGTGTGAAA
TTGTTATCCGCTCACAATTCCACACAACATACGAGCCGGAAGCATAAAGTGTAAAGCCTGGGGTGCCTAATGAGTGA
GCTAACTCACATTAATTGCGTTGCGCTCACTGCCCGCTTTCCAGTCGGGAAACCTGTCGTGCCAGCTGCATTAATGA
ATCGGCCAACGCGCGGGGAGAGGCGGTTTGCGTATTGGGCGCTCTTCCGCTTCCTCGCTCACTGACTCGCTGCGCTC
GGTCGTTCGGCTGCGGCGAGCGGTATCAGCTCACTCAAAGGCGGTAATACGGTTATCCACAGAATCAGGGGATAACG
```

-continued

CAGGAAAGAACATGTGAGCAAAAGGCCAGCAAAAGGCCAGGAACCGTAAAAAGGCCGCGTTGCTGGCGTTTTTCCAT

AGGCTCCGCCCCCTGACGAGCATCACAAAAATCGACGCTCAAGTCAGAGGTGGCGAAACCCGACAGGACTATAAAG

ATACCAGGCGTTTCCCCCTGGAAGCTCCCTCGTGCGCTCTCCTGTTCCGACCCTGCCGCTTACCGGATACCTGTCCG

CCTTTCTCCCTTCGGGAAGCGTGGCGCTTTCTCATAGCTCACGCTGTAGGTATCTCAGTTCGGTGTAGGTCGTTCGC

TCCAAGCTGGGCTGTGTGCACGAACCCCCCGTTCAGCCCGACCGCTGCGCCTTATCCGGTAACTATCGTCTTGAGTC

CAACCCGGTAAGACACGACTTATCGCCACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGAACAGTATTTGGTATCTGCGCTCTGCTG

AAGCCAGTTACCTTCGGAAAAAGAGTTGGTAGCTCTTGATCCGGCAAACAAACCACCGCTGGTAGCGGTTTTTTTGT

TTGCAAGCAGCAGATTACGCGCAGAAAAAAAGGATCTCAAGAAGATCCTTTGATCTTTTCTACGGGGTCTGACGCTC

AGTGGAACGAAAACTCACGTTAAGGGATTTTGGTCATGAGATTATCAAAAAGGATCTTCACCTAGATCCTTTTAAAT

TAAAAATGAAGTTTTAAATCAATCTAAAGTATATATGAGTAAACTTGGTCTGACAGTTACCAATGCTTAATCAGTGA

GGCACCTATCTCAGCGATCTGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACGTTGTTGCCATTGCTACAGGCATCGTGG

TGTCACGCTCGTCGTTTGGTATGGCTTCATTCAGCTCCGGTTCCCAACGATCAAGGCGAGTTACATGATCCCCCATG

TTGTGCAAAAAAGCGGTTAGCTCCTTCGGTCCTCCGATCGTTGTCAGAAGTAAGTTGGCCGCAGTGTTATCACTCAT

GGTTATGGCAGCACTGCATAATTCTCTTACTGTCATGCCATCCGTAAGATGCTTTTCTGTGACTGGTGAGTACTCAA

CCAAGTCATTCTGAGAATAGTGTATGCGGCGACCGAGTTGCTCTTGCCCGGCGTCAATACGGGATAATACCGCGCCA

CATAGCAGAACTTTAAAAGTGCTCATCATTGGAAAACGTTCTTCGGGGCGAAAACTCTCAAGGATCTTACCGCTGTT

GAGATCCAGTTCGATGTAACCCACTCGTGCACCCAACTGATCTTCAGCATCTTTTACTTTCACCAGCGTTTCTGGGT

GAGCAAAAACAGGAAGGCAAAATGCCGCAAAAAAGGGAATAAGGGCGACACGGAAATGTTGAATACTCATACTCTTC

CTTTTTCAATATTATTGAAGCATTTATCAGGGTTATTGTCTCATGAGCGGATACATATTTGAATGTATTTAGAAAAA

TAAACAAATAGGGGTTCCGCGCACATTTCCCCGAAAAGTGCCACCTGACGTCGACGGATCGGGAGATCTCCCGATCC

CCTATGGTGCACTCTCAGTACAATCTGCTCTGATGCCGCATAGTTAAGCCAGTATCTGCTCCCTGCTTGTGTGTTGG

AGGTCGCTGAGTAGTGCGCGAGCAAAATTTAAGCTACAACAAGGCAAGGCTTGACCGACAATTGCATGAAGAATCTG

CTTAGGGTTAGGCGTTTTGCGCTGCTTCGCGATGTACGGGCCAGATATACGC.

The plasmid that codes for SEQ ID NO: 10 has an identity (SEQ ID NO: 22)
GTTGACATTGATTATTGACTAGTTATTAATAGTAATCAATTACGGGGTCATTAGTTCATAGCCCATATATGGAGTTC

CGCGTTACATAACTTACGGTAAATGGCCCGCCTGGCTGACCGCCCAACGACCCCCGCCCATTGACGTCAATAATGAC

GTATGTTCCCATAGTAACGCCAATAGGGACTTTCCATTGACGTCAATGGGTGGAGTATTTACGGTAAACTGCCCACT

TGGCAGTACATCAAGTGTATCATATGCCAAGTACGCCCCCTATTGACGTCAATGACGGTAAATGGCCCGCCTGGCAT

TATGCCCAGTACATGACCTTATGGGACTTTCCTACTTGGCAGTACATCTACGTATTAGTCATCGCTATTACCATGGT

GATGCGGTTTTGGCAGTACATCAATGGGCGTGGATAGCGGTTTGACTCACGGGGATTTCCAAGTCTCCACCCCATTG

ACGTCAATGGGAGTTTGTTTTGGCACCAAAATCAACGGGACTTTCCAAAATGTCGTAACAACTCCGCCCCATTGACG

CAAATGGGCGGTAGGCGTGTACGGTGGGAGGTCTATATAAGCAGAGCTCTCTGGCTAACTAGAGAACCCACTGCTTA

CTGGCTTATCGAAATTAATACGACTCACTATAGGGAGACCCAAGCTGGCTAGCGCCACCATGGACTACAAAGACCAT

GACGGTGATTATAAAGATCATGACATCGATTACAAGGATGACGATGACAAGATGGCCCCCAAGAAGAAGAGGAAGGT

GGGCATTCACCGCGGGGTACCTATGGTGGACTTGAGGACACTCGGTTATTCGCAACAGCAACAGGAGAAAATCAAGC

-continued

```
CTAAGGTCAGGAGCACCGTCGCGCAACACCACGAGGCGCTTGTGGGGCATGGCTTCACTCATGCGCATATTGTCGCG
CTTTCACAGCACCCTGCGGCGCTTGGGACGGTGGCTGTCAAATACCAAGATATGATTGCGGCCCTGCCCGAAGCCAC
GCACGAGGCAATTGTAGGGGTCGGTAAACAGTGGTCGGGAGCGCGAGCACTTGAGGCGCTGCTGACTGTGGCGGGTG
AGCTTAGGGGGCCTCCGCTCCAGCTCGACACCGGGCAGCTGCTGAAGATCGCGAAGAGAGGGGGAGTAACAGCGGTA
GAGGCAGTGCACGCCTGGCGCAATGCGCTCACCGGTGCCCCCTGAACCTGACCCCGGACCAAGTGGTGGCTATCGC
CAGCCACGATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACATTGGCGGCAAGCAAGCGCTCGAAACGGTGCAGCGGCTGTTGCCG
GTGCTGTGCCAGGACCATGGCCTGACTCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACTCCGGACCAAGTGGTGGCTATCGCCA
GCCACGATGGCGGCAAGCAAGCGCTCGAAACGGTGCAGCGGCTGTTGCCGGTGCTGTGCCAGGACCATGGCCTGACC
CCGGACCAAGTGGTGGCTATCGCCAGCAACGGTGGCGGCAAGCAAGCGCTCGAAACGGTGCAGCGGCTGTTGCCGGT
GCTGTGCCAGGACCATGGCCTGACCCCGGACCAAGTGGTGGCTATCGCCAGCAACGGTGGCGGCAAGCAAGCGCTCG
AAACGGTGCAGCGGCTGTTGCCGGTGCTGTGCCAGGACCATGGCCTGACCCCGGACCAAGTGGTGGCTATCGCCAGC
AACAAGGGCGGCAAGCAAGCGCTCGAAACGGTGCAGCGGCTGTTGCCGGTGCTGTGCCAGGACCATGGCCTGACTCC
GGACCAAGTGGTGGCTATCGCCAGCCACGATGGCGGCAAGCAAGCGCTCGAAACGGTGCAGCGGCTGTTGCCGGTGC
TGTGCCAGGACCATGGCCTGACTCCGGACCAAGTGGTGGCTATCGCCAGCCACGATGGCGGCAAGCAAGCGCTCGAA
ACGGTGCAGCGGCTGTTGCCGGTGCTGTGCCAGGACCATGGCCTGACTCCGGACCAAGTGGTGGCTATCGCCAGCCA
CGATGGCGGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCCGGTGCTG
TGCCAGGACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACTCCGGACCAAGTGGTGGCTATCGCCAGCCACG
ATGGCGGCAAGCAAGCGCTCGAAACGGTGCAGCGGCTGTTGCCGGTGCTGTGCCAGGACCATGGCCTGACCCCGGAC
CAAGTGGTGGCTATCGCCAGCAACATTGGCGGCAAGCAAGCGCTCGAAACGGTGCAGCGGCTGTTGCCGGTGCTGTG
CCAGGACCATGGCCTGACCCCGGACCAAGTGGTGGCTATCGCCAGCAACAAGGGCGGCAAGCAAGCGCTCGAAACGG
TGCAGCGGCTGTTGCCGGTGCTGTGCCAGGACCATGGCCTGACCCCGGACCAAGTGGTGGCTATCGCCAGCAACAAG
GGCGGCAAGCAAGCGCTCGAAACGGTGCAGCGGCTGTTGCCGGTGCTGTGCCAGGACCATGGCCTGACCCCGGACCA
AGTGGTGGCTATCGCCAGCAACAAGGGCGGCAAGCAAGCGCTCGAAACGGTGCAGCGGCTGTTGCCGGTGCTGTGCC
AGGACCATGGCCTGACTCCGGACCAAGTGGTGGCTATCGCCAGCCACGATGGCGGCAAGCAAGCGCTCGAAACGGTG
CAGCGGCTGTTGCCGGTGCTGTGCCAGGACCATGGCCTGACCCCGGACCAAGTGGTGGCTATCGCCAGCAACATTGG
CGGCAAGCAAGCGCTCGAAACGGTGCAGCGGCTGTTGCCGGTGCTGTGCCAGGACCATGGCCTGACCCCGGACCAAG
TGGTGGCTATCGCCAGCAACAAGGGCGGCAAGCAAGCGCTCGAAACGGTGCAGCGGCTGTTGCCGGTGCTGTGCCAG
GACCATGGCCTGACCCCGGACCAAGTGGTGGCTATCGCCAGCAACGGTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAACATTGGCG
GCAAGCAAGCGCTCGAAACGGTGCAGCGGCTGTTGCCGGTGCTGTGCCAGGACCATGGCCTGACCCCGGACCAAGTG
GTGGCTATCGCCAGCAACATTGGCGGCAAGCAAGCGCTCGAAACGGTGCAGCGGCTGTTGCCGGTGCTGTGCCAGGA
CCATGGCCTGACCCCGGACCAAGTGGTGGCTATCGCCAGCCACGATGGCGGCAAGCAAGCGCTCGAAAGCATTGTGG
CCCAGCTGAGCCGGCCTGATCCGGCGTTGGCCGCGTTGACCAACGACCATCTGGTGGCGTTGGCATGTCTTGGTGGA
CGACCCGCGCTCGATGCAGTCAAAAAGGGTCTGCCTCATGCTCCCGCATTGATCAAAAGAACCAACCGGCGGATTCC
CGAGAGAACTTCCCATCGAGTCGCGGGATCCCAGCTGGTGAAGAGCGAGCTGGAGGAGAAGAAGTCCGAGCTGCGGC
ACAAGCTGAAGTACGTGCCCCACGAGTACATCGAGCTGATCGAGATCGCCAGGAACAGCACCCAGGACCGCATCCTG
GAGATGAAGGTGATGGAGTTCTTCATGAAGGTGTACGGCTACAGGGGAAAGCACCTGGGCGGAAGCAGAAAGCCTGA
```

-continued

```
CGGCGCCATCTATACAGTGGGCAGCCCCATCGATTACGGCGTGATCGTGGACACAAAGGCCTACAGCGGCGGCTACA
ATCTGCCTATCGGCCAGGCCGACGAGATGCAGAGATACGTGGAGGAGAACCAGACCCGGAATAAGCACATCAACCCC
AACGAGTGGTGGAAGGTGTACCCTAGCAGCGTGACCGAGTTCAAGTTCCTGTTCGTGAGCGGCCACTTCAAGGGCAA
CTACAAGGCCCAGCTGACCAGGCTGAACCACATCACCAACTGCAATGGCGCCGTGCTGAGCGTGGAGGAGCTGCTGA
TCGGCGGCGAGATGATCAAAGCCGGCACCCTGACACTGGAGGAGGTGCGGCGCAAGTTCAACAACGGCGAGATCAAC
TTCTGATAACTTAAGTTTAAACCGCTGATCAGCCTCGACTGTGCCTTCTAGTTGCCAGCCATCTGTTGTTTGCCCCT
CCCCCGTGCCTTCCTTGACCCTGGAAGGTGCCACTCCCACTGTCCTTTCCTAATAAAATGAGGAAATTGCATCGCAT
TGTCTGAGTAGGTGTCATTCTATTCTGGGGGGTGGGGTGGGGCAGGACAGCAAGGGGGAGGATTGGGAAGACAATAG
CAGGCATGCTGGGGATGCGGTGGGCTCTATGGCTTCTGAGGCGGAAAGAACCAGCTGGGGCTCTAGGGGGTATCCCC
ACGCGCCCTGTAGCGGCGCATTAAGCGCGGCGGGTGTGGTGGTTACGCGCAGCGTGACCGCTACACTTGCCAGCGCC
CTAGCGCCCGCTCCTTTCGCTTTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAACTTGATTAGGGTGATGGTTCAC
GTAGTGGGCCATCGCCCTGATAGACGGTTTTTCGCCCTTTGACGTTGGAGTCCACGTTCTTTAATAGTGGACTCTTG
TTCCAAACTGGAACAACACTCAACCCTATCTCGGTCTATTCTTTTGATTTATAAGGGATTTTGCCGATTTCGGCCTA
TTGGTTAAAAAATGAGCTGATTTAACAAAAATTTAACGCGAATTAATTCTGTGGAATGTGTGTCAGTTAGGGTGTGG
AAAGTCCCCAGGCTCCCCAGCAGGCAGAAGTATGCAAAGCATGCATCTCAATTAGTCAGCAACCAGGTGTGGAAAGT
CCCCAGGCTCCCCAGCAGGCAGAAGTATGCAAAGCATGCATCTCAATTAGTCAGCAACCATAGTCCCGCCCCTAACT
CCGCCCATCCCGCCCCTAACTCCGCCCAGTTCCGCCCATTCTCCGCCCCATGGCTGACTAATTTTTTTTATTTATGC
AGAGGCCGAGGCCGCCTCTGCCTCTGAGCTATTCCAGAAGTAGTGAGGAGGCTTTTTGGAGGCCTAGGCTTTTGCA
AAAAGCTCCCGGGAGCTTGTATATCCATTTTCGGATCTGATCAAGAGACAGGATGAGGATCGTTTCGCATGATTGAA
CAAGATGGATTGCACGCAGGTTCTCCGGCCGCTTGGGTGGAGAGGCTATTCGGCTATGACTGGGCACAACAGACAAT
CGGCTGCTCTGATGCCGCCGTGTTCCGGCTGTCAGCGCAGGGGCGCCCGGTTCTTTTTGTCAAGACCGACCTGTCCG
GTGCCCTGAATGAACTGCAGGACGAGGCAGCGCGGCTATCGTGGCTGGCCACGACGGGCGTTCCTTGCGCAGCTGTG
CTCGACGTTGTCACTGAAGCGGGAAGGGACTGGCTGCTATTGGGCGAAGTGCCGGGGCAGGATCTCCTGTCATCTCA
CCTTGCTCCTGCCGAGAAAGTATCCATCATGGCTGATGCAATGCGGCGGCTGCATACGCTTGATCCGGCTACCTGCC
CATTCGACCACCAAGCGAAACATCGCATCGAGCGAGCACGTACTCGGATGGAAGCCGGTCTTGTCGATCAGGATGAT
CTGGACGAAGAGCATCAGGGGCTCGCGCCAGCCGAACTGTTCGCCAGGCTCAAGGCGCGCATGCCCGACGGCGAGGA
TCTCGTCGTGACCCATGGCGATGCCTGCTTGCCGAATATCATGGTGGAAAATGGCCGCTTTTCTGGATTCATCGACT
GTGGCCGGCTGGGTGTGGCGGACCGCTATCAGGACATAGCGTTGGCTACCCGTGATATTGCTGAAGAGCTTGGCGGC
GAATGGGCTGACCGCTTCCTCGTGCTTTACGGTATCGCCGCTCCCGATTCGCAGCGCATCGCCTTCTATCGCCTTCT
TGACGAGTTCTTCTGAGCGGGACTCTGGGGTTCGAAATGACCGACCAAGCGACGCCCAACCTGCCATCACGAGATTT
CGATTCCACCGCCGCCTTCTATGAAAGGTTGGGCTTCGGAATCGTTTTCCGGGACGCCGGCTGGATGATCCTCCAGC
GCGGGGATCTCATGCTGGAGTTCTTCGCCCACCCCAACTTGTTTATTGCAGCTTATAATGGTTACAAATAAAGCAAT
AGCATCACAAATTTCACAAATAAAGCATTTTTTTCACTGCATTCTAGTTGTGGTTTGTCCAAACTCATCAATGTATC
TTATCATGTCTGTATACCGTCGACCTCTAGCTAGAGCTTGGCGTAATCATGGTCATAGCTGTTTCCTGTGTGAAATT
GTTATCCGCTCACAATTCCACACAACATACGAGCCGGAAGCATAAAGTGTAAAGCCTGGGGTGCCTAATGAGTGAGC
TAACTCACATTAATTGCGTTGCGCTCACTGCCCGCTTTCCAGTCGGGAAACCTGTCGTGCCAGCTGCATTAATGAAT
CGGCCAACGCGCGGGGAGAGGCGGTTTGCGTATTGGGCGCTCTTCCGCTTCCTCGCTCACTGACTCGCTGCGCTCGG
TCGTTCGGCTGCGGCGAGCGGTATCAGCTCACTCAAAGGCGGTAATACGGTTATCCACAGAATCAGGGGATAACGCA
GGAAAGAACATGTGAGCAAAAGGCCAGCAAAAGGCCAGGAACCGTAAAAAGGCCGCGTTGCTGGCGTTTTTCCATAG
```

-continued

```
GCTCCGCCCCCTGACGAGCATCACAAAAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTCGGTGTAGGTCGTTCGCTC
CAAGCTGGGCTGTGTGCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCGAGGTATGTAGGCGGT
GCTACAGAGTTCTTGAAGTGGTGGCCTAACTACGGCTACACTAGAAGAACAGTATTTGGTATCTGCGCTCTGCTGAA
GCCAGTTACCTTCGGAAAAAGAGTTGGTAGCTCTTGATCCGGCAAACAAACCACCGCTGGTAGCGGTTTTTTTGTTT
GCAAGCAGCAGATTACGCGCAGAAAAAAAGGATCTCAAGAAGATCCTTTGATCTTTTCTACGGGGTCTGACGCTCAG
TGGAACGAAAACTCACGTTAAGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTACCAATGCTTAATCAGTGAGG
CACCTATCTCAGCGATCTGTCTATTTCGTTCATCCATAGTTGCCTGACTCCCCGTCGTGTAGATAACTACGATACGG
GAGGGCTTACCATCTGGCCCCAGTGCTGCAATGATACCGCGAGACCCACGCTCACCGGCTCCAGATTTATCAGCAAT
AAACCAGCCAGCCGGAAGGGCCGAGCGCAGAAGTGGTCCTGCAACTTTATCCGCCTCCATCCAGTCTATTAATTGTT
GCCGGGAAGCTAGAGTAAGTAGTTCGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTAAGTTGGCCGCAGTGTTATCACTCATGG
TTATGGCAGCACTGCATAATTCTCTTACTGTCATGCCATCCGTAAGATGCTTTTCTGTGACTGGTGAGTACTCAACC
AAGTCATTCTGAGAATAGTGTATGCGGCGACCGAGTTGCTCTTGCCCGGCGTCAATACGGGATAATACCGCGCCACA
TAGCAGAACTTTAAAAGTGCTCATCATTGGAAAACGTTCTTCGGGGCGAAAACTCTCAAGGATCTTACCGCTGTTGA
GATCCAGTTCGATGTAACCCACTCGTGCACCCAACTGATCTTCAGCATCTTTTACTTTCACCAGCGTTTCTGGGTGA
GCAAAAACAGGAAGGCAAAATGCCGCAAAAAAGGGAATAAGGGCGACACGGAAATGTTGAATACTCATACTCTTCCT
TTTTCAATATTATTGAAGCATTTATCAGGGTTATTGTCTCATGAGCGGATACATATTTGAATGTATTTAGAAAAATA
AACAAATAGGGGTTCCGCGCACATTTCCCCGAAAAGTGCCACCTGACGTCGACGGATCGGGAGATCTCCCGATCCCC
TATGGTGCACTCTCAGTACAATCTGCTCTGATGCCGCATAGTTAAGCCAGTATCTGCTCCCTGCTTGTGTGTTGGAG
GTCGCTGAGTAGTGCGCGAGCAAAATTTAAGCTACAACAAGGCAAGGCTTGACCGACAATTGCATGAAGAATCTGCT
TAGGGTTAGGCGTTTTGCGCTGCTTCGCGATGTACGGGCCAGATATACGC.
```

The plasmid that codes for SEQ ID NO: 11 has an identity (SEQ ID NO: 23)
```
GTTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCAT
TATGCCCAGTACATGACCTTATGGGACTTTCCTACTTGGCAGTACATCTACGTATTAGTCATCGCTATTACCATGGT
GATGCGGTTTTGGCAGTACATCAATGGGCGTGGATAGCGGTTTGACTCACGGGGATTTCCAAGTCTCCACCCCATTG
ACGTCAATGGGAGTTTGTTTTGGCACCAAAATCAACGGGACTTTCCAAAATGTCGTAACAACTCCGCCCCATTGACG
CAAATGGGCGGTAGGCGTGTACGGTGGGAGGTCTATATAAGCAGAGCTCTCTGGCTAACTAGAGAACCCACTGCTTA
CTGGCTTATCGAAATTAATACGACTCACTATAGGGAGACCCAAGCTGGCTAGCGCCACCATGGACTACAAAGACCAT
GACGGTGATTATAAAGATCATGACATCGATTACAAGGATGACGATGACAAGATGGCCCCCAAGAAGAAGAGGAAGGT
GGGCATTCACCGCGGGGTACCTATGGTGGACTTGAGGACACTCGGTTATTCGCAACAGCAACAGGAGAAAATCAAGC
CTAAGGTCAGGAGCACCGTCGCGCAACACCACGAGGCGCTTGTGGGGCATGGCTTCACTCATGCGCATATTGTCGCG
```

-continued

```
CTTTCACAGCACCCTGCGGCGCTTGGGACGGTGGCTGTCAAATACCAAGATATGATTGCGGCCCTGCCCGAAGCCAC
GCACGAGGCAATTGTAGGGGTCGGTAAACAGTGGTCGGGAGCGCGAGCACTTGAGGCGCTGCTGACTGTGGCGGGTG
AGCTTAGGGGGCCTCCGCTCCAGCTCGACACCGGGCAGCTGCTGAAGATCGCGAAGAGAGGGGGAGTAACAGCGGTA
GAGGCAGTGCACGCCTGGCGCAATGCGCTCACCGGTGCCCCCCTGAACCTGACCCCGGACCAAGTGGTGGCTATCGC
CAGCCACGATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACATTGGCGGCAAGCAAGCGCTCGAAACGGTGCAGCGGCTGTTGCCG
GTGCTGTGCCAGGACCATGGCCTGACTCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACTCCGGACCAAGTGGTGGCTATCGCCA
GCCACGATGGCGGCAAGCAAGCGCTCGAAACGGTGCAGCGGCTGTTGCCGGTGCTGTGCCAGGACCATGGCCTGACC
CCGGACCAAGTGGTGGCTATCGCCAGCAACGGTGGCGGCAAGCAAGCGCTCGAAACGGTGCAGCGGCTGTTGCCGGT
GCTGTGCCAGGACCATGGCCTGACCCCGGACCAAGTGGTGGCTATCGCCAGCAACGGTGGCGGCAAGCAAGCGCTCG
AAACGGTGCAGCGGCTGTTGCCGGTGCTGTGCCAGGACCATGGCCTGACCCCGGACCAAGTGGTGGCTATCGCCAGC
AACAATGGCGGCAAGCAAGCGCTCGAAACGGTGCAGCGGCTGTTGCCGGTGCTGTGCCAGGACCATGGCCTGACTCC
GGACCAAGTGGTGGCTATCGCCAGCCACGATGGCGGCAAGCAAGCGCTCGAAACGGTGCAGCGGCTGTTGCCGGTGC
TGTGCCAGGACCATGGCCTGACTCCGGACCAAGTGGTGGCTATCGCCAGCCACGATGGCGGCAAGCAAGCGCTCGAA
ACGGTGCAGCGGCTGTTGCCGGTGCTGTGCCAGGACCATGGCCTGACTCCGGACCAAGTGGTGGCTATCGCCAGCCA
CGATGGCGGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCCGGTGCTG
TGCCAGGACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACTCCGGACCAAGTGGTGGCTATCGCCAGCCACG
ATGGCGGCAAGCAAGCGCTCGAAACGGTGCAGCGGCTGTTGCCGGTGCTGTGCCAGGACCATGGCCTGACCCCGGAC
CAAGTGGTGGCTATCGCCAGCAACATTGGCGGCAAGCAAGCGCTCGAAACGGTGCAGCGGCTGTTGCCGGTGCTGTG
CCAGGACCATGGCCTGACCCCGGACCAAGTGGTGGCTATCGCCAGCAACAATGGCGGCAAGCAAGCGCTCGAAACGG
TGCAGCGGCTGTTGCCGGTGCTGTGCCAGGACCATGGCCTGACCCCGGACCAAGTGGTGGCTATCGCCAGCAACAAT
GGCGGCAAGCAAGCGCTCGAAACGGTGCAGCGGCTGTTGCCGGTGCTGTGCCAGGACCATGGCCTGACCCCGGACCA
AGTGGTGGCTATCGCCAGCAACAATGGCGGCAAGCAAGCGCTCGAAACGGTGCAGCGGCTGTTGCCGGTGCTGTGCC
AGGACCATGGCCTGACTCCGGACCAAGTGGTGGCTATCGCCAGCCACGATGGCGGCAAGCAAGCGCTCGAAACGGTG
CAGCGGCTGTTGCCGGTGCTGTGCCAGGACCATGGCCTGACCCCGGACCAAGTGGTGGCTATCGCCAGCAACATTGG
CGGCAAGCAAGCGCTCGAAACGGTGCAGCGGCTGTTGCCGGTGCTGTGCCAGGACCATGGCCTGACCCCGGACCAAG
TGGTGGCTATCGCCAGCAACAATGGCGGCAAGCAAGCGCTCGAAACGGTGCAGCGGCTGTTGCCGGTGCTGTGCCAG
GACCATGGCCTGACCCCGGACCAAGTGGTGGCTATCGCCAGCAACGGTGGCGGCAAGCAAGCGCTCGAAAGCATTGT
GGCCCAGCTGAGCCGGCCTGATCCGGCGTTGGCCGCGTTGACCAACGACCATCTGGTGGCGTTGGCATGTCTTGGTG
GACGACCCGCGCTCGATGCAGTCAAAAAGGGTCTGCCTCATGCTCCCGCATTGATCAAAAGAACCAACCGGCGGATT
CCCGAGAGAACTTCCCATCGAGTCGCGGGATCCCAGCTGGTGAAGAGCGAGCTGGAGGAGAAGAAGTCCGAGCTGCG
GCACAAGCTGAAGTACGTGCCCCACGAGTACATCGAGCTGATCGAGATCGCCAGGAACAGCACCCAGGACCGCATCC
TGGAGATGAAGGTGATGGAGTTCTTCATGAAGGTGTACGGCTACAGGGGAAAGCACCTGGGCGGAAGCAGAAAGCCT
GACGGCGCCATCTATACAGTGGGCAGCCCCATCGATTACGGCGTGATCGTGGACACAAAGGCCTACAGCGGCGGCTA
CAATCTGCCTATCGGCCAGGCCGACGAGATGCAGAGATACGTGGAGGAGAACCAGACCCGGAATAAGCACATCAACC
CCAACGAGTGGTGGAAGGTGTACCCTAGCAGCGTGACCGAGTTCAAGTTCCTGTTCGTGAGCGGCCACTTCAAGGGC
AACTACAAGGCCCAGCTGACCAGGCTGAACCACATCACCAACTGCAATGGCGCCGTGCTGAGCGTGGAGGAGCTGCT
GATCGGCGGCGAGATGATCAAAGCCGGCACCCTGACACTGGAGGAGGTGCGGCGCAAGTTCAACAACGGCGAGATCA
```

-continued

```
ACTTCTGATAACTTAAGTTTAAACCGCTGATCAGCCTCGACTGTGCCTTCTAGTTGCCAGCCATCTGTTGTTTGCCC
CTCCCCCGTGCCTTCCTTGACCCTGGAAGGTGCCACTCCCACTGTCCTTTCCTAATAAAATGAGGAAATTGCATCGC
ATTGTCTGAGTAGGTGTCATTCTATTCTGGGGGGTGGGGTGGGGCAGGACAGCAAGGGGGAGGATTGGGAAGACAAT
AGCAGGCATGCTGGGGATGCGGTGGGCTCTATGGCTTCTGAGGCGGAAAGAACCAGCTGGGGCTCTAGGGGGTATCC
CCACGCGCCCTGTAGCGGCGCATTAAGCGCGGCGGGTGTGGTGGTTACGCGCAGCGTGACCGCTACACTTGCCAGCG
CCCTAGCGCCCGCTCCTTTCGCTTTCTTCCCTTCCTTTCTCGCCACGTTCGCCGGCTTTCCCCGTCAAGCTCTAAAT
CGGGGGCTCCCTTTAGGGTTCCGATTTAGTGCTTTACGGCACCTCGACCCCAAAAAACTTGATTAGGGTGATGGTTC
ACGTAGTGGGCCATCGCCCTGATAGACGGTTTTTCGCCCTTTGACGTTGGAGTCCACGTTCTTTAATAGTGGACTCT
TGTTCCAAACTGGAACAACACTCAACCCTATCTCGGTCTATTCTTTTGATTTATAAGGGATTTTGCCGATTTCGGCC
TATTGGTTAAAAAATGAGCTGATTTAACAAAAATTTAACGCGAATTAATTCTGTGGAATGTGTGTCAGTTAGGGTGT
GGAAAGTCCCCAGGCTCCCCAGCAGGCAGAAGTATGCAAAGCATGCATCTCAATTAGTCAGCAACCAGGTGTGGAAA
GTCCCCAGGCTCCCCAGCAGGCAGAAGTATGCAAAGCATGCATCTCAATTAGTCAGCAACCATAGTCCCGCCCCTAA
CTCCGCCCATCCCGCCCCTAACTCCGCCCAGTTCCGCCCATTCTCCGCCCCATGGCTGACTAATTTTTTTATTTAT
GCAGAGGCCGAGGCCGCCTCTGCCTCTGAGCTATTCCAGAAGTAGTGAGGAGGCTTTTTTGGAGGCCTAGGCTTTTG
CAAAAAGCTCCCGGGAGCTTGTATATCCATTTTCGGATCTGATCAAGAGACAGGATGAGGATCGTTTCGCATGATTG
AACAAGATGGATTGCACGCAGGTTCTCCGGCCGCTTGGGTGGAGAGGCTATTCGGCTATGACTGGGCACAACAGACA
ATCGGCTGCTCTGATGCCGCCGTGTTCCGGCTGTCAGCGCAGGGGCGCCCGGTTCTTTTTGTCAAGACCGACCTGTC
CGGTGCCCTGAATGAACTGCAGGACGAGGCAGCGCGGCTATCGTGGCTGGCCACGACGGGCGTTCCTTGCGCAGCTG
TGCTCGACGTTGTCACTGAAGCGGGAAGGGACTGGCTGCTATTGGGCGAAGTGCCGGGGCAGGATCTCCTGTCATCT
CACCTTGCTCCTGCCGAGAAAGTATCCATCATGGCTGATGCAATGCGGCGGCTGCATACGCTTGATCCGGCTACCTG
CCCATTCGACCACCAAGCGAAACATCGCATCGAGCGAGCACGTACTCGGATGGAAGCCGGTCTTGTCGATCAGGATG
ATCTGGACGAAGAGCATCAGGGGCTCGCGCCAGCCGAACTGTTCGCCAGGCTCAAGGCGCGCATGCCCGACGGCGAG
GATCTCGTCGTGACCCATGGCGATGCCTGCTTGCCGAATATCATGGTGGAAAATGGCCGCTTTTCTGGATTCATCGA
CTGTGGCCGGCTGGGTGTGGCGGACCGCTATCAGGACATAGCGTTGGCTACCCGTGATATTGCTGAAGAGCTTGGCG
GCGAATGGGCTGACCGCTTCCTCGTGCTTTACGGTATCGCCGCTCCCGATTCGCAGCGCATCGCCTTCTATCGCCTT
CTTGACGAGTTCTTCTGAGCGGGACTCTGGGGTTCGAAATGACCGACCAAGCGACGCCCAACCTGCCATCACGAGAT
TTCGATTCCACCGCCGCCTTCTATGAAAGGTTGGGCTTCGGAATCGTTTTCCGGGACGCCGGCTGGATGATCCTCCA
GCGCGGGGATCTCATGCTGGAGTTCTTCGCCCACCCCAACTTGTTTATTGCAGCTTATAATGGTTACAAATAAAGCA
ATAGCATCACAAATTTCACAAATAAAGCATTTTTTTCACTGCATTCTAGTTGTGGTTTGTCCAAACTCATCAATGTA
TCTTATCATGTCTGTATACCGTCGACCTCTAGCTAGAGCTTGGCGTAATCATGGTCATAGCTGTTTCCTGTGTGAAA
TTGTTATCCGCTCACAATTCCACACAACATACGAGCCGGAAGCATAAAGTGTAAAGCCTGGGGTGCCTAATGAGTGA
GCTAACTCACATTAATTGCGTTGCGCTCACTGCCCGCTTTCCAGTCGGGAAACCTGTCGTGCCAGCTGCATTAATGA
ATCGGCCAACGCGCGGGGAGAGGCGGTTTGCGTATTGGGCGCTCTTCCGCTTCCTCGCTCACTGACTCGCTGCGCTC
GGTCGTTCGGCTGCGGCGAGCGGTATCAGCTCACTCAAAGGCGGTAATACGGTTATCCACAGAATCAGGGGATAACG
CAGGAAAGAACATGTGAGCAAAAGGCCAGCAAAAGGCCAGGAACCGTAAAAAGGCCGCGTTGCTGGCGTTTTTCCAT
AGGCTCCGCCCCCCTGACGAGCATCACAAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAACTATCGTCTTGAGTC
CAACCCGGTAAGACACGACTTATCGCCACTGGCAGCAGCCACTGGTAACAGGATTAGCAGAGCGAGGTATGTAGGCG
```

-continued

```
GTGCTACAGAGTTCTTGAAGTGGTGGCCTAACTACGGCTACACTAGAAGAACAGTATTTGGTATCTGCGCTCTGCTG

AAGCCAGTTACCTTCGGAAAAAGAGTTGGTAGCTCTTGATCCGGCAAACAAACCACCGCTGGTAGCGGTTTTTTTGT

TTGCAAGCAGCAGATTACGCGCAGAAAAAAGGATCTCAAGAAGATCCTTTGATCTTTTCTACGGGGTCTGACGCTC

AGTGGAACGAAAACTCACGTTAAGGGATTTTGGTCATGAGATTATCAAAAAGGATCTTCACCTAGATCCTTTTAAAT

TAAAAATGAAGTTTTAAATCAATCTAAAGTATATATGAGTAAACTTGGTCTGACAGTTACCAATGCTTAATCAGTGA

GGCACCTATCTCAGCGATCTGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACGTTGTTGCCATTGCTACAGGCATCGTGG

TGTCACGCTCGTCGTTTGGTATGGCTTCATTCAGCTCCGGTTCCCAACGATCAAGGCGAGTTACATGATCCCCCATG

TTGTGCAAAAAAGCGGTTAGCTCCTTCGGTCCTCCGATCGTTGTCAGAAGTAAGTTGGCCGCAGTGTTATCACTCAT

GGTTATGGCAGCACTGCATAATTCTCTTACTGTCATGCCATCCGTAAGATGCTTTTCTGTGACTGGTGAGTACTCAA

CCAAGTCATTCTGAGAATAGTGTATGCGGCGACCGAGTTGCTCTTGCCCGGCGTCAATACGGGATAATACCGCGCCA

CATAGCAGAACTTTAAAAGTGCTCATCATTGGAAAACGTTCTTCGGGGCGAAAACTCTCAAGGATCTTACCGCTGTT

GAGATCCAGTTCGATGTAACCCACTCGTGCACCCAACTGATCTTCAGCATCTTTTACTTTCACCAGCGTTTCTGGGT

GAGCAAAAACAGGAAGGCAAAATGCCGCAAAAAAGGGAATAAGGGCGACACGGAAATGTTGAATACTCATACTCTTC

CTTTTTCAATATTATTGAAGCATTTATCAGGGTTATTGTCTCATGAGCGGATACATATTTGAATGTATTTAGAAAAA

TAAACAAATAGGGGTTCCGCGCACATTTCCCCGAAAAGTGCCACCTGACGTCGACGGATCGGGAGATCTCCCGATCC

CCTATGGTGCACTCTCAGTACAATCTGCTCTGATGCCGCATAGTTAAGCCAGTATCTGCTCCCTGCTTGTGTGTTGG

AGGTCGCTGAGTAGTGCGCGAGCAAAATTTAAGCTACAACAAGGCAAGGCTTGACCGACAATTGCATGAAGAATCTG

CTTAGGGTTAGGCGTTTTGCGCTGCTTCGCGATGTACGGGCCAGATATACGC.
```

The plasmid that codes for SEQ ID NO: 12 has an identity (SEQ ID NO: 24)
```
GTTGACATTGATTATTGACTAGTTATTAATAGTAATCAATTACGGGGTCATTAGTTCATAGCCCATATATGGAGTTC

CGCGTTACATAACTTACGGTAAATGGCCCGCCTGGCTGACCGCCCAACGACCCCCGCCCATTGACGTCAATAATGAC

GTATGTTCCCATAGTAACGCCAATAGGGACTTTCCATTGACGTCAATGGGTGGAGTATTTACGGTAAACTGCCCACT

TGGCAGTACATCAAGTGTATCATATGCCAAGTACGCCCCCTATTGACGTCAATGACGGTAAATGGCCCGCCTGGCAT

TATGCCCAGTACATGACCTTATGGGACTTTCCTACTTGGCAGTACATCTACGTATTAGTCATCGCTATTACCATGGT

GATGCGGTTTTGGCAGTACATCAATGGGCGTGGATAGCGGTTTGACTCACGGGGATTTCCAAGTCTCCACCCCATTG

ACGTCAATGGGAGTTTGTTTTGGCACCAAAATCAACGGGACTTTCCAAAATGTCGTAACAACTCCGCCCCATTGACG

CAAATGGGCGGTAGGCGTGTACGGTGGGAGGTCTATATAAGCAGAGCTCTCTGGCTAACTAGAGAACCCACTGCTTA

CTGGCTTATCGAAATTAATACGACTCACTATAGGGAGACCCAAGCTGGCTAGCGCCACCATGGACTACAAAGACCAT

GACGGTGATTATAAAGATCATGACATCGATTACAAGGATGACGATGACAAGATGGCCCCCAAGAAGAAGAGGAAGGT

GGGCATTCACCGCGGGTACCTATGGTGGACTTGAGGACACTCGGTTATTCGCAACAGCAACAGGAGAAAATCAAGC

CTAAGGTCAGGAGCACCGTCGCGCAACACCACGAGGCGCTTGTGGGCATGGCTTCACTCATGCGCATATTGTCGCG

CTTTCACAGCACCCTGCGGCGCTTGGGACGGTGGCTGTCAAATACCAAGATATGATTGCGGCCCTGCCCGAAGCCAC

GCACGAGGCAATTGTAGGGGTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAGAGGGGGAGTAACAGCGGTA

GAGGCAGTGCACGCCTGGCGCAATGCGCTCACCGGTGCCCCCCTGAACCTGACCCCGGACCAAGTGGTGGCTATCGC

CAGCCACGATGGCGGCAAGCAAGCGCTCGAAACGGTGCAGCGGCTGTTGCCGGTGCTGTGCCAGGACCATGGCCTGA
```

-continued

```
CCCCGGACCAAGTGGTGGCTATCGCCAGCAACATTGGCGGCAAGCAAGCGCTCGAAACGGTGCAGCGGCTGTTGCCG
GTGCTGTGCCAGGACCATGGCCTGACTCCGGACCAAGTGGTGGCTATCGCCAGCCACGATGGCGGCAAGCAAGCGCT
CGAAACGGTGCAGCGGCTGTTGCCGGTGCTGTGCCAGGACCATGGCCTGACTCCGGACCAAGTGGTGGCTATCGCCA
GCCACGATGGCGGCAAGCAAGCGCTCGAAACGGTGCAGCGGCTGTTGCCGGTGCTGTGCCAGGACCATGGCCTGACC
CCGGACCAAGTGGTGGCTATCGCCAGCAACGGTGGCGGCAAGCAAGCGCTCGAAACGGTGCAGCGGCTGTTGCCGGT
GCTGTGCCAGGACCATGGCCTGACCCCGGACCAAGTGGTGGCTATCGCCAGCAACGGTGGCGGCAAGCAAGCGCTCG
AAACGGTGCAGCGGCTGTTGCCGGTGCTGTGCCAGGACCATGGCCTGACCCCGGACCAAGTGGTGGCTATCGCCAGC
AACAATGGCGGCAAGCAAGCGCTCGAAACGGTGCAGCGGCTGTTGCCGGTGCTGTGCCAGGACCATGGCCTGACTCC
GGACCAAGTGGTGGCTATCGCCAGCCACGATGGCGGCAAGCAAGCGCTCGAAACGGTGCAGCGGCTGTTGCCGGTGC
TGTGCCAGGACCATGGCCTGACTCCGGACCAAGTGGTGGCTATCGCCAGCCACGATGGCGGCAAGCAAGCGCTCGAA
ACGGTGCAGCGGCTGTTGCCGGTGCTGTGCCAGGACCATGGCCTGACTCCGGACCAAGTGGTGGCTATCGCCAGCCA
CGATGGCGGCAAGCAAGCGCTCGAAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGGTGCAGCGGCTGTTGCCGGTGCTG
TGCCAGGACCATGGCCTGACCCCGGACCAAGTGGTGGCTATCGCCAGCAACATTGGCGGCAAGCAAGCGCTCGAAAC
GGTGCAGCGGCTGTTGCCGGTGCTGTGCCAGGACCATGGCCTGACTCCGGACCAAGTGGTGGCTATCGCCAGCCACG
ATGGCGGCAAGCAAGCGCTCGAAACGGTGCAGCGGCTGTTGCCGGTGCTGTGCCAGGACCATGGCCTGACCCCGGAC
CAAGTGGTGGCTATCGCCAGCAACATTGGCGGCAAGCAAGCGCTCGAAACGGTGCAGCGGCTGTTGCCGGTGCTGTG
CCAGGACCATGGCCTGACCCCGGACCAAGTGGTGGCTATCGCCAGCAACAATGGCGGCAAGCAAGCGCTCGAAACGG
TGCAGCGGCTGTTGCCGGTGCTGTGCCAGGACCATGGCCTGACCCCGGACCAAGTGGTGGCTATCGCCAGCAACAAT
GGCGGCAAGCAAGCGCTCGAAACGGTGCAGCGGCTGTTGCCGGTGCTGTGCCAGGACCATGGCCTGACCCCGGACCA
AGTGGTGGCTATCGCCAGCAACAATGGCGGCAAGCAAGCGCTCGAAACGGTGCAGCGGCTGTTGCCGGTGCTGTGCC
AGGACCATGGCCTGACTCCGGACCAAGTGGTGGCTATCGCCAGCCACGATGGCGGCAAGCAAGCGCTCGAAACGGTG
CAGCGGCTGTTGCCGGTGCTGTGCCAGGACCATGGCCTGACCCCGGACCAAGTGGTGGCTATCGCCAGCAACATTGG
CGGCAAGCAAGCGCTCGAAACGGTGCAGCGGCTGTTGCCGGTGCTGTGCCAGGACCATGGCCTGACCCCGGACCAAG
TGGTGGCTATCGCCAGCAACAATGGCGGCAAGCAAGCGCTCGAAACGGTGCAGCGGCTGTTGCCGGTGCTGTGCCAG
GACCATGGCCTGACCCCGGACCAAGTGGTGGCTATCGCCAGCAACGGTGGCGGCAAGCAAGCGCTCGAAACGGTGCA
GCGGCTGTTGCCGGTGCTGTGCCAGGACCATGGCCTGACCCCGGACCAAGTGGTGGCTATCGCCAGCAACATTGGCG
GCAAGCAAGCGCTCGAAACGGTGCAGCGGCTGTTGCCGGTGCTGTGCCAGGACCATGGCCTGACCCCGGACCAAGTG
GTGGCTATCGCCAGCAACATTGGCGGCAAGCAAGCGCTCGAAACGGTGCAGCGGCTGTTGCCGGTGCTGTGCCAGGA
CCATGGCCTGACCCCGGACCAAGTGGTGGCTATCGCCAGCCACGATGGCGGCAAGCAAGCGCTCGAAAGCATTGTGG
CCCAGCTGAGCCGGCCTGATCCGGCGTTGGCCGCGTTGACCAACGACCATCTGGTGGCGTTGGCATGTCTTGGTGGA
CGACCCGCGCTCGATGCAGTCAAAAAGGGTCTGCCTCATGCTCCCGCATTGATCAAAAGAACCAACCGGCGGATTCC
CGAGAGAACTTCCCATCGAGTCGCGGGATCCCAGCTGGTGAAGAGCGAGCTGGAGGAGAAGAAGTCCGAGCTGCGGC
ACAAGCTGAAGTACGTGCCCCACGAGTACATCGAGCTGATCGAGATCGCCAGGAACAGCACCCAGGACCGCATCCTG
GAGATGAAGGTGATGGAGTTCTTCATGAAGGTGTACGGCTACAGGGGAAAGCACCTGGGCGGAAGCAGAAAGCCTGA
CGGCGCCATCTATACAGTGGGCAGCCCCATCGATTACGGCGTGATCGTGGACACAAAGGCCTACAGCGGCGGCTACA
ATCTGCCTATCGGCCAGGCCGACGAGATGCAGAGATACGTGGAGGAGAACCAGACCCGGAATAAGCACATCAACCCC
AACGAGTGGTGGAAGGTGTACCCTAGCAGCGTGACCGAGTTCAAGTTCCTGTTCGTGAGCGGCCACTTCAAGGGCAA
CTACAAGGCCCAGCTGACCAGGCTGAACCACATCACCAACTGCAATGGCGCCGTGCTGAGCGTGGAGGAGCTGCTGA
TCGGCGGCGAGATGATCAAAGCCGGCACCCTGACACTGGAGGAGGTGCGGCGCAAGTTCAACAACGGCGAGATCAAC
TTCTGATAACTTAAGTTTAAACCGCTGATCAGCCTCGACTGTGCCTTCTAGTTGCCAGCCATCTGTTGTTTGCCCCT
```

-continued

```
CCCCCGTGCCTTCCTTGACCCTGGAAGGTGCCACTCCCACTGTCCTTTCCTAATAAAATGAGGAAATTGCATCGCAT

TGTCTGAGTAGGTGTCATTCTATTCTGGGGGTGGGGTGGGGCAGGACAGCAAGGGGAGGATTGGGAAGACAATAG

CAGGCATGCTGGGGATGCGGTGGGCTCTATGGCTTCTGAGGCGGAAAGAACCAGCTGGGGCTCTAGGGGGTATCCCC

ACGCGCCCTGTAGCGGCGCATTAAGCGCGGCGGGTGTGGTGGTTACGCGCAGCGTGACCGCTACACTTGCCAGCGCC

CTAGCGCCCGCTCCTTTCGCTTTCTTCCCTTCCTTTCTCGCCACGTTCGCCGGCTTTCCCCGTCAAGCTCTAAATCG

GGGGCTCCCTTTAGGGTTCCGATTTAGTGCTTTACGGCACCTCGACCCCAAAAAACTTGATTAGGGTGATGGTTCAC

GTAGTGGGCCATCGCCCTGATAGACGGTTTTTCGCCCTTTGACGTTGGAGTCCACGTTCTTTAATAGTGGACTCTTG

TTCCAAACTGGAACAACACTCAACCCTATCTCGGTCTATTCTTTTGATTTATAAGGGATTTTGCCGATTTCGGCCTA

TTGGTTAAAAAATGAGCTGATTTAACAAAAATTTAACGCGAATTAATTCTGTGGAATGTGTGTCAGTTAGGGTGTGG

AAAGTCCCCAGGCTCCCCAGCAGGCAGAAGTATGCAAAGCATGCATCTCAATTAGTCAGCAACCAGGTGTGGAAAGT

CCCCAGGCTCCCCAGCAGGCAGAAGTATGCAAAGCATGCATCTCAATTAGTCAGCAACCATAGTCCCGCCCCTAACT

CCGCCCATCCCGCCCCTAACTCCGCCCAGTTCCGCCCATTCTCCGCCCCATGGCTGACTAATTTTTTTTATTTATGC

AGAGGCCGAGGCCGCCTCTGCCTCTGAGCTATTCCAGAAGTAGTGAGGAGGCTTTTTGGAGGCCTAGGCTTTTGCA

AAAAGCTCCCGGGAGCTTGTATATCCATTTTCGGATCTGATCAAGAGACAGGATGAGGATCGTTTCGCATGATTGAA

CAAGATGGATTGCACGCAGGTTCTCCGGCCGCTTGGGTGGAGAGGCTATTCGGCTATGACTGGGCACAACAGACAAT

CGGCTGCTCTGATGCCGCCGTGTTCCGGCTGTCAGCGCAGGGGCGCCCGGTTCTTTTTGTCAAGACCGACCTGTCCG

GTGCCCTGAATGAACTGCAGGACGAGGCAGCGCGGCTATCGTGGCTGGCCACGACGGGCGTTCCTTGCGCAGCTGTG

CTCGACGTTGTCACTGAAGCGGGAAGGGACTGGCTGCTATTGGGCGAAGTGCCGGGGCAGGATCTCCTGTCATCTCA

CCTTGCTCCTGCCGAGAAAGTATCCATCATGGCTGATGCAATGCGGCGGCTGCATACGCTTGATCCGGCTACCTGCC

CATTCGACCACCAAGCGAAACATCGCATCGAGCGAGCACGTACTCGGATGGAAGCCGGTCTTGTCGATCAGGATGAT

CTGGACGAAGAGCATCAGGGGCTCGCGCCAGCCGAACTGTTCGCCAGGCTCAAGGCGCGCATGCCCGACGGCGAGGA

TCTCGTCGTGACCCATGGCGATGCCTGCTTGCCGAATATCATGGTGGAAAATGGCCGCTTTTCTGGATTCATCGACT

GTGGCCGGCTGGGTGTGGCGGACCGCTATCAGGACATAGCGTTGGCTACCCGTGATATTGCTGAAGAGCTTGGCGGC

GAATGGGCTGACCGCTTCCTCGTGCTTTACGGTATCGCCGCTCCCGATTCGCAGCGCATCGCCTTCTATCGCCTTCT

TGACGAGTTCTTCTGAGCGGGACTCTGGGGTTCGAAATGACCGACCAAGCGACGCCCAACCTGCCATCACGAGATTT

CGATTCCACCGCCGCCTTCTATGAAAGGTTGGGCTTCGGAATCGTTTTCCGGGACGCCGGCTGGATGATCCTCCAGC

GCGGGGATCTCATGCTGGAGTTCTTCGCCCACCCCAACTTGTTTATTGCAGCTTATAATGGTTACAAATAAAGCAAT

AGCATCACAAATTTCACAAATAAAGCATTTTTTTCACTGCATTCTAGTTGTGGTTTGTCCAAACTCATCAATGTATC

TTATCATGTCTGTATACCGTCGACCTCTAGCTAGAGCTTGGCGTAATCATGGTCATAGCTGTTTCCTGTGTGAAATT

GTTATCCGCTCACAATTCCACACAACATACGAGCCGGAAGCATAAAGTGTAAAGCCTGGGGTGCCTAATGAGTGAGC

TAACTCACATTAATTGCGTTGCGCTCACTGCCCGCTTTCCAGTCGGGAAACCGTCGTGCCAGCTGCATTAATGAAT

CGGCCAACGCGCGGGAGAGGCGGTTTGCGTATTGGGCGCTCTTCCGCTTCCTCGCTCACTGACTCGCTGCGCTCGG

TCGTTCGGCTGCGGCGAGCGGTATCAGCTCACTCAAAGGCGGTAATACGGTTATCCACAGAATCAGGGGATAACGCA

GGAAAGAACATGTGAGCAAAAGGCCAGCAAAAGGCCAGGAACCGTAAAAAGGCCGCGTTGCTGGCGTTTTTCCATAG

GCTCCGCCCCCTGACGAGCATCACAAAAATCGACGCTCAAGTCAGAGGTGGCGAAACCCGACAGGACTATAAAGAT

ACCAGGCGTTTCCCCCTGGAAGCTCCCTCGTGCGCTCTCCTGTTCCGACCCTGCCGCTTACCGGATACCTGTCCGCC

TTTCTCCCTTCGGGAAGCGTGGCGCTTTCTCATAGCTCACGCTGTAGGTATCTCAGTTCGGTGTAGGTCGTTCGCTC

CAAGCTGGGCTGTGTGCACGAACCCCCCGTTCAGCCCGACCGCTGCGCCTTATCCGGTAACTATCGTCTTGAGTCCA

ACCCGGTAAGACACGACTTATCGCCACTGGCAGCAGCCACTGGTAACAGGATTAGCAGAGCGAGGTATGTAGGCGGT

GCTACAGAGTTCTTGAAGTGGTGGCCTAACTACGGCTACACTAGAAGAACAGTATTTGGTATCTGCGCTCTGCTGAA
```

-continued

```
GCCAGTTACCTTCGGAAAAAGAGTTGGTAGCTCTTGATCCGGCAAACAAACCACCGCTGGTAGCGGTTTTTTGTTT

GCAAGCAGCAGATTACGCGCAGAAAAAAAGGATCTCAAGAAGATCCTTTGATCTTTTCTACGGGGTCTGACGCTCAG

TGGAACGAAAACTCACGTTAAGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTACCAATGCTTAATCAGTGAGG

CACCTATCTCAGCGATCTGTCTATTTCGTTCATCCATAGTTGCCTGACTCCCCGTCGTGTAGATAACTACGATACGG

GAGGGCTTACCATCTGGCCCCAGTGCTGCAATGATACCGCGAGACCCACGCTCACCGGCTCCAGATTTATCAGCAAT

AAACCAGCCAGCCGGAAGGGCCGAGCGCAGAAGTGGTCCTGCAACTTTATCCGCCTCCATCCAGTCTATTAATTGTT

GCCGGGAAGCTAGAGTAAGTAGTTCGCCAGTTAATAGTTTGCGCAACGTTGTTGCCATTGCTACAGGCATCGTGGTG

TCACGCTCGTCGTTTGGTATGGCTTCATTCAGCTCCGGTTCCCAACGATCAAGGCGAGTTACATGATCCCCCATGTT

GTGCAAAAAAGCGGTTAGCTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTGACTGGTGAGTACTCAACC

AAGTCATTCTGAGAATAGTGTATGCGGCGACCGAGTTGCTCTTGCCCGGCGTCAATACGGGATAATACCGCGCCACA

TAGCAGAACTTTAAAAGTGCTCAT+32TGGAAAACGTTCTTCGGGGCGAAAACTCTCAAGGATCTTACCGCTGTTGA

GATCCAGTTCGATGTAACCCACTCGTGCACCCAACTGATCTTCAGCATCTTTTACTTTCACCAGCGTTTCTGGGTGA

GCAAAAACAGGAAGGCAAAATGCCGCAAAAAAGGGAATAAGGGCGACACGGAAATGTTGAATACTCATACTCTTCCT

TTTTCAATATTATTGAAGCATTTATCAGGGTTATTGTCTCATGAGCGGATACATATTTGAATGTATTTAGAAAAATA

AACAAATAGGGGTTCCGCGCACATTTCCCCGAAAAGTGCCACCTGACGTCGACGGATCGGGAGATCTCCCGATCCCC

TATGGTGCACTCTCAGTACAATCTGCTCTGATGCCGCATAGTTAAGCCAGTATCTGCTCCCTGCTTGTGTGTTGGAG

GTCGCTGAGTAGTGCGCGAGCAAAATTTAAGCTACAACAAGGCAAGGCTTGACCGACAATTGCATGAAGAATCTGCT

TAGGGTTAGGCGTTTTGCGCTGCTTCGCGATGTACGGGCCAGATATACGC.
```

138 of the most highly ranked genomic loci were interrogated for off-target activity. Off-target activity was observed in 13 cases, 9 of which were outside the globin gene family. Table 6 provides a summary of the results. While NN TALENs imparted higher activity than NK TALENs, in agreement with previous reports, NN-TALENs had higher off-target cleavage activity than the corresponding NK-TALENs. This study was the first to uncover off-target cleavage for NK-TALENs, as well as TALEN off-target cleavage at sites lacking a 5' pyrimidine, and at a site with a spacer longer than 24 bp. For ZFNs, the 4F-ZFNs had no significant off-target cleavage at any of the sites interrogated while having higher on-target activity than the corresponding 3F-ZFNs, which had off-target cleavage at five sites. The rankings provided good agreement with the modification frequency observed in the 293T Cell line.

The methods provided a user-friendly, web-based tool for rapid identification of potential nuclease off-target cleavage sites that can be further confirmed using standard molecular biology techniques. The bioinformatics-based ranking algorithms can identify potential nuclease off-target cleavage sites with a success rate comparable to existing experimental methods. This novel approach could serve as a screening tool for selecting nuclease binding sites that give both high on-target cleavage and low (or no) off-target activity, as well as allowing the selection of the optimal architecture and type of nuclease. The algorithms are flexible and can be readily modified to incorporate additional search criteria as they become available.

TABLE 6

SMRT Sequencing confirms on -target and off-target activity at site ranked by PROGNOS

| Nucleases | Closest Gene | Match Type | Mutations per half-site (+) | Mutations per half-site (−) | (+) half-site | (−) half-site | Computed Rankings H | Computed Rankings RK | Computed Rankings RN | 293T Cell Line Modification Frequency RVD Targeting Guanosine NK | 293T Cell Line Modification Frequency RVD Targeting Guanosine NN |
|---|---|---|---|---|---|---|---|---|---|---|---|
| TALENs | | | | | | | | | | | |
| S2/S5 TALENs | HBB | L-16-R | 0 | 1 | TCACCTTGCCCCACAGGGCAGT | tCAGGAGTCAGGTGCA | 1 | 1 | 1 | 19.6%* | 44.9%*^ |
| | FAM3D | R-17-R | 3 | 3 | TGCcCCTGACTCCTta | AaAtGAGgCAGGTGCA | 4 | 439 | 25 | 0.09%* | 0.06% |
| | HBD | L-16-R | 2 | 2 | TCACtTTGCCCCACAGGGCAtT | tCAGGAGTCAGaTGCA | 2 | 2 | 2 | 0% | 4.5%*^ |

TABLE 6-continued

SMRT Sequencing confirms on-target and off-target activity at site ranked by PROGNOS

| Nucleases | Closest Gene | Match Type | Mutations per half-site (+) | Mutations per half-site (−) | (+) half-site | (−) half-site | Computed Rankings H | RK | RN | 293T Cell Line Modification Frequency RVD Targeting Guanosine NK | NN |
|---|---|---|---|---|---|---|---|---|---|---|---|
| | GPR6 | R-30-R | 2 | 2 | TcCACCTGgCTCCTGT | gCAGGAGTtAaGgGtA | 21 | 241 | 16 | 0% | 0.07%*^ |
| | | | | | | Total Sites Interrogated: | | | | 21 | 20 |
| S1/S7 TALENs | HBB | L-15-R | 0 | 0 | TCACCTTGCCCCACAGGGCAGTAAC | AGGAGTCAGGTGCACCA | 1 | 1 | 1 | 0.2%* | 39.2%*^ |
| | LINC00299 | R-23-R | 3 | 5 | TGGaGCACCTGACcCCa | AGGAGaaAaGgGCACCt | 17 | 8 | 60 | 0.1%* | 0.06% |
| | HBD | L-15-R | 3 | 1 | TCACtTTGCCCCACAGGGCAtTgAC | AGGAGTCAGaTGCACCA | 2 | 2 | 3 | 0% | 4.2%*^ |
| | FAM3D | R-21-R | 3 | 5 | ctGTGCcCCTGACTCCT | AtGAGgCAGGTGCAttt | 8 | 4 | 2 | 0% | 0.2%*^ |
| | | | | | | Total Sites Interrogated: | | | | 24 | 25 |

ZFNs

| | Closest Gene | Match Type | Mutations per half-site (+) | Mutations per half-site (−) | (+) half-site | (−) half-site | H | C | ZFN Activity |
|---|---|---|---|---|---|---|---|---|---|
| 4F ZFNs | HBB | L5R | 0 | 0 | TCACCTTGCCCC | GCAGTAACGGCA | 1 | 1 | 6.0%* |
| | | | | | | Total Sites Interrogated: | | | 23 |
| 3F ZFNs | HBB | L-5-R | 0 | 0 | CCTTGCCCC | GCAGTAACG | 1 | 1 | 1.4%* |
| | ATG7 | L-6-L | 1 | 0 | CCTTGgCCC | GGGGCAAGG | 3 | 7 | 0.5%* |
| | PARD3B | L-5-L | 0 | 1 | CCTTGCCCC | GGGGCAAGc | 5 | 8 | 1.0%* |
| | GLIS2 | L-6-L | 1 | 0 | CCTgGCCCC | GGGGCAAGG | 9 | 6 | 0.6%* |
| | AFF3 | L-6-L | 2 | 0 | CCTaGgCCC | GGGGCAAGG | 16 | 37 | 2.3%* |
| | RGS10 | L-6-L | 0 | 2 | CCTTGCCCC | GGGGCAgaG | 22 | 39 | 5.0%* |
| | | | | | | Total Sites Interrogated: | | | 23 |

We interrogated 138 highly ranked genomic loci with SMRT sequencing, and observed off-target activity in 13 cases, 9 of which were outside the globin gene family. The match type indicates the orientation of the left (L) and right (R) nucleases at the site and the length of the spacer sequence. In sequences, lowercase letters indicate mutations compared to the target. Site sequences are listed as 5'-(+) half-site-spacer-(−) half-site-3'. Therefore, the (−) half-site for TALENs and the (+) half-site for ZFNs are listed in the reverse sense orientation compared to the DNA sequence that the nuclease binds. Rankings by the PROGNOS algorithms Homology (H), RVDs for NK (RK), RVDs for NN (RN), and Conserved G's (C) are displayed. 293T Modification Frequency is the frequency of observed sequences showing evidence of nonhomologous end-joining repair.
*indicates P < 0.05 in cells expressing active nuclease compared to cells expressing empty vector.
^indicates P < 0.05 for the difference in activity between NK and NN at that site.

Table 6 discloses the "(+)half-site" sequences as SEQ ID NOS 165-173, respectively, in order of appearance and the "(−)half-site" sequences as SEQ ID NOS 174-182, respectively, in order of appearance.

Example 2

Prediction of TALEN Activity

Materials and Methods
Assembly of TALENs
All TALENs were assembled using a two-step Golden Gate cloning method6 to link DNA-binding repeats (plasmids kindly provided by Daniel F. Voytas, University of Minnesota) containing RVDs HD, NI, NG, and NK to recognize C, A, T, and G, respectively. A pcDNA3.1(−)-based backbone vector was constructed containing a Kozak sequence, a triple FLAG epitope tag, and a previously described TALEN framework8. The repeats were cloned into the backbone vector using BsmBI restriction sites to replace a lacZ gene stuffer fragment for blue/white screening.

Assembly of SSA Reporter Plasmids
The SSA reporter plasmid backbone contains an EGFP gene, interrupted after 327 bp with a stop codon, the target site for a pair of GFP-targeted ZFNs19, an AscI and an SbfI cloning site. The downstream portion of the EGFP gene includes a 42-bp region repeating the sequence of the EGFP gene before the stop codon. SSA reporters were constructed using oligonucleotide pairs containing the left target site, the spacer, and the right target site ligated into the vector's AscI and SbfI sites.

Single Strand Annealing (SSA) Activity Assay
HEK293T cells (ATCC) were cultured in Dulbecco's Modified Eagle Medium (Sigma) supplemented with 10% FBS and 2 mM L-Glutamine. Cells were seeded 80,000 per well of a 24-well plate. After 4 h, cells were transfected with 200 ng of the TALEN plasmid (or 100 ng of each TALEN for hetero-dimeric pairs) and 10 ng of the corresponding SSA reporter plasmid using calcium phosphate transfection. Three control transfections were included: 1) 200 ng of an empty TALEN backbone and 10 ng of an SSA reporter plasmid, 2) 200 ng of an empty TALEN backbone and 10 ng of a pEGFP plasmid, and 3) 100 ng of each GFP-ZFN and 10 ng of an SSA reporter plasmid. Cells were harvested 48 h after transfection. The percentages of pEGFP-transfected samples expressing GFP were determined using an Accuri C6 flow cytometer, as an indication of transfection efficiency. Genomic DNA was isolated using QuickExtract DNA extraction solution (Epicentre) as described20. Sample were PCR amplified for 35 cycles (95° C., 30 s; 60° C., 30 s; 72° C., 60 s) in a 50 μl reaction that contains 2 μl of the extracted DNA, 2.5 μl of each 10 μM target region amplification primer (SSA-Cell-F4, 5'-TCGTGAC-CACCCTGACCTACGG (SEQ ID NO: 183); SSA-Cell-R4, 5'-TGCCGTCCTCGATGTTGTGGCG (SEQ ID NO: 184)), and 25 μl of GoTaq green master mix (Promega). PCR reactions were then separated on 2% agarose gels and the percentages of SSA-repaired products were quantified using ImageJ.

Standard Curve for SSA Assay
To generate the standard curve, EGFP plasmid (pEGFP), with a sequence identical to the SSA-repaired target plasmid, and a target plasmid were mixed at different ratios. HEK293T cells were transfected with the mixtures and an empty TALEN backbone, the genomic DNA harvested and the SSA assay performed, as above. The results from three transfections were averaged and plotted comparing the percentage of the EGFP plasmid versus the percentage of the smaller band (345 bp).

T7 Endonuclease I (T7E1) Mutation Detection Assay for Measuring Endogenous Gene Modification The gene modification efficiency of hetero-dimeric TALEN pairs was quantified based on the level of imperfect repair of double-stranded breaks by NHEJ. HEK293T cells were seeded 40,000 per well of a 24-well plate. After 24 hours, cells were transfected with 500 ng of each nuclease (TALEN or ZFN) plasmid and 10 ng of pEGFP plasmid using 3.4 µl FuGene HD (Promega), following manufacturer's instructions. Cells were harvested 72 hours after transfection and analyzed with an Accuri C6 flow cytometer to quantify GFP fluorescence, as a measurement of transfection efficiency. Cell pellets were then collected and genomic DNA isolated using QuickExtract DNA extraction solution (Epicentre), as described[20]. T7E1 assays were performed, as described previously[7]. The digestions were separated on 2% agarose gels. The cleavage bands were quantified using ImageJ. The percentage of gene modification=100×(1−(1−fraction cleaved)$^{0.5}$), as described. All PCR reactions were performed using AccuPrime Taq DNA Polymerase High Fidelity (Life Technologies) following manufacturer's instructions for 35 cycles (94° C., 30 s; 60° C., 30 s; 68° C., 60 s) in a 50 µl reaction containing 2 µl of the extracted DNA, 2.5 µl of each 10 µM target region amplification primer, and 5% DMSO. The PCR reactions for the FANCE locus gave non-specific bands under standard conditions and were amplified after addition of 1 M betaine.

SMRT Sequencing of NHEJ Induced Mutations

The same PCR products used for T7E1 assays were pooled for SMRT sequencing following the manufacturer's instructions (Pacific Biosciences). NHEJ mutations were detected and analyzed using algorithms developed in-house (manuscript under preparation).

Statistical Analysis

To calculate the p-value for correlation in, the correlation coefficient R was converted to t-statistic using the following equation $t=(R^2 \times (n-2)/(1-R^2))^{1/2}$, and the two-tailed p-value was obtained from this t-statistic.

Method for Predicting TALEN Activity

The algorithm contains an optimized set of dummy variables and continuous variables. Dummy variables were used to describe base identities of the first five and the last five nucleotides in the monomer target sequence, whereas cubic functions were used to characterize the effect of changes in other variables, including the length of the target sequence, the overall percentages of each nucleotide in the target sequence, percentages of each nucleotide in the first five or the last five nucleotides, and the maximum numbers of consecutive As and Gs9.

The method defines a score that represents the activity of TALEN monomers as shown in Equation (5) above. The score of each monomer target sequence is calculated as the sum of seven terms. There are a total of 55 variables and 86 parameters. To fully establish the algorithm, 116 NK-TALENs (See Table 7 for complete list) were individually tested for their monomer SSA activity in cultured cells. The experimental results were used to determine the parameters in the algorithm by minimizing the total squared differences between computed scores and measured SSA activities of the training set (116 TALENs), which allows the computed score to best predict cellular SSA activity of newly designed TALENs. The parameters of the algorithm were optimized using the Generalized Reduced Gradient non-linear optimization algorithm13, 14.

TABLE 7

Summary of results and % SSA activities for 116 TALENs targeted the β-globin (SEQ ID NOS 185-326, respectively, in order of appearance)

| Target gene | Index name of TALEN | Target sequence (excluding the 5'T present before the 5'end of all TALEN half-sites) | Average % SSA activity | s.e.m. of % SSA activity | Computed Score |
|---|---|---|---|---|---|
| | | Training set | | | |
| HBB | S-01 | GGTGCACCTGACTCCT | 5.2 | 0.7 | 8.6 |
| HBB | S-02 | GCACCTGACTCCTGT | 23.0 | 3.9 | 19.5 |
| HBB | S-03 | CAAACAGACACCATGGTGCACCT | 4.9 | 1.0 | 4.7 |
| HBB | S-04 | CAAACAGACACCATGGTGCACCTGA | 2.5 | 0.7 | −0.4 |
| HBB | S-05 | CACCTTGCCCCACAGGGCAGT | 6.1 | 1.0 | 5.4 |
| HBB | S-06 | CACCTTGCCCCACAGGGCAGTAA | 5.3 | 1.2 | 4.7 |
| HBB | S-07 | CACCTTGCCCCACAGGGCAGTAAC | 7.5 | 0.5 | 3.9 |
| HBB | S-08 | CACCTTGCCCCACAGGGCAGTA | 1.9 | 0.4 | 1.8 |
| HBB | S-09 | GCCCCACAGGGCAGTAACGGCAGA | 6.2 | 0.6 | 6.6 |
| HBB | S-10 | GCTTACATTTGCTTCTGACACAACTGTGTT | 8.4 | 0.6 | 5.3 |
| HBB | S-11 | ACAAGACAGGTTTAAGGAGACCAAT | 1.5 | 0.1 | 2.5 |
| HBB | S-12 | TGCCCCACAGGGCAGT | 11.0 | 0.1 | 6.5 |

TABLE 7-continued

Summary of results and % SSA activities for
116 TALENs targeted the β-globin
(SEQ ID NOS 185-326, respectively,
in order of appearance)

| Target gene | Index name of TALEN | Target sequence (excluding the 5'T present before the 5'end of all TALEN half-sites) | Average % SSA activity | s.e.m. of % SSA activity | Computed Score |
|---|---|---|---|---|---|
| HBB | S-13 | CTTGGGTTTCTGATAGGCACTGACTCTCT | 13.0 | 1.1 | 6.4 |
| HBB | S-14 | CCTGTGGAGAAGTCT | 0.6 | 0.2 | 1.1 |
| HBB | S-15 | CCTGTGGAGAAGTCTGCCGT | 3.0 | 0.4 | 0.6 |
| HBB | S-16 | CTGATAGGCACTGACTCT | 30.9 | 1.6 | 20.2 |
| HBB | S-17 | CTGATAGGCACTGACTCTCT | 29.2 | 1.1 | 24.1 |
| HBB | S-18 | CTGATAGGCACTGACTCTCT | 26.2 | 1.1 | 24.7 |
| HBB | S-19 | CTGATAGGCACTGACTCTCTGCCT | 17.2 | 0.5 | 14.5 |
| HBB | S-20 | CTGATAGGCACTGACTCTCTGCCTAT | 16.6 | 1.3 | 20.6 |
| HBB | S-21 | CTGATAGGCACTGACTCTCTGCCTATT | 21.8 | 2.4 | 17.1 |
| HBB | S-22 | CCACGTTCACCTTGCCCCACAGGGCAGT | 4.5 | 0.2 | 9.1 |
| HBB | S-23 | AGACCACCAGCAGCCT | 11.6 | 0.6 | 10.5 |
| HBB | S-24 | CCAAGGGTAGACCACCAGCAGCCT | 1.3 | 0.1 | 0.2 |
| HBB | S-25 | CTCCACAGGAGTCAGGTGCACCAT | 11.1 | 0.0 | 12.2 |
| HBB | S-26 | ATCAGAAACCCAAGAGTCTTCTCTGT | 11.7 | 1.4 | 9.5 |
| HBB | S-27 | GCCTATCAGAAACCCAAGAGTCTTCTCTGT | 3.5 | 0.7 | 4.7 |
| HBB | S-28 | ATCAGAAACCCAAGAGTCTTCTCT | 15.3 | 0.8 | 12.9 |
| HBB | S-29 | GCCTATCAGAAACCCAAGAGTCTTCTCT | 5.3 | 0.0 | 6.6 |
| HBB | S-30 | ATCAGAAACCCAAGAGTCTTCT | 17.9 | 1.2 | 15.2 |
| HBB | S-31 | GCCTATCAGAAACCCAAGAGTCTTCT | 9.7 | 0.2 | 8.6 |
| HBB | S-32 | ATCAGAAACCCAAGAGTCTT | 10.5 | 1.2 | 12.2 |
| HBB | S-33 | GCCTATCAGAAACCCAAGAGTCTT | 4.9 | 0.3 | 5.8 |
| HBB | S-34 | ATCAGAAACCCAAGAGTCT | 14.8 | 0.1 | 15.8 |
| HBB | S-35 | GCCTATCAGAAACCCAAGAGTCT | 8.1 | 0.3 | 8.4 |
| HBB | S-36 | ATCAGAAACCCAAGAGT | 7.3 | 1.1 | 8.3 |
| HBB | S-37 | GCCTATCAGAAACCCAAGAGT | 4.8 | 0.6 | 1.0 |
| HBB | S-38 | CTATTGCTTACATTTGCTTCTGACACAACT | 3.7 | 0.3 | 5.1 |
| HBB | S-39 | GGGTTTCTGATAGGCACTGACTCTCT | 5.0 | 0.3 | 8.8 |
| HBB | S-40 | ATTGCTTACATTTGCTTCTGACACAACT | 2.5 | 0.4 | 2.6 |
| HBB | S-41 | ATTGCTTACATTTGCTTCTGACACAACTGT | 3.1 | 0.3 | 5.9 |
| HBB | S-42 | GCTTACATTTGCTTCTGACACAACT | 4.3 | 0.2 | 3.6 |
| HBB | S-43 | GCTTACATTTGCTTCTGACACAACTGT | 4.1 | 0.6 | 6.5 |
| HBB | S-44 | GCTTACATTTGCTTCTGACACAACTGTGT | 3.2 | 0.2 | 3.0 |
| HBB | S-55 | AAGGAGACCAATAGAAACT | 0.3 | 0.3 | -1.4 |
| HBB | S-56 | TAAGGAGACCAATAGAAACT | 0.3 | 0.1 | -1.9 |
| HBB | S-57 | TTAAGGAGACCAATAGAAACT | 0.4 | 0.2 | 1.9 |
| HBB | S-68 | TGCCCCACAGGGCAGTA | 1.1 | 0.1 | 4.5 |

TABLE 7-continued

Summary of results and % SSA activities for
116 TALENs targeted the β-globin
(SEQ ID NOS 185-326, respectively,
in order of appearance)

| Target gene | Index name of TALEN | Target sequence (excluding the 5'T present before the 5'end of all TALEN half-sites) | Average % SSA activity | s.e.m. of % SSA activity | Computed Score |
|---|---|---|---|---|---|
| HBB | S-74 | CAAACAGACACCATG | 5.2 | 0.3 | 4.1 |
| HBB | S-75 | CAAACAGACACCATGGT | 10.1 | 0.8 | 13.6 |
| HBB | S-76 | AGACACCATGGTGCAC | 3.0 | 0.1 | 2.9 |
| HBB | S-77 | CAAACAGACACCATGGTGCACC | 7.4 | 0.3 | 7.6 |
| HBB | S-78 | AACGGCAGACTTCTCCA | 2.4 | 0.3 | -0.8 |
| HBB | S-79 | AACGGCAGACTTCT | 1.5 | 0.2 | 4.1 |
| HBB | S-80 | GCAGTAACGGCAGACT | 0.9 | 0.1 | 4.9 |
| HBB | S-81 | CCTTGCCCCACAGGGCAGTAACGGCAGACT | 1.1 | 0.2 | 0.5 |
| n/a | S-82 | GCACCTGACTCCTGG | 14.1 | 0.6 | 16.3 |
| n/a | S-83 | CTGATAGGCACTGACTCG | 17.9 | 1.0 | 18.2 |
| n/a | S-84 | ATCAGAAACCCAAGAGTCTTCTCG | 9.2 | 0.5 | 8.4 |
| n/a | S-85 | CACCTTGCCCCACAGGGCAGG | 10.1 | 1.2 | 8.9 |
| n/a | S-86 | GGTGCACCTGACTCCG | 8.3 | 0.6 | 7.3 |
| n/a | S-87 | GCCCCACAGGGCAGTAACGGCAGG | 12.5 | 1.1 | 14.1 |
| HBB | S-88 | GCACCTGACTCCTGA | 14.5 | 0.2 | 13.7 |
| n/a | S-89 | CTGATAGGCACTGACTCA | 14.0 | 0.6 | 11.9 |
| n/a | S-90 | ATCAGAAACCCAAGAGTCTTCTCA | 4.5 | 0.8 | 7.5 |
| n/a | S-91 | CACCTTGCCCCACAGGGCAGA | 1.7 | 0.3 | 3.7 |
| n/a | S-92 | GGTGCACCTGACTCCA | 1.4 | 0.3 | 2.8 |
| n/a | S-93 | GCCCCACAGGGCAGTAACGGCAGT | 5.7 | 0.9 | 7.1 |
| n/a | S-94 | GCACCTGACTCCTGC | 16.3 | 1.1 | 15.0 |
| n/a | S-95 | CTGATAGGCACTGACTCC | 11.0 | 1.7 | 13.3 |
| n/a | S-96 | ATCAGAAACCCAAGAGTCTTCTCC | 5.2 | 0.9 | 2.6 |
| n/a | S-97 | CACCTTGCCCCACAGGGCAGC | 3.6 | 1.0 | 6.9 |
| n/a | S-98 | GGTGCACCTGACTCCC | 7.8 | 1.0 | 2.9 |
| n/a | S-99 | GCCCCACAGGGCAGTAACGGCAGC | 8.6 | 1.0 | 5.8 |
| n/a | S-100 | TCACCTGACTCCTGT | 19.5 | 1.0 | 17.6 |
| n/a | S-101 | TTGATAGGCACTGACTCT | 18.9 | 2.1 | 17.7 |
| n/a | S-102 | TTCAGAAACCCAAGAGTCTTCTCT | 8.4 | 0.7 | 13.5 |
| n/a | S-103 | TACCTTGCCCCACAGGGCAGT | 4.2 | 0.7 | 3.3 |
| n/a | S-104 | TGTGCACCTGACTCCT | 0.0 | 0.0 | 3.1 |
| n/a | S-105 | TCCCCACAGGGCAGTAACGGCAGA | 8.5 | 0.6 | 2.1 |
| n/a | S-106 | GAACCTGACTCCTGT | 16.9 | 1.8 | 13.3 |
| n/a | S-107 | CAGATAGGCACTGACTCT | 6.0 | 0.2 | 12.2 |
| n/a | S-108 | AACAGAAACCCAAGAGTCTTCTCT | 3.9 | 0.3 | 9.0 |

TABLE 7-continued

Summary of results and % SSA activities for
116 TALENs targeted the β-globin
(SEQ ID NOS 185-326, respectively,
in order of appearance)

| Target gene | Index name of TALEN | Target sequence (excluding the 5'T present before the 5'end of all TALEN half-sites) | Average % SSA activity | s.e.m. of % SSA activity | Computed Score |
|---|---|---|---|---|---|
| n/a | S-109 | CTCCTTGCCCCACAGGGCAGT | 4.7 | 0.9 | 12.7 |
| n/a | S-110 | GATGCACCTGACTCCT | 0.0 | 0.0 | 6.1 |
| n/a | S-111 | GACCCACAGGGCAGTAACGGCAGA | 4.7 | 0.6 | 6.6 |
| HBB | S-114 | TCCCACCCTTAGGCT | 21.7 | 1.6 | 17.3 |
| HBB | S-115 | CACTAGCAACCTCAAACA | 3.7 | 0.1 | 0.3 |
| HBB | S-116 | CTGCCGTTACTGCCCTGT | 29.6 | 2.9 | 30.0 |
| HBB | S-117 | CAAAGAACCTCTGGGTCCAA | 0.5 | 0.0 | -2.9 |
| HBB | S-118 | TCACCTTGCCCCACA | 25.6 | 2.3 | 27.0 |
| HBB | S-119 | TCTCCACAGGAGTCA | 5.5 | 0.4 | 10.0 |
| HBB | S-120 | CACCACCAACTTCAT | 23.5 | 0.1 | 19.4 |
| HBB | S-121 | AGCAACCTCAAACAGACACCAT | 3.0 | 0.3 | 2.5 |
| HBB | S-122 | AACGGCAGACTTCTCCACA | 5.0 | 1.2 | 4.1 |
| CFTR | S-125 | TATGCCTGGCACCA | 0.0 | 0.0 | 1.7 |
| CFTR | S-126 | CATCATAGGAAACACCAAT | 13.2 | 0.7 | 12.6 |
| HBB | S-127 | CTCTCTGCCTATTGGTC | 9.7 | 0.8 | 10.4 |
| HBB | S-128 | CCAAGGGTAGACCACCAGC | 0.1 | 0.1 | 1.2 |
| HBB | S-129 | GGTGCACCTGACTCC | 8.0 | 0.2 | 3.5 |
| HBB | S-130 | TGCCCCACAGGGCAGTAAC | 8.3 | 0.8 | 8.3 |
| HBB | S-131 | GCCTATTGGTCTATTTTCC | 14.1 | 0.1 | 13.9 |
| HBB | S-132 | CCAAGGGTAGACCACC | 0.6 | 0.2 | 1.4 |
| HBB | S-133 | GTGTTCACTAGCAACCTC | 12.6 | 1.0 | 10.0 |
| HBB | S-134 | TCTCCACAGGAGTCAGGTGC | 4.2 | 1.4 | 3.8 |
| CXADR | C-01 | TCTTTTCCCCTTTTATGC | 7.7 | 0.6 | 8.5 |
| CXADR | C-02 | GAGGCATGACAACGC | 0.8 | 0.1 | 1.3 |
| CFTR | F-01 | TTTATTTCCAGACTTC | 2.2 | 1.1 | 1.6 |
| CFTR | F-02 | CTGAAGGCTCCAGTTCTCC | 1.8 | 0.7 | 9.0 |
| CFTR | F-03 | TTCCAGACTTCACTTC | 1.8 | 0.6 | 3.8 |
| CFTR | F-04 | CTGAAGGCTCCAGTTCTC | 2.0 | 0.7 | 5.5 |
| CFTR | F-05 | GAAGGCTCCAGTTCTCCC | 0.9 | 0.4 | 2.2 |
| ERCC5 | J-03 | TTTCGAATTCGTCCTATTT | 25.5 | 1.8 | 24.3 |
| ERCC5 | J-04 | CTGTTTCTTCAATAGTGGAGCAT | 5.7 | 0.3 | 8.5 |
| ERCC5 | J-09 | CGGCTCTGCAAACTCTTATTTTTT | 17.9 | 3.7 | 19.3 |
| ERCC5 | J-10 | CCCCATCAAACACAAA | 15.9 | 2.5 | 20.1 |
| Test Set | | | | | |
| CXADR | C-03 | CTCTTTTTTTCTTTTGT | 24.6 | 0.6 | 50.4 |
| CXADR | C-04 | GTAATTCCATCAGTC | 8.9 | 1.0 | 5.5 |

TABLE 7-continued

Summary of results and % SSA activities for
116 TALENs targeted the β-globin
(SEQ ID NOS 185-326, respectively,
in order of appearance)

| Target gene | Index name of TALEN | Target sequence (excluding the 5'T present before the 5'end of all TALEN half-sites) | Average % SSA activity | s.e.m. of % SSA activity | Computed Score |
|---|---|---|---|---|---|
| CFTR | F-06 | GAACCCTTCACACTACCCA | 14.8 | 1.9 | 19.6 |
| CFTR | F-07 | AGACTAACCGATTGAATAT | 20.2 | 3.1 | 8.8 |
| CFTR | F-08 | TTATTTCCAGACTTCACTTCT | 21.8 | 1.5 | 24.7 |
| CFTR | F-09 | ACCCTCTGAAGGCTCCAGTTCT | 12.8 | 2.9 | 26.9 |
| CFTR | F-10 | TCACTTCTAATGGTGAT | 23.6 | 2.6 | 15.5 |
| CFTR | F-11 | GTGCTTAATTTTACCCTCTGAA | 8.8 | 1.8 | 22.6 |
| AAVS1 | G-01 | CTGCCTAACAGGAGGTG | 11.7 | 1.4 | 22.1 |
| AAVS1 | G-02 | CCTCCTTCCTAGTCTCCTGAT | 18.0 | 3.7 | 28.9 |
| AAVS1 | G-03 | GTCCCTAGTGGCCCCACT | 10.8 | 2.5 | 33.5 |
| AAVS1 | G-04 | CTGGTTCTGGGTACTTTTAT | 4.0 | 1.9 | 8.6 |
| CDH1 | J-01 | CTCGGCGCTGCTGCTGCTGCT | 81.4 | 5.4 | 95.7 |
| CDH1 | J-02 | GCGTCCCTCGCAAGTCAG | 16.7 | 1.1 | 19.1 |
| HOXD13 | J-05 | TTCTCTCCGCGCCT | 80.7 | 1.5 | 90.6 |
| HOXD13 | J-06 | GCCGCCGCCGCCGCCCGCCCCGAAT | 66.3 | 1.9 | 40.7 |
| CDH1 | J-07 | CGGCGCTGCTGCTGCTGCT | 73.9 | 2.7 | 99.1 |
| CDH1 | J-08 | GCGTCCCTCGCAAGTCAGGG | 52.9 | 2.7 | 21.3 |
| HOXD13 | J-11 | GCGCTCAAGTCATCGCCGCA | 54.0 | 2.6 | 25.5 |
| HOXD13 | J-12 | GTACTTCTCCACGGGAA | 28.1 | 0.3 | 23.8 |
| FANCE | J-13 | CGCTTGCTCGAGGCCCT | 21.4 | 7.0 | 13.5 |
| FANCE | J-14 | CAGGCCCCTGCACGACC | 8.2 | 3.0 | 19.6 |
| KIT | J-15 | GGGATTTTCTCTGCGTTCT | 1.3 | 0.2 | 6.7 |
| KIT | J-16 | GTCCCACCTGTCTGGACG | 77.3 | 2.3 | 19.1 |
| TGFBR2 | J-17 | CGTCCTGTGGACGCGTAT | 66.0 | 5.0 | 22.1 |
| TGFBR2 | J-18 | CACCCGACTTCTGAACGTGCGGT | 16.8 | 1.9 | 3.5 |

Results

Figure 18A:
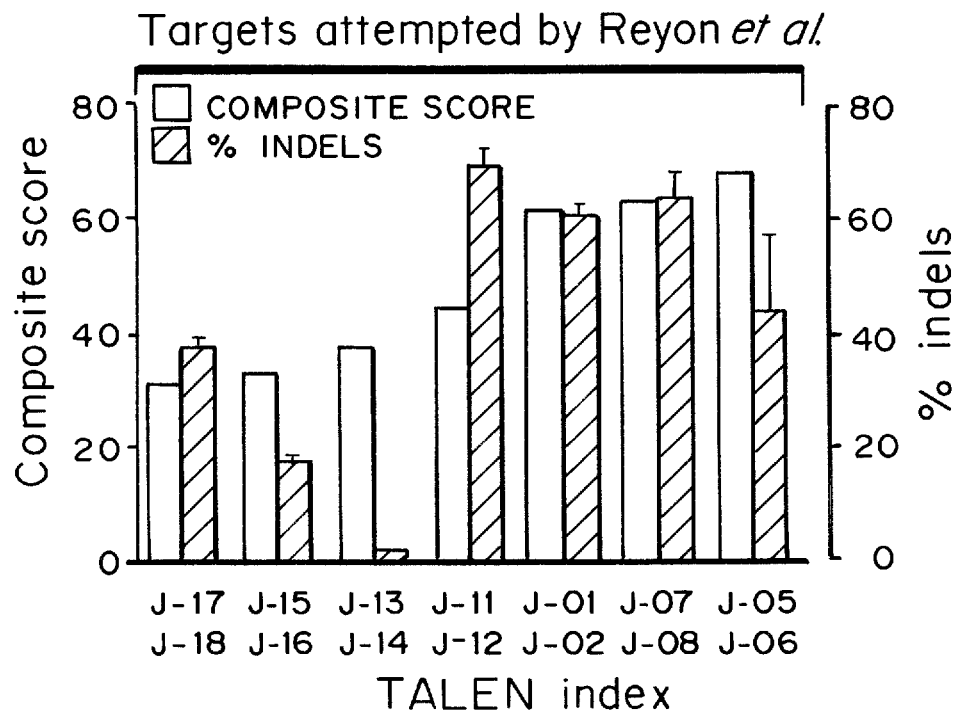
FIGS. 18A and 18B are bar graphs showing a comparison of predicted TALEN nuclease activity to endogenous gene modification efficiency as determined by T7E1 assay.
Figure 18B:
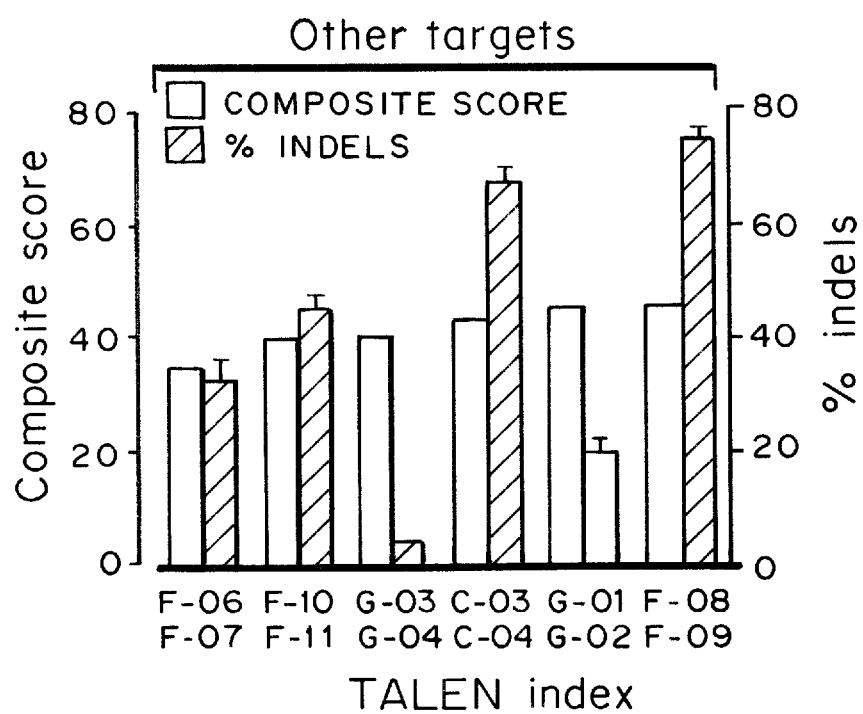

The measured SSA activities of 116 NK-TALENs were used to establish the algorithm, which contains a total of 55 variables and 86 parameters. With specific target features indicated in Table 8 as variables, the scoring function gives a numerical value that predicts TALEN activity (a high score predicts a high activity). The scoring function contains variables reflecting the existing design guidelines and new design rules established in this study. The parameters in the algorithm were optimized by minimizing the total squared differences between computed scores and the measured TALEN SSA activities using the Generalized Reduced Gradient (GRG2) algorithm, which gave rise to an excellent correlation ($R^2$=0.849, correlation p=1.09×10$^{-4}$). See FIG. 18. All of the optimized parameters for the NK-TALENS are reported in Table 9.

TABLE 8

Evaluation of existing design guidelines and development of new design rules

| Feature in target site | Existing guidelines | Optimal value[a] from this study | Relative importance[b] | Recommendation |
|---|---|---|---|---|
| Comparison with previously published guidelines | | | | |
| Base identities at 5' (Pos. 1), 2nd nt. from 5' (Pos. 2), and 3' ends[6] | No T at Pos. 1<br>No A at Pos. 2<br>T at the 3' end | G at Pos. 1<br>T at Pos. 2<br>T at 3' end | + | It may not be necessary to choose specific nucleotides at these positions |
| Overall base composition[6] | A 31 ± 16%<br>C 37 ± 13%<br>G 9 ± 8%<br>T 22 ± 10% | 6%<br>53%<br>11%<br>30% | +++ | Choose target sequences with a large percentage of C[c] |
| Length of target sequence[7] | 15-20 bp | 15-25 bp | + | The length of a target sequence should be 15~25 bp[c] |
| Spacer length[7] | 16-19 bp | 14-19 bp[d] | n/a | Spacer length should be 14~19 bp |
| New design rules | | | | |
| Base composition of the first 5 nt | | A 0%<br>C 60%<br>G 20%<br>T 20% | +++ | The first 5 nt of the target sequence should contain a large % C[c] |
| Base composition of the last 5 nt | | A 20%<br>C 0%<br>G 0%<br>T 80% | +++ | The last 5 nt of the target sequence should contain a large % T[c] |
| Max. num of consecutive A's | | ≤3 | + | Shorter stretches of As will give higher activity |
| Max. num of consecutive G's | | ≤3 | ++ | Shorter stretches of G's will give higher activity |

[a]Optimal value shows the value of a certain variable that maximizes its contribution to the score, with the constraint that the value of this variable should be within the range of training set data.
[b]Relative importance of each design feature was rated by its magnitude of contribution to the score.
[c]Target sequence refers to a half-site targeted by a TALEN monomer, excluding the 5'-T immediately before the 5' end of the half-site.
[d]Acceptable values for spacer length were observed from T7E1 assays of TALEN pairs.

TABLE 9

Optimized parameters for computed activity of NK TALENs

Functional form for dummy variables below $F(d_i) = \beta_{i,A} * d_{i,A} + \beta_{i,C} * d_{i,C} + \beta_{i,G} * d_{i,G} + \beta_{i,T} * d_{i,T}$
Note: the dummy variable $d_{i,x}$ is either 1 (if the nucleotide at the position i is x) or 0 (otherwise)

| Dummy (binary) variable at position i | $\beta_{i,A}$ for nucleotide A | $\beta_{i,C}$ for nucleotide C | $\beta_{i,G}$ for nucleotide G | $\beta_{i,T}$ for nucleotide T |
|---|---|---|---|---|
| Nucleotide at Position 1 | 1.11433716 | −1.22042567 | 3.25882341 | −0.72100039 |
| Nucleotide at Position 2 | 0.16643637 | −0.67777093 | −2.08510160 | 4.53610911 |
| Nucleotide at Position 3 | 3.26245840 | −1.26286071 | 3.33703849 | −1.18880012 |
| Nucleotide at Position 4 | 0.27183271 | 5.28517844 | −2.80586719 | 1.39150978 |
| Nucleotide at Position 5 | −2.03792471 | 2.05093483 | 3.86725339 | 0.26624990 |
| Nucleotide at Position N-4* | 0.22866487 | 0.57623096 | 1.41121369 | −0.00372175 |
| Nucleotide at Position N-3* | 0.00705890 | 1.16632665 | −1.21664522 | 1.45240812 |
| Nucleotide at Position N-2* | −1.25387232 | −0.96628728 | 3.05173874 | 1.37859062 |
| Nucleotide at Position N-1* | 3.72999716 | 2.25921914 | −0.66544520 | −3.11696420 |
| Nucleotide at Position N* | −1.42576406 | −2.52986421 | 2.97702904 | 3.18118714 |

*N denotes the length of the target half-site excluding the 5'T that precedes each half-site.
Functional form for continuous variables below $Q(x) = A*x^3 + b*x^2 + c*x$

| Continuous variable | Cubic term a | Quadratic term b | Linear term c |
|---|---|---|---|
| Length of target sequence N | 0.00738946 | −0.56145540 | 13.46857733 |
| % A | 0.00033476 | −0.00872130 | −4.71326638 |
| % C | 0.00207823 | −0.21733864 | 3.14534539 |
| % G | 0.00119139 | −0.07234300 | −3.32523560 |
| % T | −0.00022177 | 0.01381322 | −4.68766605 |
| % A in the first 5 nt (% AFS) | 0.00015418 | −0.01126741 | 1.63469641 |
| % C in the first 5 nt (% CFS) | −0.00003225 | 0.00342139 | 1.52796728 |
| % G in the first 5 nt (% GFS) | 0.00009642 | −0.01125353 | 1.90075140 |

TABLE 9-continued

| Optimized parameters for computed activity of NK TALENs | | | |
|---|---|---|---|
| % T in the first 5 nt (% TFS) | 0.00010591 | −0.01091288 | 1.90173488 |
| % A in the last 5 nt (% ALS) | 0.00007195 | −0.00931559 | 2.02607277 |
| % C in the last 5 nt (% CLS) | −0.00001250 | 0.00297156 | 1.53220695 |
| % G in the last 5 nt (% GLS) | 0.00016059 | −0.01565351 | 2.06463117 |
| % T in the last 5 nt (% TLS) | −0.00007828 | 0.01322284 | 1.24917563 |
| Max. num of consecutive Gs (GCONS) | −4.42724656 | 21.32113536 | −28.76487390 |
| Max. num of consecutive As (ACONS) | −12.32918215 | 71.80249537 | −128.69530619 |
| Final content ($C_s$) | | 10.76815666 | |

Figure 14:
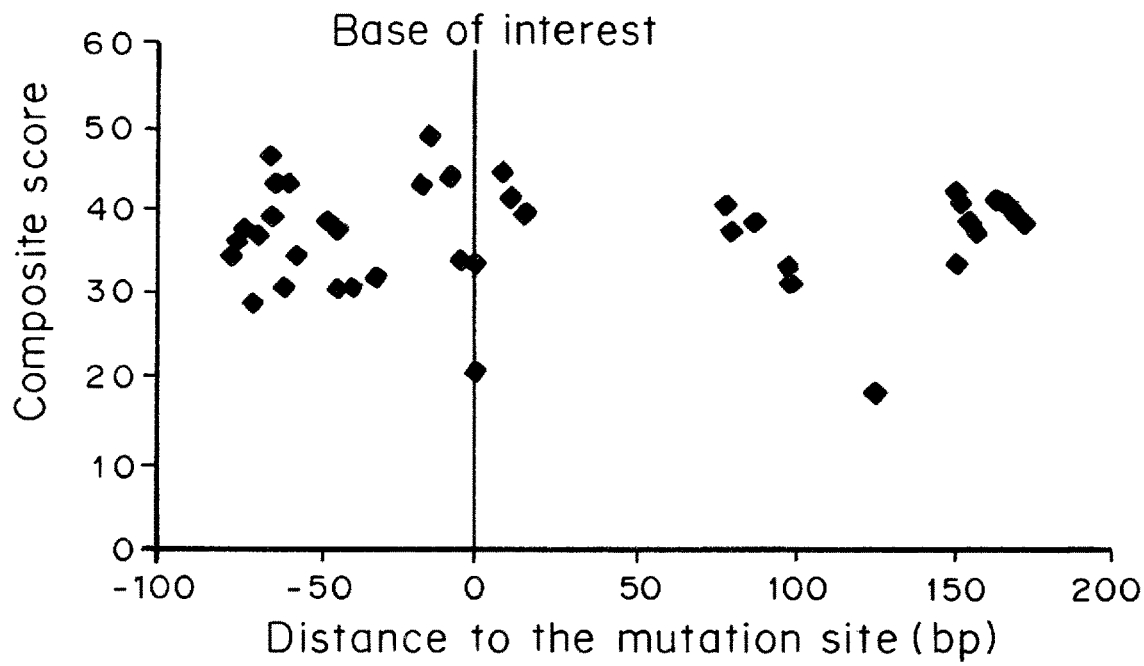
FIG. 14 is an example output showing composite scores for TALEN activity in a β-globin segment plotted against distances to the mutation site, marked as base zero. When brackets are placed around the base of interest in the input gene segment the program plots the composite scores as a function of the distance to the base of interest indicated by the vertical line at distance zero.

To help researchers identify optimal TALEN target sites, a user-friendly web interface was established that outputs a ranked list of scores and the associated target sites. An example output can be found in FIG. 14. The DNA sequence of interest, together with the ranges of acceptable target and spacer lengths are entered into the web interface, which then outputs the ranked scores for each TALEN pair, together with the corresponding target sequences with the nucleotide preceding each target half-site specified[6,7]. For each pair of TALENs, a single numerical value—the composite score—is defined based on the scores of the left and right TALENs in a way that favors pairs with balanced left and right scores using Composite Score $5+4\times\sqrt{LS}+4\times\sqrt{RS}$, where LS is the L-score (left TALEN score), and RS is the R-score (right TALEN score).

Figure 19:
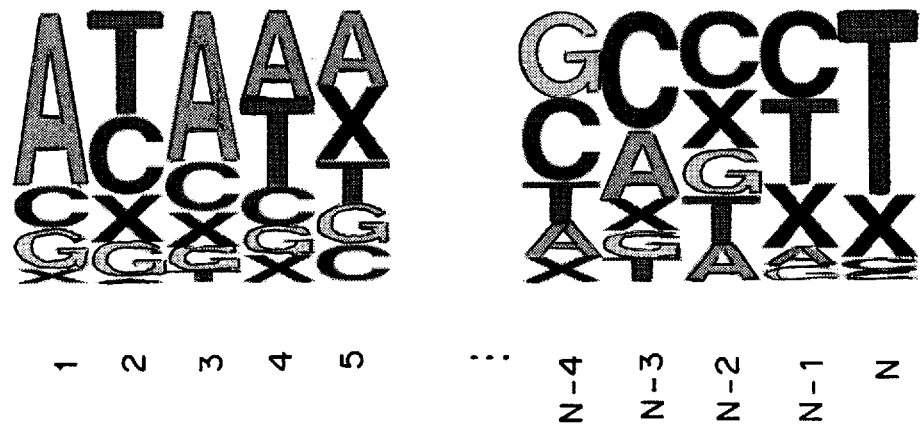
FIG. 19 depicts nucleotide frequencies at the termini of 109 naturally-occurring TAL effector target sites larger than 10 bp, based on the RVDs in the TAL effectors. N denotes the length of target site. X in the target site corresponds to RVDs that do not have a known single base preference.
Figure 20:
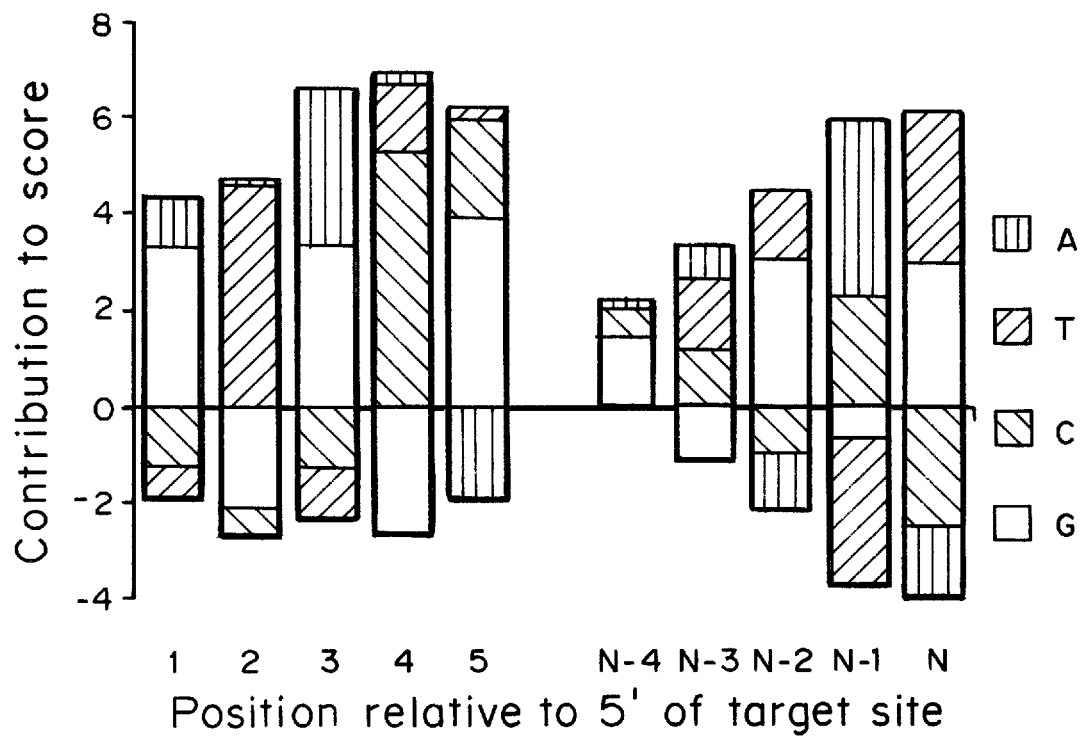
FIG. 20 depicts the score contribution of each nucleotide at the termini of a TALEN target site to the computed TALEN activity approximation. T at position 2 and T at position N give the highest positive scores among nucleotides at their positions, which is consistent with the high frequencies of these nucleotides present in naturally existing TAL effectors depicted in FIG. 19.
Figure 21:
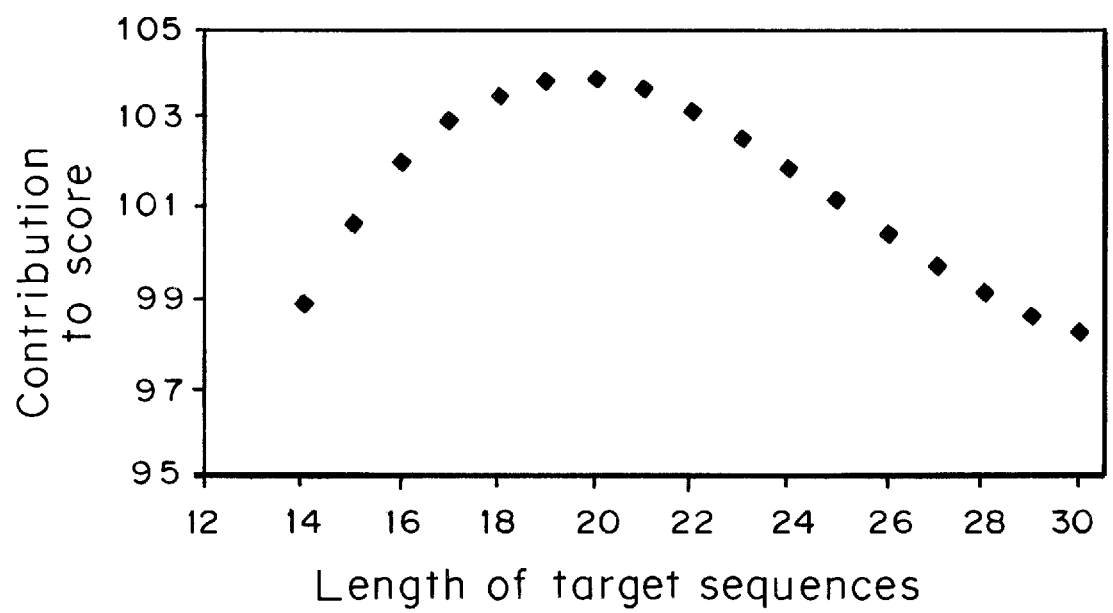
FIG. 21 depicts the contribution of different target lengths to the computed TALEN activity approximation. Full width at half maximum (FWHM) of this graph is 10 bp (15~25 bp). The peak value is achieved at 20 bp of target length.
Figure 22:
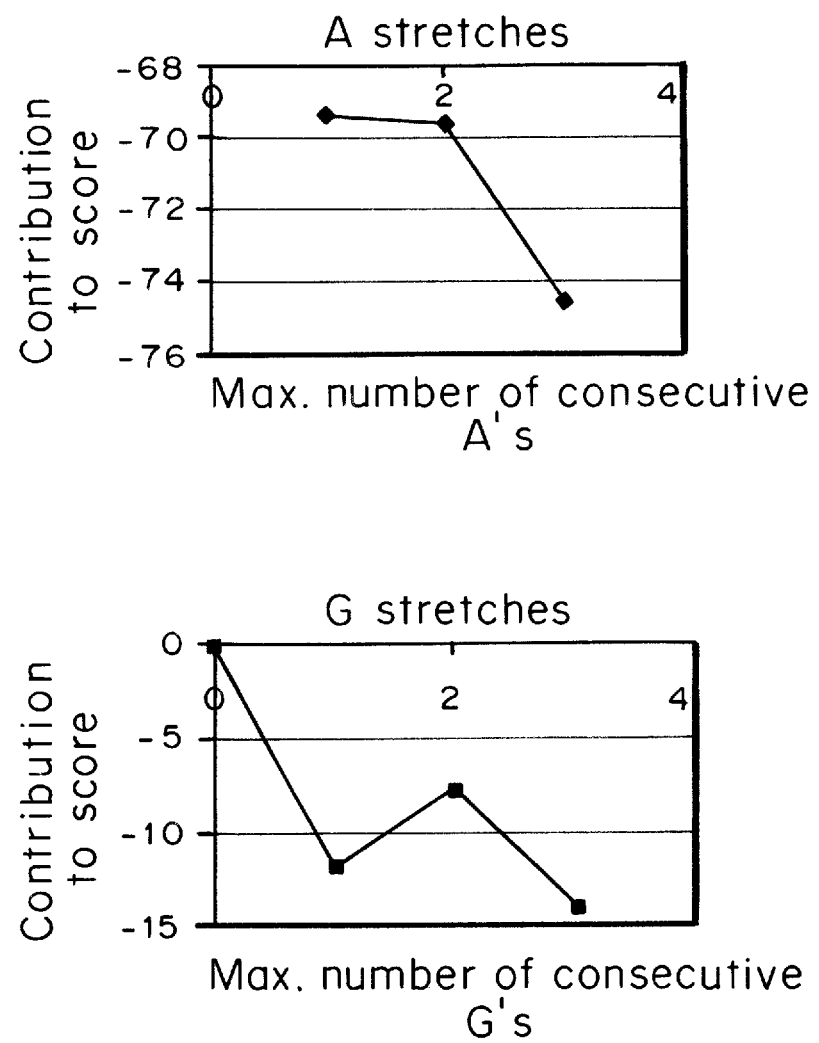
FIG. 22 depicts the contribution of different length stretches of consecutive A's or G's to the computed TALEN activity approximation. Longer stretches of A or G lower the score for predicted activity.
Figure 23:
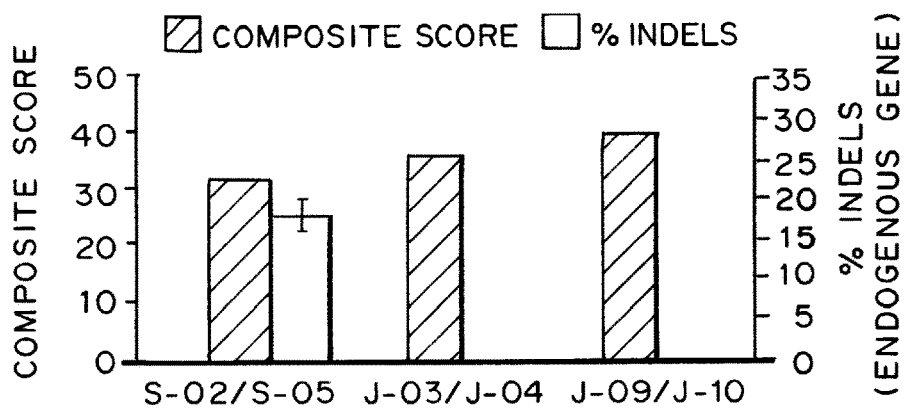
FIG. 23 is a bar graph for ERCC5-targeting TALEN pairs showing a comparison of the composite score for the predicted activity to the percentage of indels observed in a T7E1 assay for endogenous gene activity.

The method was validated by testing an additional 26 TALENs (test-set) targeting CXADR, CFTR, AAVS1 and five cancer-related genes (CDH1, HOXD13, FANCE, KIT, and TGFBR2). For each gene segment, the ranges of target and spacer lengths were set to be 14-25 bp and 14-19 bp, respectively, and TALEN pairs with high composite scores output by the online tool were chosen. The intracellular monomer activity of TALENs in the test-set was measured by SSA activity, as above. Most TALENs in the test-set had SSA activities correlated well with the computed scores ($R^2$=0.559, correlation p=1.13×10$^{-5}$) (See FIG. 17). Several TALEN pairs had SSA activities differed from the prediction by more than one standard deviation since their SSA activities (or computed scores) were far beyond the range in the training set. The activity of designed TALEN pairs was quantified by measuring their NHEJ-mediated endogenous gene modification using a T7 endonuclease I (T7E1) assay. Each of the six designed NK-TALEN pairs successfully cleaved their targets in the CXADR, CFTR and AAVS1 genes, resulting in NHEJ-induced mutation rates from 3.4% to 74.5%. To further demonstrate the potential, nine TALEN pairs were evaluated that targeted six cancer-related genes (ERCC5, CDH1, HOXD13, FANCE, KIT and TGFBR2) attempted previously, but showed no TALEN cleavage activity. See Reyon et al. (2012), Nat. Biotechnology 30:460-465. The two TALEN pairs in the training set targeting the ERCC5 gene showed no endogenous gene-targeting activity (FIG. 23), whereas the seven designed TALEN pairs targeting the other five cancer genes had a gene modification rate from 1.6% to 69.2% (FIG. 19). Single Molecule Real Time (SMRT) sequencing confirmed the mutation frequencies determined by the T7E1 assay. Overall, designed NK-TALEN pairs had a mean gene-targeting efficiency of 41.2%. This compares favorably with the NN-TALEN pairs evaluated by Reyon et al, which had activity levels ranging from zero to 55.8% with a mean of 22.2%.

Figure 24:
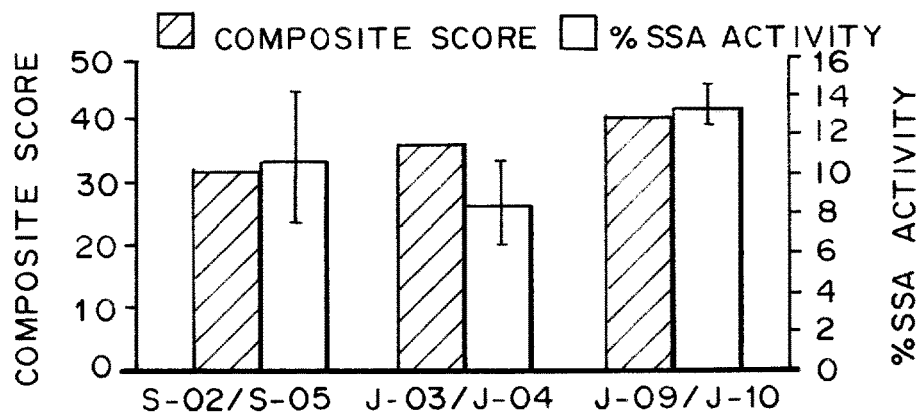
FIG. 24 is a bar graph for ERCC5-targeting TALEN pairs showing a comparison of the composite score for the predicted activity to the activity measured by SSA assay.
Figure 25:
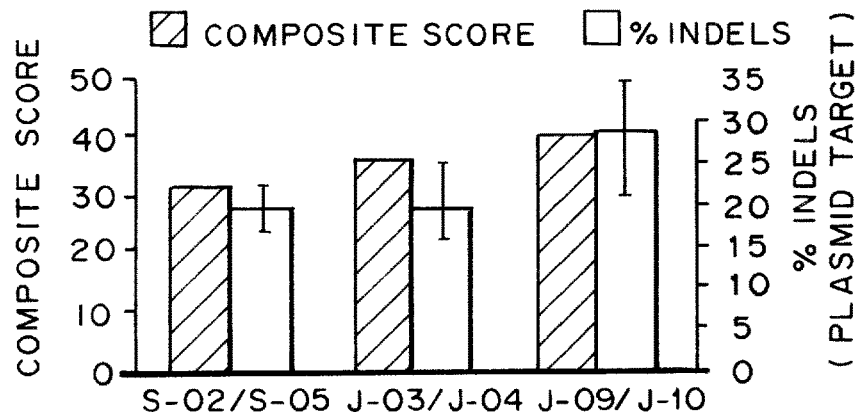
FIG. 25 is a bar graph for ERCC5-targeting TALEN pairs showing a comparison of the composite score for the predicted activity to the percentage of indels observed in a T7E1 assay at plasmid targets.
Figure 26:
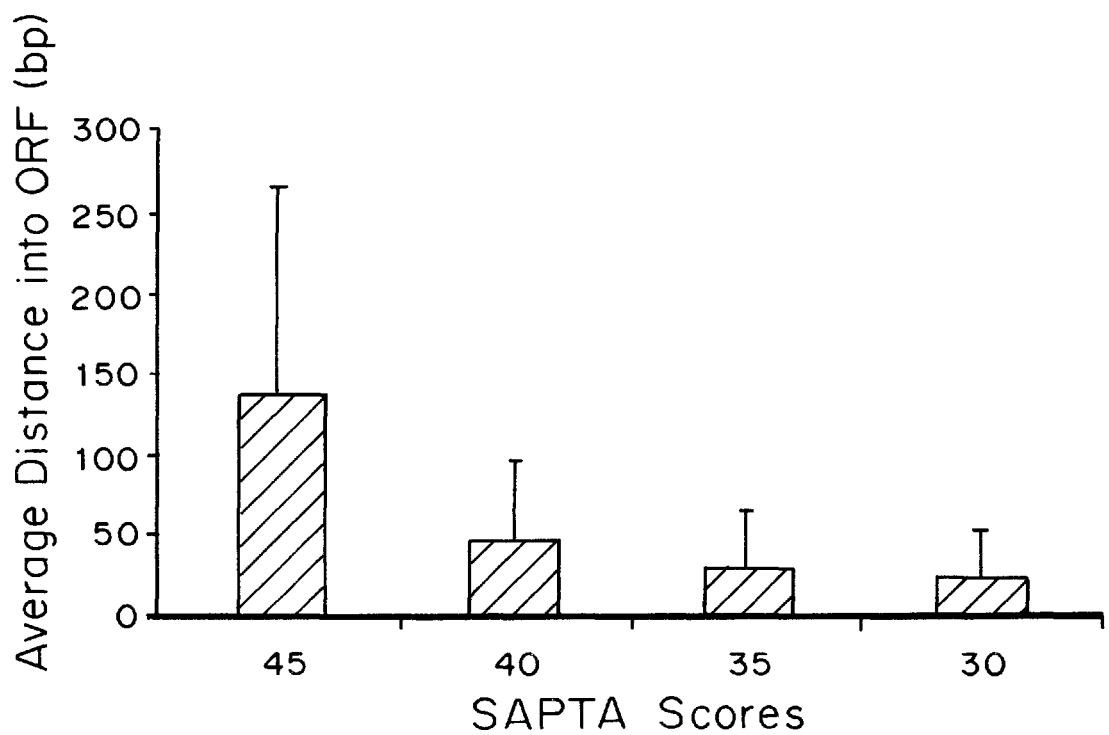
FIG. 26 is a bar graph depicting the average distance from the start codon to the closest site with a predicted TALEN activity above 30, 35, 40, or 45 in the first 500 base pairs of the open reading frames of the first 48 genes listed in Reyon et al.
Figure 27:
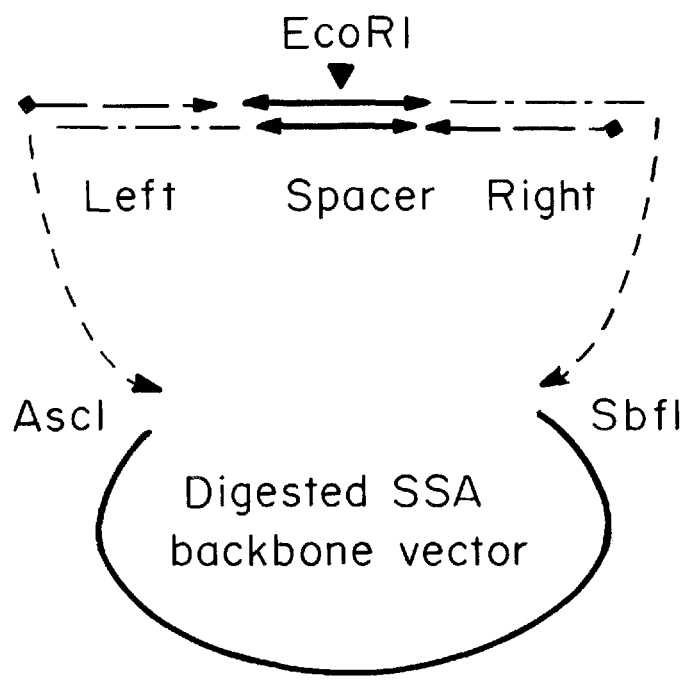
FIG. 27 is a schematic of target plasmid assembly. Three pairs of oligonucleotides that contain the left TALEN half-site, a spacer with an EcoRI site, and the right TALEN half-site are ligated into the vector. This robust, high-throughput method allows flexibility in constructing target plasmids.

In summary the method incorporates a significantly wider range of TALEN design rules than existing design guidelines, thus representing a significant advance over available design tools (e.g. TALE-NT 2.0). Designed NK-TALENs can achieve near 100% success rate, much higher than the 14% success rate for NK-TALENs designed without these methods, and even higher than the 88% success rate previously shown with NN-TALENs by Reyon et al. The designed NK-TALENs generally gave high gene modifying efficiencies, particularly those with composite scores above 40 (FIG. 19). A CFTR-targeting TALEN pair reached a targeting efficiency of 74.5%, which is one of the highest among TALENs tested by T7E1 assays. Using the method presented here to identify multiple high-scoring target sites is advantageous, since a well-designed TALEN does not necessarily have high gene-targeting efficiency possibly due to genomic context, even if the TALEN expression level is sufficient. For example, the two TALEN pairs targeting ERCC5 showed high activity with extrachromosomal plasmid targets in cells, but had undetectable activity at endogenous target sites (FIGS. 24 and 26). The scoring function on average identifies high-scoring target sites within the first 29 bp in a search through the coding sequences of 48 human genes, therefore enabling robust and flexible gene editing without extensive experimental screening of TALENs.

Although is optimized for NK-TALENs, it can also identify highly active target sites for TALENs with NN and NH RVDs. The methods can aid the design of TALENs with other RVDs, including NN and NH, by incorporating additional design rules than existing guidelines, even though the ranked list is optimized for NK-TALENs. NK-TALENs designed have an average endogenous gene modification of 41%. Due to the higher binding affinity of NN and NH RVDs, targeting the same sites with NN- and NH-TALENs may result in even higher average gene modification rates, since NN and NH RVDs have a higher DNA binding affinity than NK RVD.

The NN and NH versions of several designed NK-TALEN pairs were made (i.e., TALENs with identical target sequences but with different RVDs targeting G) and found that they had high cleavage activities (data not shown). Therefore, it is likely that the method would also work for selecting target sites for TALENs with NN or NH.

TABLE 11

Ranking results for eight target sites provided by a search using TALEN-NT 2.0[3]

| Gene | L-TALEN | L-score | R-TALEN | R-score | Composite score* | % indels ± s.e.m. |
|---|---|---|---|---|---|---|
| HBB | S-116 | 30.0 | S-120 | 19.4 | 44.5 | 43.4 ± 1.4 |
| HBB | S-02 | 19.5 | S-12 | 6.5 | 32.9 | 7.6 ± 0.7 |

TABLE 11-continued

Ranking results for eight target sites provided by a search using TALEN-NT 2.0[3]

| Gene | L-TALEN | L-score | R-TALEN | R-score | Composite score* | % indels ± s.e.m. |
|---|---|---|---|---|---|---|
| HBB | S-133 | 10.0 | S-134 | 3.8 | 25.4 | 0 |
| HBB | S-131 | 13.9 | S-132 | 1.4 | 24.6 | 0 |
| HBB | S-129 | 3.5 | S-130 | 8.3 | 24.0 | 0 |
| HBB | S-127 | 10.4 | S-128 | 1.2 | 22.2 | 0 |
| HBB | S-115 | 0.3 | S-119 | 10.0 | 19.8 | 0 |
| HBB | S-114 | 17.3 | S-117 | -2.9 | N/A** | 0 |

*Composite Score = $5 + 4 \times \sqrt{LS} + 4 \times \sqrt{RS}$, where LS is the L-score (left TALEN score), and RS is the R-score (right TALEN score).
**Ignored due to a negative score for the right TALEN.

Cellular activity measured as % indels using the T7 assay is shown for pairs of TALEN target sites tested in this study that were found in the 3612 pairs in the TALEN-NT 2.0 output for this gene segment. The computed composite score is shown for each pair and is used to select higher scoring sites for TALEN targeting and to screen against using sub-optimal sites (composite score <30), such as the third through eighth row below. The TALEN pairs with composite scores above 30 had detectable endogenous gene targeting, whereas those with lower scores, did not have detectable activity.

Example 3

Newly Designed TALENs

The TALENs designed for parameterizing and validating the activity ranking and additional new TALENs have been generated with the method for predicting TALEN activity from Example 2.

The plasmid backbone used for TALEN expression has the identity:

(SEQ ID NO: 25)
GACGGATCGGGAGATCTCCCGATCCCCTATGGTGCACTCTCAGTACA

ATCTGCTCTGATGCCGCATAGTTAAGCCAGTATCTGCTCCCTGCTTG

TGTGTTGGAGGTCGCTGAGTAGTGCGCGAGCAAAATTTAAGCTACAA

CAAGGCAAGGCTTGACCGACAATTGCATGAAGAATCTGCTTAGGGTT

AGGCGTTTTGCGCTGCTTCGCGATGTACGGGCCAGATATACGCGTTG

ACATTGATTATTGACTAGTTATTAATAGTAATCAATTACGGGGTCAT

TAGTTCATAGCCCATATATGGAGTTCCGCGTTACATAACTTACGGTA

AATGGCCCGCCTGGCTGACCGCCCAACGACCCCCGCCCATTGACGTC

AATAATGACGTATGTTCCCATAGTAACGCCAATAGGGACTTTCCATT

GACGTCAATGGGTGGAGTATTTACGGTAAACTGCCCACTTGGCAGTA

CATCAAGTGTATCATATGCCAAGTACGCCCCCTATTGACGTCAATGA

CGGTAAATGGCCCGCCTGGCATTATGCCCAGTACATGACCTTATGGG

ACTTTCCTACTTGGCAGTACATCTACGTATTAGTCATCGCTATTACC

ATGGTGATGCGGTTTTGGCAGTACATCAATGGGCGTGGATAGCGGTT

TGACTCACGGGGATTTCCAAGTCTCCACCCCATTGACGTCAATGGGA

GTTTGTTTTGGCACCAAAATCAACGGGACTTTCCAAAATGTCGTAAC

AACTCCGCCCCATTGACGCAAATGGGCGGTAGGCGTGTACGGTGGGA

GGTCTATATAAGCAGAGCTCTCTGGCTAACTAGAGAACCCACTGCTT

ACTGGCTTATCGAAATTAATACGACTCACTATAGGGAGACCCAAGCT

GGCTAGCGCCACCATGGACTACAAAGACCATGACGGTGATTATAAAG

ATCATGACATCGATTACAAGGATGACGATGACAAGATGGCCCCCAAG

AAGAAGAGGAAGGTGGGCATTCACCGCGGGGTACCTATGGTGGACTT

GAGGACACTCGGTTATTCGCAACAGCAACAGGAGAAAATCAAGCCTA

AGGTCAGGAGCACCGTCGCGCAACACCACGAGGCGCTTGTGGGGCAT

GGCTTCACTCATGCGCATATTGTCGCGCTTTCACAGCACCCTGCGGC

GCTTGGGACGGTGGCTGTCAAATACCAAGATATGATTGCGGCCCTGC

CCGAAGCCACGCACGAGGCAATTGTAGGGGTCGGTAAACAGTGGTCG

GGAGCGCGAGCACTTGAGGCGCTGCTGACTGTGGCGGGTGAGCTTAG

GGGGCCTCCGCTCCAGCTCGACACCGGGCAGCTGCTGAAGATCGCGA

AGAGAGGGGGAGTAACAGCGGTAGAGGCAGTGCACGCCTGGCGCAAT

GCGCTCACCGGtGCCCCCCTGGAGACGGGCGCCGCTACAGGGCGCGT

CCCATTCGCCATTCAGGCTGCGCAACTGTTGGGAAGGGCGATCGGTG

CGGGCCTCTTCGCTATTACGCCAGCTGGCGAAAGGGGATGTGCTGC

AAGGCGATTAAGTTGGGTAACGCCAGGGTTTTCCCAGTCACGACGTT

GTAAAACGACGGCCAGTGAGCGCGCGTAATACGACTCACTATAGGGC

GAATTGGGTACCGGGCCCCCCCTCGAGGTCCTCCAGCTTTTGTTCCC

TTTAGTGAGGGTTAATTGCGCGCTTGGCGTAATCATGGTCATAGCTG

TTTCCTGTGTGAAATTGTTATCCGCTCACAATTCCACACAACATACG

AGCCGGAAGCATAAAGTGTAAAGCCTGGGGTGCCTAATGAGTGAGCT

AACTCACATTAATTGCGTTGCGCTCACTGCCCGCTTTCCACCGGTCG

TCTCCAACGACCATCTGGTGGCGTTGGCATGTCTTGGTGGACGACCC

GCGCTCGATGCAGTCAAAAAGGGTCTGCCTCATGCTCCCGCATTGAT

CAAAAGAACCAACCGGCGGATTCCCGAGAGAACTTCCCATCGAGTCG

CGGGATCCCAGCTGGTGAAGAGCGAGCTGGAGGAGAAGAAGTCCGAG

CTGCGGCACAAGCTGAAGTACGTGCCCCACGAGTACATCGAGCTGAT

CGAGATCGCCAGGAACAGCACCCAGGACCGCATCCTGGAGATGAAGG

TGATGGAGTTCTTCATGAAGGTGTACGGCTACAGGGGAAAGCACCTG

GGCGGAAGCAGAAAGCCTGACGGCGCCATCTATACAGTGGGCAGCCC

CATCGATTACGGCGTGATCGTGGACACAAAGGCCTACAGCGGCGGCT

ACAATCTGCCTATCGGCCAGGCCGACGAGATGCAGAGATACGTGGAG

GAGAACCAGACCCGGAATAAGCACATCAACCCCAACGAGTGGTGGAA

GGTGTACCCTAGCAGCGTGACCGAGTTCAAGTTCCTGTTCGTGAGCG

GCCACTTCAAGGGCAACTACAAGGCCCAGCTGACCAGGCTGAACCAC

ATCACCAACTGCAATGGCGCCGTGCTGAGCGTGGAGGAGCTGCTGAT

CGGCGGCGAGATGATCAAAGCCGGCACCCTGACACTGGAGGAGGTGC

GGCGCAAGTTCAACAACGGCGAGATCAACTTCTGATAACTTAAGTTT

AAACCGCTGATCAGCCTCGACTGTGCCTTCTAGTTGCCAGCCATCTG

TTGTTTGCCCCTCCCCCGTGCCTTCCTTGACCCTGGAAGGTGCCACT
CCCACTGTCCTTTCCTAATAAAATGAGGAAATTGCATCGCATTGTCT
GAGTAGGTGTCATTCTATTCTGGGGGGTGGGGTGGGGCAGGACAGCA
AGGGGGAGGATTGGGAAGACAAATAGCAGGCATGCTGGGGATGCGGTG
GGCTCTATGGCTTCTGAGGCGGAAAGAACCAGCTGGGGCTCTAGGGG
GTATCCCCACGCGCCCTGTAGCGGCGCATTAAGCGCGGCGGGTGTGG
TGGTTACGCGCAGCGTGACCGCTACACTTGCCAGCGCCCTAGCGCCC
GCTCCTTTCGCTTTCTTCCCTTCCTTTCTCGCCACGTTCGCCGGCTT
TCCCCGTCAAGCTCTAAATCGGGGCTCCCTTTAGGGTTCCGATTTA
GTGCTTTACGGCACCTCGACCCCAAAAAACTTGATTAGGGTGATGGT
TCACGTAGTGGGCCATCGCCCTGATAGACGGTTTTTCGCCCTTTGAC
GTTGGAGTCCACGTTCTTTAATAGTGGACTCTTGTTCCAAACTGGAA
CAACACTCAACCCTATCTCGGTCTATTCTTTTGATTTATAAGGGATT
TTGCCGATTTCGGCCTATTGGTTAAAAAATGAGCTGATTTAACAAAA
ATTTAACGCGAATTAATTCTGTGGAATGTGTGTCAGTTAGGGTGTGG
AAAGTCCCCAGGCTCCCCAGCAGGCAGAAGTATGCAAAGCATGCATC
TCAATTAGTCAGCAACCAGGTGTGGAAAGTCCCCAGGCTCCCCAGCA
GGCAGAAGTATGCAAAGCATGCATCTCAATTAGTCAGCAACCATAGT
CCCGCCCCTAACTCCGCCCATCCCGCCCCTAACTCCGCCCAGTTCCG
CCCATTCTCCGCCCCATGGCTGACTAATTTTTTTTATTTATGCAGAG
GCCGAGGCCGCCTCTGCCTCTGAGCTATTCCAGAAGTAGTGAGGAGG
CTTTTTTGGAGGCCTAGGCTTTTGCAAAAAGCTCCCGGGAGCTTGTA
TATCCATTTTCGGATCTGATCAAGAGACAGGATGAGGATCGTTTCGC
ATGATTGAACAAGATGGATTGCACGCAGGTTCTCCGGCCGCTTGGGT
GGAGAGGCTATTCGGCTATGACTGGGCACAACAGACAATCGGCTGCT
CTGATGCCGCCGTGTTCCGGCTGTCAGCGCAGGGGCGCCCGGTTCTT
TTTGTCAAGACCGACCTGTCCGGTGCCCTGAATGAACTGCAGGACGA
GGCAGCGCGGCTATCGTGGCTGGCCACGACGGGCGTTCCTTGCGCAG
CTGTGCTCGACGTTGTCACTGAAGCGGGAAGGGACTGGCTGCTATTG
GGCGAAGTGCCGGGGCAGGATCTCCTGTCATCTCACCTTGCTCCTGC
CGAGAAAGTATCCATCATGGCTGATGCAATGCGGCGGCTGCATACGC
TTGATCCGGCTACCTGCCCATTCGACCACCAAGCGAAACATCGCATC
GAGCGAGCACGTACTCGGATGGAAGCCGGTCTTGTCGATCAGGATGA
TCTGGACGAAGAGCATCAGGGGCTCGCGCCAGCCGAACTGTTCGCCA
GGCTCAAGGCGCGCATGCCCGACGGCGAGGATCTCGTCGTGACCCAT
GGCGATGCCTGCTTGCCGAATATCATGGTGGAAAATGGCCGCTTTTC
TGGATTCATCGACTGTGGCCGGCTGGGTGTGGCGGACCGCTATCAGG
ACATAGCGTTGGCTACCCGTGATATTGCTGAAGAGCTTGGCGGCGAA
TGGGCTGACCGCTTCCTCGTGCTTTACGGTATCGCCGCTCCCGATTC
GCAGCGCATCGCCTTCTATCGCCTTCTTGACGAGTTCTTCTGAGCGG

GACTCTGGGGTTCGAAATGACCGACCAAGCGACGCCCAACCTGCCAT
CACGAGATTTCGATTCCACCGCCGCCTTCTATGAAAGGTTGGGCTTC
GGAATCGTTTTCCGGGACGCCGGCTGGATGATCCTCCAGCGCGGGGA
TCTCATGCTGGAGTTCTTCGCCCACCCCAACTTGTTTATTGCAGCTT
ATAATGGTTACAAATAAAGCAATAGCATCACAAATTTCACAAATAAA
GCATTTTTTTCACTGCATTCTAGTTGTGGTTTGTCCAAACTCATCAA
TGTATCTTATCATGTCTGTATACCGTCGACCTCTAGCTAGAGCTTGG
CGTAATCATGGTCATAGCTGTTTCCTGTGTGAAATTGTTATCCGCTC
ACAATTCCACACAACATACGAGCCGGAAGCATAAAGTGTAAAGCCTG
GGGTGCCTAATGAGTGAGCTAACTCACATTAATTGCGTTGCGCTCAC
TGCCCGCTTTCCAGTCGGGAAACCTGTCGTGCCAGCTGCATTAATGA
ATCGGCCAACGCGCGGGGAGAGGCGGTTTGCGTATTGGGCGCTCTTC
CGCTTCCTCGCTCACTGACTCGCTGCGCTCGGTCGTTCGGCTGCGGC
GAGCGGTATCAGCTCACTCAAAGGCGGTAATACGGTTATCCACAGAA
TCAGGGGATAACGCAGGAAAGAACATGTGAGCAAAAGGCCAGCAAAA
GGCCAGGAACCGTAAAAAGGCCGCGTTGCTGGCGTTTTTCCATAGGC
TCCGCCCCCCTGACGAGCATCACAAAAATCGACGCTCAAGTCAGAGG
TGGCGAAACCCGACAGGACTATAAAGATACCAGGCGTTTCCCCCTGG
AAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCT
GGGCTGTGTGCACGAACCCCCCGTTCAGCCCGACCGCTGCGCCTTAT
CCGGTAACTATCGTCTTGAGTCCAACCCGGTAAGACACGACTTATCG
CCACTGGCAGCAGCCACTGGTAACAGGATTAGCAGAGCGAGGTATGT
AGGCGGTGCTACAGAGTTCTTGAAGTGGTGGCCTAACTACGGCTACA
CTAGAAGAACAGTATTTGGTATCTGCGCTCTGCTGAAGCCAGTTACC
TTCGGAAAAAGAGTTGGTAGCTCTTGATCCGGCAAACAAACCACCGC
TGGTAGCGGTTTTTTTGTTTGCAAGCAGCAGATTACGCGCAGAAAAA
AAGGATCTCAAGAAGATCCTTTGATCTTTTCTACGGGGTCTGACGCT
CAGTGGAACGAAAACTCACGTTAAGGGATTTTGGTCATGAGATTATC
AAAAAGGATCTTCACCTAGATCCTTTTAAATTAAAAATGAAGTTTTA
AATCAATCTAAAGTATATATGAGTAAACTTGGTCTGACAGTTACCAA
TGCTTAATCAGTGAGGCACCTATCTCAGCGATCTGTCTATTTCGTTC
ATCCATAGTTGCCTGACTCCCCGTCGTGTAGATAACTACGATACGGG
AGGGCTTACCATCTGGCCCCAGTGCTGCAATGATACCGCGAGACCCA
CGCTCACCGGCTCCAGATTTATCAGCAATAAACCAGCCAGCGGAAG
GGCCGAGCGCAGAAGTGGTCCTGCAACTTTATCCGCCTCCATCCAGT
CTATTAATTGTTGCCGGGAAGCTAGAGTAAGTAGTTCGCCAGTTAAT
AGTTTGCGCAACGTTGTTGCCATTGCTACAGGCATCGTGGTGTCACG
CTCGTCGTTTGGTATGGCTTCATTCAGCTCCGGTTCCCAACGATCAA
GGCGAGTTACATGATCCCCCATGTTGTGCAAAAAAGCGGTTAGCTCC

TTCGGTCCTCCGATCGTTGTCAGAAGTAAGTTGGCCGCAGTGTTATC

ACTCATGGTTATGGCAGCACTGCATAATTCTCTTACTGTCATGCCAT

CCGTAAGATGCTTTTCTGTGACTGGTGAGTACTCAACCAAGTCATTC

TGAGAATAGTGTATGCGGCGACCGAGTTGCTCTTGCCCGGCGTCAAT

ACGGGATAATACCGCGCCACATAGCAGAACTTTAAAAGTGCTCATCA

TTGGAAAACGTTCTTCGGGGCGAAAACTCTCAAGGATCTTACCGCTG

TTGAGATCCAGTTCGATGTAACCCACTCGTGCACCCAACTGATCTTC

AGCATCTTTTACTTTCACCAGCGTTTCTGGGTGAGCAAAAACAGGAA

GGCAAAATGCCGCAAAAAAGGGAATAAGGGCGACACGGAAATGTTGA

ATACTCATACTCTTCCTTTTTCAATATTATTGAAGCATTTATCAGGG

TTATTGTCTCATGAGCGGATACATATTTGAATGTATTTAGAAAAATA

AACAAATAGGGGTTCCGCGCACATTTCCCCGAAAAGTGCCACCTGAC

GTC.

Two BsmBI sites were used to clone the repeat arrays assembled from the Cermak tool kit into this backbone.

The plasmid backbone for the SSA reporter assays has the identity:

(SEQ ID NO: 26)
GACGGATCGGGAGATCTCCCGATCCCCTATGGTCGACTCTCAGTACA

ATCTGCTCTGATGCCGCATAGTTAAGCCAGTATCTGCTCCCTGCTTG

TGTGTTGGAGGTCGCTGAGTAGTGCGCGAGCAAAATTTAAGCTACAA

CAAGGCAAGGCTTGACCGACAATTGCATGAAGAATCTGCTTAGGGTT

AGGCGTTTTGCGCTGCTTCGCGATGTACGGGCCAGATATACGCGTTG

ACATTGATTATTGACTAGTTATTAATAGTAATCAATTACGGGGTCAT

TAGTTCATAGCCCATATATGGAGTTCCGCGTTACATAACTTACGGTA

AATGGCCCGCCTGGCTGACCGCCCAACGACCCCCGCCCATTGACGTC

AATAATGACGTATGTTCCCATAGTAACGCCAATAGGGACTTTCCATT

GACGTCAATGGGTGGACTATTTACGGTAAACTGCCCACTTGGCAGTA

CATCAAGTGTATCATATGCCAAGTACGCCCCCTATTGACGTCAATGA

CGGTAAATGGCCCGCCTGGCATTATGCCCAGTACATGACCTTATGGG

ACTTTCCTACTTGGCAGTACATCTACGTATTAGTCATCGCTATTACC

ATGGTGATGCGGTTTTGGCAGTACATCAATGGGCGTGGATAGCGGTT

TGACTCACGGGGATTTCCAAGTCTCCACCCCATTGACGTCAATGGGA

GTTTGTTTTGGCACCAAAATCAACGGGACTTTCCAAAATGTCGTAAC

AACTCCGCCCCATTGACGCAAATGGGCGGTAGGCGTGTACGGTGGGA

GGTCTATATAAGCAGAGCTCTCTGGCTAACTAGAGAACCCACTGCTT

ACTGGCTTATCGAAATTAATACGACTCACTATAGGGAGACCCAAGCT

TGGTACCGAGCTCGGATCGATATCTGCGGCCGCACCATGGTGAGCAA

GGGCGAGGAGCTGTTCACCGGGGTGGTGCCCATCCTGGTCGAGCTGG

ACGGCGACGTAAACGGCCACAAGTTCAGCGTGTCCGGCGAGGGCGAG

GGCGATGCCACCTACGGCAAGCTGACCCTGAAGTTCATCTGCACCAC

CGGCAAGCTGCCCGTGCCCTGGCCCACCCTCGTGACCACCCTGACCT

ACGGCGTGCAGTGCTTCAGCCGCTACCCCGACCACATGAAGCAGCAC

GACTTCTTCAAGTCCGCCATGCCCGAAGGCTACGTCCAGGAGCGCAC

AATTTTTTTCAAGGATGATGGAAACTACAAGTAAGGCGCGACCATCT

TCTTCAAGGACGACGGCGCGCCTGGGATCCTGCAGGCAGGAGCGCAC

AATTTTTTTCAAGGATGATGGAAACTACAAGACCCGCGCCGAGGTGA

AGTTCGAGGGCGACACCCTGGTGAACCGCATCGAGCTGAAGGGCATC

GACTTCAAGGAGGACGGCAACATCCTGGGGCACAAGCTGGAGTACAA

CTACAACAGCCACAACGTCTATATCATGGCCGACAAGCAGAAGAACG

GCATCAAGGTGAACTTCAAGATCCGCCACAACATCGAGGACGGCAGC

GTGCAGCTCGCCGACCACTACCAGCAGAACACCCCCATCGGCGACNG

CCCCGTGCTGCTGCCCGACAACCACTACCTGAGCACCCAGTCCGCCC

TGAGCAAAGACCCCAACGAGAAGCGCGATCACATGGTCCTGCTGGAG

TTCGTGACCGCCGCCGGGATCACTCTCGGCATGGACGAGCTGTACAA

GTAAGGATCCACTAGTAACGGCCGCCAGTGTGCTGGAATTAATTCGC

TGTCTGCGAGGGCCAGCTGTTGGGGTGAGTACTCCCTCTCAAAAGCG

GGCATGACTTCTGCGCTAAGATTGTCAGTTTCCAAAAACGAGGAGGA

TTTGATATTCACCTGGCCCGCGGTGATGCCTTTGAGGGTGGCCGCGT

CCATCTGGTCAGAAAAGACAATCTTTTTGTTGTCAAGCTTGAGGTGT

GGCAGGCTTGAGATCTGGCCATACACTTGAGTGACAATGACATCCAC

TTTGCCTTTCTCTCCACAGGTGTCCACTCCCAGGTCCAACTGCAGGT

CGAGCATGCATCTAGGGCGGCCAATTCCGCCCCTCTCCCTCCCCCCC

CCCTAACGTTACTGGCCGAAGCCGCTTGGAATAAGGCCGGTGTGCGT

TTGTCTATATGTGATTTTCCACCATATTGCCGTCTTTTGGCAATGTG

AGGGCCCGGAAACCTGGCCCTGTCTTCTTGACGAGCATTCCTAGGGG

TCTTTCCCCTCTCGCCAAAGGAATGCAAGGTCTGTTGAATGTCGTGA

AGGAAGCAGTTCCTCTGGAAGCTTCTTGAAGACAAACAACGTCTGTA

GCGACCCTTTGCAGGCAGCGGAACCCCCCACCTGGCGACAGGTGCCT

CTGCGGCCAAAAGCCACGTGTATAAGATACACCTGCAAAGGCGGCAC

AACCCCAGTGCCACGTTGTGAGTTGGATAGTTGTGGAAAGAGTCAAA

TGGCTCTCCTCAAGCGTATTCAACAAGGGGCTGAAGGATGCCCAGAA

GGTACCCCATTGTATGGGATCTGATCTGGGGCCTCGGTGCACATGCT

TTACATGTGTTTAGTCGAGGTTAAAAAAACGTCTAGGCCCCCCGAAC

CACGGGGACGTGGTTTTCCTTTGAAAAACACGATGATAAGCTTGCCA

CAACCCACAAGGAGACGACCTTCCATGACCGAGTACAAGCCCACGGT

GCGCCTCGCCACCCGCGACGACGTCCCCCGGGCCGTACGCACCCTCG

CCGCCGCGTTCGCCGACTACCCCGCCACGCGCCACACCGTCGACCCG

```
GACCGCCACATCGAGCGGGTCACCGAGCTGCAAGAACTCTTCCTCAC
GCGCGTCGGGCTCGACATCGGCAAGGTGTGGGTCGCGGACGACGGCG
CCGCGGTGGCGGTCTGGACCACGCCGGAGAGCGTCGAAGCGGGGGCG
GTGTTCGCCGAGATCGGCCCGCGCATGGCCGAGTTGAGCGGTTCCCG
GCTGGCCGCGCAGCAACAGATGGAAGGCCTCCTGGCGCCGCACCGGC
CCAAGGAGCCCGCGTGGTTCCTGGCCACCGTCGGCGTCTCGCCCGAC
CACCAGGGCAAGGGTCTGGGCAGCGCCGTCGTGCTCCCCGGAGTGGA
GGCGGCCGAGCGCGCCGGGGTGCCCGCCTTCCTGGAGACCTCCGCGC
CCCGCAACCTCCCCTTCTACGAGCGGCTCGGCTTCACCGTCACCGCC
GACGTCGAGTGCCCGAAGGACCGCGCGACCTGGTGCATGACCCGCAA
GCCCGGTGCCTGACGCCCGCCCCACGACCCGCAGCGCCCGACCGAAA
GGAGCGCACGACCCCATGGCTCCGACCGAAGCCGACCCGGGCGGCCC
CGCCGACCCCGCACCCGCCCCGAGGCCCACCGACTCTAGAGCTCGC
TGATCAGCCTCGACTGTGCCTTCTAGTTGCCAGCCATCTGTTGTTTG
CCCCTCCCCGTGCCTTCCTTGACCCTGGAAGGTGCCACTCCCACTG
TCCTTTCCTAATAAAATGAGGAAATTGCATCGCATTGTCTGAGTAGG
TGTCATTCTATTCTGGGGGGTGGGGTGGGGCAGGACAGCAAGGGGGA
GGATTGGGAAGACAATAGCAGGCATGCTGGGGATGCGGTGGGCTCTA
TGGCTTCTGAGGCGGAAAGAACCAGCTGGGGCTCGAGTGCATTCTAG
TTGTGGTTTGTCCAAACTCATCAATGTATCTTATCATGTCTGTATAC
CGTCGACCTCTAGCTAGAGCTTGGCGTAATCATGGTCATAGCTGTTT
CCTGTGTGAAATTGTTATCCGCTCACAATTCCACACAACATACGAGC
CGGAAGCATAAAGTGTAAAGCCTGGGGTGCCTAATGAGTGAGCTAAC
TCACATTAATTGCGTTGCGCTCACTGCCCGCTTTCCAGTCGGGAAAC
CTGTCGTGCCAGCTGCATTAATGAATCGGCCAACGCGCGGGGAGAGG
CGGTTTGCGTATTGGGCGCTCTTCCGCTTCCTCGCTCACTGACTCGC
TGCGCTCGGTCGTTCGGCTGCGGCGAGCGGTATCAGCTCACTCAAAG
GCGGTAATACGGTTATCCACAGAATCAGGGGATAACGCAGGAAAGAA
CATGTGAGCAAAAGGCCAGCAAAAGGCCAGGAACCGTAAAAAGGCCG
CGTTGCTGGCGTTTTTCCATAGGCTCCGCCCCCCTGACGAGCATCAC
AAAAATCGACGCTCAAGTCAGAGGTGGCGAAACCCGACAGGACTATA
AAGATACCAGGCGTTTCCCCCTGGAAGCTCCCTCGTGCGCTCTCCTG
TTCCGACCCTGCCGCTTACCGGATACCTGTCCGCCTTTCTCCCTTCG
GGAAGCGTGGCGCTTTCTCAATGCTCACGCTGTAGGTATCTCAGTTC
GGTGTAGGTCGTTCGCTCCAAGCTGGGCTGTGTGCACGAACCCCCCG
TTCAGCCCGACCGCTGCGCCTTATCCGGTAACTATCGTCTTGAGTCC
AACCCGGTAAGACACGACTTATCGCCACTGGCAGCAGCCACTGGTAA
CAGGATTAGCAGAGCGAGGTATGTAGGCGGTGCTACAGAGTTCTTGA
AGTGGTGGCCTAACTACGGCTACACTAGAAGGACAGTATTTGGTATC
TGCGCTCTGCTGAAGCCAGTTACCTTCGGAAAAAGAGTTGGTAGCTC
TTGATCCGGCAAACAAACCACCGCTGGTAGCGGTGGTTTTTTTGTTT
GCAAGCAGCAGATTACGCGCAGAAAAAAAGGATCTCAAGAAGATCCT
TTGATCTTTTCTACGGGGTCTGACGCTCAGTGGAACGAAAACTCACG
TTAAGGGATTTTGGTCATGAGATTATCAAAAAGGATCTTCACCTAGA
TCCTTTTAAATTAAAAATGAAGTTTTAAATCAATCTAAAGTATATAT
GAGTAAACTTGGTCTGACAGTTACCAATGCTTAATCAGTGAGGCACC
TATCTCAGCGATCTGTCTATTTCGTTCATCCATAGTTGCCTGACTCC
CCGTCGTGTAGATAACTACGATACGGGAGGGCTTACCATCTGGCCCC
AGTGCTGCAATGATACCGCGAGACCCACGCTCACCGGCTCCAGATTT
ATCAGCAATAAACCAGCCAGCCGGAAGGGCCGAGCGCAGAAGTGGTC
CTGCAACTTTATCCGCCTCCATCCAGTCTATTAATTGTTGCCGGGAA
GCTAGAGTAAGTAGTTCGCCAGTTAATAGTTTGCGCAACGTTGTTGC
CATTGCTACAGGCATCGTGGTGTCACGCTCGTCGTTTGGTATGGCTT
CATTCAGCTCCGGTTCCCAACGATCAAGGCGAGTTACATGATCCCCC
ATGTTGTGCAAAAAAGCGGTTAGCTCCTTCGGTCCTCCGATCGTTGT
CAGAAGTAAGTTGGCCGCAGTGTTATCACTCATGGTTATGGCAGCAC
TGCATAATTCTCTTACTGTCATGCCATCCGTAAGATGCTTTTCTGTG
ACTGGTGAGTACTCAACCAAGTCATTCTGAGAATAGTGTATGCGGCG
ACCGAGTTGCTCTTGCCCGGCGTCAATACGGGATAATACCGCGCCAC
ATAGCAGAACTTTAAAAGTGCTCATCATTGGAAAACGTTCTTCGGGG
CGAAAACTCTCAAGGATCTTACCGCTGTTGAGATCCAGTTCGATGTA
ACCCACTCGTGCACCCAACTGATCTTCAGCATCTTTTACTTTCACCA
GCGTTTCTGGGTGAGCAAAAACAGGAAGGCAAAATGCCGCAAAAAAG
GGAATAAGGGCGACACGGAAATGTTGAATACTCATACTCTTCCTTTT
TCAATATTATTGAAGCATTTATCAGGGTTATTGTCTCATGAGCGGAT
ACATATTTGAATGTATTTAGAAAAATAAACAAATAGGGGTTCCGCGC
ACATTTCCCCGAAAAGTGCCACCTGACGTC.
```

AscI and SbfI sites were used for inserting specific oligonucleotide pairs containing the target half-sites and the spacer into the backbone.

TABLE 12

TALEN target gene, TALEN index, Target
Sequence, and RVD array for newly designed TALENs

| Target gene | TALEN Index | Target sequence (excluding the 5'T present before the 5'end of all TALEN half-sites) | TALEN RVD array |
|---|---|---|---|
| | | Training set | |
| HBB | S-01 | GGTGCACCTGACTCCT | NK NK NG NK HD NI HD HD NG NK NI HD NG HD HD NG |
| HBB | S-02 | GCACCTGACTCCTGT | NK HD NI HD HD NG NK NI HD NG HD HD NG NK NG |
| HBB | S-03 | CAAACAGACACCATGGTGCACCT | HD NI NI NI HD NI NK NI HD NI HD HD NI NG NK NK NG NK HD NI HD HD NG |
| HBB | S-04 | CAAACAGACACCATGGTGCACCTGA | HD NI NI NI HD NI NK NI HD NI HD HD NI NG NK NK NG NK HD NI HD HD NG NK NI |
| HBB | S-05 | CACCTTGCCCCACAGGGCAGT | HD NI HD HD NG NG NK HD HD HD HD NI HD NI NK NK NK HD NI NK NG |
| HBB | S-06 | CACCTTGCCCCACAGGGCAGTAA | HD NI HD HD NG NG NK HD HD HD HD NI HD NI NK NK NK HD NI NK NG NI NI |
| HBB | S-07 | CACCTTGCCCCACAGGGCAGTAAC | HD NI HD HD NG NG NK HD HD HD HD NI HD NI NK NK NK HD NI NK NG NI NI HD |
| HBB | S-08 | CACCTTGCCCCACAGGGCAGTA | HD NI HD HD NG NG NK HD HD HD HD NI HD NI NK NK NK HD NI NK NG NI |
| HBB | S-09 | GCCCCACAGGGCAGTAACGGCAGA | NK HD HD HD HD NI HD NI NK NK NK HD NI NK NG NI NI HD NK NK HD NI NK NI |
| HBB | S-10 | GCTTACATTTGCTTCTGACACAACTGTGT T | NK HD NG NG NI HD NI NG NG NG NK HD NG NG HD NG NK NI HD NI HD NI NI HD NG NK NG NK NG NG |
| HBB | S-11 | ACAAGACAGGTTTAAGGAGACCAAT | NI HD NI NI NK NI HD NI NK NK NG NG NG NI NI NK NK NI NK NI HD HD NI NI NG |
| HBB | S-12 | TGCCCCACAGGGCAGT | NG NK HD HD HD HD NI HD NI NK NK NK HD NI NK NG |
| HBB | S-13 | CTTGGGTTTCTGATAGGCACTGACTCTCT | HD NG NG NK NK NK NG NG NG HD NG NK NI NG NI NK NK HD NI HD NG NK NI HD NG HD NG HD NG |
| HBB | S-14 | CCTGTGGAGAAGTCT | HD HD NG NK NG NK NK NI NK NI NI NK NG HD NG |

TABLE 12-continued

TALEN target gene, TALEN index, Target Sequence, and RVD array for newly designed TALENs

| Target gene | TALEN Index | Target sequence (excluding the 5'T present before the 5'end of all TALEN half-sites) | TALEN RVD array |
|---|---|---|---|
| HBB | S-15 | CCTGTGGAGAAGTCTGCCGT | HD HD NG NK NG NK NK NI NK NI NI NK NG HD NG NK HD HD NK NG |
| HBB | S-16 | CTGATAGGCACTGACTCT | HD NG NK NI NG NI NK NK HD NI HD NG NK NI HD NG HD NG |
| HBB | S-17 | CTGATAGGCACTGACTCTCT | HD NG NK NI NG NI NK NK HD NI HD NG NK NI HD NG HD NG HD NG |
| HBB | S-18 | CTGATAGGCACTGACTCTCTCT | HD NG NK NI NG NI NK NK HD NI HD NG NK NI HD NG HD NG HD NG HD NG |
| HBB | S-19 | CTGATAGGCACTGACTCTCTCTGCCT | HD NG NK NI NG NI NK NK HD NI HD NG NK NI HD NG HD NG HD NG NK HD HD NG |
| HBB | S-20 | CTGATAGGCACTGACTCTCTCTGCCTAT | HD NG NK NI NG NI NK NK HD NI HD NG NK NI HD NG HD NG HD NG HD NG NK HD HD NG NI NG |
| HBB | S-21 | CTGATAGGCACTGACTCTCTCTGCCTATT | HD NG NK NI NG NI NK NK HD NI HD NG NK NI HD NG HD NG HD NG NK HD HD NG NI NG NG |
| HBB | S-22 | CCACGTTCACCTTGCCCCACAGGGCAGT | HD HD NI HD NK NG NG HD NI HD HD NG NG NK HD HD HD HD NI HD NI NK NK NK HD NI NK NG |
| HBB | S-23 | AGACCACCAGCAGCCT | NI NK NI HD HD NI HD HD NI NK HD NI NK HD HD NG |
| HBB | S-24 | CCAAGGGTAGACCACCAGCAGCCT | HD HD NI NI NK NK NK NG NI NK NI HD HD NI HD HD NI NK HD NI NK HD HD NG |
| HBB | S-25 | CTCCACAGGAGTCAGGTGCACCAT | HD NG HD HD NI HD NI NK NK NI NK NG HD NI NK NK NG NK HD NI HD HD NI NG |
| HBB | S-26 | ATCAGAAACCCAAGAGTCTTCTCTGT | NI NG HD NI NK NI NI NI HD HD HD NI NI NK NI NK HD NG NG HD NG HD NG NK NG |
| HBB | S-27 | GCCTATCAGAAACCCAAGAGTCTTCTCTGT | NK HD HD NG NI NG HD NI NK NI NI NI HD HD HD NI NI NK NI NK HD NG NG HD NG HD NG NK NG |
| HBB | S-28 | ATCAGAAACCCAAGAGTCTTCTCT | NI NG HD NI NK NI NI NI HD HD HD NI |

TABLE 12-continued

TALEN target gene, TALEN index, Target
Sequence, and RVD array for newly designed TALENs

| Target gene | TALEN Index | Target sequence (excluding the 5'T present before the 5'end of all TALEN half-sites) | TALEN RVD array |
|---|---|---|---|
| | | | NI NK NI NK NG HD<br>NG NG HD NG HD NG |
| HBB | S-29 | GCCTATCAGAAACCCAAGAGTCTTCTCT | NK HD HD NG NI NG<br>HD NI NK NI NI NI<br>HD HD HD NI NI NK<br>NI NK NG HD NG NG<br>HD NG HD NG |
| HBB | S-30 | ATCAGAAACCCAAGAGTCTTCT | NI NG HD NI NK NI<br>NI NI HD HD HD NI<br>NI NK NI NK NG HD<br>NG NG HD NG |
| HBB | S-31 | GCCTATCAGAAACCCAAGAGTCTTCT | NK HD HD NG NI NG<br>HD NI NK NI NI NI<br>HD HD HD NI NI NK<br>NI NK NG HD NG NG<br>HD NG |
| HBB | S-32 | ATCAGAAACCCAAGAGTCTT | NI NG HD NI NK NI<br>NI NI HD HD HD NI<br>NI NK NI NK NG HD<br>NG NG |
| HBB | S-33 | GCCTATCAGAAACCCAAGAGTCTT | NK HD HD NG NI NG<br>HD NI NK NI NI NI<br>HD HD HD NI NI NK<br>NI NK NG HD NG NG |
| HBB | S-34 | ATCAGAAACCCAAGAGTCT | NI NG HD NI NK NI<br>NI NI HD HD HD NI<br>NI NK NI NK NG HD<br>NG |
| HBB | S-35 | GCCTATCAGAAACCCAAGAGTCT | NK HD HD NG NI NG<br>HD NI NK NI NI NI<br>HD HD HD NI NI NK<br>NI NK NG HD NG |
| HBB | S-36 | ATCAGAAACCCAAGAGT | NI NG HD NI NK NI<br>NI NI HD HD HD NI<br>NI NK NI NK NG |
| HBB | S-37 | GCCTATCAGAAACCCAAGAGT | NK HD HD NG NI NG<br>HD NI NK NI NI NI<br>HD HD HD NI NI NK<br>NI NK NG |
| HBB | S-38 | CTATTGCTTACATTTGCTTCTGACACAACT | HD NG NI NG NG NK<br>HD NG NG NI HD NI<br>NG NG NG NK HD NG<br>NG HD NG NK NI HD<br>NI HD NI NI HD NG |
| HBB | S-39 | GGGTTTCTGATAGGCACTGACTCTCTCT | NK NK NK NG NG NG<br>HD NG NK NI NG NI<br>NK NK HD NI HD NG<br>NK NI HD NG HD NG<br>HD NG HD NG |
| HBB | S-40 | ATTGCTTACATTTGCTTCTGACACAACT | NI NG NG NK HD NG<br>NG NI HD NI NG NG<br>NG NK HD NG NG HD<br>NG NK NI HD NI HD<br>NI NI HD NG |
| HBB | S-41 | ATTGCTTACATTTGCTTCTGACACAACTGT | NI NG NG NK HD NG<br>NG NI HD NI NG NG<br>NG NK HD NG NG HD<br>NG NK NI HD NI HD<br>NI NI HD NG NK NG |

TABLE 12-continued

TALEN target gene, TALEN index, Target
Sequence, and RVD array for newly designed TALENs

| Target gene | TALEN Index | Target sequence (excluding the 5'T present before the 5'end of all TALEN half-sites) | TALEN RVD array |
|---|---|---|---|
| HBB | S-42 | GCTTACATTTGCTTCTGACACAACT | NK HD NG NG NI HD NI NG NG NG NK HD NG NG HD NG NK NI HD NI HD NI NI HD NG |
| HBB | S-43 | GCTTACATTTGCTTCTGACACAACTGT | NK HD NG NG NI HD NI NG NG NG NK HD NG NG HD NG NK NI HD NI HD NI NI HD NG NK NG |
| HBB | S-44 | GCTTACATTTGCTTCTGACACAACTGTGT | NK HD NG NG NI HD NI NG NG NG NK HD NG NG HD NG NK NI HD NI HD NI NI HD NG NK NG NK NG |
| HBB | S-55 | AAGGAGACCAATAGAAACT | NI NI NK NK NI NK NI HD HD NI NI NG NI NK NI NI NI HD NG |
| HBB | S-56 | TAAGGAGACCAATAGAAACT | NG NI NI NK NK NI NK NI HD HD NI NI NG NI NK NI NI NI HD NG |
| HBB | S-57 | TTAAGGAGACCAATAGAAACT | NG NG NI NI NK NK NI NK NI HD HD NI NI NG NI NK NI NI NI HD NG |
| HBB | S-68 | TGCCCCACAGGGCAGTA | NG NK HD HD HD HD NI HD NI NK NK NK HD NI NK NG NI |
| HBB | S-74 | CAAACAGACACCATG | HD NI NI NI HD NI NK NI HD NI HD HD NI NG NK |
| HBB | S-75 | CAAACAGACACCATGGT | HD NI NI NI HD NI NK NI HD NI HD HD NI NG NK NK NG |
| HBB | S-76 | AGACACCATGGTGCAC | NI NK NI HD NI HD HD NI NG NK NK NG NK HD NI HD |
| HBB | S-77 | CAAACAGACACCATGGTGCACC | HD NI NI NI HD NI NK NI HD NI HD HD NI NG NK NK NG NK HD NI HD HD |
| HBB | S-78 | AACGGCAGACTTCTCCA | NI NI HD NK NK HD NI NK NI HD NG NG HD NG HD HD NI |
| HBB | S-79 | AACGGCAGACTTCT | NI NI HD NK NK HD NI NK NI HD NG NG HD NG |
| HBB | S-80 | GCAGTAACGGCAGACT | NK HD NI NK NG NI NI HD NK NK HD NI NK NI HD NG |
| HBB | S-81 | CCTTGCCCCACAGGGCAGTAACGGCAGACT | HD HD NG NG NK HD HD HD HD NI HD NI NK NK NK HD NI NK NG NI NI HD NK NK HD NI NK NI HD NG |

TABLE 12-continued

TALEN target gene, TALEN index, Target
Sequence, and RVD array for newly designed TALENs

| Target gene | TALEN Index | Target sequence (excluding the 5'T present before the 5'end of all TALEN half-sites) | TALEN RVD array |
|---|---|---|---|
| n/a | S-82 | GCACCTGACTCCTGG | NK HD NI HD HD NG NK NI HD NG HD HD NG NK NK |
| n/a | S-83 | CTGATAGGCACTGACTCG | HD NG NK NI NG NI NK NK HD NI HD NG NK NI HD NG HD NK |
| n/a | S-84 | ATCAGAAACCCAAGAGTCTTCTCG | NI NG HD NI NK NI NI NI HD HD HD NI NI NK NI NK NG HD NG NG HD NG HD NK |
| n/a | S-85 | CACCTTGCCCCACAGGGCAGG | HD NI HD HD NG NG NK HD HD HD HD NI HD NI NK NK NK HD NI NK NK |
| n/a | S-86 | GGTGCACCTGACTCCG | NK NK NG NK HD NI HD HD NG NK NI HD NG HD HD NK |
| n/a | S-87 | GCCCCACAGGGCAGTAACGGCAGG | NK HD HD HD HD NI HD NI NK NK NK HD NI NK NG NI NI HD NK NK HD NI NK NK |
| HBB | S-88 | GCACCTGACTCCTGA | NK HD NI HD HD NG NK NI HD NG HD HD NG NK NI |
| n/a | S-89 | CTGATAGGCACTGACTCA | HD NG NK NI NG NI NK NK HD NI HD NG NK NI HD NG HD NI |
| n/a | S-90 | ATCAGAAACCCAAGAGTCTTCTCA | NI NG HD NI NK NI NI NI HD HD HD NI NI NK NI NK NG HD NG NG HD NG HD NI |
| n/a | S-91 | CACCTTGCCCCACAGGGCAGA | HD NI HD HD NG NG NK HD HD HD HD NI HD NI NK NK NK HD NI NK NI |
| n/a | S-92 | GGTGCACCTGACTCCA | NK NK NG NK HD NI HD HD NG NK NI HD NG HD HD NI |
| n/a | S-93 | GCCCCACAGGGCAGTAACGGCAGT | NK HD HD HD HD NI HD NI NK NK NK HD NI NK NG NI NI HD NK NK HD NI NK NG |
| n/a | S-94 | GCACCTGACTCCTGC | NK HD NI HD HD NG NK NI HD NG HD HD NG NK HD |
| n/a | S-95 | CTGATAGGCACTGACTCC | HD NG NK NI NG NI NK NK HD NI HD NG NK NI HD NG HD HD |
| n/a | S-96 | ATCAGAAACCCAAGAGTCTTCTCC | NI NG HD NI NK NI NI NI HD HD HD NI NI NK NI NK NG HD NG NG HD NG HD HD |
| n/a | S-97 | CACCTTGCCCCACAGGGCAGC | HD NI HD HD NG NG NK HD HD HD HD NI HD NI NK NK NK HD NI NK HD |

TABLE 12-continued

TALEN target gene, TALEN index, Target
Sequence, and RVD array for newly designed TALENs

| Target gene | TALEN Index | Target sequence (excluding the 5'T present before the 5'end of all TALEN half-sites) | TALEN RVD array |
|---|---|---|---|
| n/a | S-98 | GGTGCACCTGACTCCC | NK NK NG NK HD NI HD HD NG NK NI HD NG HD HD HD |
| n/a | S-99 | GCCCCACAGGGCAGTAACGGCAGC | NK HD HD HD HD NI HD NI NK NK NK HD NI NK NG NI NI HD NK NK HD NI NK HD |
| n/a | S-100 | TCACCTGACTCCTGT | NG HD NI HD HD NG NK NI HD NG HD HD NG NK NG |
| n/a | S-101 | TTGATAGGCACTGACTCT | NG NG NK NI NG NI NK NK HD NI HD NG NK NI HD NG HD NG |
| n/a | S-102 | TTCAGAAACCCAAGAGTCTTCTCT | NG NG HD NI NK NI NI NI HD HD HD NI NI NK NI NK NG HD NG NG HD NG HD NG |
| n/a | S-103 | TACCTTGCCCCACAGGGCAGT | NG NI HD HD NG NG NK HD HD HD HD NI HD NI NK NK NK HD NI NK NG |
| n/a | S-104 | TGTGCACCTGACTCCT | NG NK NG NK HD NI HD HD NG NK NI HD NG HD HD NG |
| n/a | S-105 | TCCCCACAGGGCAGTAACGGCAGA | NG HD HD HD HD NI HD NI NK NK NK HD NI NK NG NI NI HD NK NK HD NI NK NI |
| n/a | S-106 | GAACCTGACTCCTGT | NK NI NI HD HD NG NK NI HD NG HD HD NG NK NG |
| n/a | S-107 | CAGATAGGCACTGACTCT | HD NI NK NI NG NI NK NK HD NI HD NG NK NI HD NG HD NG |
| n/a | S-108 | AACAGAAACCCAAGAGTCTTCTCT | NI NI HD NI NK NI NI NI HD HD HD NI NI NK NI NK NG HD NG NG HD NG HD NG |
| n/a | S-109 | CTCCTTGCCCCACAGGGCAGT | HD NG HD HD NG NG NK HD HD HD HD NI HD NI NK NK NK HD NI NK NG |
| n/a | S-110 | GATGCACCTGACTCCT | NK NI NG NK HD NI HD HD NG NK NI HD NG HD HD NG |
| n/a | S-111 | GACCCACAGGGCAGTAACGGCAGA | NK NI HD HD HD NI HD NI NK NK NK HD NI NK NG NI NI HD NK NK HD NI NK NI |
| HBB | S-114 | TCCCACCCTTAGGCT | NG HD HD HD NI HD HD HD NG NG NI NK NK HD NG |
| HBB | S-115 | CACTAGCAACCTCAAACA | HD NI HD NG NI NK HD NI NI HD HD NG HD NI NI NI HD NI |

TABLE 12-continued

TALEN target gene, TALEN index, Target Sequence, and RVD array for newly designed TALENs

| Target gene | TALEN Index | Target sequence (excluding the 5'T present before the 5'end of all TALEN half-sites) | TALEN RVD array |
| --- | --- | --- | --- |
| HBB | S-116 | CTGCCGTTACTGCCCTGT | HD NG NK HD HD NK NG NG NI HD NG NK HD HD HD NG NK NG |
| HBB | S-117 | CAAAGAACCTCTGGGTCCAA | HD NI NI NI NK NI NI HD HD NG HD NG NK NK NK NG HD HD NI NI |
| HBB | S-118 | TCACCTTGCCCCACA | NG HD NI HD HD NG NG NK HD HD HD HD NI HD NI |
| HBB | S-119 | TCTCCACAGGAGTCA | NG HD NG HD HD NI HD NI NK NK NI NK NG HD NI |
| HBB | S-120 | CACCACCAACTTCAT | HD NI HD HD NI HD HD NI NI HD NG NG HD NI NG |
| HBB | S-121 | AGCAACCTCAAACAGACACCAT | NI NK HD NI NI HD HD NG HD NI NI NI HD NI NK NI HD NI HD HD NI NG |
| HBB | S-122 | AACGGCAGACTTCTCCACA | NI NI HD NK NK HD NI NK NI HD NG NG HD NG HD HD NI HD NI |
| CFTR | S-125 | TATGCCTGGCACCA | NG NI NG NK HD HD NG NK NK HD NI HD HD NI |
| CFTR | S-126 | CATCATAGGAAACACCAAT | HD NI NG HD NI NG NI NK NK NI NI NI HD NI HD HD NI NI NG |
| HBB | S-127 | CTCTCTGCCTATTGGTC | HD NG HD NG HD NG NK HD HD NG NI NG NG NK NK NG HD |
| HBB | S-128 | CCAAGGGTAGACCACCAGC | HD HD NI NI NK NK NK NG NI NK NI HD HD NI HD HD NI NK HD |
| HBB | S-129 | GGTGCACCTGACTCC | NK NK NG NK HD NI HD HD NG NK NI HD NG HD HD |
| HBB | S-130 | TGCCCCACAGGGCAGTAAC | NG NK HD HD HD HD NI HD NI NK NK NK HD NI NK NG NI NI HD |
| HBB | S-131 | GCCTATTGGTCTATTTTCC | NK HD HD NG NI NG NG NK NK NG HD NG NI NG NG NG NG HD HD |
| HBB | S-132 | CCAAGGGTAGACCACC | HD HD NI NI NK NK NK NG NI NK NI HD HD NI HD HD |
| HBB | S-133 | GTGTTCACTAGCAACCTC | NK NG NK NG NG HD NI HD NG NI NK HD NI NI HD HD NG HD |

TABLE 12-continued

TALEN target gene, TALEN index, Target Sequence, and RVD array for newly designed TALENs

| Target gene | TALEN Index | Target sequence (excluding the 5'T present before the 5'end of all TALEN half-sites) | TALEN RVD array |
|---|---|---|---|
| HBB | S-134 | TCTCCACAGGAGTCAGGTGC | NG HD NG HD HD NI HD NI NK NK NI NK NG HD NI NK NK NG NK HD |
| CXADR | C-01 | TCTTTTCCCCTTTTATGC | NG HD NG NG NG NG HD HD HD HD NG NG NG NG NI NG NK HD |
| CXADR | C-02 | GAGGCATGACAACGC | NK NI NK NK HD NI NG NK NI HD NI NI HD NK HD |
| CFTR | F-01 | TTTATTTCCAGACTTC | NG NG NG NI NG NG NG HD HD NI NK NI HD NG NG HD |
| CFTR | F-02 | CTGAAGGCTCCAGTTCTCC | HD NG NK NI NI NK NK HD NG HD HD NI NK NG NG HD NG HD HD |
| CFTR | F-03 | TTCCAGACTTCACTTC | NG NG HD HD NI NK NI HD NG NG HD NI HD NG NG HD |
| CFTR | F-04 | CTGAAGGCTCCAGTTCTC | HD NG NK NI NI NK NK HD NG HD HD NI NK NG NG HD NG HD |
| CFTR | F-05 | GAAGGCTCCAGTTCTCCC | NK NI NI NK NK HD NG HD HD NI NK NG NG HD NG HD HD HD |
| ERCC5 | J-03 | TTTCGAATTCGTCCTATTT | NG NG NG HD NK NI NI NG NG HD NK NG HD HD NG NI NG NG NG |
| ERCC5 | J-04 | CTGTTTCTTCAATAGTGGAGCAT | HD NG NK NG NG NG HD NG NG HD NG NI NI NG NI NK NG NK NK NI NK HD NI NG |
| ERCC5 | J-09 | CGGCTCTGCAAACTCTTATTTTTT | HD NK NK HD NG HD NG NK HD NI NI NI HD NG HD NG NG NI NG NG NG NG NG NG |
| ERCC5 | J-10 | CCCCATCAAACACAAA | HD HD HD HD NI NG HD NI NI NI HD NI HD NI NI NI |

Test Set

| CXADR | C-03 | CTCTTTTTTTCTTTTGT | HD NG HD NG NG NG NG NG NG NG HD NG NG NG NG NG NK NG |
| CXADR | C-04 | GTAATTCCATCAGTC | NK NG NI NI NG NG HD HD NI NG HD NI NK NG HD |
| CFTR | F-06 | GAACCCTTCACACTACCCA | NK NI NI HD HD HD NG NG HD NI HD NI HD NG NI HD HD HD NI |
| CFTR | F-07 | AGACTAACCGATTGAATAT | NI NK NI HD NG NI NI HD HD NK NI NG |

TABLE 12-continued

TALEN target gene, TALEN index, Target
Sequence, and RVD array for newly designed TALENs

| Target gene | TALEN Index | Target sequence (excluding the 5'T present before the 5'end of all TALEN half-sites) | TALEN RVD array |
|---|---|---|---|
| | | | NG NK NI NI NG NI NG |
| CFTR | F-08 | TTATTTCCAGACTTCACTTCT | NG NG NI NG NG NG HD HD NI NK NI HD NG NG HD NI HD NG NG HD NG |
| CFTR | F-09 | ACCCTCTGAAGGCTCCAGTTCT | NI HD HD HD NG HD NG NK NI NI NK NK HD NG HD HD NI NK NG NG HD NG |
| CFTR | F-10 | TCACTTCTAATGGTGAT | NG HD NI HD NG NG HD NG NI NI NG NK NK NG NK NI NG |
| CFTR | F-11 | GTGCTTAATTTTACCCTCTGAA | NK NG NK HD NG NG NI NI NG NG NG NG NI HD HD HD NG HD NG NK NI NI |
| AAVS1 | G-01 | CTGCCTAACAGGAGGTG | HD NG NK HD HD NG NI NI HD NI NK NK NI NK NK NG NK |
| AAVS1 | G-02 | CCTCCTTCCTAGTCTCCTGAT | HD HD NG HD HD NG NG HD HD NG NI NK NG HD NG HD HD NG NK NI NG |
| AAVS1 | G-03 | GTCCCTAGTGGCCCCACT | NK NG HD HD HD NG NI NK NG NK NK HD HD HD HD NI HD NG |
| AAVS1 | G-04 | CTGGTTCTGGGTACTTTTAT | HD NG NK NK NG NG HD NG NK NK NK NG NI HD NG NG NG NG NI NG |
| CDH1 | J-01 | CTCGGCGCTGCTGCTGCTGCT | HD NG HD NK NK HD NK HD NK NK HD NG NK HD NG NK HD NG NK HD NG |
| CDH1 | J-02 | GCGTCCCTCGCAAGTCAG | NK HD NK NG HD HD HD NG HD NK HD NI NI NK NG HD NI NK |
| HOXD13 | J-05 | TTCTCTCCGCGCCT | NG NG HD NG HD NG HD HD NK HD HD HD NG |
| HOXD13 | J-06 | GCCGCCGCCGCCGCCCGCCCCGAAT | NK HD HD NK HD HD NK HD HD NK HD HD NK HD HD HD NK HD HD HD NK NI NI NG |
| CDH1 | J-07 | CGGCGCTGCTGCTGCTGCT | HD NK NK HD NK HD NG NK HD NG NK HD NG NK HD NG NK HD NG |
| CDH1 | J-08 | GCGTCCCTCGCAAGTCAGGG | NK HD NK NG HD HD HD NG HD NK HD NI NI NK NG HD NI NK NK NK |
| HOXD13 | J-11 | GCGCTCAAGTCATCGCCGCA | NK HD NK HD NG HD NI NI NK NG HD NI |

TABLE 12-continued

TALEN target gene, TALEN index, Target
Sequence, and RVD array for newly designed TALENs

| Target gene | TALEN Index | Target sequence (excluding the 5'T present before the 5'end of all TALEN half-sites) | TALEN RVD array |
|---|---|---|---|
| | | | NG HD NK HD HD NK HD NI |
| HOXD13 | J-12 | GTACTTCTCCACGGGAA | NK NG NI HD NG NG HD NG HD HD NI HD NK NK NK NI NI |
| FANCE | J-13 | CGCTTGCTCGAGGCCCT | HD NK HD NG NG NK HD NG HD NK NI NK NK HD HD HD NG |
| FANCE | J-14 | CAGGCCCCTGCACGACC | HD NI NK NK HD HD HD HD NG NK HD NI HD NK NI HD HD |
| KIT | J-15 | GGGATTTTCTCTGCGTTCT | NK NK NK NI NG NG NG NG HD NG HD NG NK HD NK NG NG HD NG |
| KIT | J-16 | GTCCCACCTGTCTGGACG | NK NG HD HD NI HD HD NG NK NG HD NG NK NK NI HD NK |
| TGFBR2 | J-17 | CGTCCTGTGGACGCGTAT | HD NK NG HD HD NG NK NG NK NK NI HD NK HD NK NG NI NG |
| TGFBR2 | J-18 | CACCCGACTTCTGAACGTGCGGT | HD NI HD HD HD NK NI HD NG NG HD NG NK NI NI HD NK NG NK HD NK NK NG |
| AXIN2 | J-0036 | CTTCCCCTGGCACTGG | HD NG NG HD HD HD HD NG NN NN HD NI HD NG NN NN |
| AXIN2 | J-0037 | CCCGGACCCCAGCAGCAGCTTCCG | HD HD HD NN NN NI HD HD HD HD NI NN HD NI NN HD NI NN HD NG NG HD HD NN |
| EXT2 | J-0038 | GGCCTGCGGCATCCCT | NN NN HD HD NG NN HD NN NN HD NI NG HD HD HD NG |
| EXT2 | J-0039 | TCCCTACCTCGTCCCACGG | NG HD HD HD NG NI HD HD NG HD NG NN NG HD HD HD NI HD NN NN |
| FANCA | J-0040 | ACCCAGCAGCTCGGCCCAG | NI HD HD HD NI NN HD NI NN NG HD NN NN HD HD HD NI NN |
| FANCA | J-0041 | CCGCCTCGGGCCAGGACCC | HD HD NN HD HD NG HD NN NN NN HD HD NI NN NN NI HD HD HD |
| FLT4 | J-0042 | TCGCCGCGCTCACCGTCCA | NG HD NN HD HD NN HD NN HD NG HD NI HD HD NN NG HD HD NI |
| FLT4 | J-0043 | GCCTGCGACTGTGGCT | NN HD HD NG NN HD NN NI HD NG NN NG NN NN HD NG |

TABLE 12-continued

TALEN target gene, TALEN index, Target Sequence, and RVD array for newly designed TALENs

| Target gene | TALEN Index | Target sequence (excluding the 5'T present before the 5'end of all TALEN half-sites) | TALEN RVD array |
|---|---|---|---|
| HMGA2 | J-0044 | CCACTTCAGCCCAGG | HD HD NI HD NG NG HD NI NN HD HD HD NI NN NN |
| HMGA2 | J-0045 | CCTCTCTTCTGAGGCG | HD HD NG HD NG HD NG NG HD NG NN NI NN NN HD NN |
| ATF4 | G-0041 | GTCCCCCTTCGACCAG | NK NG HD HD HD HD HD NG NG HD NK NI HD HD NI NK |
| ATF4 | G-0042 | CTAAGAGACCTAGGCTTTCT | HD NG NI NI NK NI NK NI HD HD NG NI NK NK HD NG NG NG HD NG |
| ATF4 | G-0043 | CCTCCGAATGGCTGGCTGTGGAT | HD HD NG HD HD NK NI NI NG NK NK HD NG NK NK HD NG NK NG NK NK NI NG |
| ATF4 | G-0044 | GGCCCACTCACCCTTGCTGTTGTT | NK NK HD HD HD NI HD NG HD NI HD HD HD NG NG NK HD NG NK NG NG NK NG NG |
| EIF2AK1 | G-0045 | CCGATCCCTCACCGTCAT | HD HD NK NI NG HD HD HD NG HD NI HD HD NK NG HD NI NG |
| EIF2AK1 | G-0046 | CGACTTTCCCGCCGAGGG | HD NK NI HD NG NG NG HD HD HD NK HD HD NK NI NK NK NK |
| EIF2AK1 | G-0047 | GCTCCAGCAAAGAAACCAGCAAGAG | NK HD NG HD HD NI NK HD NI NI NI NI NK NI NI NI HD NI NK HD NI NI NK NI NK |
| EIF2AK1 | G-0048 | ACAACAGCCAACCTTCCCTTTTG | NI HD NI NI HD NI NK HD HD NI NI HD HD NG NG HD HD HD NG NG NG NG NK |
| EIF2AK2 | G-0049 | CCCTGCTTCTGACGGTATGTAT | HD HD HD NG NK HD NG NG HD NG NK NI HD NK NK NG NI NG NK NG NI NG |
| EIF2AK2 | G-0050 | CTTTCAGCAGGTTTCT | HD NG NG NG HD NI NK HD NI NK NK NG NG NG HD NG |
| EIF2AK2 | G-0051 | ACTACTCCCTGCTTCTGACGGTAT | NI HD NG NI HD NG HD HD HD NG NK HD NG NK HD NG NK NI HD NK NK NG NI NG |
| EIF2AK2 | G-0052 | CTTTCAGCAGGTTTCTTCAT | HD NG NG NG HD NI NK HD NI NK NK NG NG NG HD NG NI NG |
| EIF2AK3 | G-0053 | CACCTCGGCCGCAGCCACG | HD NI HD HD NG HD NK NK HD HD NK HD NI NK HD HD NI HD NK |

TABLE 12-continued

TALEN target gene, TALEN index, Target Sequence, and RVD array for newly designed TALENs

| Target gene | TALEN Index | Target sequence (excluding the 5'T present before the 5'end of all TALEN half-sites) | TALEN RVD array |
|---|---|---|---|
| EIF2AK3 | G-0054 | GCTCCCACCTCAGCGACGCG | NK HD NG HD HD HD NI HD HD NG HD NI NK HD NK NI HD NK HD NK |
| EIF2AK3 | G-0055 | CCCACATCCAAATCCCACT | HD HD HD NI HD NI NG HD HD NI NI NI NG HD HD HD NI HD NG |
| EIF2AK3 | G-0056 | GCTGCCTTGGATCCTGAA | NK HD NG NK HD HD NG NG NK NK NI NG HD HD NG NK NI NI |
| EIF2AK4 | G-0057 | CTACGGCGCGGACTTCCAAG | HD NG NI HD NK NK HD NK HD NK NK NI HD NG NG HD HD NI NI NK |
| EIF2AK4 | G-0058 | CCTACCGGTCCGCAAG | HD HD NG NI HD HD NK NK NG HD HD NK HD NI NI NK |
| DMPK | G-0019 | TTGCCCATCCACGTCAG | NG NG NK HD HD HD NI NG HD HD NI HD NK NG HD NI NK |
| DMPK | G-0020 | CACAGACCATTTCTTTCT | HD NI HD NI NK NI HD HD NI NG NG NG HD NG NG NG HD NG |
| PAH | G-0021 | GTCCAAGACCTCAATCCTTTGG | NK NG HD HD NI NI NK NI HD HD NG HD NI NI NG HD HD NG NG NG NK NK |
| PAH | G-0022 | ACCTCGGCCCTTCTCAG | NI HD HD NG HD NK NK HD HD HD NG NG HD NG HD NI NK |

Table 12 lists the target sequence and the TALEN RVD sequence for the TALENs designed in this work. The full protein sequence can be obtained by starting with the N-terminal sequence having the identity:

(SEQ ID NO: 27)
MDYKDHDGDYKDHDIDYKDDDDKMAPKKKRKVGIHRGVPMVDLR

TLGYSQQQQEKIKPKVRSTVAQHHEALVGHGFTHAHIVALSQHP

AALGTVAVKYQDMIAALPEATHEAIVGVGKQWSGARALEALLTV

AGELRGPPLQLDTGQLLKIAKRGGVTAVEAVHAWRNALTGAPLN

LTPDQVVAIAS.

Each RVD pair from the sequence is then added (reading from left to right in Table 12), separated by the TALEN repeat having the identity (SEQ ID NO: 28)
GGKQALETVQRLLPVLCQDHGLTPDQVVAIAS.

The 3'-terminus sequence is added to the last RVD. The 3'-terminus sequence has the identity (SEQ ID NO: 29)
GGKQALESIVAQLSRPDPALAALTNDHLVALACLGGRPALDAVK

KGLPHAPALIKRTNRRIPERTSHRVAGSQLVKSELEEKKSELRH

KLKYVPHEYIELIEIARNSTQDRILEMKVMEFFMKVYGYRGKHL

GGSRKPDGAIYTVGSPIDYGVIVDTKAYSGGYNLPIGQADEMQR

YVEENQTRNKHINPNEWWKVYPSSVTEFKFLFVSGHFKGNYKAQ

LTRLNHITNCNGAVLSVEELLIGGEMIKAGTLTLEEVRRKFNNG

EINF.

We claim:

1. A method for synthesizing a nuclease with reduced off-site cleavage comprising:

scanning complete genomic sequence data for the off-target cleavage locations of each nuclease from a group of nucleases to return off-target cleavage locations in the genome, wherein scanning comprises iteratively comparing a user-provided target site to the genomic sequence to identify mismatches between the target site and the genomic sequence, wherein the target site comprises a left half and a right half;

locating all potential cleavage sites of each nuclease including mismatches in the left and right half target sites, assigning a score to each nuclease based upon the returned off-target cleavage locations indicative of the predictive likelihood of off-target cleavage wherein the score is calculated using the algorithm $$SCORE_H = (N_{MAX}+1-N_L)^2 + (N_{MAX}+1-N_R)^2$$

wherein $N_L$ and $N_R$ are the number of mismatches in the left and right half target sites respectively and $N_{MAX}$ is the maximum number of mismatches allowed per half site;

ranking the nucleases using the score calculated based upon the off-target cleavage locations, wherein a higher score indicates a nuclease with more potential off-target cleavage sites compared to a nuclease with a lower score;

synthesizing the nuclease with the lowest number of predicted off-target cleavage locations;

contacting the synthesized nuclease with the genomic sequence;

and assaying the genomic sequence after nuclease treatment to ensure specific genome editing, wherein scanning the genomic sequence, locating cleavage sites, assigning a score, and ranking the off-target cleavage locations are performed in a computer system.

2. The method of claim 1, wherein the nuclease uses a guide RNA strand, such as the CRISPR, and/or Cas9 systems.

3. The method of claim 1, further comprising the step of designating the off-target cleavage location as being in an exon, intron, promoter or regulatory, or intergenic region.

* * * * *

SEQUENCE LISTING

<160> NUMBER OF SEQ ID NOS: 370

<210> SEQ ID NO 1
<211> LENGTH: 307
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Met Asp Tyr Lys Asp His Asp Gly Asp Tyr Lys Asp His Asp Ile Asp
1               5                   10                  15

Tyr Lys Asp Asp Asp Asp Lys Pro Lys Lys Arg Lys Val Pro Phe
                20                  25                  30

Ala Cys Asp Ile Cys Gly Arg Lys Phe Ala Arg Thr Asp Thr Leu Arg
            35                  40                  45

Asp His Thr Lys Ile His Thr Gly Glu Lys Pro Phe Gln Cys Arg Ile
        50                  55                  60

Cys Met Arg Asn Phe Ser Gln Ser Ser Ser Leu Val Arg His Ile Arg
65                  70                  75                  80

Thr His Thr Gly Glu Lys Pro Phe Ala Cys Asp Ile Cys Gly Arg Lys
                85                  90                  95

Phe Ala Gln Ser Gly Asp Leu Thr Arg His Gln Arg Thr His Gly Ser
            100                 105                 110

Gln Leu Val Lys Ser Glu Leu Glu Glu Lys Lys Ser Glu Leu Arg His
        115                 120                 125

Lys Leu Lys Tyr Val Pro His Glu Tyr Ile Glu Leu Ile Glu Ile Ala
130                 135                 140

Arg Asn Ser Thr Gln Asp Arg Ile Leu Glu Met Lys Val Met Glu Phe
145                 150                 155                 160

Phe Met Lys Val Tyr Gly Tyr Arg Gly Lys His Leu Gly Gly Ser Arg
                165                 170                 175

Lys Pro Asp Gly Ala Ile Tyr Thr Val Gly Ser Pro Ile Asp Tyr Gly
            180                 185                 190

Val Ile Val Asp Thr Lys Ala Tyr Ser Gly Gly Tyr Asn Leu Pro Ile
        195                 200                 205

Gly Gln Ala Asp Glu Met Gln Arg Tyr Val Glu Glu Asn Gln Thr Arg
    210                 215                 220

Asn Lys His Ile Asn Pro Asn Glu Trp Trp Lys Val Tyr Pro Ser Ser
225                 230                 235                 240

Val Thr Glu Phe Lys Phe Leu Phe Val Ser Gly His Phe Lys Gly Asn
                245                 250                 255

Tyr Lys Ala Gln Leu Thr Arg Leu Asn His Ile Thr Asn Cys Asn Gly
            260                 265                 270

Ala Val Leu Ser Val Glu Glu Leu Leu Ile Gly Gly Glu Met Ile Lys
        275                 280                 285

Ala Gly Thr Leu Thr Leu Glu Glu Val Arg Arg Lys Phe Asn Asn Gly
    290                 295                 300

Glu Ile Asn
305

<210> SEQ ID NO 2
<211> LENGTH: 308
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 2

Met Asp Tyr Lys Asp His Asp Gly Asp Tyr Lys Asp His Asp Ile Asp
1               5                   10                  15

Tyr Lys Asp Asp Asp Asp Lys Pro Lys Lys Arg Lys Val Pro Phe
                20                  25                  30

Ala Cys Asp Ile Cys Gly Arg Lys Phe Ala Arg Ser Asp His Leu Thr
                35                  40                  45

Asn His Thr Lys Ile His Thr Gly Glu Lys Pro Phe Gln Cys Arg Ile
    50                  55                  60

Cys Met Arg Asn Phe Ser Gln Ser Gly Asp Leu Thr Arg His Ile Arg
65                  70                  75                  80

Thr His Thr Gly Glu Lys Pro Phe Ala Cys Asp Ile Cys Gly Arg Lys
                85                  90                  95

Phe Ala Arg Ser Asp His Leu Ser Arg His Gln Arg Thr His Gly Ser
                100                 105                 110

Gln Leu Val Lys Ser Glu Leu Glu Lys Lys Ser Glu Leu Arg His
                115                 120                 125

Lys Leu Lys Tyr Val Pro His Glu Tyr Ile Glu Leu Ile Glu Ile Ala
    130                 135                 140

Arg Asn Ser Thr Gln Asp Arg Ile Leu Glu Met Lys Val Met Glu Phe
145                 150                 155                 160

Phe Met Lys Val Tyr Gly Tyr Arg Gly Lys His Leu Gly Gly Ser Arg
                165                 170                 175

Lys Pro Asp Gly Ala Ile Tyr Thr Val Gly Ser Pro Ile Asp Tyr Gly
                180                 185                 190

Val Ile Val Asp Thr Lys Ala Tyr Ser Gly Gly Tyr Asn Leu Pro Ile
    195                 200                 205

Gly Gln Ala Asp Glu Met Gln Arg Tyr Val Glu Glu Asn Gln Thr Arg
    210                 215                 220

Asn Lys His Ile Asn Pro Asn Glu Trp Trp Lys Val Tyr Pro Ser Ser
225                 230                 235                 240

Val Thr Glu Phe Lys Phe Leu Phe Val Ser Gly His Phe Lys Gly Asn
                245                 250                 255

Tyr Lys Ala Gln Leu Thr Arg Leu Asn His Ile Thr Asn Cys Asn Gly
                260                 265                 270

Ala Val Leu Ser Val Glu Glu Leu Leu Ile Gly Gly Glu Met Ile Lys
                275                 280                 285

Ala Gly Thr Leu Thr Leu Glu Glu Val Arg Arg Lys Phe Asn Asn Gly
                290                 295                 300

Glu Ile Asn Phe
305

<210> SEQ ID NO 3
<211> LENGTH: 337
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3
```

```
Met Asp Tyr Lys Asp His Asp Gly Asp Tyr Lys Asp His Asp Ile Asp
1               5                   10                  15

Tyr Lys Asp Asp Asp Lys Pro Lys Lys Arg Lys Val Pro Phe
            20                  25                  30

Gln Cys Arg Ile Cys Met Arg Asn Phe Ser Gln Ser Gly Ser Leu Thr
            35                  40                  45

Arg His Ile Arg Thr His Thr Gly Glu Lys Pro Phe Ala Cys Asp Ile
        50                  55                  60

Cys Gly Arg Lys Phe Ala Arg Thr Asp Thr Leu Arg Asp His Thr Lys
65                  70                  75                  80

Ile His Thr Gly Gly Glu Lys Pro Phe Gln Cys Arg Ile Cys Met Arg
                85                  90                  95

Asn Phe Ser Gln Ser Ser Ser Leu Val Arg His Ile Arg Thr His Thr
                100                 105                 110

Gly Glu Lys Pro Phe Ala Cys Asp Ile Cys Gly Arg Lys Phe Ala Gln
            115                 120                 125

Ser Gly Asp Leu Thr Arg His Gln Arg Thr His Gly Ser Gln Leu Val
    130                 135                 140

Lys Ser Glu Leu Glu Glu Lys Lys Ser Glu Leu Arg His Lys Leu Lys
145                 150                 155                 160

Tyr Val Pro His Glu Tyr Ile Glu Leu Ile Glu Ile Ala Arg Asn Ser
                165                 170                 175

Thr Gln Asp Arg Ile Leu Glu Met Lys Val Met Glu Phe Phe Met Lys
                180                 185                 190

Val Tyr Gly Tyr Arg Gly Lys His Leu Gly Gly Ser Arg Lys Pro Asp
    195                 200                 205

Gly Ala Ile Tyr Thr Val Gly Ser Pro Ile Asp Tyr Gly Val Ile Val
    210                 215                 220

Asp Thr Lys Ala Tyr Ser Gly Gly Tyr Asn Leu Pro Ile Gly Gln Ala
225                 230                 235                 240

Asp Glu Met Gln Arg Tyr Val Glu Glu Asn Gln Thr Arg Asn Lys His
                245                 250                 255

Ile Asn Pro Asn Glu Trp Trp Lys Val Tyr Pro Ser Ser Val Thr Glu
                260                 265                 270

Phe Lys Phe Leu Phe Val Ser Gly His Phe Lys Gly Asn Tyr Lys Ala
            275                 280                 285

Gln Leu Thr Arg Leu Asn His Ile Thr Asn Cys Asn Gly Ala Val Leu
    290                 295                 300

Ser Val Glu Glu Leu Leu Ile Gly Gly Glu Met Ile Lys Ala Gly Thr
305                 310                 315                 320

Leu Thr Leu Glu Glu Val Arg Arg Lys Phe Asn Asn Gly Glu Ile Asn
                325                 330                 335

Phe
```

```
<210> SEQ ID NO 4
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4
```

```
Met Asp Tyr Lys Asp His Asp Gly Asp Tyr Lys Asp His Asp Ile Asp
1               5                   10                  15
```

Tyr Lys Asp Asp Asp Asp Lys Pro Lys Lys Arg Lys Val Pro Phe
            20                  25                  30

Gln Cys Arg Ile Cys Met Arg Asn Phe Ser Gln Ser Gly His Leu Ala
         35                  40                  45

Ser His Ile Arg Thr His Thr Gly Glu Lys Pro Phe Ala Cys Asp Ile
 50                  55                  60

Cys Gly Arg Lys Phe Ala Arg Ser Asp His Leu Thr Asn His Thr Lys
 65                  70                  75                  80

Ile His Thr Gly Gly Gly Ser Glu Lys Pro Phe Gln Cys Arg Ile Cys
                 85                  90                  95

Met Arg Asn Phe Ser Gln Ser Gly Asp Leu Thr Arg His Ile Arg Thr
            100                 105                 110

His Thr Gly Glu Lys Pro Phe Ala Cys Asp Ile Cys Gly Arg Lys Phe
            115                 120                 125

Ala Arg Ser Asp His Leu Ser Arg His Gln Arg Thr His Gly Ser Gln
130                 135                 140

Leu Val Lys Ser Glu Leu Glu Glu Lys Lys Ser Glu Leu Arg His Lys
145                 150                 155                 160

Leu Lys Tyr Val Pro His Glu Tyr Ile Glu Leu Ile Glu Ile Ala Arg
                165                 170                 175

Asn Ser Thr Gln Asp Arg Ile Leu Glu Met Lys Val Met Glu Phe Phe
            180                 185                 190

Met Lys Val Tyr Gly Tyr Arg Gly Lys His Leu Gly Gly Ser Arg Lys
            195                 200                 205

Pro Asp Gly Ala Ile Tyr Thr Val Gly Ser Pro Ile Asp Tyr Gly Val
            210                 215                 220

Ile Val Asp Thr Lys Ala Tyr Ser Gly Gly Tyr Asn Leu Pro Ile Gly
225                 230                 235                 240

Gln Ala Asp Glu Met Gln Arg Tyr Val Glu Glu Asn Gln Thr Arg Asn
                245                 250                 255

Lys His Ile Asn Pro Asn Glu Trp Trp Lys Val Tyr Pro Ser Ser Val
            260                 265                 270

Thr Glu Phe Lys Phe Leu Phe Val Ser Gly His Phe Lys Gly Asn Tyr
            275                 280                 285

Lys Ala Gln Leu Thr Arg Leu Asn His Ile Thr Asn Cys Asn Gly Ala
290                 295                 300

Val Leu Ser Val Glu Glu Leu Leu Ile Gly Gly Glu Met Ile Lys Ala
305                 310                 315                 320

Gly Thr Leu Thr Leu Glu Glu Val Arg Arg Lys Phe Asn Asn Gly Glu
                325                 330                 335

Ile Asn Phe

<210> SEQ ID NO 5
<211> LENGTH: 967
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val

```
                    20                  25                  30
        Gly Ile His Arg Gly Val Pro Met Val Asp Leu Arg Thr Leu Gly Tyr
                        35                  40                  45

Ser Gln Gln Gln Glu Lys Ile Lys Pro Lys Val Arg Ser Thr Val
            50                  55                  60

Ala Gln His His Glu Ala Leu Val Gly His Gly Phe Thr His Ala His
        65                  70                  75                  80

Ile Val Ala Leu Ser Gln His Pro Ala Ala Leu Gly Thr Val Ala Val
                        85                  90                  95

Lys Tyr Gln Asp Met Ile Ala Ala Leu Pro Glu Ala Thr His Glu Ala
                        100                 105                 110

Ile Val Gly Val Gly Lys Gln Trp Ser Gly Ala Arg Ala Leu Glu Ala
                        115                 120                 125

Leu Leu Thr Val Ala Gly Glu Leu Arg Gly Pro Pro Leu Gln Leu Asp
                        130                 135                 140

Thr Gly Gln Leu Leu Lys Ile Ala Lys Arg Gly Gly Val Thr Ala Val
        145                 150                 155                 160

Glu Ala Val His Ala Trp Arg Asn Ala Leu Thr Gly Ala Pro Leu Asn
                        165                 170                 175

Leu Thr Pro Asp Gln Val Val Ala Ile Ala Ser Asn Lys Gly Gly Lys
                        180                 185                 190

Gln Ala Leu Glu Thr Val Gln Arg Leu Leu Pro Val Leu Cys Gln Asp
                        195                 200                 205

His Gly Leu Thr Pro Asp Gln Val Val Ala Ile Ala Ser Asn Lys Gly
                        210                 215                 220

Gly Lys Gln Ala Leu Glu Thr Val Gln Arg Leu Leu Pro Val Leu Cys
        225                 230                 235                 240

Gln Asp His Gly Leu Thr Pro Asp Gln Val Val Ala Ile Ala Ser Asn
                        245                 250                 255

Gly Gly Gly Lys Gln Ala Leu Glu Thr Val Gln Arg Leu Leu Pro Val
                        260                 265                 270

Leu Cys Gln Asp His Gly Leu Thr Pro Asp Gln Val Val Ala Ile Ala
                        275                 280                 285

Ser Asn Lys Gly Gly Lys Gln Ala Leu Glu Thr Val Gln Arg Leu Leu
                        290                 295                 300

Pro Val Leu Cys Gln Asp His Gly Leu Thr Pro Asp Gln Val Val Ala
        305                 310                 315                 320

Ile Ala Ser His Asp Gly Gly Lys Gln Ala Leu Glu Thr Val Gln Arg
                        325                 330                 335

Leu Leu Pro Val Leu Cys Gln Asp His Gly Leu Thr Pro Asp Gln Val
                        340                 345                 350

Val Ala Ile Ala Ser Asn Ile Gly Gly Lys Gln Ala Leu Glu Thr Val
                        355                 360                 365

Gln Arg Leu Leu Pro Val Leu Cys Gln Asp His Gly Leu Thr Pro Asp
                        370                 375                 380

Gln Val Val Ala Ile Ala Ser His Asp Gly Gly Lys Gln Ala Leu Glu
        385                 390                 395                 400

Thr Val Gln Arg Leu Leu Pro Val Leu Cys Gln Asp His Gly Leu Thr
                        405                 410                 415

Pro Asp Gln Val Val Ala Ile Ala Ser His Asp Gly Gly Lys Gln Ala
                        420                 425                 430

Leu Glu Thr Val Gln Arg Leu Leu Pro Val Leu Cys Gln Asp His Gly
                        435                 440                 445
```

```
Leu Thr Pro Asp Gln Val Val Ala Ile Ala Ser Asn Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Lys Gly
                485                 490                 495

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Ser Asn
        515                 520                 525

Ile Gly Gly Lys Gln Ala Leu Glu Thr Val Gln Arg Leu Leu Pro Val
    530                 535                 540

Leu Cys Gln Asp His Gly Leu Thr Pro Asp Gln Val Val Ala Ile Ala
545                 550                 555                 560

Ser His Asp Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser Asn Gly Gly Lys Gln Ala Leu Glu Thr Val Gln Arg
        595                 600                 605

Leu Leu Pro Val Leu Cys Gln Asp His Gly Leu Thr Pro Asp Gln Val
    610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser His Asp Gly Gly Lys Gln Ala Leu Glu
            660                 665                 670

Thr Val Gln Arg Leu Leu Pro Val Leu Cys Gln Asp His Gly Leu Thr
        675                 680                 685

Pro Asp Gln Val Val Ala Ile Ala Ser Asn Gly Gly Lys Gln Ala
    690                 695                 700

Leu Glu Ser Ile Val Ala Gln Leu Ser Arg Pro Asp Pro Ala Leu Ala
705                 710                 715                 720

Ala Leu Thr Asn Asp His Leu Val Ala Leu Ala Cys Leu Gly Gly Arg
                725                 730                 735

Pro Ala Leu Asp Ala Val Lys Lys Gly Leu Pro His Ala Pro Ala Leu
            740                 745                 750

Ile Lys Arg Thr Asn Arg Arg Ile Pro Glu Arg Thr Ser His Arg Val
        755                 760                 765

Ala Gly Ser Gln Leu Val Lys Ser Glu Leu Glu Glu Lys Lys Ser Glu
    770                 775                 780

Leu Arg His Lys Leu Lys Tyr Val Pro His Glu Tyr Ile Glu Leu Ile
785                 790                 795                 800

Glu Ile Ala Arg Asn Ser Thr Gln Asp Arg Ile Leu Glu Met Lys Val
                805                 810                 815

Met Glu Phe Phe Met Lys Val Tyr Gly Tyr Arg Gly Lys His Leu Gly
            820                 825                 830

Gly Ser Arg Lys Pro Asp Gly Ala Ile Tyr Thr Val Gly Ser Pro Ile
        835                 840                 845

Asp Tyr Gly Val Ile Val Asp Thr Lys Ala Tyr Ser Gly Gly Tyr Asn
    850                 855                 860
```

```
Leu Pro Ile Gly Gln Ala Asp Glu Met Gln Arg Tyr Val Glu Glu Asn
865                 870                 875                 880

Gln Thr Arg Asn Lys His Ile Asn Pro Asn Glu Trp Trp Lys Val Tyr
            885                 890                 895

Pro Ser Ser Val Thr Glu Phe Lys Phe Leu Phe Val Ser Gly His Phe
        900                 905                 910

Lys Gly Asn Tyr Lys Ala Gln Leu Thr Arg Leu Asn His Ile Thr Asn
        915                 920                 925

Cys Asn Gly Ala Val Leu Ser Val Glu Glu Leu Leu Ile Gly Gly Glu
        930                 935                 940

Met Ile Lys Ala Gly Thr Leu Thr Leu Glu Glu Val Arg Arg Lys Phe
945                 950                 955                 960

Asn Asn Gly Glu Ile Asn Phe
                965

<210> SEQ ID NO 6
<211> LENGTH: 933
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
        50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser Asn Lys Gly Gly Lys
            180                 185                 190

Gln Ala Leu Glu Thr Val Gln Arg Leu Leu Pro Val Leu Cys Gln Asp
        195                 200                 205

His Gly Leu Thr Pro Asp Gln Val Val Ala Ile Ala Ser His Asp Gly
    210                 215                 220

Gly Lys Gln Ala Leu Glu Thr Val Gln Arg Leu Leu Pro Val Leu Cys
225                 230                 235                 240

Gln Asp His Gly Leu Thr Pro Asp Gln Val Val Ala Ile Ala Ser Asn
```

-continued

```
                245                 250                 255
Ile Gly Gly Lys Gln Ala Leu Glu Thr Val Gln Arg Leu Leu Pro Val
            260                 265                 270
Leu Cys Gln Asp His Gly Leu Thr Pro Asp Gln Val Val Ala Ile Ala
            275                 280                 285
Ser His Asp Gly Gly Lys Gln Ala Leu Glu Thr Val Gln Arg Leu Leu
            290                 295                 300
Pro Val Leu Cys Gln Asp His Gly Leu Thr Pro Asp Gln Val Val Ala
305                 310                 315                 320
Ile Ala Ser His Asp Gly Gly Lys Gln Ala Leu Glu Thr Val Gln Arg
                325                 330                 335
Leu Leu Pro Val Leu Cys Gln Asp His Gly Leu Thr Pro Asp Gln Val
            340                 345                 350
Val Ala Ile Ala Ser Asn Gly Gly Lys Gln Ala Leu Glu Thr Val
            355                 360                 365
Gln Arg Leu Leu Pro Val Leu Cys Gln Asp His Gly Leu Thr Pro Asp
    370                 375                 380
Gln Val Val Ala Ile Ala Ser Asn Lys Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser Asn Ile Gly Gly Lys Gln Ala
            420                 425                 430
Leu Glu Thr Val Gln Arg Leu Leu Pro Val Leu Cys Gln Asp His Gly
            435                 440                 445
Leu Thr Pro Asp Gln Val Val Ala Ile Ala Ser His Asp Gly Gly Lys
            450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Ser Asn Gly Gly
                485                 490                 495
Gly Lys Gln Ala Leu Glu Thr Val Gln Arg Leu Leu Pro Val Leu Cys
            500                 505                 510
Gln Asp His Gly Leu Thr Pro Asp Gln Val Val Ala Ile Ala Ser His
            515                 520                 525
Asp Gly Gly Lys Gln Ala Leu Glu Thr Val Gln Arg Leu Leu Pro Val
            530                 535                 540
Leu Cys Gln Asp His Gly Leu Thr Pro Asp Gln Val Val Ala Ile Ala
545                 550                 555                 560
Ser His Asp Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
            580                 585                 590
Ile Ala Ser Asn Gly Gly Lys Gln Ala Leu Glu Thr Val Gln Arg
            595                 600                 605
Leu Leu Pro Val Leu Cys Gln Asp His Gly Leu Thr Pro Asp Gln Val
    610                 615                 620
Val Ala Ile Ala Ser Asn Lys Gly Gly Lys Gln Ala Leu Glu Thr Val
625                 630                 635                 640
Gln Arg Leu Leu Pro Val Leu Cys Gln Asp His Gly Leu Thr Pro Asp
                645                 650                 655
Gln Val Val Ala Ile Ala Ser Asn Gly Gly Gly Lys Gln Ala Leu Glu
            660                 665                 670
```

```
Ser Ile Val Ala Gln Leu Ser Arg Pro Asp Pro Ala Leu Ala Ala Leu
            675                 680                 685

Thr Asn Asp His Leu Val Ala Leu Ala Cys Leu Gly Gly Arg Pro Ala
    690                 695                 700

Leu Asp Ala Val Lys Lys Gly Leu Pro His Ala Pro Ala Leu Ile Lys
705                 710                 715                 720

Arg Thr Asn Arg Arg Ile Pro Glu Arg Thr Ser His Arg Val Ala Gly
                725                 730                 735

Ser Gln Leu Val Lys Ser Glu Leu Glu Glu Lys Ser Glu Leu Arg
            740                 745                 750

His Lys Leu Lys Tyr Val Pro His Glu Tyr Ile Glu Leu Ile Glu Ile
            755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
            835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
            915                 920                 925

Gly Glu Ile Asn Phe
    930

<210> SEQ ID NO 7
<211> LENGTH: 967
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
        50                  55                  60

Ala Gln His His Glu Ala Leu Val Gly His Gly Phe Thr His Ala His
65                  70                  75                  80
```

```
Ile Val Ala Leu Ser Gln His Pro Ala Ala Leu Gly Thr Val Ala Val
                85                  90                  95
Lys Tyr Gln Asp Met Ile Ala Ala Leu Pro Glu Ala Thr His Glu Ala
            100                 105                 110
Ile Val Gly Val Gly Lys Gln Trp Ser Gly Ala Arg Ala Leu Glu Ala
            115                 120                 125
Leu Leu Thr Val Ala Gly Glu Leu Arg Gly Pro Pro Leu Gln Leu Asp
130                 135                 140
Thr Gly Gln Leu Leu Lys Ile Ala Lys Arg Gly Gly Val Thr Ala Val
145                 150                 155                 160
Glu Ala Val His Ala Trp Arg Asn Ala Leu Thr Gly Ala Pro Leu Asn
                165                 170                 175
Leu Thr Pro Asp Gln Val Val Ala Ile Ala Ser Asn Asn Gly Gly Lys
            180                 185                 190
Gln Ala Leu Glu Thr Val Gln Arg Leu Leu Pro Val Leu Cys Gln Asp
            195                 200                 205
His Gly Leu Thr Pro Asp Gln Val Val Ala Ile Ala Ser Asn Asn Gly
    210                 215                 220
Gly Lys Gln Ala Leu Glu Thr Val Gln Arg Leu Leu Pro Val Leu Cys
225                 230                 235                 240
Gln Asp His Gly Leu Thr Pro Asp Gln Val Val Ala Ile Ala Ser Asn
                245                 250                 255
Gly Gly Gly Lys Gln Ala Leu Glu Thr Val Gln Arg Leu Leu Pro Val
            260                 265                 270
Leu Cys Gln Asp His Gly Leu Thr Pro Asp Gln Val Val Ala Ile Ala
            275                 280                 285
Ser Asn Asn Gly Gly Lys Gln Ala Leu Glu Thr Val Gln Arg Leu Leu
            290                 295                 300
Pro Val Leu Cys Gln Asp His Gly Leu Thr Pro Asp Gln Val Val Ala
305                 310                 315                 320
Ile Ala Ser His Asp Gly Gly Lys Gln Ala Leu Glu Thr Val Gln Arg
                325                 330                 335
Leu Leu Pro Val Leu Cys Gln Asp His Gly Leu Thr Pro Asp Gln Val
            340                 345                 350
Val Ala Ile Ala Ser Asn Ile Gly Gly Lys Gln Ala Leu Glu Thr Val
            355                 360                 365
Gln Arg Leu Leu Pro Val Leu Cys Gln Asp His Gly Leu Thr Pro Asp
            370                 375                 380
Gln Val Val Ala Ile Ala Ser His Asp Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser His Asp Gly Gly Lys Gln Ala
            420                 425                 430
Leu Glu Thr Val Gln Arg Leu Leu Pro Val Leu Cys Gln Asp His Gly
            435                 440                 445
Leu Thr Pro Asp Gln Val Val Ala Ile Ala Ser Asn Gly Gly Gly Lys
            450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Ser Asn Asn Gly
                485                 490                 495
Gly Lys Gln Ala Leu Glu Thr Val Gln Arg Leu Leu Pro Val Leu Cys
```

```
                500             505             510
Gln Asp His Gly Leu Thr Pro Asp Gln Val Ala Ile Ala Ser Asn
            515             520             525
Ile Gly Gly Lys Gln Ala Leu Glu Thr Val Gln Arg Leu Leu Pro Val
        530             535             540
Leu Cys Gln Asp His Gly Leu Thr Pro Asp Gln Val Val Ala Ile Ala
545             550             555             560
Ser His Asp Gly Gly Lys Gln Ala Leu Glu Thr Val Gln Arg Leu Leu
                565             570             575
Pro Val Leu Cys Gln Asp His Gly Leu Thr Pro Asp Gln Val Val Ala
            580             585             590
Ile Ala Ser Asn Gly Gly Lys Gln Ala Leu Glu Thr Val Gln Arg
        595             600             605
Leu Leu Pro Val Leu Cys Gln Asp His Gly Leu Thr Pro Asp Gln Val
        610             615             620
Val Ala Ile Ala Ser His Asp Gly Gly Lys Gln Ala Leu Glu Thr Val
625             630             635             640
Gln Arg Leu Leu Pro Val Leu Cys Gln Asp His Gly Leu Thr Pro Asp
            645             650             655
Gln Val Val Ala Ile Ala Ser His Asp Gly Gly Lys Gln Ala Leu Glu
            660             665             670
Thr Val Gln Arg Leu Leu Pro Val Leu Cys Gln Asp His Gly Leu Thr
        675             680             685
Pro Asp Gln Val Val Ala Ile Ala Ser Asn Gly Gly Lys Gln Ala
        690             695             700
Leu Glu Ser Ile Val Ala Gln Leu Ser Arg Pro Asp Pro Ala Leu Ala
705             710             715             720
Ala Leu Thr Asn Asp His Leu Val Ala Leu Ala Cys Leu Gly Gly Arg
            725             730             735
Pro Ala Leu Asp Ala Val Lys Lys Gly Leu Pro His Ala Pro Ala Leu
            740             745             750
Ile Lys Arg Thr Asn Arg Arg Ile Pro Glu Arg Thr Ser His Arg Val
        755             760             765
Ala Gly Ser Gln Leu Val Lys Ser Glu Leu Glu Glu Lys Lys Ser Glu
        770             775             780
Leu Arg His Lys Leu Lys Tyr Val Pro His Glu Tyr Ile Glu Leu Ile
785             790             795             800
Glu Ile Ala Arg Asn Ser Thr Gln Asp Arg Ile Leu Glu Met Lys Val
            805             810             815
Met Glu Phe Phe Met Lys Val Tyr Gly Tyr Arg Gly Lys His Leu Gly
            820             825             830
Gly Ser Arg Lys Pro Asp Gly Ala Ile Tyr Thr Val Gly Ser Pro Ile
        835             840             845
Asp Tyr Gly Val Ile Val Asp Thr Lys Ala Tyr Ser Gly Gly Tyr Asn
850             855             860
Leu Pro Ile Gly Gln Ala Asp Glu Met Gln Arg Tyr Val Glu Glu Asn
865             870             875             880
Gln Thr Arg Asn Lys His Ile Asn Pro Asn Glu Trp Trp Lys Val Tyr
            885             890             895
Pro Ser Ser Val Thr Glu Phe Lys Phe Leu Phe Val Ser Gly His Phe
            900             905             910
Lys Gly Asn Tyr Lys Ala Gln Leu Thr Arg Leu Asn His Ile Thr Asn
        915             920             925
```

```
Cys Asn Gly Ala Val Leu Ser Val Glu Glu Leu Leu Ile Gly Gly Glu
            930                 935                 940

Met Ile Lys Ala Gly Thr Leu Thr Leu Glu Glu Val Arg Arg Lys Phe
945                 950                 955                 960

Asn Asn Gly Glu Ile Asn Phe
                965

<210> SEQ ID NO 8
<211> LENGTH: 933
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65              70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser Asn Asn Gly Gly Lys
            180                 185                 190

Gln Ala Leu Glu Thr Val Gln Arg Leu Leu Pro Val Leu Cys Gln Asp
        195                 200                 205

His Gly Leu Thr Pro Asp Gln Val Val Ala Ile Ala Ser His Asp Gly
    210                 215                 220

Gly Lys Gln Ala Leu Glu Thr Val Gln Arg Leu Leu Pro Val Leu Cys
225                 230                 235                 240

Gln Asp His Gly Leu Thr Pro Asp Gln Val Val Ala Ile Ala Ser Asn
                245                 250                 255

Ile Gly Gly Lys Gln Ala Leu Glu Thr Val Gln Arg Leu Leu Pro Val
            260                 265                 270

Leu Cys Gln Asp His Gly Leu Thr Pro Asp Gln Val Val Ala Ile Ala
        275                 280                 285

Ser His Asp Gly Gly Lys Gln Ala Leu Glu Thr Val Gln Arg Leu Leu
    290                 295                 300
```

```
Pro Val Leu Cys Gln Asp His Gly Leu Thr Pro Asp Gln Val Val Ala
305                 310                 315                 320
Ile Ala Ser His Asp Gly Gly Lys Gln Ala Leu Glu Thr Val Gln Arg
                325                 330                 335
Leu Leu Pro Val Leu Cys Gln Asp His Gly Leu Thr Pro Asp Gln Val
            340                 345                 350
Val Ala Ile Ala Ser Asn Gly Gly Lys Gln Ala Leu Glu Thr Val
            355                 360                 365
Gln Arg Leu Leu Pro Val Leu Cys Gln Asp His Gly Leu Thr Pro Asp
        370                 375                 380
Gln Val Val Ala Ile Ala Ser Asn Asn Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser Asn Ile Gly Gly Lys Gln Ala
            420                 425                 430
Leu Glu Thr Val Gln Arg Leu Leu Pro Val Leu Cys Gln Asp His Gly
            435                 440                 445
Leu Thr Pro Asp Gln Val Val Ala Ile Ala Ser His Asp Gly Gly Lys
        450                 455                 460
Gln Ala Leu Glu Thr Val Gln Arg Leu Leu Pro Val Leu Cys Gln Asp
465                 470                 475                 480
His Gly Leu Thr Pro Asp Gln Val Val Ala Ile Ala Ser Asn Gly Gly
                485                 490                 495
Gly Lys Gln Ala Leu Glu Thr Val Gln Arg Leu Leu Pro Val Leu Cys
            500                 505                 510
Gln Asp His Gly Leu Thr Pro Asp Gln Val Val Ala Ile Ala Ser His
            515                 520                 525
Asp Gly Gly Lys Gln Ala Leu Glu Thr Val Gln Arg Leu Leu Pro Val
        530                 535                 540
Leu Cys Gln Asp His Gly Leu Thr Pro Asp Gln Val Val Ala Ile Ala
545                 550                 555                 560
Ser His Asp Gly Gly Lys Gln Ala Leu Glu Thr Val Gln Arg Leu Leu
                565                 570                 575
Pro Val Leu Cys Gln Asp His Gly Leu Thr Pro Asp Gln Val Val Ala
            580                 585                 590
Ile Ala Ser Asn Gly Gly Gly Lys Gln Ala Leu Glu Thr Val Gln Arg
            595                 600                 605
Leu Leu Pro Val Leu Cys Gln Asp His Gly Leu Thr Pro Asp Gln Val
        610                 615                 620
Val Ala Ile Ala Ser Asn Asn Gly Gly Lys Gln Ala Leu Glu Thr Val
625                 630                 635                 640
Gln Arg Leu Leu Pro Val Leu Cys Gln Asp His Gly Leu Thr Pro Asp
                645                 650                 655
Gln Val Val Ala Ile Ala Ser Asn Gly Gly Lys Gln Ala Leu Glu
            660                 665                 670
Ser Ile Val Ala Gln Leu Ser Arg Pro Asp Pro Ala Leu Ala Ala Leu
            675                 680                 685
Thr Asn Asp His Leu Val Ala Leu Ala Cys Leu Gly Gly Arg Pro Ala
        690                 695                 700
Leu Asp Ala Val Lys Lys Gly Leu Pro His Ala Pro Ala Leu Ile Lys
705                 710                 715                 720
Arg Thr Asn Arg Arg Ile Pro Glu Arg Thr Ser His Arg Val Ala Gly
```

```
                    725                 730                 735

Ser Gln Leu Val Lys Ser Glu Leu Glu Glu Lys Ser Glu Leu Arg
                740                 745                 750

His Lys Leu Lys Tyr Val Pro His Glu Tyr Ile Glu Leu Ile Glu Ile
                755                 760                 765

Ala Arg Asn Ser Thr Gln Asp Arg Ile Leu Glu Met Lys Val Met Glu
                770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
                820                 825                 830

Ile Gly Gln Ala Asp Glu Met Gln Arg Tyr Val Glu Glu Asn Gln Thr
                835                 840                 845

Arg Asn Lys His Ile Asn Pro Asn Glu Trp Trp Lys Val Tyr Pro Ser
                850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
                900                 905                 910

Lys Ala Gly Thr Leu Thr Leu Glu Glu Val Arg Arg Lys Phe Asn Asn
                915                 920                 925

Gly Glu Ile Asn Phe
                930

<210> SEQ ID NO 9
<211> LENGTH: 1137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Arg Gly Val Pro Met Val Asp Leu Arg Thr Leu Gly Tyr
                35                  40                  45

Ser Gln Gln Gln Gln Glu Lys Ile Lys Pro Lys Val Arg Ser Thr Val
                50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
                100                 105                 110

Ile Val Gly Val Gly Lys Gln Trp Ser Gly Ala Arg Ala Leu Glu Ala
                115                 120                 125

Leu Leu Thr Val Ala Gly Glu Leu Arg Gly Pro Pro Leu Gln Leu Asp
                130                 135                 140
```

```
Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser His Asp Gly Gly Lys
            180                 185                 190

Gln Ala Leu Glu Thr Val Gln Arg Leu Leu Pro Val Leu Cys Gln Asp
        195                 200                 205

His Gly Leu Thr Pro Asp Gln Val Val Ala Ile Ala Ser Asn Ile Gly
    210                 215                 220

Gly Lys Gln Ala Leu Glu Thr Val Gln Arg Leu Leu Pro Val Leu Cys
225                 230                 235                 240

Gln Asp His Gly Leu Thr Pro Asp Gln Val Val Ala Ile Ala Ser His
                245                 250                 255

Asp Gly Gly Lys Gln Ala Leu Glu Thr Val Gln Arg Leu Leu Pro Val
            260                 265                 270

Leu Cys Gln Asp His Gly Leu Thr Pro Asp Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Asp His Gly Leu Thr Pro Asp Gln Val Val Ala
305                 310                 315                 320

Ile Ala Ser Asn Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Ser Asn Gly Gly Lys Gln Ala Leu Glu Thr Val
        355                 360                 365

Gln Arg Leu Leu Pro Val Leu Cys Gln Asp His Gly Leu Thr Pro Asp
    370                 375                 380

Gln Val Val Ala Ile Ala Ser Asn Lys Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser His Asp Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser His Asp Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Ser His
        515                 520                 525

Asp Gly Gly Lys Gln Ala Leu Glu Thr Val Gln Arg Leu Leu Pro Val
    530                 535                 540

Leu Cys Gln Asp His Gly Leu Thr Pro Asp Gln Val Val Ala Ile Ala
545                 550                 555                 560
```

```
Ser Asn Ile Gly Gly Lys Gln Ala Leu Glu Thr Val Gln Arg Leu Leu
            565                 570                 575

Pro Val Leu Cys Gln Asp His Gly Leu Thr Pro Asp Gln Val Val Ala
            580                 585                 590

Ile Ala Ser His Asp Gly Gly Lys Gln Ala Leu Glu Thr Val Gln Arg
            595                 600                 605

Leu Leu Pro Val Leu Cys Gln Asp His Gly Leu Thr Pro Asp Gln Val
            610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser Asn Lys Gly Gly Lys Gln Ala Leu Glu
                660                 665                 670

Thr Val Gln Arg Leu Leu Pro Val Leu Cys Gln Asp His Gly Leu Thr
            675                 680                 685

Pro Asp Gln Val Val Ala Ile Ala Ser Asn Lys Gly Gly Lys Gln Ala
            690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Lys Gly Gly Lys
                725                 730                 735

Gln Ala Leu Glu Thr Val Gln Arg Leu Leu Pro Val Leu Cys Gln Asp
                740                 745                 750

His Gly Leu Thr Pro Asp Gln Val Val Ala Ile Ala Ser His Asp Gly
            755                 760                 765

Gly Lys Gln Ala Leu Glu Thr Val Gln Arg Leu Leu Pro Val Leu Cys
            770                 775                 780

Gln Asp His Gly Leu Thr Pro Asp Gln Val Val Ala Ile Ala Ser Asn
785                 790                 795                 800

Ile Gly Gly Lys Gln Ala Leu Glu Thr Val Gln Arg Leu Leu Pro Val
                805                 810                 815

Leu Cys Gln Asp His Gly Leu Thr Pro Asp Gln Val Val Ala Ile Ala
                820                 825                 830

Ser Asn Lys Gly Gly Lys Gln Ala Leu Glu Thr Val Gln Arg Leu Leu
            835                 840                 845

Pro Val Leu Cys Gln Asp His Gly Leu Thr Pro Asp Gln Val Val Ala
            850                 855                 860

Ile Ala Ser Asn Gly Gly Gly Lys Gln Ala Leu Glu Ser Ile Val Ala
865                 870                 875                 880

Gln Leu Ser Arg Pro Asp Pro Ala Leu Ala Ala Leu Thr Asn Asp His
                885                 890                 895

Leu Val Ala Leu Ala Cys Leu Gly Gly Arg Pro Ala Leu Asp Ala Val
                900                 905                 910

Lys Lys Gly Leu Pro His Ala Pro Ala Leu Ile Lys Arg Thr Asn Arg
            915                 920                 925

Arg Ile Pro Glu Arg Thr Ser His Arg Val Ala Gly Ser Gln Leu Val
930                 935                 940

Lys Ser Glu Leu Glu Lys Lys Ser Glu Leu Arg His Lys Leu Lys
945                 950                 955                 960

Tyr Val Pro His Glu Tyr Ile Glu Leu Ile Glu Ile Ala Arg Asn Ser
                965                 970                 975

Thr Gln Asp Arg Ile Leu Glu Met Lys Val Met Glu Phe Phe Met Lys
```

```
                      980             985             990
Val Tyr Gly Tyr Arg Gly Lys His Leu Gly Gly Ser Arg Lys Pro Asp
                995             1000            1005

Gly Ala Ile Tyr Thr Val Gly Ser Pro Ile Asp Tyr Gly Val Ile
        1010            1015            1020

Val Asp Thr Lys Ala Tyr Ser Gly Gly Tyr Asn Leu Pro Ile Gly
        1025            1030            1035

Gln Ala Asp Glu Met Gln Arg Tyr Val Glu Glu Asn Gln Thr Arg
        1040            1045            1050

Asn Lys His Ile Asn Pro Asn Glu Trp Trp Lys Val Tyr Pro Ser
        1055            1060            1065

Ser Val Thr Glu Phe Lys Phe Leu Phe Val Ser Gly His Phe Lys
        1070            1075            1080

Gly Asn Tyr Lys Ala Gln Leu Thr Arg Leu Asn His Ile Thr Asn
        1085            1090            1095

Cys Asn Gly Ala Val Leu Ser Val Glu Glu Leu Leu Ile Gly Gly
        1100            1105            1110

Glu Met Ile Lys Ala Gly Thr Leu Thr Leu Glu Glu Val Arg Arg
        1115            1120            1125

Lys Phe Asn Asn Gly Glu Ile Asn Phe
        1130            1135

<210> SEQ ID NO 10
<211> LENGTH: 1239
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
        50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
            115                 120                 125

Leu Leu Thr Val Ala Gly Glu Leu Arg Gly Pro Pro Leu Gln Leu Asp
        130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser His Asp Gly Gly Lys
            180                 185                 190
```

```
Gln Ala Leu Glu Thr Val Gln Arg Leu Leu Pro Val Leu Cys Gln Asp
        195                 200                 205

His Gly Leu Thr Pro Asp Gln Val Val Ala Ile Ala Ser Asn Ile Gly
        210                 215                 220

Gly Lys Gln Ala Leu Glu Thr Val Gln Arg Leu Leu Pro Val Leu Cys
225                 230                 235                 240

Gln Asp His Gly Leu Thr Pro Asp Gln Val Val Ala Ile Ala Ser His
                245                 250                 255

Asp Gly Gly Lys Gln Ala Leu Glu Thr Val Gln Arg Leu Leu Pro Val
                260                 265                 270

Leu Cys Gln Asp His Gly Leu Thr Pro Asp Gln Val Val Ala Ile Ala
                275                 280                 285

Ser His Asp Gly Gly Lys Gln Ala Leu Glu Thr Val Gln Arg Leu Leu
        290                 295                 300

Pro Val Leu Cys Gln Asp His Gly Leu Thr Pro Asp Gln Val Val Ala
305                 310                 315                 320

Ile Ala Ser Asn Gly Gly Lys Gln Ala Leu Glu Thr Val Gln Arg
                325                 330                 335

Leu Leu Pro Val Leu Cys Gln Asp His Gly Leu Thr Pro Asp Gln Val
                340                 345                 350

Val Ala Ile Ala Ser Asn Gly Gly Lys Gln Ala Leu Glu Thr Val
        355                 360                 365

Gln Arg Leu Leu Pro Val Leu Cys Gln Asp His Gly Leu Thr Pro Asp
        370                 375                 380

Gln Val Val Ala Ile Ala Ser Asn Lys Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser His Asp Gly Gly Lys Gln Ala
                420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser His Asp Gly Gly Lys
        450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser His Asp Gly
                485                 490                 495

Gly Lys Gln Ala Leu Glu Thr Val Gln Arg Leu Leu Pro Val Leu Cys
                500                 505                 510

Gln Asp His Gly Leu Thr Pro Asp Gln Val Val Ala Ile Ala Ser His
                515                 520                 525

Asp Gly Gly Lys Gln Ala Leu Glu Thr Val Gln Arg Leu Leu Pro Val
        530                 535                 540

Leu Cys Gln Asp His Gly Leu Thr Pro Asp Gln Val Val Ala Ile Ala
545                 550                 555                 560

Ser Asn Ile Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
                580                 585                 590

Ile Ala Ser His Asp Gly Gly Lys Gln Ala Leu Glu Thr Val Gln Arg
                595                 600                 605
```

```
Leu Leu Pro Val Leu Cys Gln Asp His Gly Leu Thr Pro Asp Gln Val
    610                 615                 620
Val Ala Ile Ala Ser Asn Ile Gly Gly Lys Gln Ala Leu Glu Thr Val
625                 630                 635                 640
Gln Arg Leu Leu Pro Val Leu Cys Gln Asp His Gly Leu Thr Pro Asp
                645                 650                 655
Gln Val Val Ala Ile Ala Ser Asn Lys Gly Gly Lys Gln Ala Leu Glu
            660                 665                 670
Thr Val Gln Arg Leu Leu Pro Val Leu Cys Gln Asp His Gly Leu Thr
        675                 680                 685
Pro Asp Gln Val Val Ala Ile Ala Ser Asn Lys Gly Gly Lys Gln Ala
690                 695                 700
Leu Glu Thr Val Gln Arg Leu Leu Pro Val Leu Cys Gln Asp His Gly
705                 710                 715                 720
Leu Thr Pro Asp Gln Val Val Ala Ile Ala Ser Asn Lys Gly Gly Lys
                725                 730                 735
Gln Ala Leu Glu Thr Val Gln Arg Leu Leu Pro Val Leu Cys Gln Asp
            740                 745                 750
His Gly Leu Thr Pro Asp Gln Val Val Ala Ile Ala Ser His Asp Gly
        755                 760                 765
Gly Lys Gln Ala Leu Glu Thr Val Gln Arg Leu Leu Pro Val Leu Cys
770                 775                 780
Gln Asp His Gly Leu Thr Pro Asp Gln Val Val Ala Ile Ala Ser Asn
785                 790                 795                 800
Ile Gly Gly Lys Gln Ala Leu Glu Thr Val Gln Arg Leu Leu Pro Val
                805                 810                 815
Leu Cys Gln Asp His Gly Leu Thr Pro Asp Gln Val Val Ala Ile Ala
            820                 825                 830
Ser Asn Lys Gly Gly Lys Gln Ala Leu Glu Thr Val Gln Arg Leu Leu
        835                 840                 845
Pro Val Leu Cys Gln Asp His Gly Leu Thr Pro Asp Gln Val Val Ala
850                 855                 860
Ile Ala Ser Asn Gly Gly Gly Lys Gln Ala Leu Glu Thr Val Gln Arg
865                 870                 875                 880
Leu Leu Pro Val Leu Cys Gln Asp His Gly Leu Thr Pro Asp Gln Val
                885                 890                 895
Val Ala Ile Ala Ser Asn Ile Gly Gly Lys Gln Ala Leu Glu Thr Val
            900                 905                 910
Gln Arg Leu Leu Pro Val Leu Cys Gln Asp His Gly Leu Thr Pro Asp
        915                 920                 925
Gln Val Val Ala Ile Ala Ser Asn Ile Gly Gly Lys Gln Ala Leu Glu
930                 935                 940
Thr Val Gln Arg Leu Leu Pro Val Leu Cys Gln Asp His Gly Leu Thr
945                 950                 955                 960
Pro Asp Gln Val Val Ala Ile Ala Ser His Asp Gly Gly Lys Gln Ala
                965                 970                 975
Leu Glu Ser Ile Val Ala Gln Leu Ser Arg Pro Asp Pro Ala Leu Ala
            980                 985                 990
Ala Leu Thr Asn Asp His Leu Val Ala Leu Ala Cys Leu Gly Gly Arg
        995                 1000                1005
Pro Ala Leu Asp Ala Val Lys Lys Gly Leu Pro His Ala Pro Ala
        1010                1015                1020
Leu Ile Lys Arg Thr Asn Arg Arg Ile Pro Glu Arg Thr Ser His
```

```
                    1025                1030                1035

Arg Val Ala Gly Ser Gln Leu Val Lys Ser Glu Leu Glu Glu Lys
            1040                1045                1050

Lys Ser Glu Leu Arg His Lys Leu Lys Tyr Val Pro His Glu Tyr
    1055                1060                1065

Ile Glu Leu Ile Glu Ile Ala Arg Asn Ser Thr Gln Asp Arg Ile
    1070                1075                1080

Leu Glu Met Lys Val Met Glu Phe Phe Met Lys Val Tyr Gly Tyr
    1085                1090                1095

Arg Gly Lys His Leu Gly Gly Ser Arg Lys Pro Asp Gly Ala Ile
    1100                1105                1110

Tyr Thr Val Gly Ser Pro Ile Asp Tyr Gly Val Ile Val Asp Thr
    1115                1120                1125

Lys Ala Tyr Ser Gly Gly Tyr Asn Leu Pro Ile Gly Gln Ala Asp
    1130                1135                1140

Glu Met Gln Arg Tyr Val Glu Glu Asn Gln Thr Arg Asn Lys His
    1145                1150                1155

Ile Asn Pro Asn Glu Trp Trp Lys Val Tyr Pro Ser Ser Val Thr
    1160                1165                1170

Glu Phe Lys Phe Leu Phe Val Ser Gly His Phe Lys Gly Asn Tyr
    1175                1180                1185

Lys Ala Gln Leu Thr Arg Leu Asn His Ile Thr Asn Cys Asn Gly
    1190                1195                1200

Ala Val Leu Ser Val Glu Glu Leu Leu Ile Gly Gly Glu Met Ile
    1205                1210                1215

Lys Ala Gly Thr Leu Thr Leu Glu Glu Val Arg Arg Lys Phe Asn
    1220                1225                1230

Asn Gly Glu Ile Asn Phe
    1235

<210> SEQ ID NO 11
<211> LENGTH: 1137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125
```

```
Leu Leu Thr Val Ala Gly Glu Leu Arg Gly Pro Leu Gln Leu Asp
        130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser His Asp Gly Gly Lys
            180                 185                 190

Gln Ala Leu Glu Thr Val Gln Arg Leu Leu Pro Val Leu Cys Gln Asp
        195                 200                 205

His Gly Leu Thr Pro Asp Gln Val Val Ala Ile Ala Ser Asn Ile Gly
210                 215                 220

Gly Lys Gln Ala Leu Glu Thr Val Gln Arg Leu Leu Pro Val Leu Cys
225                 230                 235                 240

Gln Asp His Gly Leu Thr Pro Asp Gln Val Val Ala Ile Ala Ser His
                245                 250                 255

Asp Gly Gly Lys Gln Ala Leu Glu Thr Val Gln Arg Leu Leu Pro Val
            260                 265                 270

Leu Cys Gln Asp His Gly Leu Thr Pro Asp Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Asp His Gly Leu Thr Pro Asp Gln Val Val Ala
305                 310                 315                 320

Ile Ala Ser Asn Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Ser Asn Gly Gly Lys Gln Ala Leu Glu Thr Val
        355                 360                 365

Gln Arg Leu Leu Pro Val Leu Cys Gln Asp His Gly Leu Thr Pro Asp
370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser His Asp Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser His Asp Gly Gly Lys
450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Ser His
        515                 520                 525

Asp Gly Gly Lys Gln Ala Leu Glu Thr Val Gln Arg Leu Leu Pro Val
530                 535                 540
```

```
Leu Cys Gln Asp His Gly Leu Thr Pro Asp Gln Val Val Ala Ile Ala
545                 550                 555                 560

Ser Asn Ile Gly Gly Lys Gln Ala Leu Glu Thr Val Gln Arg Leu Leu
        565                 570                 575

Pro Val Leu Cys Gln Asp His Gly Leu Thr Pro Asp Gln Val Val Ala
            580                 585                 590

Ile Ala Ser His Asp Gly Gly Lys Gln Ala Leu Glu Thr Val Gln Arg
        595                 600                 605

Leu Leu Pro Val Leu Cys Gln Asp His Gly Leu Thr Pro Asp Gln Val
    610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
            645                 650                 655

Gln Val Val Ala Ile Ala Ser Asn Asn Gly Gly Lys Gln Ala Leu Glu
            660                 665                 670

Thr Val Gln Arg Leu Leu Pro Val Leu Cys Gln Asp His Gly Leu Thr
        675                 680                 685

Pro Asp Gln Val Val Ala Ile Ala Ser Asn Asn Gly Gly Lys Gln Ala
690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Asn Gly Gly Lys
            725                 730                 735

Gln Ala Leu Glu Thr Val Gln Arg Leu Leu Pro Val Leu Cys Gln Asp
            740                 745                 750

His Gly Leu Thr Pro Asp Gln Val Val Ala Ile Ala Ser His Asp Gly
        755                 760                 765

Gly Lys Gln Ala Leu Glu Thr Val Gln Arg Leu Leu Pro Val Leu Cys
        770                 775                 780

Gln Asp His Gly Leu Thr Pro Asp Gln Val Val Ala Ile Ala Ser Asn
785                 790                 795                 800

Ile Gly Gly Lys Gln Ala Leu Glu Thr Val Gln Arg Leu Leu Pro Val
            805                 810                 815

Leu Cys Gln Asp His Gly Leu Thr Pro Asp Gln Val Val Ala Ile Ala
            820                 825                 830

Ser Asn Asn Gly Gly Lys Gln Ala Leu Glu Thr Val Gln Arg Leu Leu
        835                 840                 845

Pro Val Leu Cys Gln Asp His Gly Leu Thr Pro Asp Gln Val Val Ala
    850                 855                 860

Ile Ala Ser Asn Gly Gly Gly Lys Gln Ala Leu Glu Ser Ile Val Ala
865                 870                 875                 880

Gln Leu Ser Arg Pro Asp Pro Ala Leu Ala Ala Leu Thr Asn Asp His
            885                 890                 895

Leu Val Ala Leu Ala Cys Leu Gly Gly Arg Pro Ala Leu Asp Ala Val
            900                 905                 910

Lys Lys Gly Leu Pro His Ala Pro Ala Leu Ile Lys Arg Thr Asn Arg
        915                 920                 925

Arg Ile Pro Glu Arg Thr Ser His Arg Val Ala Gly Ser Gln Leu Val
        930                 935                 940

Lys Ser Glu Leu Glu Glu Lys Lys Ser Glu Leu Arg His Lys Leu Lys
945                 950                 955                 960

Tyr Val Pro His Glu Tyr Ile Glu Leu Ile Glu Ile Ala Arg Asn Ser
```

```
                      965                 970                 975
Thr Gln Asp Arg Ile Leu Glu Met Lys Val Met Glu Phe Phe Met Lys
                  980                 985                 990

Val Tyr Gly Tyr Arg Gly Lys His Leu Gly Gly Ser Arg Lys Pro Asp
            995                 1000                1005

Gly Ala Ile Tyr Thr Val Gly Ser Pro Ile Asp Tyr Gly Val Ile
        1010                1015                1020

Val Asp Thr Lys Ala Tyr Ser Gly Gly Tyr Asn Leu Pro Ile Gly
        1025                1030                1035

Gln Ala Asp Glu Met Gln Arg Tyr Val Glu Glu Asn Gln Thr Arg
        1040                1045                1050

Asn Lys His Ile Asn Pro Asn Glu Trp Trp Lys Val Tyr Pro Ser
        1055                1060                1065

Ser Val Thr Glu Phe Lys Phe Leu Phe Val Ser Gly His Phe Lys
        1070                1075                1080

Gly Asn Tyr Lys Ala Gln Leu Thr Arg Leu Asn His Ile Thr Asn
        1085                1090                1095

Cys Asn Gly Ala Val Leu Ser Val Glu Glu Leu Leu Ile Gly Gly
        1100                1105                1110

Glu Met Ile Lys Ala Gly Thr Leu Thr Leu Glu Glu Val Arg Arg
        1115                1120                1125

Lys Phe Asn Asn Gly Glu Ile Asn Phe
        1130                1135

<210> SEQ ID NO 12
<211> LENGTH: 1239
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
        50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
                100                 105                 110

Ile Val Gly Val Gly Lys Gln Trp Ser Gly Ala Arg Ala Leu Glu Ala
            115                 120                 125

Leu Leu Thr Val Ala Gly Glu Leu Arg Gly Pro Pro Leu Gln Leu Asp
        130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175
```

```
Leu Thr Pro Asp Gln Val Val Ala Ile Ala Ser His Asp Gly Gly Lys
            180                 185                 190

Gln Ala Leu Glu Thr Val Gln Arg Leu Leu Pro Val Leu Cys Gln Asp
        195                 200                 205

His Gly Leu Thr Pro Asp Gln Val Val Ala Ile Ala Ser Asn Ile Gly
    210                 215                 220

Gly Lys Gln Ala Leu Glu Thr Val Gln Arg Leu Leu Pro Val Leu Cys
225                 230                 235                 240

Gln Asp His Gly Leu Thr Pro Asp Gln Val Val Ala Ile Ala Ser His
                245                 250                 255

Asp Gly Gly Lys Gln Ala Leu Glu Thr Val Gln Arg Leu Leu Pro Val
            260                 265                 270

Leu Cys Gln Asp His Gly Leu Thr Pro Asp Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Asp His Gly Leu Thr Pro Asp Gln Val Val Ala
305                 310                 315                 320

Ile Ala Ser Asn Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Ser Asn Gly Gly Lys Gln Ala Leu Glu Thr Val
        355                 360                 365

Gln Arg Leu Leu Pro Val Leu Cys Gln Asp His Gly Leu Thr Pro Asp
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser His Asp Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser His Asp Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Asp His Gly Leu Thr Pro Asp Gln Val Val Ala Ile Ala Ser His
        515                 520                 525

Asp Gly Gly Lys Gln Ala Leu Glu Thr Val Gln Arg Leu Leu Pro Val
    530                 535                 540

Leu Cys Gln Asp His Gly Leu Thr Pro Asp Gln Val Val Ala Ile Ala
545                 550                 555                 560

Ser Asn Ile Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590
```

```
Ile Ala Ser His Asp Gly Gly Lys Gln Ala Leu Glu Thr Val Gln Arg
            595                 600                 605

Leu Leu Pro Val Leu Cys Gln Asp His Gly Leu Thr Pro Asp Gln Val
    610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser Asn Gly Gly Lys Gln Ala Leu Glu
            660                 665                 670

Thr Val Gln Arg Leu Leu Pro Val Leu Cys Gln Asp His Gly Leu Thr
        675                 680                 685

Pro Asp Gln Val Val Ala Ile Ala Ser Asn Asn Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Asn Gly Gly Lys
                725                 730                 735

Gln Ala Leu Glu Thr Val Gln Arg Leu Leu Pro Val Leu Cys Gln Asp
            740                 745                 750

His Gly Leu Thr Pro Asp Gln Val Val Ala Ile Ala Ser His Asp Gly
        755                 760                 765

Gly Lys Gln Ala Leu Glu Thr Val Gln Arg Leu Leu Pro Val Leu Cys
    770                 775                 780

Gln Asp His Gly Leu Thr Pro Asp Gln Val Val Ala Ile Ala Ser Asn
785                 790                 795                 800

Ile Gly Gly Lys Gln Ala Leu Glu Thr Val Gln Arg Leu Leu Pro Val
                805                 810                 815

Leu Cys Gln Asp His Gly Leu Thr Pro Asp Gln Val Val Ala Ile Ala
            820                 825                 830

Ser Asn Asn Gly Gly Lys Gln Ala Leu Glu Thr Val Gln Arg Leu Leu
        835                 840                 845

Pro Val Leu Cys Gln Asp His Gly Leu Thr Pro Asp Gln Val Val Ala
    850                 855                 860

Ile Ala Ser Asn Gly Gly Lys Gln Ala Leu Glu Thr Val Gln Arg
865                 870                 875                 880

Leu Leu Pro Val Leu Cys Gln Asp His Gly Leu Thr Pro Asp Gln Val
                885                 890                 895

Val Ala Ile Ala Ser Asn Ile Gly Gly Lys Gln Ala Leu Glu Thr Val
            900                 905                 910

Gln Arg Leu Leu Pro Val Leu Cys Gln Asp His Gly Leu Thr Pro Asp
        915                 920                 925

Gln Val Val Ala Ile Ala Ser Asn Ile Gly Gly Lys Gln Ala Leu Glu
    930                 935                 940

Thr Val Gln Arg Leu Leu Pro Val Leu Cys Gln Asp His Gly Leu Thr
945                 950                 955                 960

Pro Asp Gln Val Val Ala Ile Ala Ser His Asp Gly Gly Lys Gln Ala
                965                 970                 975

Leu Glu Ser Ile Val Ala Gln Leu Ser Arg Pro Asp Pro Ala Leu Ala
            980                 985                 990

Ala Leu Thr Asn Asp His Leu Val Ala Leu Ala Cys Leu Gly Gly Arg
        995                 1000                1005

Pro Ala Leu Asp Ala Val Lys Lys Gly Leu Pro His Ala Pro Ala
```

Leu Ile Lys Arg Thr Asn Arg Arg Ile Pro Glu Arg Thr Ser His
1025                1030                1035

Arg Val Ala Gly Ser Gln Leu Val Lys Ser Glu Leu Glu Glu Lys
1040                1045                1050

Lys Ser Glu Leu Arg His Lys Leu Lys Tyr Val Pro His Glu Tyr
1055                1060                1065

Ile Glu Leu Ile Glu Ile Ala Arg Asn Ser Thr Gln Asp Arg Ile
1070                1075                1080

Leu Glu Met Lys Val Met Glu Phe Phe Met Lys Val Tyr Gly Tyr
1085                1090                1095

Arg Gly Lys His Leu Gly Gly Ser Arg Lys Pro Asp Gly Ala Ile
1100                1105                1110

Tyr Thr Val Gly Ser Pro Ile Asp Tyr Gly Val Ile Val Asp Thr
1115                1120                1125

Lys Ala Tyr Ser Gly Gly Tyr Asn Leu Pro Ile Gly Gln Ala Asp
1130                1135                1140

Glu Met Gln Arg Tyr Val Glu Glu Asn Gln Thr Arg Asn Lys His
1145                1150                1155

Ile Asn Pro Asn Glu Trp Trp Lys Val Tyr Pro Ser Ser Val Thr
1160                1165                1170

Glu Phe Lys Phe Leu Phe Val Ser Gly His Phe Lys Gly Asn Tyr
1175                1180                1185

Lys Ala Gln Leu Thr Arg Leu Asn His Ile Thr Asn Cys Asn Gly
1190                1195                1200

Ala Val Leu Ser Val Glu Glu Leu Leu Ile Gly Gly Glu Met Ile
1205                1210                1215

Lys Ala Gly Thr Leu Thr Leu Glu Glu Val Arg Arg Lys Phe Asn
1220                1225                1230

Asn Gly Glu Ile Asn Phe
1235

<210> SEQ ID NO 13
<211> LENGTH: 6280
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 13
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600

```
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
accatggact acaaagacca tgacggtgat tataaagatc atgacatcga ttacaaggat    960
gacgatgaca agccaaaaaa gaagcgaaag gtaccttttg cctgcgacat ctgcggccgc   1020
aagttcgccc ggactgacac cctgagggat cacaccaaaa tccacactgg agagaagccc   1080
ttccagtgca gaatctgcat gcgcaacttt agccagagct cctctctggt gaggcacatt   1140
agaacacaca ccggcgaaaa gcccttcgct tgtgatatct gtggtcgtaa atttgcccag   1200
agcggggacc tgacaagaca ccagcgcact catggatccc agctggtgaa gagcgagctg   1260
gaggagaaga agtccgagct gcggcacaag ctgaagtacg tgccccacga gtacatcgag   1320
ctgatcgaga tcgccaggaa cagcacccag gaccgcatcc tggagatgaa ggtgatggag   1380
ttcttcatga aggtgtacgg ctacaggga aagcacctgg gcggaagcag aaagcctgac   1440
ggcgccatct atacagtggg cagccccatc gattacggcg tgatcgtgga cacaaaggcc   1500
tacagcggcg gctacaatct gcctatcggc caggccgacg agatgcagag atacgtggag   1560
gagaaccaga cccggaataa gcacatcaac cccaacgagt ggtggaaggt gtaccctagc   1620
agcgtgaccg agttcaagtt cctgttcgtg agcggccact tcaagggcaa ctacaaggcc   1680
cagctgacca ggctgaacca catcaccaac tgcaatggcg ccgtgctgag cgtggaggag   1740
ctgctgatcg gcggcgagat gatcaaagcc ggcaccctga cactggagga ggtgcggcgc   1800
aagttcaaca acgcgagat caacttctga taactcgagc ggccgccact gtgctggata   1860
aaccgctgat cagcctcgac tgtgccttct agttgccagc catctgttgt ttgcccctcc   1920
cccgtgcctt ccttgaccct ggaaggtgcc actcccactg tcctttccta ataaaatgag   1980
gaaattgcat cgcattgtct gagtaggtgt cattctattc tggggggtgg ggtggggcag   2040
gacagcaagg gggaggattg ggaagacaat agcaggcatg ctgggggatgc ggtgggctct   2100 atggcttctg aggcggaaag aaccagctgg ggctctaggg ggtatcccca cgcgccctgt   2160
agcggcgcat taagcgcggc gggtgtggtg gttacgcgca gcgtgaccgc tacacttgcc   2220
agcgccctag cgcccgctcc tttcgctttc ttcccttcct ttctcgccac gttcgccggc   2280
tttccccgtc aagctctaaa tcgggggctc cctttagggt tccgatttag tgctttacgg   2340
cacctcgacc ccaaaaaact tgattagggt gatggttcac gtagtgggcc atcgccctga   2400
tagacggttt ttcgcccttt gacgttggag tccacgttct ttaatagtgg actcttgttc   2460
caaactggaa caacactcaa ccctatctcg gtctattctt ttgatttata agggattttg   2520
ccgatttcgg cctattggtt aaaaaatgag ctgatttaac aaaaatttaa cgcgaattaa   2580
ttctgtggaa tgtgtgtcag ttagggtgtg gaaagtcccc aggctcccca gcaggcagaa   2640
gtatgcaaag catgcatctc aattagtcag caaccaggtg tggaaagtcc caggctccc    2700 cagcaggcag aagtatgcaa agcatgcatc tcaattagtc agcaaccata gtcccgcccc   2760
taactccgcc catcccgccc ctaactccgc ccagttccgc ccattctccg ccccatggct   2820
gactaatttt ttttatttat gcagaggccg aggccgcctc tgcctctgag ctattccaga   2880
agtagtgagg aggcttttt ggaggcctag gcttttgcaa aaagctcccg ggagcttgta   2940
tatccatttt cggatctgat caagagacag gatgaggatc gtttcgcatg attgaacaag   3000
```

```
atggattgca cgcaggttct ccggccgctt gggtggagag gctattcggc tatgactggg    3060
cacaacagac aatcggctgc tctgatgccg ccgtgttccg gctgtcagcg caggggcgcc    3120
cggttctttt tgtcaagacc gacctgtccg gtgccctgaa tgaactgcag gacgaggcag    3180
cgcggctatc gtggctggcc acgacgggcg ttccttgcgc agctgtgctc gacgttgtca    3240
ctgaagcggg aagggactgg ctgctattgg gcgaagtgcc ggggcaggat ctcctgtcat    3300
ctcaccttgc tcctgccgag aaagtatcca tcatggctga tgcaatgcgg cggctgcata    3360
cgcttgatcc ggctacctgc ccattcgacc accaagcgaa acatcgcatc gagcgagcac    3420
gtactcggat ggaagccggt cttgtcgatc aggatgatct ggacgaagag catcaggggc    3480
tcgcgccagc cgaactgttc gccaggctca aggcgcgcat gcccgacggc gaggatctcg    3540
tcgtgaccca tggcgatgcc tgcttgccga atatcatggt ggaaaatggc cgcttttctg    3600
gattcatcga ctgtggccgg ctgggtgtgg cggaccgcta tcaggacata gcgttggcta    3660
cccgtgatat tgctgaagag cttggcggcg aatgggctga ccgcttcctc gtgctttacg    3720
gtatcgccgc tcccgattcg cagcgcatcg ccttctatcg ccttcttgac gagttcttct    3780
gagcgggact ctggggttcg aaatgaccga ccaagcgacg cccaacctgc catcacgaga    3840
tttcgattcc accgccgcct tctatgaaag gttgggcttc ggaatcgttt tccgggacgc    3900
cggctggatg atcctccagc gcggggatct catgctggag ttcttcgccc accccaactt    3960
gtttattgca gcttataatg gttacaaata aagcaatagc atcacaaatt tcacaaataa    4020
agcatttttt tcactgcatt ctagttgtgg tttgtccaaa ctcatcaatg tatcttatca    4080
tgtctgtata ccgtcgacct ctagctagag cttggcgtaa tcatggtcat agctgtttcc    4140
tgtgtgaaat tgttatccgc tcacaattcc acacaacata cgagccggaa gcataaagtg    4200
taaagcctgg ggtgcctaat gagtgagcta actcacatta attgcgttgc gctcactgcc    4260
cgctttccag tcgggaaacc tgtcgtgcca gctgcattaa tgaatcggcc aacgcgcggg    4320
gagaggcggt ttgcgtattg ggcgctcttc cgcttcctcg ctcactgact cgctgcgctc    4380
ggtcgttcgg ctgcggcgag cggtatcagc tcactcaaag gcggtaatac ggttatccac    4440
agaatcaggg gataacgcag gaaagaacat gtgagcaaaa ggccagcaaa aggccaggaa    4500
ccgtaaaaag gccgcgttgc tggcgttttt ccataggctc cgcccccctg acgagcatca    4560
caaaaatcga cgctcaagtc agaggtggcg aaacccgaca ggactataaa gataccaggc    4620
gtttccccct ggaagctccc tcgtgcgctc tcctgttccg accctgccgc ttaccggata    4680
cctgtccgcc tttctccctt cgggaagcgt ggcgctttct catagctcac gctgtaggta    4740
tctcagttcg gtgtaggtcg ttcgctccaa gctgggctgt gtgcacgaac cccccgttca    4800
gcccgaccgc tgcgccttat ccggtaacta tcgtcttgag tccaacccgg taagacacga    4860
cttatcgcca ctggcagcag ccactggtaa caggattagc agagcgaggt atgtaggcgg    4920
tgctacagag ttcttgaagt ggtggcctaa ctacggctac actagaagaa cagtatttgg    4980
tatctgcgct ctgctgaagc cagttacctt cggaaaaaga gttggtagct cttgatccgg    5040
caaacaaacc accgctggta gcggtttttt tgtttgcaag cagcagatta cgcgcagaaa    5100
aaaaggatct caagaagatc ctttgatctt ttctacgggg tctgacgctc agtggaacga    5160
aaactcacgt taagggattt tggtcatgag attatcaaaa aggatcttca cctagatcct    5220
tttaaattaa aaatgaagtt ttaaatcaat ctaaagtata tatgagtaaa cttggtctga    5280
cagttaccaa tgcttaatca gtgaggcacc tatctcagcg atctgtctat ttcgttcatc    5340
```

| | |
|---|---|
| catagttgcc tgactcccg tcgtgtagat aactacgata cgggagggct taccatctgg | 5400 |
| ccccagtgct gcaatgatac cgcgagaccc acgctcaccg gctccagatt tatcagcaat | 5460 |
| aaaccagcca gccggaaggg ccgagcgcag aagtggtcct gcaactttat ccgcctccat | 5520 |
| ccagtctatt aattgttgcc gggaagctag agtaagtagt tcgccagtta atagtttgcg | 5580 |
| caacgttgtt gccattgcta caggcatcgt ggtgtcacgc tcgtcgtttg gtatggcttc | 5640 |
| attcagctcc ggttcccaac gatcaaggcg agttacatga tcccccatgt tgtgcaaaaa | 5700 |
| agcggttagc tccttcggtc ctccgatcgt tgtcagaagt aagttggccg cagtgttatc | 5760 |
| actcatggtt atggcagcac tgcataattc tcttactgtc atgccatccg taagatgctt | 5820 |
| ttctgtgact ggtgagtact caaccaagtc attctgagaa tagtgtatgc ggcgaccgag | 5880 |
| ttgctcttgc ccggcgtcaa tacgggataa taccgcgcca catagcagaa ctttaaaagt | 5940 |
| gctcatcatt ggaaaacgtt cttcggggcg aaaactctca aggatcttac cgctgttgag | 6000 |
| atccagttcg atgtaaccca ctcgtgcacc caactgatct tcagcatctt ttactttcac | 6060 |
| cagcgtttct gggtgagcaa aaacaggaag gcaaaatgcc gcaaaaaagg gaataagggc | 6120 |
| gacacggaaa tgttgaatac tcatactctt ccttttcaa tattattgaa gcatttatca | 6180 |
| gggttattgt ctcatgagcg gatacatatt tgaatgtatt tagaaaaata aacaaatagg | 6240 |
| ggttccgcgc acatttcccc gaaaagtgcc acctgacgtc | 6280 |

<210> SEQ ID NO 14
<211> LENGTH: 6280
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

| | |
|---|---|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccaccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| accatggact acaaagacca tgacggtgat tataaagatc atgacatcga ttacaaggat | 960 |
| gacgatgaca agccaaaaaa gaagcgaaag gtaccttttg cctgcgacat ctgcggccgc | 1020 |
| aagttcgcca gaagcgacca cctgaccaac cacaccaaaa tccacactgg agagaagccc | 1080 |

```
ttccagtgca gaatctgcat gcgcaacttt agccagagcg gcgacctgac cagacacatt    1140
agaacacaca ccggcgaaaa gcccttcgct tgtgatatct gtggtcgtaa atttgccaga    1200
agcgaccacc tgagcagaca ccagcgcact catggatccc agctggtgaa gagcgagctg    1260
gaggagaaga agtccgagct gcggcacaag ctgaagtacg tgccccacga gtacatcgag    1320
ctgatcgaga tcgccaggaa cagcacccag gaccgcatcc tggagatgaa ggtgatggag    1380
ttcttcatga aggtgtacgg ctacagggga aagcacctgg gcggaagcag aaagcctgac    1440
ggcgccatct atacagtggg cagccccatc gattacggcg tgatcgtgga cacaaaggcc    1500
tacagcggcg gctacaatct gcctatcggc caggccgacg agatgcagag atacgtggag    1560
gagaaccaga cccggaataa gcacatcaac cccaacgagt ggtggaaggt gtaccctagc    1620
agcgtgaccg agttcaagtt cctgttcgtg agcggccact tcaagggcaa ctacaaggcc    1680
cagctgacca ggctgaacca catcaccaac tgcaatggcg ccgtgctgag cgtggaggag    1740
ctgctgatcg gcgcgagat gatcaaagcc ggcacccctga cactggagga ggtgcggcgc    1800
aagttcaaca acggcgagat caacttctga taactcgagc ggccgccact gtgctggata    1860
aaccgctgat cagcctcgac tgtgccttct agttgccagc catctgttgt ttgcccctcc    1920
cccgtgcctt ccttgaccct ggaaggtgcc actcccactg tcctttccta ataaaatgag    1980
gaaattgcat cgcattgtct gagtaggtgt cattctattc tggggggtgg ggtggggcag    2040
gacagcaagg gggaggattg gaagacaat agcaggcatg ctggggatgc ggtgggctct    2100
atggcttctg aggcggaaag aaccagctgg ggctctaggg ggtatcccca cgcgccctgt    2160
agcggcgcat taagcgcggc gggtgtggtg gttacgcgca gcgtgaccgc tacacttgcc    2220
agcgccctag cgcccgctcc tttcgctttc ttcccttcct ttctcgccac gttcgccggc    2280
tttccccgtc aagctctaaa tcgggggctc cctttagggt tccgatttag tgctttacgg    2340
cacctcgacc ccaaaaaact tgattagggt gatggttcac gtagtgggcc atcgccctga    2400
tagacggttt ttcgcccttt gacgttggag tccacgttct ttaatagtgg actcttgttc    2460
caaactggaa caacactcaa ccctatctcg gtctattctt ttgatttata agggattttg    2520
ccgatttcgg cctattggtt aaaaaatgag ctgatttaac aaaaatttaa cgcgaattaa    2580
ttctgtggaa tgtgtgtcag ttagggtgtg gaaagtcccc aggctcccca gcaggcagaa    2640
gtatgcaaag catgcatctc aattagtcag caaccaggtg tggaaagtcc ccaggctccc    2700
cagcaggcag aagtatgcaa agcatgcatc tcaattagtc agcaaccata gtcccgcccc    2760
taactccgcc catcccgccc ctaactccgc ccagttccgc ccattctccg ccccatggct    2820
gactaatttt ttttatttat gcagaggccg aggccgcctc tgcctctgag ctattccaga    2880
agtagtgagg aggcttttt ggaggcctag gcttttgcaa aaagctcccg ggagcttgta    2940
tatccatttt cggatctgat caagagacag gatgaggatc gtttcgcatg attgaacaag    3000
atggattgca cgcaggttct ccggccgctt ggtggagag gctattcggc tatgactggg    3060
cacaacagac aatcggctgc tctgatgccg ccgtgttccg gctgtcagcg caggggcgcc    3120
cggttctttt tgtcaagacc gacctgtccg gtgccctgaa tgaactgcag gacgaggcag    3180
cgcggctatc gtggctggcc acgacgggcg ttccttgcgc agctgtgctc gacgttgtca    3240
ctgaagcggg aagggactgg ctgctattgg gcgaagtgcc ggggcaggat ctcctgtcat    3300
ctcaccttgc tcctgccgag aaagtatcca tcatggctga tgcaatgcgg cggctgcata    3360
cgcttgatcc ggctacctgc ccattcgacc accaagcgaa acatcgcatc gagcgagcac    3420
```

-continued

| | |
|---|---|
| gtactcggat ggaagccggt cttgtcgatc aggatgatct ggacgaagag catcaggggc | 3480 |
| tcgcgccagc cgaactgttc gccaggctca aggcgcgcat gcccgacggc gaggatctcg | 3540 |
| tcgtgaccca tggcgatgcc tgcttgccga atatcatggt ggaaaatggc cgcttttctg | 3600 |
| gattcatcga ctgtggccgg ctgggtgtgg cggaccgcta tcaggacata gcgttggcta | 3660 |
| cccgtgatat tgctgaagag cttggcggcg aatgggctga ccgcttcctc gtgctttacg | 3720 |
| gtatcgccgc tcccgattcg cagcgcatcg ccttctatcg ccttcttgac gagttcttct | 3780 |
| gagcgggact ctggggttcg aaatgaccga ccaagcgacg cccaacctgc catcacgaga | 3840 |
| tttcgattcc accgccgcct tctatgaaag gttgggcttc ggaatcgttt tccgggacgc | 3900 |
| cggctggatg atcctccagc gcggggatct catgctggag ttcttcgccc accccaactt | 3960 |
| gtttattgca gcttataatg gttacaaata aagcaatagc atcacaaatt tcacaaataa | 4020 |
| agcattttt tcactgcatt ctagttgtgg tttgtccaaa ctcatcaatg tatcttatca | 4080 |
| tgtctgtata ccgtcgacct ctagctagag cttggcgtaa tcatggtcat agctgtttcc | 4140 |
| tgtgtgaaat tgttatccgc tcacaattcc acacaacata cgagccggaa gcataaagtg | 4200 |
| taaagcctgg ggtgcctaat gagtgagcta actcacatta attgcgttgc gctcactgcc | 4260 |
| cgctttccag tcgggaaacc tgtcgtgcca gctgcattaa tgaatcggcc aacgcgcggg | 4320 |
| gagaggcggt ttgcgtattg ggcgctcttc cgcttcctcg ctcactgact cgctgcgctc | 4380 |
| ggtcgttcgg ctgcggcgag cggtatcagc tcactcaaag gcggtaatac ggttatccac | 4440 |
| agaatcaggg gataacgcag gaaagaacat gtgagcaaaa ggccagcaaa aggccaggaa | 4500 |
| ccgtaaaaag gccgcgttgc tggcgttttt ccataggctc cgcccccctg acgagcatca | 4560 |
| caaaaatcga cgctcaagtc agaggtggcg aaacccgaca ggactataaa gataccaggc | 4620 |
| gtttccccct ggaagctccc tcgtgcgctc tcctgttccg accctgccgc ttaccggata | 4680 |
| cctgtccgcc tttctccctt cgggaagcgt ggcgctttct catagctcac gctgtaggta | 4740 |
| tctcagttcg gtgtaggtcg ttcgctccaa gctgggctgt gtgcacgaac cccccgttca | 4800 |
| gcccgaccgc tgcgccttat ccggtaacta tcgtcttgag tccaacccgg taagacacga | 4860 |
| cttatcgcca ctggcagcag ccactggtaa caggattagc agagcgaggt atgtaggcgg | 4920 |
| tgctacagag ttcttgaagt ggtggcctaa ctacggctac actagaagaa cagtatttgg | 4980 |
| tatctgcgct ctgctgaagc cagttacctt cggaaaaaga gttggtagct cttgatccgg | 5040 |
| caaacaaacc accgctggta gcggtttttt tgtttgcaag cagcagatta cgcgcagaaa | 5100 |
| aaaaggatct caagaagatc ctttgatctt ttctacgggg tctgacgctc agtggaacga | 5160 |
| aaactcacgt taagggattt tggtcatgag attatcaaaa aggatcttca cctagatcct | 5220 |
| tttaaattaa aaatgaagtt ttaaatcaat ctaaagtata tatgagtaaa cttggtctga | 5280 |
| cagttaccaa tgcttaatca gtgaggcacc tatctcagcg atctgtctat ttcgttcatc | 5340 |
| catagttgcc tgactccccg tcgtgtagat aactacgata cgggagggct taccatctgg | 5400 |
| ccccagtgct gcaatgatac cgcgagaccc acgctcaccg gctccagatt tatcagcaat | 5460 |
| aaaccagcca gccggaaggg ccgagcgcag aagtggtcct gcaactttat ccgcctccat | 5520 |
| ccagtctatt aattgttgcc gggaagctag agtaagtagt tcgccagtta atagtttgcg | 5580 |
| caacgttgtt gccattgcta caggcatcgt ggtgtcacgc tcgtcgtttg gtatggcttc | 5640 |
| attcagctcc ggttcccaac gatcaaggcg agttacatga tcccccatgt tgtgcaaaaa | 5700 |
| agcggttagc tccttcggtc ctccgatcgt tgtcagaagt aagttggccg cagtgttatc | 5760 |
| actcatggtt atggcagcac tgcataattc tcttactgtc atgccatccg taagatgctt | 5820 |

```
ttctgtgact ggtgagtact caaccaagtc attctgagaa tagtgtatgc ggcgaccgag    5880
ttgctcttgc ccggcgtcaa tacgggataa taccgcgcca catagcagaa ctttaaaagt    5940
gctcatcatt ggaaaacgtt cttcggggcg aaaactctca aggatcttac cgctgttgag    6000
atccagttcg atgtaaccca ctcgtgcacc caactgatct tcagcatctt ttactttcac    6060
cagcgtttct gggtgagcaa aaacaggaag gcaaaatgcc gcaaaaaagg gaataagggc    6120
gacacggaaa tgttgaatac tcatactctt ccttttcaa tattattgaa gcatttatca     6180
gggttattgt ctcatgagcg gatacatatt tgaatgtatt tagaaaaata aacaaatagg    6240
ggttccgcgc acatttcccc gaaaagtgcc acctgacgtc                          6280
```

<210> SEQ ID NO 15
<211> LENGTH: 6367
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
accatggact acaaagacca tgacggtgat tataaagatc atgacatcga ttacaaggat     960
gacgatgaca agccaaaaaa gaagcgaaag gtaccattcc agtgccgcat tgtatgcgc    1020 aatttcagcc agagtggaag tctgacccgg catatccgta cccacaccgg tgagaaacct    1080
tttgcctgcg acatctgcgg ccgcaagttc gcccggactg acacctgag ggatcacacc     1140 aaaatccaca ctggaggcga gaagcccttc cagtgcagaa tctgcatgcg caactttagc    1200
cagagctcct ctctggtgag gcacattaga acacacaccg gcgaaaagcc cttcgcttgt    1260
gatatctgtg gtcgtaaatt tgcccagagc ggggacctga agacacca gcgcactcat      1320 ggatcccagc tggtgaagag cgagctggag gagaagaagt ccgagctgcg gcacaagctg    1380
aagtacgtgc cccacgagta catcgagctg atcgagatcg ccaggaacag cacccaggac    1440
cgcatcctgg agatgaaggt gatggagttc ttcatgaagg tgtacggcta caggggaaag    1500
```

```
cacctgggcg gaagcagaaa gcctgacggc gccatctata cagtgggcag ccccatcgat    1560
tacggcgtga tcgtggacac aaaggcctac agcggcggct acaatctgcc tatcggccag    1620
gccgacgaga tgcagagata cgtggaggag aaccagaccc ggaataagca catcaacccc    1680
aacgagtggt ggaaggtgta ccctagcagc gtgaccgagt tcaagttcct gttcgtgagc    1740
ggccacttca agggcaacta caaggcccag ctgaccaggc tgaaccacat caccaactgc    1800
aatggcgccg tgctgagcgt ggaggagctg ctgatcggcg cgagatgat caaagccggc     1860 accctgacac tggaggaggt gcggcgcaag ttcaacaacg gcgagatcaa cttctgataa    1920
ctcgagcggc cgccactgtg ctggataaac cgctgatcag cctcgactgt gccttctagt    1980
tgccagccat ctgttgtttg cccctcccc gtgccttcct tgaccctgga aggtgccact      2040
cccactgtcc tttcctaata aaatgaggaa attgcatcgc attgtctgag taggtgtcat    2100
tctattctgg ggggtggggt ggggcaggac agcaaggggg aggattggga agacaatagc    2160
aggcatgctg gggatgcggt gggctctatg gcttctgagg cggaaagaac cagctggggc    2220 tctaggggt atccccacgc gccctgtagc ggcgcattaa gcgcggcggg tgtggtggtt     2280
acgcgcagcg tgaccgctac acttgccagc gccctagcgc ccgctccttt cgctttcttc    2340
ccttcctttc tcgccacgtt cgccggcttt ccccgtcaag ctctaaatcg gggctccct    2400 ttagggttcc gatttagtgc tttacggcac ctcgacccca aaaaacttga ttagggtgat    2460
ggttcacgta gtgggccatc gccctgatag acggtttttc gccctttgac gttggagtcc    2520
acgttcttta atagtggact cttgttccaa actggaacaa cactcaaccc tatctcggtc    2580
tattcttttg atttataagg gattttgccg atttcggcct attggttaaa aaatgagctg    2640
atttaacaaa aatttaacgc gaattaattc tgtggaatgt gtgtcagtta gggtgtggaa    2700
agtccccagg ctccccagca ggcagaagta tgcaaagcat gcatctcaat tagtcagcaa    2760
ccaggtgtgg aaagtcccca ggctccccag caggcagaag tatgcaaagc atgcatctca    2820
attagtcagc aaccatagtc ccgcccctaa ctccgcccat cccgccccta actccgccca    2880
gttccgccca ttctccgccc catggctgac taatttttt tatttatgca gaggccgagg     2940
ccgcctctgc ctctgagcta ttccagaagt agtgaggagg cttttttgga ggcctaggct    3000
tttgcaaaaa gctcccggga gcttgtatat ccattttcgg atctgatcaa gagacaggat    3060
gaggatcgtt tcgcatgatt gaacaagatg gattgcacgc aggttctccg gccgcttggg    3120
tggagaggct attcggctat gactgggcac aacagacaat cggctgctct gatgccgccg    3180
tgttccggct gtcagcgcag gggcgcccgg ttcttttgt caagaccgac ctgtccggtg      3240
ccctgaatga actgcaggac gaggcagcgc ggctatcgtg gctggccacg acgggcgttc    3300
cttgcgcagc tgtgctcgac gttgtcactg aagcgggaag ggactggctg ctattgggcg    3360
aagtgccggg gcaggatctc ctgtcatctc accttgctcc tgccgagaaa gtatccatca    3420
tggctgatgc aatgcggcgg ctgcatacgc ttgatccggc tacctgccca ttcgaccacc    3480
aagcgaaaca tcgcatcgag cgagcacgta ctcggatgga agccggtctt gtcgatcagg    3540
atgatctgga cgaagagcat caggggctcg cgccagccga actgttcgcc aggctcaagg    3600
cgcgcatgcc cgacggcgag gatctcgtcg tgacccatgg cgatgcctgc ttgccgaata    3660
tcatggtgga aaatggccgc ttttctggat tcatcgactg tggccggctg ggtgtggcgg    3720
accgctatca ggacatagcg ttggctaccc gtgatattgc tgaagagctt ggcggcgaat    3780
gggctgaccg cttcctcgtg ctttacggta tcgccgctcc cgattcgcag cgcatcgcct    3840
tctatcgcct tcttgacgag ttcttctgag cgggactctg gggttcgaaa tgaccgacca    3900
```

| | | | | |
|---|---|---|---|---|
| agcgacgccc | aacctgccat | cacgagattt | cgattccacc | gccgccttct | atgaaaggtt | 3960 |
| gggcttcgga | atcgttttcc | gggacgccgg | ctgatgatc | ctccagcgcg | ggatctcat | 4020 |
| gctggagttc | ttcgcccacc | ccaacttgtt | tattgcagct | tataatggtt | acaaataaag | 4080 |
| caatagcatc | acaaatttca | caaataaagc | attttttca | ctgcattcta | gttgtggttt | 4140 |
| gtccaaactc | atcaatgtat | cttatcatgt | ctgtataccg | tcgacctcta | gctagagctt | 4200 |
| ggcgtaatca | tggtcatagc | tgtttcctgt | gtgaaattgt | tatccgctca | caattccaca | 4260 |
| caacatacga | gccggaagca | taaagtgtaa | agcctggggt | gcctaatgag | tgagctaact | 4320 |
| cacattaatt | gcgttgcgct | cactgcccgc | tttccagtcg | ggaaacctgt | cgtgccagct | 4380 |
| gcattaatga | atcggccaac | gcgcgggag | aggcggtttg | cgtattgggc | gctcttccgc | 4440 |
| ttcctcgctc | actgactcgc | tgcgctcggt | cgttcggctg | cggcgagcgg | tatcagctca | 4500 |
| ctcaaaggcg | gtaatacggt | tatccacaga | atcaggggat | aacgcaggaa | agaacatgtg | 4560 |
| agcaaaaggc | cagcaaaagg | ccaggaaccg | taaaaaggcc | gcgttgctgg | cgtttttcca | 4620 |
| taggctccgc | cccctgacg | agcatcacaa | aaatcgacgc | tcaagtcaga | ggtggcgaaa | 4680 |
| cccgacagga | ctataaagat | accaggcgtt | tccccctgga | agctccctcg | tgcgctctcc | 4740 |
| tgttccgacc | ctgccgctta | ccggatacct | gtccgccttt | ctcccttcgg | gaagcgtggc | 4800 |
| gctttctcat | agctcacgct | gtaggtatct | cagttcggtg | taggtcgttc | gctccaagct | 4860 |
| gggctgtgtg | cacgaacccc | ccgttcagcc | cgaccgctgc | gccttatccg | gtaactatcg | 4920 |
| tcttgagtcc | aacccggtaa | gacacgactt | atcgccactg | gcagcagcca | ctggtaacag | 4980 |
| gattagcaga | gcgaggtatg | taggcggtgc | tacagagttc | ttgaagtggt | ggcctaacta | 5040 |
| cggctacact | agaagaacag | tatttggtat | ctgcgctctg | ctgaagccag | ttaccttcgg | 5100 |
| aaaaagagtt | ggtagctctt | gatccggcaa | acaaaccacc | gctggtagcg | gtttttttgt | 5160 |
| ttgcaagcag | cagattacgc | gcagaaaaaa | aggatctcaa | gaagatcctt | tgatcttttc | 5220 |
| tacgggtct | gacgctcagt | ggaacgaaaa | ctcacgttaa | gggattttgg | tcatgagatt | 5280 |
| atcaaaaagg | atcttcacct | agatcctttt | aaattaaaaa | tgaagtttta | aatcaatcta | 5340 |
| aagtatatat | gagtaaactt | ggtctgacag | ttaccaatgc | ttaatcagtg | aggcacctat | 5400 |
| ctcagcgatc | tgtctatttc | gttcatccat | agttgcctga | ctccccgtcg | tgtagataac | 5460 |
| tacgatacgg | gagggcttac | catctggccc | cagtgctgca | atgataccgc | gagacccacg | 5520 |
| ctcaccggct | ccagatttat | cagcaataaa | ccagccagcc | ggaagggccg | agcgcagaag | 5580 |
| tggtcctgca | actttatccg | cctccatcca | gtctattaat | tgttgccggg | aagctagagt | 5640 |
| aagtagttcg | ccagttaata | gtttgcgcaa | cgttgttgcc | attgctacag | gcatcgtggt | 5700 |
| gtcacgctcg | tcgtttggta | tggcttcatt | cagctccggt | tcccaacgat | caaggcgagt | 5760 |
| tacatgatcc | cccatgttgt | gcaaaaaagc | ggttagctcc | ttcggtcctc | cgatcgttgt | 5820 |
| cagaagtaag | ttggccgcag | tgttatcact | catggttatg | gcagcactgc | ataattctct | 5880 |
| tactgtcatg | ccatccgtaa | gatgcttttc | tgtgactggt | gagtactcaa | ccaagtcatt | 5940 |
| ctgagaatag | tgtatgcggc | gaccgagttg | ctcttgcccg | gcgtcaatac | gggataatac | 6000 |
| cgcgccacat | agcagaactt | taaaagtgct | catcattgga | aaacgttctt | cggggcgaaa | 6060 |
| actctcaagg | atcttaccgc | tgttgagatc | cagttcgatg | taacccactc | gtgcacccaa | 6120 |
| ctgatcttca | gcatctttta | ctttcaccag | cgtttctggg | tgagcaaaaa | caggaaggca | 6180 |
| aaatgccgca | aaaaagggaa | taaggcgac | acggaaatgt | tgaatactca | tactcttcct | 6240 |

```
ttttcaatat tattgaagca tttatcaggg ttattgtctc atgagcggat acatatttga    6300
atgtatttag aaaaataaac aaataggggt tccgcgcaca tttccccgaa aagtgccacc    6360
tgacgtc                                                              6367

<210> SEQ ID NO 16
<211> LENGTH: 6373
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
accatggact acaaagacca tgacggtgat tataaagatc atgacatcga ttacaaggat     960
gacgatgaca agccaaaaaa gaagcgaaag gtaccattcc agtgccgcat ttgtatgcgc    1020
aatttcagcc agagcggcca cctggccagc catatccgta cccacaccgg tgagaaacct    1080
tttgcctgcg acatctgcgg ccgcaagttc gccagaagcg accacctgac caaccacacc    1140
aaaatccaca ctggaggcgg atctgagaag cccttccagt gcagaatctg catgcgcaac    1200
tttagccaga gcggcgacct gaccagacac attagaacac acaccggcga aaagcccttc    1260
gcttgtgata tctgtggtcg taaatttgcc agaagcgacc acctgagcag acaccagcgc    1320
actcatggat cccagctggt gaagagcgag ctggaggaga agaagtccga gctgcggcac    1380
aagctgaagt acgtgcccca cgagtacatc gagctgatcg agatcgccag gaacagcacc    1440
caggaccgca tcctggagat gaaggtgatg gagttcttca tgaaggtgta cggctacagg    1500
ggaaagcacc tgggcggaag cagaaagcct gacggcgcca tctatacagt gggcagcccc    1560
atcgattacg gcgtgatcgt ggacacaaag gcctacagcg gcggctacaa tctgcctatc    1620
ggccaggccg acgagatgca gagatacgtg gaggagaacc agacccggaa taagcacatc    1680
aaccccaacg agtggtggaa ggtgtaccct agcagcgtga ccgagttcaa gttcctgttc    1740
gtgagcggcc acttcaaggg caactacaag gcccagctga ccaggctgaa ccacatcacc    1800
aactgcaatg gcgccgtgct gagcgtggag gagctgctga tcggcggcga gatgatcaaa    1860
```

```
gccggcaccc tgacactgga ggaggtgcgg cgcaagttca acaacggcga gatcaacttc    1920
tgataactcg agcggccgcc actgtgctgg ataaaccgct gatcagcctc gactgtgcct    1980
tctagttgcc agccatctgt tgtttgcccc tcccccgtgc cttccttgac cctggaaggt    2040
gccactccca ctgtcctttc ctaataaaat gaggaaattg catcgcattg tctgagtagg    2100
tgtcattcta ttctgggggg tggggtgggg caggacagca agggggagga ttgggaagac    2160
aatagcaggc atgctgggga tgcggtgggc tctatggctt ctgaggcgga aagaaccagc    2220
tggggctcta gggggtatcc ccacgcgccc tgtagcggcg cattaagcgc ggcgggtgtg    2280
gtggttacgc gcagcgtgac cgctacactt gccagcgccc tagcgcccgc tcctttcgct    2340
ttcttccctt cctttctcgc cacgttcgcc ggctttcccc gtcaagctct aaatcggggg    2400
ctccctttag ggttccgatt tagtgcttta cggcacctcg accccaaaaa acttgattag    2460
ggtgatggtt cacgtagtgg gccatcgccc tgatagacgg ttttcgccc tttgacgttg    2520 gagtccacgt tctttaatag tggactcttg ttccaaactg gaacaacact caaccctatc    2580
tcggtctatt cttttgattt ataagggatt ttgccgattt cggcctattg gttaaaaaat    2640
gagctgattt aacaaaaatt taacgcgaat taattctgtg gaatgtgtgt cagttagggt    2700
gtggaaagtc cccaggctcc ccagcaggca gaagtatgca aagcatgcat ctcaattagt    2760
cagcaaccag gtgtggaaag tccccaggct ccccagcagg cagaagtatg caaagcatgc    2820
atctcaatta gtcagcaacc atagtcccgc ccctaactcc gcccatcccg ccctaactc    2880 cgcccagttc cgcccattct ccgccccatg gctgactaat ttttttatt tatgcagagg    2940 ccgaggccgc ctctgcctct gagctattcc agaagtagtg aggaggcttt tttggaggcc    3000
taggcttttg caaaaagctc ccgggagctt gtatatccat tttcggatct gatcaagaga    3060
caggatgagg atcgtttcgc atgattgaac aagatggatt gcacgcaggt tctccggccg    3120
cttgggtgga gaggctattc ggctatgact gggcacaaca gacaatcggc tgctctgatg    3180
ccgccgtgtt ccggctgtca gcgcaggggc gcccggttct ttttgtcaag accgacctgt    3240
ccggtgccct gaatgaactg caggacgagg cagcgcggct atcgtggctg gccacgacgg    3300
gcgttccttg cgcagctgtg ctcgacgttg tcactgaagc gggaagggac tggctgctat    3360
tgggcgaagt gccggggcag gatctcctgt catctcacct tgctcctgcc gagaaagtat    3420
ccatcatggc tgatgcaatg cggcggctgc atacgcttga tccggctacc tgcccattcg    3480
accaccaagc gaaacatcgc atcgagcgag cacgtactcg gatggaagcc ggtcttgtcg    3540
atcaggatga tctggacgaa gagcatcagg ggctcgcgcc agccgaactg ttcgccaggc    3600
tcaaggcgcg catgcccgac ggcgaggatc tcgtcgtgac ccatggcgat gcctgcttgc    3660
cgaatatcat ggtggaaaat ggccgctttt ctggattcat cgactgtggc cggctgggtg    3720
tggcggaccg ctatcaggac atagcgttgg ctacccgtga tattgctgaa gagcttggcg    3780
gcgaatgggc tgaccgcttc ctcgtgcttt acggtatcgc cgctcccgat tcgcagcgca    3840
tcgccttcta tcgccttctt gacgagttct tctgagcggg actctggggt tcgaaatgac    3900
cgaccaagcg acgcccaacc tgccatcacg agatttcgat tccaccgccg ccttctatga    3960
aaggttgggc ttcggaatcg ttttccggga cgccggctgg atgatcctcc agcgcgggga    4020
tctcatgctg gagttcttcg cccacccca cttgtttatt gcagcttata atggttacaa    4080
ataaagcaat agcatcacaa atttcacaaa taaagcattt ttttcactgc attctagttg    4140
tggtttgtcc aaactcatca atgtatctta tcatgtctgt ataccgtcga cctctagcta    4200
```

```
gagcttggcg taatcatggt catagctgtt tcctgtgtga aattgttatc cgctcacaat    4260
tccacacaac atacgagccg gaagcataaa gtgtaaagcc tggggtgcct aatgagtgag    4320
ctaactcaca ttaattgcgt tgcgctcact gcccgctttc cagtcgggaa acctgtcgtg    4380
ccagctgcat taatgaatcg gccaacgcgc ggggagaggc ggtttgcgta ttgggcgctc    4440
ttccgcttcc tcgctcactg actcgctgcg ctcggtcgtt cggctgcggc gagcggtatc    4500
agctcactca aaggcggtaa tacggttatc cacagaatca ggggataacg caggaaagaa    4560
catgtgagca aaaggccagc aaaaggccag gaaccgtaaa aaggccgcgt tgctggcgtt    4620
tttccatagg ctccgccccc ctgacgagca tcacaaaaat cgacgctcaa gtcagaggtg    4680
gcgaaacccg acaggactat aaagatacca ggcgtttccc cctggaagct ccctcgtgcg    4740
ctctcctgtt ccgaccctgc cgcttaccgg atacctgtcc gcctttctcc cttcgggaag    4800
cgtggcgctt tctcatagct cacgctgtag gtatctcagt tcggtgtagg tcgttcgctc    4860
caagctgggc tgtgtgcacg aaccccccgt tcagcccgac cgctgcgcct tatccggtaa    4920
ctatcgtctt gagtccaacc cggtaagaca cgacttatcg ccactggcag cagccactgg    4980
taacaggatt agcagagcga ggtatgtagg cggtgctaca gagttcttga agtggtggcc    5040
taactacggc tacactagaa gaacagtatt tggtatctgc gctctgctga agccagttac    5100
cttcggaaaa agagttggta gctcttgatc cggcaaacaa accaccgctg gtagcggttt    5160
ttttgtttgc aagcagcaga ttacgcgcag aaaaaaagga tctcaagaag atcctttgat    5220
cttttctacg gggtctgacg ctcagtggaa cgaaaactca cgttaaggga ttttggtcat    5280
gagattatca aaaaggatct tcacctagat ccttttaaat taaaaatgaa gttttaaatc    5340
aatctaaagt atatatgagt aaacttggtc tgacagttac caatgcttaa tcagtgaggc    5400
acctatctca gcgatctgtc tatttcgttc atccatagtt gcctgactcc ccgtcgtgta    5460
gataactacg atacgggagg gcttaccatc tggccccagt gctgcaatga taccgcgaga    5520
cccacgctca ccggctccag atttatcagc aataaaccag ccagccggaa gggccgagcg    5580
cagaagtggt cctgcaactt tatccgcctc catccagtct attaattgtt gccgggaagc    5640
tagagtaagt agttcgccag ttaatagttt gcgcaacgtt gttgccattg ctacaggcat    5700
cgtggtgtca cgctcgtcgt ttggtatggc ttcattcagc tccggttccc aacgatcaag    5760
gcgagttaca tgatccccca tgttgtgcaa aaaagcggtt agctccttcg gtcctccgat    5820
cgttgtcaga agtaagttgg ccgcagtgtt atcactcatg gttatggcag cactgcataa    5880
ttctcttact gtcatgccat ccgtaagatg cttttctgtg actggtgagt actcaaccaa    5940
gtcattctga gaatagtgta tgcggcgacc gagttgctct tgcccggcgt caatacggga    6000
taataccgcg ccacatagca gaactttaaa agtgctcatc attggaaaac gttcttcggg    6060
gcgaaaactc tcaaggatct taccgctgtt gagatccagt tcgatgtaac ccactcgtgc    6120
acccaactga tcttcagcat cttttacttt caccagcgtt tctgggtgag caaaaacagg    6180
aaggcaaaat gccgcaaaaa agggaataag ggcgacacgg aaatgttgaa tactcatact    6240 cttcctttt caatattatt gaagcattta tcagggttat tgtctcatga gcggatacat    6300
atttgaatgt atttagaaaa ataaacaaat aggggttccg cgcacatttc cccgaaaagt    6360
gccacctgac gtc                                                       6373
```

<210> SEQ ID NO 17
<211> LENGTH: 8243
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17

```
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtgatgc ggttttggca gtacatcaat gggcgtggat     420
agcggtttga ctcacgggga tttccaagtc tccacccccat tgacgtcaat gggagtttgt     480
tttggcacca aaatcaacgg gactttccaa aatgtcgtaa caactccgcc ccattgacgc     540
aaatgggcgg taggcgtgta cggtgggagg tctatataag cagagctctc tggctaacta     600
gagaacccac tgcttactgg cttatcgaaa ttaatacgac tcactatagg gagacccaag     660
ctggctagcg ccaccatgga ctacaaagac catgacggtg attataaaga tcatgacatc     720
gattacaagg atgacgatga caagatggcc cccaagaaga agaggaaggt gggcattcac     780
cgcggggtac ctatggtgga cttgaggaca ctcggttatt cgcaacagca acaggagaaa     840
atcaagccta aggtcaggag caccgtcgcg caacaccacg aggcgcttgt ggggcatggc     900
ttcactcatg cgcatattgt cgcgctttca cagcaccctg cggcgcttgg gacggtggct     960
gtcaaatacc aagatatgat tgcggccctg cccgaagcca cgcacgaggc aattgtaggg    1020
gtcggtaaac agtggtcggg agcgcgagca cttgaggcgc tgctgactgt ggcgggtgag    1080
cttaggggc ctccgctcca gctcgacacc gggcagctgc tgaagatcgc gaagagaggg    1140
ggagtaacag cggtagaggc agtgcacgcc tggcgcaatg cgctcaccgg tgcccccctg    1200
aacctgaccc cggaccaagt ggtggctatc gccagcaaca agggcggcaa gcaagcgctc    1260
gaaacggtgc agcggctgtt gccggtgctg tgccaggacc atggcctgac cccggaccaa    1320
gtggtggcta tcgccagcaa caagggcggc aagcaagcgc tcgaaacggt gcagcggctg    1380
ttgccggtgc tgtgccagga ccatggcctg accccgacc aagtggtggc tatcgccagc    1440
aacggtggcg gcaagcaagc gctcgaaacg gtgcagcggc tgttgccggt gctgtgccag    1500
gaccatggcc tgaccccgga ccaagtggtg gctatcgcca gcaacaaggg cggcaagcaa    1560
gcgctcgaaa cggtgcagcg gctgttgccg gtgctgtgcc aggaccatgg cctgactccg    1620
gaccaagtgg tggctatcgc cagccacgat ggcggcaagc aagcgctcga acggtgcag    1680
cggctgttgc cggtgctgtg ccaggaccat ggcctgaccc cggaccaagt ggtggctatc    1740
gccagcaaca ttggcggcaa gcaagcgctc gaaacggtgc agcggctgtt gccggtgctg    1800
tgccaggacc atggcctgac tccggaccaa gtggtggcta tcgccagcca cgatggcggc    1860
aagcaagcgc tcgaaacggt gcagcggctg ttgccggtgc tgtgccagga ccatggcctg    1920
actccggacc aagtggtggc tatcgccagc acgatggcg gcaagcaagc gctcgaaacg    1980
gtgcagcggc tgttgccggt gctgtgccag gaccatggcc tgaccccgga ccaagtggtg    2040
gctatcgcca gcaacggtgg cggcaagcaa gcgctcgaaa cggtgcagcg gctgttgccg    2100
gtgctgtgcc aggaccatgg cctgaccccg gaccaagtgg tggctatcgc cagcaacaag    2160
```

```
ggcggcaagc aagcgctcga aacggtgcag cggctgttgc cggtgctgtg ccaggaccat    2220
ggcctgaccc cggaccaagt ggtggctatc gccagcaaca ttggcggcaa gcaagcgctc    2280
gaaacggtgc agcggctgtt gccggtgctg tgccaggacc atggcctgac tccggaccaa    2340
gtggtggcta tcgccagcca cgatggcggc aagcaagcgc tcgaaacggt gcagcggctg    2400
ttgccggtgc tgtgccagga ccatggcctg accccggacc aagtggtggc tatcgccagc    2460
aacggtggcg gcaagcaagc gctcgaaacg gtgcagcggc tgttgccggt gctgtgccag    2520
gaccatggcc tgactccgga ccaagtggtg gctatcgcca gccacgatgg cggcaagcaa    2580
gcgctcgaaa cggtgcagcg gctgttgccg gtgctgtgcc aggaccatgg cctgactccg    2640
gaccaagtgg tggctatcgc cagccacgat ggcggcaagc aagcgctcga aacggtgcag    2700
cggctgttgc cggtgctgtg ccaggaccat ggcctgaccc cggaccaagt ggtggctatc    2760
gccagcaacg gtggcggcaa gcaagcgctc gaaagcattg tgcccagct gagccggcct     2820
gatccggcgt tggccgcgtt gaccaacgac catctggtgg cgttggcatg tcttggtgga    2880
cgacccgcgc tcgatgcagt caaaaagggt ctgcctcatg ctcccgcatt gatcaaaaga    2940
accaaccggc ggattcccga gagaacttcc catcgagtcg cgggatccca gctggtgaag    3000
agcgagctga aggagaagaa gtccgagctg cggcacaagc tgaagtacgt gccccacgag    3060
tacatcgagc tgatcgagat cgccaggaac agcacccagg accgcatcct ggagatgaag    3120
gtgatggagt cttcatgaa ggtgtacggc tacaggggaa agcacctggg cggaagcaga     3180
aagcctgacg gcgccatcta tacagtgggc agcccatcg attacggcgt gatcgtggac     3240
acaaaggcct acagcggcgg ctacaatctg cctatcggcc aggccgacga gatgcagaga    3300
tacgtggagg agaaccagac ccggaataag cacatcaacc caacgagtg gtggaaggtg     3360
taccctagca gcgtgaccga gttcaagttc ctgttcgtga cggccactt caagggcaac     3420
tacaaggccc agctgaccag gctgaaccac atcaccaact gcaatggcgc cgtgctgagc    3480
gtggaggagc tgctgatcgg cggcgagatg atcaaagccg gcaccctgac actggaggag    3540
gtgcggcgca gttcaacaa cggcgagatc aacttctgat aacttaagtt taaaccgctg    3600
atcagcctcg actgtgcctt ctagttgcca gccatctgtt gtttgcccct cccccgtgcc    3660
ttccttgacc ctggaaggtg ccactcccac tgtcctttcc taataaaatg aggaaattgc    3720
atcgcattgt ctgagtaggt gtcattctat tctggggggt ggggtggggc aggacagcaa    3780
gggggaggat tgggaagaca atagcaggca tgctggggat gcggtgggct ctatggcttc    3840
tgaggcggaa agaaccagct ggggctctag ggggtatccc cacgcgccct gtagcggcgc    3900
attaagcgcg gcgggtgtgg tggttacgcg cagcgtgacc gctacacttg ccagcgccct    3960
agcgcccgct cctttcgctt tcttcccttc ctttctcgcc acgttcgccg gctttccccg    4020
tcaagctcta aatcggggggc tccctttagg gttccgattt agtgctttac ggcacctcga    4080
ccccaaaaaa cttgattagg gtgatggttc acgtagtggg ccatcgccct gatagacggt    4140
ttttcgccct ttgacgttgg agtccacgtt ctttaatagt ggactcttgt tccaaactgg    4200
aacaacactc aaccctatct cggtctattc ttttgattta agggattt tgccgatttc     4260
ggcctattgg ttaaaaaatg agctgattta acaaaaattt aacgcgaatt aattctgtgg    4320
aatgtgtgtc agttagggtg tggaaagtcc ccaggctccc cagcaggcag aagtatgcaa    4380
agcatgcatc tcaattagtc agcaaccagg tgtggaaagt ccccaggctc ccagcaggc    4440
agaagtatgc aaagcatgca tctcaattag tcagcaacca tagtcccgcc cctaactccg    4500
cccatcccgc ccctaactcc gcccagttcc gcccattctc cgccccatgg ctgactaatt    4560
```

```
tttttattt atgcagaggc cgaggccgcc tctgcctctg agctattcca gaagtagtga    4620
ggaggctttt ttggaggcct aggcttttgc aaaaagctcc cgggagcttg tatatccatt    4680
ttcggatctg atcaagagac aggatgagga tcgtttcgca tgattgaaca agatggattg    4740
cacgcaggtt ctccggccgc ttgggtggag aggctattcg gctatgactg ggcacaacag    4800
acaatcggct gctctgatgc cgccgtgttc cggctgtcag cgcaggggcg cccggttctt    4860
tttgtcaaga ccgacctgtc cggtgccctg aatgaactgc aggacgaggc agcgcggcta    4920
tcgtggctgg ccacgacggg cgttccttgc gcagctgtgc tcgacgttgt cactgaagcg    4980
ggaagggact ggctgctatt gggcgaagtg ccggggcagg atctcctgtc atctcacctt    5040
gctcctgccg agaaagtatc catcatggct gatgcaatgc ggcggctgca tacgcttgat    5100
ccggctacct gcccattcga ccaccaagcg aaacatcgca tcgagcgagc acgtactcgg    5160
atggaagccg gtcttgtcga tcaggatgat ctggacgaag agcatcaggg gctcgcgcca    5220
gccgaactgt tcgccaggct caaggcgcgc atgcccgacg gcgaggatct cgtcgtgacc    5280
catggcgatg cctgcttgcc gaatatcatg gtggaaaatg gccgcttttc tggattcatc    5340
gactgtggcc ggctgggtgt ggcggaccgc tatcaggaca tagcgttggc tacccgtgat    5400
attgctgaag agcttggcgg cgaatgggct gaccgcttcc tcgtgcttta cggtatcgcc    5460
gctcccgatt cgcagcgcat cgccttctat cgccttcttg acgagttctt ctgagcggga    5520
ctctggggtt cgaaatgacc gaccaagcga cgcccaacct gccatcacga tttcgatt    5580 ccaccgccgc cttctatgaa aggttgggct tcggaatcgt tttccgggac gccggctgga    5640
tgatcctcca gcgcggggat ctcatgctgg agttcttcgc ccaccccaac ttgtttattg    5700
cagcttataa tggttacaaa taaagcaata gcatcacaaa tttcacaaat aaagcatttt    5760
tttcactgca ttctagttgt ggtttgtcca aactcatcaa tgtatcttat catgtctgta    5820
taccgtcgac ctctagctag agcttggcgt aatcatggtc atagctgttt cctgtgtgaa    5880
attgttatcc gctcacaatt ccacacaaca tacgagccgg aagcataaag tgtaaagcct    5940
ggggtgccta atgagtgagc taactcacat taattgcgtt gcgctcactg cccgctttcc    6000
agtcgggaaa cctgtcgtgc cagctgcatt aatgaatcgg ccaacgcgcg gggagaggcg    6060
gtttgcgtat tgggcgctct tccgcttcct cgctcactga ctcgctgcgc tcggtcgttc    6120
ggctgcggcg agcggtatca gctcactcaa aggcggtaat acggttatcc acagaatcag    6180
gggataacgc aggaaagaac atgtgagcaa aaggccagca aaaggccagg aaccgtaaaa    6240
aggccgcgtt gctggcgttt ttccataggc tccgcccccc tgacgagcat cacaaaaatc    6300
gacgctcaag tcagaggtgg cgaaacccga caggactata agataccagg cgtttccccc    6360
ctggaagctc cctcgtgcgc tctcctgttc cgaccctgcc gcttaccgga tacctgtccg    6420
cctttctccc ttcgggaagc gtggcgcttt ctcatagctc acgctgtagg tatctcagtt    6480
cggtgtaggt cgttcgctcc aagctgggct gtgtgcacga accccccgtt cagcccgacc    6540
gctgcgcctt atccggtaac tatcgtcttg agtccaaccc ggtaagacac gacttatcgc    6600
cactggcagc agccactggt aacaggatta gcagagcgag gtatgtaggc ggtgctacag    6660
agttcttgaa gtggtggcct aactacggct acactagaag aacagtattt ggtatctgcg    6720
ctctgctgaa gccagttacc ttcggaaaaa gagttggtag ctcttgatcc ggcaaacaaa    6780
ccaccgctgg tagcggtttt tttgtttgca agcagcagat tacgcgcaga aaaaaaggat    6840
ctcaagaaga tcctttgatc ttttctacgg ggtctgacgc tcagtggaac gaaaactcac    6900
```

```
gttaagggat tttggtcatg agattatcaa aaaggatctt cacctagatc cttttaaatt    6960
aaaaatgaag ttttaaatca atctaaagta tatatgagta aacttggtct gacagttacc    7020
aatgcttaat cagtgaggca cctatctcag cgatctgtct atttcgttca tccatagttg    7080
cctgactccc cgtcgtgtag ataactacga tacgggaggg cttaccatct ggccccagtg    7140
ctgcaatgat accgcgagac ccacgctcac cggctccaga tttatcagca ataaaccagc    7200
cagccggaag ggccgagcgc agaagtggtc ctgcaacttt atccgcctcc atccagtcta    7260
ttaattgttg ccgggaagct agagtaagta gttcgccagt taatagtttg cgcaacgttg    7320
ttgccattgc tacaggcatc gtggtgtcac gctcgtcgtt tggtatggct tcattcagct    7380
ccggttccca acgatcaagg cgagttacat gatcccccat gttgtgcaaa aaagcggtta    7440
gctccttcgg tcctccgatc gttgtcagaa gtaagttggc cgcagtgtta tcactcatgg    7500
ttatggcagc actgcataat tctcttactg tcatgccatc cgtaagatgc ttttctgtga    7560
ctggtgagta ctcaaccaag tcattctgag aatagtgtat gcggcgaccg agttgctctt    7620
gcccggcgtc aatacgggat aataccgcgc cacatagcag aactttaaaa gtgctcatca    7680
ttggaaaacg ttcttcgggg cgaaaactct caaggatctt accgctgttg agatccagtt    7740
cgatgtaacc cactcgtgca cccaactgat cttcagcatc ttttactttc accagcgttt    7800
ctgggtgagc aaaaacagga aggcaaaatg ccgcaaaaaa gggaataagg gcgacacgga    7860
aatgttgaat actcatactc ttcctttttc aatattattg aagcatttat cagggttatt    7920
gtctcatgag cggatacata tttgaatgta tttagaaaaa taaacaaata ggggttccgc    7980
gcacatttcc ccgaaaagtg ccacctgacg tcgacggatc gggagatctc ccgatcccct    8040
atggtgcact ctcagtacaa tctgctctga tgccgcatag ttaagccagt atctgctccc    8100
tgcttgtgtg ttggaggtcg ctgagtagtg cgcgagcaaa atttaagcta caacaaggca    8160
aggcttgacc gacaattgca tgaagaatct gcttagggtt aggcgttttg cgctgcttcg    8220
cgatgtacgg gccagatata cgc                                            8243

<210> SEQ ID NO 18
<211> LENGTH: 8141
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtgatgc ggttttggca gtacatcaat gggcgtggat     420
agcggtttga ctcacgggga tttccaagtc tccaccccat tgacgtcaat gggagtttgt     480
tttggcacca aaatcaacgg gactttccaa aatgtcgtaa caactccgcc ccattgacgc     540
aaatgggcgg taggcgtgta cggtgggagg tctatataag cagagctctc tggctaacta     600
gagaacccac tgcttactgg cttatcgaaa ttaatacgac tcactatagg gagacccaag     660
```

-continued

| | | | |
|---|---|---|---|
| ctggctagcg ccaccatgga ctacaaagac catgacggtg attataaaga tcatgacatc | 720 |
| gattacaagg atgacgatga caagatggcc cccaagaaga agaggaaggt gggcattcac | 780 |
| cgcggggtac ctatggtgga cttgaggaca ctcggttatt cgcaacagca acaggagaaa | 840 |
| atcaagccta aggtcaggag caccgtcgcg caacaccacg aggcgcttgt ggggcatggc | 900 |
| ttcactcatg cgcatattgt cgcgctttca cagcaccctg cggcgcttgg acggtggct | 960 |
| gtcaaatacc aagatatgat tgcggccctg cccgaagcca cgcacgaggc aattgtaggg | 1020 |
| gtcggtaaac agtggtcggg agcgcgagca cttgaggcgc tgctgactgt ggcgggtgag | 1080 |
| cttagggggc ctccgctcca gctcgacacc gggcagctgc tgaagatcgc gaagagaggg | 1140 |
| ggagtaacag cggtagaggc agtgcacgcc tggcgcaatg cgctcaccgg tgccccctg | 1200 |
| aacctgaccc cggaccaagt ggtggctatc gccagcaaca agggcggcaa gcaagcgctc | 1260 |
| gaaacggtgc agcggctgtt gccggtgctg tgccaggacc atggcctgac tccggaccaa | 1320 |
| gtggtggcta tcgccagcca cgatggcggc aagcaagcgc tcgaaacggt gcagcggctg | 1380 |
| ttgccggtgc tgtgccagga ccatggcctg accccggacc aagtggtggc tatcgccagc | 1440 |
| aacattggcg gcaagcaagc gctcgaaacg gtgcagcggc tgttgccggt gctgtgccag | 1500 |
| gaccatggcc tgactccgga ccaagtggtg gctatcgcca gccacgatgg cggcaagcaa | 1560 |
| gcgctcgaaa cggtgcagcg gctgttgccg gtgctgtgcc aggaccatgg cctgactccg | 1620 |
| gaccaagtgg tggctatcgc cagccacgat ggcggcaagc aagcgctcga acggtgcag | 1680 |
| cggctgttgc cggtgctgtg ccaggaccat ggcctgaccc cggaccaagt ggtggctatc | 1740 |
| gccagcaacg gtggcggcaa gcaagcgctc gaaacggtgc agcggctgtt gccggtgctg | 1800 |
| tgccaggacc atggcctgac cccggaccaa gtggtggcta tcgccagcaa caagggcggc | 1860 |
| aagcaagcgc tcgaaacggt gcagcggctg ttgccggtgc tgtgccagga ccatggcctg | 1920 |
| accccggacc aagtggtggc tatcgccagc aacattggcg gcaagcaagc gctcgaaacg | 1980 |
| gtgcagcggc tgttgccggt gctgtgccag gaccatggcc tgactccgga ccaagtggtg | 2040 |
| gctatcgcca gccacgatgg cggcaagcaa gcgctcgaaa cggtgcagcg gctgttgccg | 2100 |
| gtgctgtgcc aggaccatgg cctgaccccg gaccaagtgg tggctatcgc cagcaacggt | 2160 |
| ggcggcaagc aagcgctcga aacggtgcag cggctgttgc cggtgctgtg ccaggaccat | 2220 |
| ggcctgaccc cggaccaagt ggtggctatc gccagcacg atggcggcaa gcaagcgctc | 2280 |
| gaaacggtgc agcggctgtt gccggtgctg tgccaggacc atggcctgac tccggaccaa | 2340 |
| gtggtggcta tcgccagcca cgatggcggc aagcaagcgc tcgaaacggt gcagcggctg | 2400 |
| ttgccggtgc tgtgccagga ccatggcctg accccggacc aagtggtggc tatcgccagc | 2460 |
| aacggtggcg gcaagcaagc gctcgaaacg gtgcagcggc tgttgccggt gctgtgccag | 2520 |
| gaccatggcc tgaccccgga ccaagtggtg gctatcgcca gcaacaaggg cggcaagcaa | 2580 |
| gcgctcgaaa cggtgcagcg gctgttgccg gtgctgtgcc aggaccatgg cctgaccccg | 2640 |
| gaccaagtgg tggctatcgc cagcaacggt ggcggcaagc aagcgctcga aagcattgtg | 2700 |
| gcccagctga gccggcctga tccggcgttg gccgcgttga ccaacgacca tctggtggcg | 2760 |
| ttggcatgtc ttggtggacg acccgcgctc gatgcagtca aaaagggtct gcctcatgct | 2820 |
| cccgcattga tcaaaagaac caaccggcgg attcccgaga gaacttccca tcgagtcgcg | 2880 |
| ggatcccagc tggtgaagag cgagctggag gagaagaagt ccgagctgcg gcacaagctg | 2940 |
| aagtacgtgc cccacgagta catcgagctg atcgagatcg ccaggaacag cacccaggac | 3000 |

```
cgcatcctgg agatgaaggt gatggagttc ttcatgaagg tgtacggcta caggggaaag    3060
cacctgggcg aagcagaaa gcctgacggc gccatctata cagtgggcag ccccatcgat    3120
tacggcgtga tcgtggacac aaaggcctac agcggcggct acaatctgcc tatcggccag    3180
gccgacgaga tgcagagata cgtggaggag aaccagaccc ggaataagca catcaacccc    3240
aacgagtggt ggaaggtgta ccctagcagc gtgaccgagt tcaagttcct gttcgtgagc    3300
ggccacttca agggcaacta caaggcccag ctgaccaggc tgaaccacat caccaactgc    3360
aatggcgccg tgctgagcgt ggaggagctg ctgatcggcg gcgagatgat caaagccggc    3420
accctgacac tggaggaggt gcggcgcaag ttcaacaacg cgagatcaa cttctgataa    3480 cttaagttta aaccgctgat cagcctcgac tgtgccttct agttgccagc catctgttgt    3540
ttgcccctcc cccgtgcctt ccttgaccct ggaaggtgcc actcccactg tcctttccta    3600
ataaaatgag gaaattgcat cgcattgtct gagtaggtgt cattctattc tggggggtgg    3660
ggtggggcag gacagcaagg gggaggattg gaagacaat agcaggcatg ctggggatgc    3720
ggtgggctct atggcttctg aggcggaaag aaccagctgg ggctctaggg ggtatcccca    3780
cgcgccctgt agcggcgcat taagcgcggc gggtgtggtg gttacgcgca gcgtgaccgc    3840
tacacttgcc agcgccctag cgcccgctcc tttcgctttc ttcccttcct ttctcgccac    3900
gttcgccggc tttccccgtc aagctctaaa tcggggctc cctttagggt tccgatttag    3960
tgctttacgg cacctcgacc ccaaaaaact tgattaggg gatggttcac gtagtgggcc    4020
atcgccctga tagacggttt ttcgcccttt gacgttggag tccacgttct ttaatagtgg    4080
actcttgttc caaactggaa caacactcaa ccctatctcg gtctattctt ttgatttata    4140
agggattttg ccgatttcgg cctattggtt aaaaaatgag ctgatttaac aaaaatttaa    4200
cgcgaattaa ttctgtggaa tgtgtgtcag ttagggtgtg aaagtcccc aggctcccca    4260 gcaggcagaa gtatgcaaag catgcatctc aattagtcag caaccaggtg tggaaagtcc    4320
ccaggctccc cagcaggcag aagtatgcaa agcatgcatc tcaattagtc agcaaccata    4380
gtcccgcccc taactccgcc catcccgccc ctaactccgc ccagttccgc ccattctccg    4440
ccccatggct gactaatttt ttttatttat gcagaggccg aggccgcctc tgcctctgag    4500
ctattccaga agtagtgagg aggcttttt ggaggcctag gcttttgcaa aaagctcccg    4560
ggagcttgta tatccatttt cggatctgat caagagacag gatgaggatc gtttcgcatg    4620
attgaacaag atggattgca cgcaggttct ccggccgctt gggtggagag gctattcggc    4680
tatgactggg cacaacagac aatcggctgc tctgatgccg ccgtgttccg gctgtcagcg    4740
caggggcgcc cggttctttt tgtcaagacc gacctgtccg gtgccctgaa tgaactgcag    4800
gacgaggcag cgcggctatc gtggctggcc acgacgggcg ttccttgcgc agctgtgctc    4860
gacgttgtca ctgaagcggg aagggactgg ctgctattgg gcgaagtgcc ggggcaggat    4920
ctcctgtcat ctcaccttgc tcctgccgag aaagtatcca tcatggctga tgcaatgcgg    4980
cggctgcata cgcttgatcc ggctacctgc ccattcgacc accaagcgaa acatcgcatc    5040
gagcgagcac gtactcggat ggaagccggt cttgtcgatc aggatgatct ggacgaagag    5100
catcaggggc tcgcgccagc cgaactgttc gccaggctca aggcgcgcat gcccgacggc    5160
gaggatctcg tcgtgaccca tggcgatgcc tgcttgccga atatcatggt ggaaaatggc    5220
cgcttttctg gattcatcga ctgtggccgg ctgggtgtgg cggaccgcta tcaggacata    5280
gcgttggcta cccgtgatat tgctgaagag cttggcggcg aatgggctga ccgcttcctc    5340
gtgctttacg gtatcgccgc tcccgattcg cagcgcatcg ccttctatcg ccttcttgac    5400
```

```
gagttcttct gagcgggact ctggggttcg aaatgaccga ccaagcgacg cccaacctgc   5460
catcacgaga tttcgattcc accgccgcct tctatgaaag gttgggcttc ggaatcgttt   5520
tccgggacgc cggctggatg atcctccagc gcggggatct catgctggag ttcttcgccc   5580
accccaactt gtttattgca gcttataatg gttacaaata aagcaatagc atcacaaatt   5640
tcacaaataa agcattttt tcactgcatt ctagttgtgg tttgtccaaa ctcatcaatg   5700
tatcttatca tgtctgtata ccgtcgacct ctagctagag cttggcgtaa tcatggtcat   5760
agctgtttcc tgtgtgaaat tgttatccgc tcacaattcc acacaacata cgagccggaa   5820
gcataaagtg taaagcctgg ggtgcctaat gagtgagcta actcacatta attgcgttgc   5880
gctcactgcc cgctttccag tcgggaaacc tgtcgtgcca gctgcattaa tgaatcggcc   5940
aacgcgcggg gagaggcggt ttgcgtattg ggcgctcttc cgcttcctcg ctcactgact   6000
cgctgcgctc ggtcgttcgg ctgcggcgag cggtatcagc tcactcaaag gcggtaatac   6060
ggttatccac agaatcaggg gataacgcag gaaagaacat gtgagcaaaa ggccagcaaa   6120
aggccaggaa ccgtaaaaag gccgcgttgc tggcgttttt ccataggctc cgcccccctg   6180
acgagcatca caaaaatcga cgctcaagtc agaggtggcg aaacccgaca ggactataaa   6240
gataccaggc gtttccccct ggaagctccc tcgtgcgctc tcctgttccg accctgccgc   6300
ttaccggata cctgtccgcc tttctccctt cgggaagcgt ggcgctttct catagctcac   6360
gctgtaggta tctcagttcg gtgtaggtcg ttcgctccaa gctgggctgt gtgcacgaac   6420
cccccgttca gcccgaccgc tgcgccttat ccggtaacta tcgtcttgag tccaacccgg   6480
taagacacga cttatcgcca ctggcagcag ccactggtaa caggattagc agagcgaggt   6540
atgtaggcgg tgctacagag ttcttgaagt ggtggcctaa ctacggctac actagaagaa   6600
cagtatttgg tatctgcgct ctgctgaagc cagttacctt cggaaaaaga gttggtagct   6660
cttgatccgg caaacaaacc accgctggta gcggtttttt tgtttgcaag cagcagatta   6720
cgcgcagaaa aaaaggatct caagaagatc ctttgatctt ttctacgggg tctgacgctc   6780
agtggaacga aaactcacgt taagggattt tggtcatgag attatcaaaa aggatcttca   6840
cctagatcct tttaaattaa aaatgaagtt ttaaatcaat ctaaagtata tatgagtaaa   6900
cttggtctga cagttaccaa tgcttaatca gtgaggcacc tatctcagcg atctgtctat   6960
ttcgttcatc catagttgcc tgactccccg tcgtgtagat aactacgata cgggagggct   7020
taccatctgg ccccagtgct gcaatgatac cgcgagaccc acgctcaccg gctccagatt   7080
tatcagcaat aaaccagcca gccggaaggg ccgagcgcag aagtggtcct gcaactttat   7140
ccgcctccat ccagtctatt aattgttgcc gggaagctag agtaagtagt tcgccagtta   7200
atagtttgcg caacgttgtt gccattgcta caggcatcgt ggtgtcacgc tcgtcgtttg   7260
gtatggcttc attcagctcc ggttcccaac gatcaaggcg agttacatga tcccccatgt   7320
tgtgcaaaaa agcggttagc tccttcggtc ctccgatcgt tgtcagaagt aagttggccg   7380
cagtgttatc actcatggtt atggcagcac tgcataattc tcttactgtc atgccatccg   7440
taagatgctt ttctgtgact ggtgagtact caaccaagtc attctgagaa tagtgtatgc   7500
ggcgaccgag ttgctcttgc ccggcgtcaa tacgggataa taccgcgcca catagcagaa   7560
ctttaaaagt gctcatcatt ggaaaacgtt cttcggggcg aaaactctca aggatcttac   7620
cgctgttgag atccagttcg atgtaaccca ctcgtgcacc caactgatct tcagcatctt   7680
ttactttcac cagcgtttct gggtgagcaa aaacaggaag gcaaaatgcc gcaaaaaagg   7740
```

```
gaataagggc gacacggaaa tgttgaatac tcatactctt cctttttcaa tattattgaa    7800
gcatttatca gggttattgt ctcatgagcg gatacatatt tgaatgtatt tagaaaaata    7860
aacaaatagg ggttccgcgc acatttcccc gaaaagtgcc acctgacgtc gacggatcgg    7920
gagatctccc gatccctat ggtgcactct cagtacaatc tgctctgatg ccgcatagtt    7980
aagccagtat ctgctccctg cttgtgtgtt ggaggtcgct gagtagtgcg cgagcaaaat    8040
ttaagctaca acaaggcaag gcttgaccga caattgcatg aagaatctgc ttagggttag    8100
gcgttttgcg ctgcttcgcg atgtacgggc cagatatacg c                       8141
```

<210> SEQ ID NO 19
<211> LENGTH: 8243
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19

```
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctctc tggctaacta    600
gagaacccac tgcttactgg cttatcgaaa ttaatacgac tcactatagg gagacccaag    660
ctggctagcg ccaccatgga ctacaaagac catgacggtg attataaaga tcatgacatc    720
gattacaagg atgacgatga caagatggcc cccaagaaga agaggaaggt gggcattcac    780
cgcggggtac ctatggtgga cttgaggaca ctcggttatt cgcaacagca acaggagaaa    840
atcaagccta aggtcaggag caccgtcgcg caacaccacg aggcgcttgt ggggcatggc    900
ttcactcatg cgcatattgt cgcgctttca cagcaccctg cggcgcttgg acggtggct    960 gtcaaatacc aagatatgat tgcggccctg cccgaagcca cgcacgaggc aattgtaggg   1020
gtcggtaaac agtggtcggg agcgcgagca cttgaggcgc tgctgactgt ggcgggtgag   1080
cttagggggc ctccgctcca gctcgacacc gggcagctgc tgaagatcgc gaagagaggg   1140
ggagtaacag cggtagaggc agtgcacgcc tggcgcaatg cgctcaccgg tgcccccctg   1200
aacctgaccc cggaccaagt ggtggctatc gccagcaaca tggcggcaa gcaagcgctc   1260 gaaacggtgc agcggctgtt gccggtgctg tgccaggacc atggcctgac cccggaccaa   1320
gtggtggcta tcgccagcaa caatggcggc aagcaagcgc tcgaaacggt gcagcggctg   1380
ttgccggtgc tgtgccagga ccatggcctg accccggacc aagtggtggc tatcgccagc   1440
aacggtggcg gcaagcaagc gctcgaaacg gtgcagcggc tgttgccggt gctgtgccag   1500
gaccatggcc tgaccccgga ccaagtggtg gctatcgcca gcaacaatgg cggcaagcaa   1560
gcgctcgaaa cggtgcagcg gctgttgccg gtgctgtgcc aggaccatgg cctgactccg   1620
```

```
gaccaagtgg tggctatcgc cagccacgat ggcggcaagc aagcgctcga aacggtgcag   1680
cggctgttgc cggtgctgtg ccaggaccat ggcctgaccc cggaccaagt ggtggctatc   1740
gccagcaaca ttggcggcaa gcaagcgctc gaaacggtgc agcggctgtt gccggtgctg   1800
tgccaggacc atggcctgac tccgaccaa gtggtggcta tcgccagcca cgatggcggc   1860
aagcaagcgc tcgaaacggt gcagcggctg ttgccggtgc tgtgccagga ccatggcctg   1920
actccggacc aagtggtggc tatcgccagc acgatggcg gcaagcaagc gctcgaaacg   1980
gtgcagcggc tgttgccggt gctgtgccag gaccatggcc tgaccccgga ccaagtggtg   2040
gctatcgcca gcaacggtgg cggcaagcaa gcgctcgaaa cggtgcagcg gctgttgccg   2100
gtgctgtgcc aggaccatgg cctgaccccg gaccaagtgg tggctatcgc cagcaacaat   2160
ggcggcaagc aagcgctcga acggtgcag cggctgttgc cggtgctgtg ccaggaccat   2220
ggcctgaccc cggaccaagt ggtggctatc gccagcaaca ttggcggcaa gcaagcgctc   2280
gaaacggtgc agcggctgtt gccggtgctg tgccaggacc atggcctgac tccgaccaa   2340 gtggtggcta tcgccagcca cgatggcggc aagcaagcgc tcgaaacggt gcagcggctg   2400
ttgccggtgc tgtgccagga ccatggcctg accccggacc aagtggtggc tatcgccagc   2460
aacggtggcg gcaagcaagc gctcgaaacg gtgcagcggc tgttgccggt gctgtgccag   2520
gaccatggcc tgactccgga ccaagtggtg gctatcgcca gccacgatgg cggcaagcaa   2580
gcgctcgaaa cggtgcagcg gctgttgccg gtgctgtgcc aggaccatgg cctgactccg   2640
gaccaagtgg tggctatcgc cagccacgat ggcggcaagc aagcgctcga aacggtgcag   2700
cggctgttgc cggtgctgtg ccaggaccat ggcctgaccc cggaccaagt ggtggctatc   2760
gccagcaacg gtggcggcaa gcaagcgctc gaaagcattg tggcccagct gagccggcct   2820
gatccggcgt tggccgcgtt gaccaacgac catctggtgg cgttggcatg tcttggtgga   2880
cgacccgcgc tcgatgcagt caaaagggt ctgcctcatg ctcccgcatt gatcaaaaga   2940
accaaccggc ggattcccga gagaacttcc catcgagtcg cgggatccca gctggtgaag   3000
agcgagctgg aggagaagaa gtccgagctg cggcacaagc tgaagtacgt gccccacgag   3060
tacatcgagc tgatcgagat cgccaggaac agcacccagg accgcatcct ggagatgaag   3120
gtgatggagt tcttcatgaa ggtgtacggc tacaggggaa agcacctggg cggaagcaga   3180
aagcctgacg cgccatccta cagtgggc agccccatcg attacggcgt gatcgtggac   3240
acaaaggcct acagcggcgg ctacaatctg cctatcggcc aggccgacga gatgcagaga   3300
tacgtggagg agaaccagac ccggaataag cacatcaacc caacgagtg gtggaaggtg   3360 taccctagca gcgtgaccga gttcaagttc ctgttcgtga gcggccactt caagggcaac   3420
tacaaggccc agctgaccag gctgaaccac atcaccaact gcaatggcgc cgtgctgagc   3480
gtggaggagc tgctgatcgg cggcgagatg atcaaagccg gcaccctgac actggaggag   3540
gtgcggcgca agttcaacaa cggcgagatc aacttctgat aacttaagtt taaaccgctg   3600
atcagcctcg actgtgcctt ctagttgcca gccatctgtt gtttgcccct cccccgtgcc   3660
ttccttgacc ctggaaggtg ccactcccac tgtcctttcc taataaaatg aggaaattgc   3720
atcgcattgt ctgagtaggt gtcattctat tctgggggt ggggtggggc aggacagcaa   3780 ggggaggat tggaagaca atagcaggca tgctgggat gcggtgggct ctatggcttc   3840
tgaggcggaa agaaccagct ggggctctag ggggtatccc cacgcgccct gtagcggcgc   3900
attaagcgcg gcgggtgtgg tggttacgcg cagcgtgacc gctacacttg ccagcgccct   3960
```

-continued

```
agcgcccgct cctttcgctt tcttcccttc ctttctcgcc acgttcgccg gctttccccg    4020
tcaagctcta atcgggggc tccctttagg gttccgattt agtgctttac ggcacctcga    4080
ccccaaaaaa cttgattagg gtgatggttc acgtagtggg ccatcgccct gatagacggt    4140
ttttcgccct tgacgttgg agtccacgtt ctttaatagt ggactcttgt tccaaactgg     4200
aacaacactc aaccctatct cggtctattc ttttgattta taagggattt tgccgatttc    4260
ggcctattgg ttaaaaaatg agctgattta acaaaaattt aacgcgaatt aattctgtgg    4320
aatgtgtgtc agttagggtg tggaaagtcc ccaggctccc cagcaggcag aagtatgcaa    4380
agcatgcatc tcaattagtc agcaaccagg tgtggaaagt ccccaggctc ccagcaggc    4440
agaagtatgc aaagcatgca tctcaattag tcagcaacca tagtcccgcc cctaactccg    4500
cccatcccgc ccctaactcc gcccagttcc gcccattctc cgcccatgg ctgactaatt     4560
ttttttattt atgcagaggc cgaggccgcc tctgcctctg agctattcca gaagtagtga    4620
ggaggctttt ttggaggcct aggcttttgc aaaaagctcc cgggagcttg tatatccatt    4680
ttcggatctg atcaagagac aggatgagga tcgtttcgca tgattgaaca agatggattg    4740
cacgcaggtt ctccggccgc ttgggtggag aggctattcg gctatgactg gcacaacag    4800
acaatcggct gctctgatgc cgccgtgttc cggctgtcag cgcaggggcg cccggttctt    4860
tttgtcaaga ccgacctgtc cggtgccctg aatgaactgc aggacgaggc agcgcggcta    4920
tcgtggctgg ccacgacggg cgttccttgc gcagctgtgc tcgacgttgt cactgaagcg    4980
ggaagggact ggctgctatt gggcgaagtg ccggggcagg atctcctgtc atctcacctt    5040
gctcctgccg agaaagtatc catcatggct gatgcaatgc ggcggctgca tacgcttgat    5100
ccggctacct gcccattcga ccaccaagcg aaacatcgca tcgagcgagc acgtactcgg    5160
atggaagccg gtcttgtcga tcaggatgat ctggacgaag agcatcaggg gctcgcgcca    5220
gccgaactgt tcgccaggct caaggcgcgc atgcccgacg gcgaggatct cgtcgtgacc    5280
catggcgatg cctgcttgcc gaatatcatg gtggaaaatg gccgcttttc tggattcatc    5340
gactgtggcc ggctgggtgt ggcggaccgc tatcaggaca tagcgttggc tacccgtgat    5400
attgctgaag agcttggcgg cgaatgggct gaccgcttcc tcgtgcttta cggtatcgcc    5460
gctcccgatt cgcagcgcat cgccttctat cgccttcttg acgagttctt ctgagcggga    5520
ctctggggtt cgaaatgacc gaccaagcga cgcccaacct gccatcacga gatttcgatt    5580
ccaccgccgc cttctatgaa aggttgggct tcggaatcgt tttccgggac gccggctgga    5640
tgatcctcca gcgcggggat ctcatgctgg agttcttcgc ccaccccaac ttgtttattg    5700
cagcttataa tggttacaaa taaagcaata gcatcacaaa tttcacaaat aaagcatttt    5760
tttcactgca ttctagttgt ggtttgtcca aactcatcaa tgtatcttat catgtctgta    5820
taccgtcgac ctctagctag agcttggcgt aatcatggtc atagctgttt cctgtgtgaa    5880
attgttatcc gctcacaatt ccacacaaca tacgagccgg aagcataaag tgtaaagcct    5940
ggggtgccta atgagtgagc taactcacat taattgcgtt gcgctcactg cccgctttcc    6000
agtcgggaaa cctgtcgtgc cagctgcatt aatgaatcgg ccaacgcgcg gggagaggcg    6060
gtttgcgtat tgggcgctct tccgcttcct cgctcactga ctcgctgcgc tcggtcgttc    6120
ggctgcggcg agcggtatca gctcactcaa aggcggtaat acggttatcc acagaatcag    6180
gggataacgc aggaaagaac atgtgagcaa aaggccagca aaaggccagg aaccgtaaaa    6240
aggccgcgtt gctggcgttt ttccataggc tccgccccc tgacgagcat cacaaaaatc    6300
gacgctcaag tcagaggtgg cgaaacccga caggactata aagataccag gcgtttcccc    6360
```

```
ctggaagctc cctcgtgcgc tctcctgttc cgaccctgcc gcttaccgga tacctgtccg    6420
cctttctccc ttcgggaagc gtggcgcttt ctcatagctc acgctgtagg tatctcagtt    6480
cggtgtaggt cgttcgctcc aagctgggct gtgtgcacga accccccgtt cagcccgacc    6540
gctgcgcctt atccggtaac tatcgtcttg agtccaaccc ggtaagacac gacttatcgc    6600
cactggcagc agccactggt aacaggatta gcagagcgag gtatgtaggc ggtgctacag    6660
agttcttgaa gtggtggcct aactacggct acactagaag aacagtattt ggtatctgcg    6720
ctctgctgaa gccagttacc ttcggaaaaa gagttggtag ctcttgatcc ggcaaacaaa    6780
ccaccgctgg tagcggtttt tttgtttgca agcagcagat tacgcgcaga aaaaaaggat    6840
ctcaagaaga tcctttgatc ttttctacgg ggtctgacgc tcagtggaac gaaaactcac    6900
gttaagggat tttggtcatg agattatcaa aaaggatctt cacctagatc cttttaaatt    6960
aaaaatgaag ttttaaatca atctaaagta tatatgagta aacttggtct gacagttacc    7020
aatgcttaat cagtgaggca cctatctcag cgatctgtct atttcgttca tccatagttg    7080
cctgactccc cgtcgtgtag ataactacga tacgggaggg cttaccatct ggccccagtg    7140
ctgcaatgat accgcgagac ccacgctcac cggctccaga tttatcagca ataaaccagc    7200
cagccggaag ggccgagcgc agaagtggtc ctgcaacttt atccgcctcc atccagtcta    7260
ttaattgttg ccgggaagct agagtaagta gttcgccagt taatagtttg cgcaacgttg    7320
ttgccattgc tacaggcatc gtggtgtcac gctcgtcgtt tggtatggct tcattcagct    7380
ccggttccca acgatcaagg cgagttacat gatccccat gttgtgcaaa aaagcggtta    7440
gctccttcgg tcctccgatc gttgtcagaa gtaagttggc cgcagtgtta tcactcatgg    7500
ttatggcagc actgcataat tctcttactg tcatgccatc cgtaagatgc ttttctgtga    7560
ctggtgagta ctcaaccaag tcattctgag aatagtgtat gcggcgaccg agttgctctt    7620
gcccggcgtc aatacgggat aataccgcgc cacatagcag aactttaaaa gtgctcatca    7680
ttggaaaacg ttcttcgggg cgaaaactct caaggatctt accgctgttg agatccagtt    7740
cgatgtaacc cactcgtgca cccaactgat cttcagcatc ttttactttc accagcgttt    7800
ctgggtgagc aaaaacagga aggcaaaatg ccgcaaaaaa gggaataagg gcgacacgga    7860
aatgttgaat actcatactc ttcctttttc aatattattg aagcatttat cagggttatt    7920
gtctcatgag cggatacata tttgaatgta tttagaaaaa taaacaaata ggggttccgc    7980
gcacatttcc ccgaaaagtg ccacctgacg tcgacggatc gggagatctc ccgatcccct    8040
atggtgcact ctcagtacaa tctgctctga tgccgcatag ttaagccagt atctgctccc    8100
tgcttgtgtg ttggaggtcg ctgagtagtg cgcgagcaaa atttaagcta caacaaggca    8160
aggcttgacc gacaattgca tgaagaatct gcttagggtt aggcgttttg cgctgcttcg    8220
cgatgtacgg gccagatata cgc                                            8243
```

<210> SEQ ID NO 20
<211> LENGTH: 8141
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20

```
gttgacattg attattgact agttattaat agtaatcaat tacggggtca ttagttcata      60
```

```
gcccatatat ggagttccgc gttacataac ttacggtaaa tggcccgcct ggctgaccgc      120
ccaacgaccc ccgcccattg acgtcaataa tgacgtatgt tcccatagta acgccaatag      180
ggactttcca ttgacgtcaa tgggtggagt atttacggta aactgcccac ttggcagtac      240
atcaagtgta tcatatgcca agtacgcccc ctattgacgt caatgacggt aaatggcccg      300
cctggcatta tgcccagtac atgaccttat gggactttcc tacttggcag tacatctacg      360
tattagtcat cgctattacc atggtgatgc ggttttggca gtacatcaat gggcgtggat      420
agcggtttga ctcacgggga tttccaagtc tccaccccat tgacgtcaat gggagtttgt      480
tttggcacca aaatcaacgg gactttccaa aatgtcgtaa caactccgcc ccattgacgc      540
aaatgggcgg taggcgtgta cggtgggagg tctatataag cagagctctc tggctaacta      600
gagaacccac tgcttactgg cttatcgaaa ttaatacgac tcactatagg gagacccaag      660
ctggctagcg ccaccatgga ctacaaagac catgacggtg attataaaga tcatgacatc      720
gattacaagg atgacgatga caagatggcc cccaagaaga agaggaaggt gggcattcac      780 cgcgggggtac ctatggtgga cttgaggaca ctcggttatt cgcaacagca acaggagaaa      840
atcaagccta aggtcaggag caccgtcgcg caacaccacg aggcgcttgt ggggcatggc      900
ttcactcatg cgcatattgt cgcgctttca cagcaccctg cggcgcttgg acggtggct      960 gtcaaatacc aagatatgat tgcggccctg cccgaagcca cgcacgaggc aattgtaggg     1020
gtcggtaaac agtggtcggg agcgcgagca cttgaggcgc tgctgactgt ggcgggtgag     1080
cttagggggc ctccgctcca gctcgacacc gggcagctgc tgaagatcgc gaagagaggg     1140
ggagtaacag cggtagaggc agtgcacgcc tggcgcaatg cgctcaccgg tgcccccctg     1200
aacctgaccc cggaccaagt ggtggctatc gccagcaaca atggcggcaa gcaagcgctc     1260
gaaacggtgc agcggctgtt gccggtgctg tgccaggacc atggcctgac tccggaccaa     1320
gtggtggcta tcgccagcca cgatggcggc aagcaagcgc tcgaaacggt gcagcggctg     1380
ttgccggtgc tgtgccagga ccatggcctg accccggacc aagtggtggc tatcgccagc     1440
aacattggcg gcaagcaagc gctcgaaacg gtgcagcggc tgttgccggt gctgtgccag     1500
gaccatggcc tgactccgga ccaagtggtg gctatcgcca gccacgatgg cggcaagcaa     1560
gcgctcgaaa cggtgcagcg gctgttgccg gtgctgtgcc aggaccatgg cctgactccg     1620
gaccaagtgg tggctatcgc cagccacgat ggcggcaagc aagcgctcga acggtgcag      1680 cggctgttgc cggtgctgtg ccaggaccat ggcctgaccc cggaccaagt ggtggctatc     1740
gccagcaacg gtggcggcaa gcaagcgctc gaaacggtgc agcggctgtt gccggtgctg     1800
tgccaggacc atggcctgac cccggaccaa gtggtggcta tcgccagcaa caatggcggc     1860
aagcaagcgc tcgaaacggt gcagcggctg ttgccggtgc tgtgccagga ccatggcctg     1920
accccggacc aagtggtggc tatcgccagc aacattggcg gcaagcaagc gctcgaaacg     1980
gtgcagcggc tgttgccggt gctgtgccag gaccatggcc tgactccgga ccaagtggtg     2040
gctatcgcca gccacgatgg cggcaagcaa gcgctcgaaa cggtgcagcg gctgttgccg     2100
gtgctgtgcc aggaccatgg cctgaccccg gaccaagtgg tggctatcgc cagcaacggt     2160
ggcggcaagc aagcgctcga aacggtgcag cggctgttgc cggtgctgtg ccaggaccat     2220
ggcctgaccc cggaccaagt ggtggctatc gccagccacg atggcggcaa gcaagcgctc     2280
gaaacggtgc agcggctgtt gccggtgctg tgccaggacc atggcctgac tccggaccaa     2340
gtggtggcta tcgccagcca cgatggcggc aagcaagcgc tcgaaacggt gcagcggctg     2400
ttgccggtgc tgtgccagga ccatggcctg accccggacc aagtggtggc tatcgccagc     2460
```

```
aacggtggcg gcaagcaagc gctcgaaacg gtgcagcggc tgttgccggt gctgtgccag    2520
gaccatggcc tgaccccgga ccaagtggtg gctatcgcca gcaacaatgg cggcaagcaa    2580
gcgctcgaaa cggtgcagcg gctgttgccg gtgctgtgcc aggaccatgg cctgaccccg    2640
gaccaagtgg tggctatcgc cagcaacggt ggcggcaagc aagcgctcga agcattgtg    2700 gcccagctga gccggcctga tccggcgttg gccgcgttga ccaacgacca tctggtggcg    2760
ttggcatgtc ttggtggacg acccgcgctc gatgcagtca aaaagggtct gcctcatgct    2820
cccgcattga tcaaaagaac caaccggcgg attcccgaga gaacttccca tcgagtcgcg    2880
ggatcccagc tggtgaagag cgagctggag gagaagaagt ccgagctgcg gcacaagctg    2940
aagtacgtgc cccacgagta catcgagctg atcgagatcg ccaggaacag caccccaggac    3000 cgcatcctgg agatgaaggt gatggagttc ttcatgaagg tgtacggcta caggggaaag    3060
cacctgggcg gaagcagaaa gcctgacggc gccatctata cagtgggcag ccccatcgat    3120 tacgcgtga tcgtggacac aaaggcctac agcggcggct acaatctgcc tatcggccag    3180
gccgacgaga tgcagagata cgtggaggag aaccagaccc ggaataagca catcaacccc    3240
aacgagtggt ggaaggtgta ccctagcagc gtgaccgagt tcaagttcct gttcgtgagc    3300
ggccacttca agggcaacta caaggcccag ctgaccaggc tgaaccacat caccaactgc    3360
aatggcgccg tgctgagcgt ggaggagctg ctgatcggcg gcgagatgat caaagccggc    3420
accctgacac tggaggaggt gcggcgcaag ttcaacaacg gcgagatcaa cttctgataa    3480
cttaagttta aaccgctgat cagcctcgac tgtgccttct agttgccagc catctgttgt    3540
ttgcccctcc cccgtgcctt ccttgaccct ggaaggtgcc actcccactg tccttttccta    3600 ataaaatgag gaaattgcat cgcattgtct gagtaggtgt cattctattc tggggggtgg    3660
ggtggggcag gacagcaagg gggaggattg ggaagacaat agcaggcatg ctggggatgc    3720
ggtgggctct atggcttctg aggcggaaag aaccagctgg ggctctaggg ggtatcccca    3780
cgcgccctgt agcggcgcat taagcgcggc gggtgtggtg gttacgcgca gcgtgaccgc    3840
tacacttgcc agcgccctag cgcccgctcc tttcgctttc ttcccttcct ttctcgccac    3900
gttcgccggc tttccccgtc aagctctaaa tcggggctc cctttagggt tccgatttag    3960
tgctttacgg cacctcgacc ccaaaaaact tgattagggt gatggttcac gtagtgggcc    4020
atcgccctga tagacggttt ttcgcccttt gacgttggag tccacgttct ttaatagtgg    4080
actcttgttc caaactggaa caacactcaa ccctatctcg gtctattctt ttgatttata    4140
agggattttg ccgatttcgg cctattggtt aaaaaatgag ctgatttaac aaaaatttaa    4200
cgcgaattaa ttctgtggaa tgtgtgtcag ttagggtgtg gaaagtcccc aggctcccca    4260
gcaggcagaa gtatgcaaag catgcatctc aattagtcag caaccaggtg tggaaagtcc    4320
ccaggctccc cagcaggcag aagtatgcaa agcatgcatc tcaattagtc agcaaccata    4380
gtcccgcccc taactccgcc catcccgccc ctaactccgc ccagttccgc ccattctccg    4440
ccccatggct gactaatttt ttttatttat gcagaggccg aggccgcctc tgcctctgag    4500
ctattccaga agtagtgagg aggcttttt ggaggcctag cttttgcaa aaagctcccg    4560 ggagcttgta tatccatttt cggatctgat caagagacag gatgaggatc gtttcgcatg    4620
attgaacaag atggattgca cgcaggttct ccggccgctt gggtggagag gctattcggc    4680
tatgactggg cacaacagac aatcggctgc tctgatgccg ccgtgttccg gctgtcagcg    4740
caggggcgcc cggttctttt tgtcaagacc gacctgtccg gtgccctgaa tgaactgcag    4800
```

```
gacgaggcag cgcggctatc gtggctggcc acgacgggcg ttccttgcgc agctgtgctc    4860
gacgttgtca ctgaagcggg aagggactgg ctgctattgg gcgaagtgcc ggggcaggat    4920
ctcctgtcat ctcaccttgc tcctgccgag aaagtatcca tcatggctga tgcaatgcgg    4980
cggctgcata cgcttgatcc ggctacctgc ccattcgacc accaagcgaa acatcgcatc    5040
gagcgagcac gtactcggat ggaagccggt cttgtcgatc aggatgatct ggacgaagag    5100
catcaggggc tcgcgccagc cgaactgttc gccaggctca aggcgcgcat gcccgacggc    5160
gaggatctcg tcgtgaccca tggcgatgcc tgcttgccga atatcatggt ggaaaatggc    5220
cgcttttctg gattcatcga ctgtggccgg ctgggtgtgg cggaccgcta tcaggacata    5280
gcgttggcta cccgtgatat tgctgaagag cttggcggcg aatgggctga ccgcttcctc    5340
gtgctttacg gtatcgccgc tcccgattcg cagcgcatcg ccttctatcg ccttcttgac    5400
gagttcttct gagcgggact ctggggttcg aaatgaccga ccaagcgacg cccaacctgc    5460
catcacgaga tttcgattcc accgccgcct tctatgaaag gttgggcttc ggaatcgttt    5520
tccgggacgc cggctggatg atcctccagc gcggggatct catgctggag ttcttcgccc    5580
accccaactt gtttattgca gcttataatg gttacaaata aagcaatagc atcacaaatt    5640
tcacaaataa agcattttt tcactgcatt ctagttgtgg tttgtccaaa ctcatcaatg    5700
tatcttatca tgtctgtata ccgtcgacct ctagctagag cttggcgtaa tcatggtcat    5760
agctgtttcc tgtgtgaaat tgttatccgc tcacaattcc acacaacata cgagccggaa    5820
gcataaagtg taaagcctgg ggtgcctaat gagtgagcta actcacatta attgcgttgc    5880
gctcactgcc cgctttccag tcgggaaacc tgtcgtgcca gctgcattaa tgaatcggcc    5940
aacgcgcggg gagaggcggt ttgcgtattg ggcgctcttc cgcttcctcg ctcactgact    6000
cgctgcgctc ggtcgttcgg ctgcggcgag cggtatcagc tcactcaaag gcggtaatac    6060
ggttatccac agaatcaggg gataacgcag gaaagaacat gtgagcaaaa ggccagcaaa    6120
aggccaggaa ccgtaaaaag gccgcgttgc tggcgttttt ccataggctc cgcccccctg    6180
acgagcatca caaaaatcga cgctcaagtc agaggtggcg aaacccgaca ggactataaa    6240
gataccaggc gtttccccct ggaagctccc tcgtgcgctc tcctgttccg accctgccgc    6300
ttaccggata cctgtccgcc tttctccctt cgggaagcgt ggcgctttct catagctcac    6360
gctgtaggta tctcagttcg gtgtaggtcg ttcgctccaa gctgggctgt gtgcacgaac    6420
cccccgttca gcccgaccgc tgcgccttat ccggtaacta tcgtcttgag tccaacccgg    6480
taagacacga cttatcgcca ctggcagcag ccactggtaa caggattagc agagcgaggt    6540
atgtaggcgg tgctacagag ttcttgaagt ggtggcctaa ctacggctac actagaagaa    6600
cagtatttgg tatctgcgct ctgctgaagc cagttacctt cggaaaaaga gttggtagct    6660
cttgatccgg caaacaaacc accgctggta gcggtttttt tgtttgcaag cagcagatta    6720
cgcgcagaaa aaaaggatct caagaagatc ctttgatctt ttctacgggg tctgacgctc    6780
agtggaacga aaactcacgt taagggattt tggtcatgag attatcaaaa aggatcttca    6840
cctagatcct tttaaattaa aaatgaagtt ttaaatcaat ctaaagtata tatgagtaaa    6900
cttggtctga cagttaccaa tgcttaatca gtgaggcacc tatctcagcg atctgtctat    6960
ttcgttcatc catagttgcc tgactccccg tcgtgtagat aactacgata cgggagggct    7020
taccatctgg ccccagtgct gcaatgatac cgcgagaccc acgctcaccg gctccagatt    7080
tatcagcaat aaaccagcca gccggaaggg ccgagcgcag aagtggtcct gcaactttat    7140
ccgcctccat ccagtctatt aattgttgcc gggaagctag agtaagtagt tcgccagtta    7200
```

```
atagtttgcg caacgttgtt gccattgcta caggcatcgt ggtgtcacgc tcgtcgtttg    7260
gtatggcttc attcagctcc ggttcccaac gatcaaggcg agttacatga tcccccatgt    7320
tgtgcaaaaa agcggttagc tccttcggtc ctccgatcgt tgtcagaagt aagttggccg    7380
cagtgttatc actcatggtt atggcagcac tgcataattc tcttactgtc atgccatccg    7440
taagatgctt ttctgtgact ggtgagtact caaccaagtc attctgagaa tagtgtatgc    7500
ggcgaccgag ttgctcttgc ccggcgtcaa tacgggataa taccgcgcca catagcagaa    7560
ctttaaaagt gctcatcatt ggaaaacgtt cttcggggcg aaaactctca aggatcttac    7620
cgctgttgag atccagttcg atgtaaccca ctcgtgcacc caactgatct tcagcatctt    7680
ttactttcac cagcgtttct gggtgagcaa aaacaggaag gcaaaatgcc gcaaaaaagg    7740
gaataagggc gacacggaaa tgttaatac tcatactctt ccttttcaa tattattgaa     7800
gcatttatca gggttattgt ctcatgagcg gatacatatt tgaatgtatt tagaaaaata   7860
aacaaatagg ggttccgcgc acatttcccc gaaaagtgcc acctgacgtc gacggatcgg    7920
gagatctccc gatcccctat ggtgcactct cagtacaatc tgctctgatg ccgcatagtt    7980
aagccagtat ctgctccctg cttgtgtgtt ggaggtcgct gagtagtgcg cgagcaaaat    8040
ttaagctaca acaaggcaag gcttgaccga caattgcatg aagaatctgc ttagggttag    8100
gcgttttgcg ctgcttcgcg atgtacgggc cagatatacg c                        8141

<210> SEQ ID NO 21
<211> LENGTH: 8753
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctctc tggctaacta    600
gagaacccac tgcttactgg cttatcgaaa ttaatacgac tcactatagg gagacccaag    660
ctggctagcg ccaccatgga ctacaaagac catgacggtg attataaaga tcatgacatc    720
gattacaagg atgacgatga caagatggcc cccaagaaga agaggaaggt gggcattcac    780
cgcggggtac ctatggtgga cttgaggaca ctcggttatt cgcaacagca acaggagaaa    840
atcaagccta aggtcaggag caccgtcgcg caacaccacg aggcgcttgt ggggcatggc    900
ttcactcatg cgcatattgt cgcgctttca cagcaccctg cggcgcttgg gacggtggct    960
gtcaaatacc aagatatgat tgcggccctg cccgaagcca cgcacgaggc aattgtaggg   1020
```

| | |
|---|---|
| gtcggtaaac agtggtcggg agcgcgagca cttgaggcgc tgctgactgt ggcgggtgag | 1080 |
| cttaggggc ctccgctcca gctcgacacc gggcagctgc tgaagatcgc gaagagaggg | 1140 |
| ggagtaacag cggtagaggc agtgcacgcc tggcgcaatg cgctcaccgg tgccccctg | 1200 |
| aacctgaccc cggaccaagt ggtggctatc gccagccacg atggcggcaa gcaagcgctc | 1260 |
| gaaacggtgc agcggctgtt gccggtgctg tgccaggacc atggcctgac cccggaccaa | 1320 |
| gtggtggcta tcgccagcaa cattggcggc aagcaagcgc tcgaaacggt gcagcggctg | 1380 |
| ttgccggtgc tgtgccagga ccatggcctg actccggacc aagtggtggc tatcgccagc | 1440 |
| cacgatggcg gcaagcaagc gctcgaaacg gtgcagcggc tgttgccggt gctgtgccag | 1500 |
| gaccatggcc tgactccgga ccaagtggtg gctatcgcca gccacgatgg cggcaagcaa | 1560 |
| gcgctcgaaa cggtgcagcg gctgttgccg gtgctgtgcc aggaccatgg cctgaccccg | 1620 |
| gaccaagtgg tggctatcgc cagcaacggt ggcggcaagc aagcgctcga acggtgcag | 1680 |
| cggctgttgc cggtgctgtg ccaggaccat ggcctgaccc cggaccaagt ggtggctatc | 1740 |
| gccagcaacg gtggcggcaa gcaagcgctc gaaacggtgc agcggctgtt gccggtgctg | 1800 |
| tgccaggacc atggcctgac cccggaccaa gtggtggcta tcgccagcaa caagggcggc | 1860 |
| aagcaagcgc tcgaaacggt gcagcggctg ttgccggtgc tgtgccagga ccatggcctg | 1920 |
| actccggacc aagtggtggc tatcgccagc cacgatggcg gcaagcaagc gctcgaaacg | 1980 |
| gtgcagcggc tgttgccggt gctgtgccag gaccatggcc tgactccgga ccaagtggtg | 2040 |
| gctatcgcca gccacgatgg cggcaagcaa gcgctcgaaa cggtgcagcg gctgttgccg | 2100 |
| gtgctgtgcc aggaccatgg cctgactccg gaccaagtgg tggctatcgc cagccacgat | 2160 |
| ggcggcaagc aagcgctcga acggtgcag cggctgttgc cggtgctgtg ccaggaccat | 2220 |
| ggcctgaccc cggaccaagt ggtggctatc gccagccacg atggcggcaa gcaagcgctc | 2280 |
| gaaacggtgc agcggctgtt gccggtgctg tgccaggacc atggcctgac cccggaccaa | 2340 |
| gtggtggcta tcgccagcaa cattggcggc aagcaagcgc tcgaaacggt gcagcggctg | 2400 |
| ttgccggtgc tgtgccagga ccatggcctg actccggacc aagtggtggc tatcgccagc | 2460 |
| cacgatggcg gcaagcaagc gctcgaaacg gtgcagcggc tgttgccggt gctgtgccag | 2520 |
| gaccatggcc tgaccccgga ccaagtggtg gctatcgcca gcaacattgg cggcaagcaa | 2580 |
| gcgctcgaaa cggtgcagcg gctgttgccg gtgctgtgcc aggaccatgg cctgaccccg | 2640 |
| gaccaagtgg tggctatcgc cagcaacaag gcggcaagc aagcgctcga acggtgcag | 2700 |
| cggctgttgc cggtgctgtg ccaggaccat ggcctgaccc cggaccaagt ggtggctatc | 2760 |
| gccagcaaca agggcggcaa gcaagcgctc gaaacggtgc agcggctgtt gccggtgctg | 2820 |
| tgccaggacc atggcctgac cccggaccaa gtggtggcta tcgccagcaa caagggcggc | 2880 |
| aagcaagcgc tcgaaacggt gcagcggctg ttgccggtgc tgtgccagga ccatggcctg | 2940 |
| actccggacc aagtggtggc tatcgccagc cacgatggcg gcaagcaagc gctcgaaacg | 3000 |
| gtgcagcggc tgttgccggt gctgtgccag gaccatggcc tgaccccgga ccaagtggtg | 3060 |
| gctatcgcca gcaacattgg cggcaagcaa gcgctcgaaa cggtgcagcg gctgttgccg | 3120 |
| gtgctgtgcc aggaccatgg cctgaccccg gaccaagtgg tggctatcgc cagcaacaag | 3180 |
| ggcggcaagc aagcgctcga acggtgcag cggctgttgc cggtgctgtg ccaggaccat | 3240 |
| ggcctgaccc cggaccaagt ggtggctatc gccagcaacg gtggcggcaa gcaagcgctc | 3300 |
| gaaagcattg tggcccagct gagccggcct gatccgcgt tggccgcgtt gaccaacgac | 3360 |
| catctggtgg cgttggcatg tcttggtgga cgacccgcgc tcgatgcagt caaaaagggt | 3420 |

```
ctgcctcatg ctcccgcatt gatcaaaaga accaaccggc ggattcccga gagaacttcc    3480
catcgagtcg cgggatccca gctggtgaag agcgagctgg aggagaagaa gtccgagctg    3540
cggcacaagc tgaagtacgt gccccacgag tacatcgagc tgatcgagat cgccaggaac    3600
agcacccagg accgcatcct ggagatgaag gtgatggagt tcttcatgaa ggtgtacggc    3660
tacaggggaa agcacctggg cggaagcaga aagcctgacg gcgccatcta tacagtgggc    3720
agccccatcg attacggcgt gatcgtggac acaaaggcct acagcggcgg ctacaatctg    3780
cctatcggcc aggccgacga gatgcagaga tacgtggagg agaaccagac ccggaataag    3840
cacatcaacc ccaacgagtg gtggaaggtg taccctagca gcgtgaccga gttcaagttc    3900
ctgttcgtga gcggccactt caagggcaac tacaagggcc agctgaccag gctgaaccac    3960
atcaccaact gcaatggcgc cgtgctgagc gtggaggagc tgctgatcgg cggcgagatg    4020
atcaaagccg gcaccctgac actggaggag gtgcggcgca gttcaacaa cggcgagatc     4080
aacttctgat aacttaagtt taaaccgctg atcagcctcg actgtgcctt ctagttgcca    4140
gccatctgtt gtttgcccct cccccgtgcc ttccttgacc ctggaaggtg ccactcccac    4200
tgtcctttcc taataaaatg aggaaattgc atcgcattgt ctgagtaggt gtcattctat    4260
tctgggggt ggggtggggc aggacagcaa ggggaggat tgggaagaca atagcaggca     4320
tgctggggat gcggtgggct ctatggcttc tgaggcggaa agaaccagct ggggctctag    4380
ggggtatccc cacgcgccct gtagcggcgc attaagcgcg gcgggtgtgg tggttacgcg    4440
cagcgtgacc gctacacttg ccagcgccct agcgcccgct cctttcgctt tcttcccttc    4500
ctttctcgcc acgttcgccg gctttccccg tcaagctcta atcgggggc tccctttagg     4560
gttccgattt agtgctttac ggcacctcga ccccaaaaaa cttgattagg gtgatggttc    4620
acgtagtggg ccatcgccct gatagacggt ttttcgccct ttgacgttgg agtccacgtt    4680
ctttaatagt ggactcttgt tccaaactgg aacaacactc aaccctatct cggtctattc    4740
ttttgattta aagggattt tgccgatttc ggcctattgg ttaaaaatg agctgattta      4800
acaaaaattt aacgcgaatt aattctgtgg aatgtgtgtc agttagggtg tggaaagtcc    4860
ccaggctccc cagcaggcag aagtatgcaa agcatgcatc tcaattagtc agcaaccagg    4920
tgtggaaagt ccccaggctc cccagcaggc agaagtatgc aaagcatgca tctcaattag    4980
tcagcaacca gtagtcccgcc cctaactccg cccatcccgc ccctaactcc gcccagttcc   5040
gcccattctc cgccccatgg ctgactaatt ttttttattt atgcagaggc cgaggccgcc    5100
tctgcctctg agctattcca gaagtagtga ggaggctttt ttggaggcct aggcttttgc    5160
aaaaagctcc cgggagcttg tatatccatt ttcggatctg atcaagagac aggatgagga    5220
tcgtttcgca tgattgaaca agatggattg cacgcaggtt ctccggccgc ttgggtggag    5280
aggctattcg gctatgactg ggcacaacag acaatcggct gctctgatgc cgccgtgttc    5340
cggctgtcag cgcaggggcg cccggttctt tttgtcaaga ccgacctgtc cggtgccctg    5400
aatgaactgc aggacgaggc agcgcggcta tcgtggctgg ccacgacggg cgttccttgc    5460
gcagctgtgc tcgacgttgt cactgaagcg ggaagggact ggctgctatt gggcgaagtg    5520
ccggggcagg atctcctgtc atctcacctt gctcctgccg agaaagtatc catcatggct    5580
gatgcaatgc ggcggctgca tacgcttgat ccggctacct gcccattcga ccaccaagcg    5640
aaacatcgca tcgagcgagc acgtactcgg atggaagccg gtcttgtcga tcaggatgat    5700
ctggacgaag agcatcaggg gctcgcgcca gccgaactgt tcgccaggct caaggcgcgc    5760
```

```
atgcccgacg gcgaggatct cgtcgtgacc catggcgatg cctgcttgcc gaatatcatg    5820
gtggaaaatg gccgctttc tggattcatc gactgtggcc ggctgggtgt ggcggaccgc    5880
tatcaggaca tagcgttggc tacccgtgat attgctgaag agcttggcgg cgaatgggct    5940
gaccgcttcc tcgtgcttta cggtatcgcc gctcccgatt cgcagcgcat cgccttctat    6000
cgccttcttg acgagttctt ctgagcggga ctctggggtt cgaaatgacc gaccaagcga    6060
cgcccaacct gccatcacga gatttcgatt ccaccgccgc cttctatgaa aggttgggct    6120
tcggaatcgt tttccgggac gccggctgga tgatcctcca gcgcgggat ctcatgctgg    6180 agttcttcgc ccaccccaac ttgtttattg cagcttataa tggttacaaa taaagcaata    6240
gcatcacaaa tttcacaaat aaagcatttt tttcactgca ttctagttgt ggtttgtcca    6300
aactcatcaa tgtatcttat catgtctgta taccgtcgac ctctagctag agcttggcgt    6360
aatcatggtc atagctgttt cctgtgtgaa attgttatcc gctcacaatt ccacacaaca    6420
tacgagccgg aagcataaag tgtaaagcct ggggtgccta atgagtgagc taactcacat    6480
taattgcgtt gcgctcactg cccgctttcc agtcggaaa cctgtcgtgc cagctgcatt    6540
aatgaatcgg ccaacgcgcg gggagaggcg gtttgcgtat tgggcgctct tccgcttcct    6600
cgctcactga ctcgctgcgc tcggtcgttc ggctgcggcg agcggtatca gctcactcaa    6660
aggcggtaat acggttatcc acagaatcag gggataacgc aggaaagaac atgtgagcaa    6720
aaggccagca aaaggccagg aaccgtaaaa aggccgcgtt gctggcgttt ttccataggc    6780 tccgccccc tgacgagcat cacaaaaatc gacgctcaag tcagaggtgg cgaaacccga    6840
caggactata aagataccag gcgtttcccc ctggaagctc cctcgtgcgc tctcctgttc    6900
cgaccctgcc gcttaccgga tacctgtccg cctttctccc ttcgggaagc gtggcgcttt    6960
ctcatagctc acgctgtagg tatctcagtt cggtgtaggt cgttcgctcc aagctgggct    7020
gtgtgcacga accccccgtt cagcccgacc gctgcgcctt atccggtaac tatcgtcttg    7080
agtccaaccc ggtaagacac gacttatcgc cactggcagc agccactggt aacaggatta    7140
gcagagcgag gtatgtaggc ggtgctacag agttcttgaa gtggtggcct aactacggct    7200
acactagaag aacagtattt ggtatctgcg ctctgctgaa gccagttacc ttcggaaaaa    7260
gagttggtag ctcttgatcc ggcaaacaaa ccaccgctgg tagcggtttt tttgtttgca    7320
agcagcagat tacgcgcaga aaaaaaggat ctcaagaaga tcctttgatc ttttctacgg    7380
ggtctgacgc tcagtggaac gaaaactcac gttaagggat tttggtcatg agattatcaa    7440
aaaggatctt cacctagatc cttttaaatt aaaaatgaag ttttaaatca atctaaagta    7500
tatatgagta aacttggtct gacagttacc aatgcttaat cagtgaggca cctatctcag    7560
cgatctgtct atttcgttca tccatagttg cctgactccc cgtcgtgtag ataactacga    7620
tacgggaggg cttaccatct ggccccagtg ctgcaatgat accgcgagac ccacgctcac    7680
cggctccaga tttatcagca ataaaccagc cagccggaag ggccgagcgc agaagtggtc    7740
ctgcaacttt atccgcctcc atccagtcta ttaattgttg ccgggaagct agagtaagta    7800
gttcgccagt taatagtttg cgcaacgttg ttgccattgc tacaggcatc gtggtgtcac    7860
gctcgtcgtt tggtatggct tcattcagct ccggttccca acgatcaagg cgagttacat    7920 gatccccat gttgtgcaaa aaagcggtta gctccttcgg tcctccgatc gttgtcagaa    7980
gtaagttggc cgcagtgtta tcactcatgg ttatggcagc actgcataat tctcttactg    8040
tcatgccatc cgtaagatgc ttttctgtga ctggtgagta ctcaaccaag tcattctgag    8100
aatagtgtat gcggcgaccg agttgctctt gcccggcgtc aatacgggat aataccgcgc    8160
```

| | |
|---|---|
| cacatagcag aactttaaaa gtgctcatca ttggaaaacg ttcttcgggg cgaaaactct | 8220 |
| caaggatctt accgctgttg agatccagtt cgatgtaacc cactcgtgca cccaactgat | 8280 |
| cttcagcatc ttttactttc accagcgttt ctgggtgagc aaaaacagga aggcaaaatg | 8340 |
| ccgcaaaaaa gggaataagg gcgacacgga aatgttgaat actcatactc ttcctttttc | 8400 |
| aatattattg aagcatttat cagggttatt gtctcatgag cggatacata tttgaatgta | 8460 |
| tttagaaaaa taaacaaata ggggttccgc gcacatttcc ccgaaaagtg ccacctgacg | 8520 |
| tcgacggatc gggagatctc ccgatcccct atggtgcact ctcagtacaa tctgctctga | 8580 |
| tgccgcatag ttaagccagt atctgctccc tgcttgtgtg ttggaggtcg ctgagtagtg | 8640 |
| cgcgagcaaa atttaagcta caacaaggca aggcttgacc gacaattgca tgaagaatct | 8700 |
| gcttaggggtt aggcgttttg cgctgcttcg cgatgtacgg gccagatata cgc | 8753 |

<210> SEQ ID NO 22
<211> LENGTH: 9059
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

| | |
|---|---|
| gttgacattg attattgact agttattaat agtaatcaat tacgggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atggtgatgc ggttttggca gtacatcaat gggcgtggat | 420 |
| agcggtttga ctcacgggga tttccaagtc tccaccccat tgacgtcaat gggagtttgt | 480 |
| tttggcacca aaatcaacgg gactttccaa aatgtcgtaa caactccgcc ccattgacgc | 540 |
| aaatgggcgg taggcgtgta cggtgggagg tctatataag cagagctctc tggctaacta | 600 |
| gagaacccac tgcttactgg cttatcgaaa ttaatacgac tcactatagg gagacccaag | 660 |
| ctggctagcg ccaccatgga ctacaaagac catgacggtg attataaaga tcatgacatc | 720 |
| gattacaagg atgacgatga caagatggcc cccaagaaga agaggaaggt gggcattcac | 780 |
| cgcggggtac ctatggtgga cttgaggaca ctcggttatt cgcaacagca acaggagaaa | 840 |
| atcaagccta aggtcaggag caccgtcgcg caacaccacg aggcgcttgt ggggcatggc | 900 |
| ttcactcatg cgcatattgt cgcgctttca cagcaccctg cggcgcttgg gacggtggct | 960 |
| gtcaaatacc aagatatgat tgcggccctg cccgaagcca cgcacgaggc aattgtaggg | 1020 |
| gtcggtaaac agtggtcggg agcgcgagca cttgaggcgc tgctgactgt ggcgggtgag | 1080 |
| cttagggggc ctccgctcca gctcgacacc gggcagctgc tgaagatcgc gaagagaggg | 1140 |
| ggagtaacag cggtagaggc agtgcacgcc tggcgcaatg cgctcaccgg tgcccccctg | 1200 |
| aacctgaccc cggaccaagt ggtggctatc gccagccacg atggcggcaa gcaagcgctc | 1260 |
| gaaacggtgc agcggctgtt gccggtgctg tgccaggacc atggcctgac cccgaccaa | 1320 |
| gtggtggcta tcgccagcaa cattggcggc aagcaagcgc tcgaaacggt gcagcggctg | 1380 |

-continued

```
ttgccggtgc tgtgccagga ccatggcctg actccggacc aagtggtggc tatcgccagc    1440
cacgatggcg gcaagcaagc gctcgaaacg gtgcagcggc tgttgccggt gctgtgccag    1500
gaccatggcc tgactccgga ccaagtggtg gctatcgcca gccacgatgg cggcaagcaa    1560
gcgctcgaaa cggtgcagcg gctgttgccg gtgctgtgcc aggaccatgg cctgaccccg    1620
gaccaagtgg tggctatcgc cagcaacggt ggcggcaagc aagcgctcga acggtgcag    1680
cggctgttgc cggtgctgtg ccaggaccat ggcctgaccc cggaccaagt ggtggctatc    1740
gccagcaacg gtggcggcaa gcaagcgctc gaaacggtgc agcggctgtt gccggtgctg    1800
tgccaggacc atggcctgac cccgaccaa gtggtggcta tcgccagcaa caagggcggc    1860
aagcaagcgc tcgaaacggt gcagcggctg ttgccggtgc tgtgccagga ccatggcctg    1920
actccggacc aagtggtggc tatcgccagc cacgatggcg gcaagcaagc gctcgaaacg    1980
gtgcagcggc tgttgccggt gctgtgccag gaccatggcc tgactccgga ccaagtggtg    2040
gctatcgcca gccacgatgg cggcaagcaa gcgctcgaaa cggtgcagcg gctgttgccg    2100
gtgctgtgcc aggaccatgg cctgactccg gaccaagtgg tggctatcgc cagccacgat    2160
ggcggcaagc aagcgctcga acggtgcag cggctgttgc cggtgctgtg ccaggaccat    2220
ggcctgaccc cggaccaagt ggtggctatc gccagcacg atggcggcaa gcaagcgctc    2280
gaaacggtgc agcggctgtt gccggtgctg tgccaggacc atggcctgac cccggaccaa    2340
gtggtggcta tcgccagcaa cattggcggc aagcaagcgc tcgaaacggt gcagcggctg    2400
ttgccggtgc tgtgccagga ccatggcctg actccggacc aagtggtggc tatcgccagc    2460
cacgatggcg gcaagcaagc gctcgaaacg gtgcagcggc tgttgccggt gctgtgccag    2520
gaccatggcc tgaccccgga ccaagtggtg gctatcgcca gcaacattgg cggcaagcaa    2580
gcgctcgaaa cggtgcagcg gctgttgccg gtgctgtgcc aggaccatgg cctgaccccg    2640
gaccaagtgg tggctatcgc cagcaacaag ggcggcaagc aagcgctcga acggtgcag    2700
cggctgttgc cggtgctgtg ccaggaccat ggcctgaccc cggaccaagt ggtggctatc    2760
gccagcaaca agggcggcaa gcaagcgctc gaaacggtgc agcggctgtt gccggtgctg    2820
tgccaggacc atggcctgac cccgaccaa gtggtggcta tcgccagcaa caagggcggc    2880
aagcaagcgc tcgaaacggt gcagcggctg ttgccggtgc tgtgccagga ccatggcctg    2940
actccggacc aagtggtggc tatcgccagc cacgatggcg gcaagcaagc gctcgaaacg    3000
gtgcagcggc tgttgccggt gctgtgccag gaccatggcc tgaccccgga ccaagtggtg    3060
gctatcgcca gcaacattgg cggcaagcaa gcgctcgaaa cggtgcagcg gctgttgccg    3120
gtgctgtgcc aggaccatgg cctgaccccg gaccaagtgg tggctatcgc cagcaacaag    3180
ggcggcaagc aagcgctcga acggtgcag cggctgttgc cggtgctgtg ccaggaccat    3240
ggcctgaccc cggaccaagt ggtggctatc gccagcaacg gtggcggcaa gcaagcgctc    3300
gaaacggtgc agcggctgtt gccggtgctg tgccaggacc atggcctgac cccggaccaa    3360
gtggtggcta tcgccagcaa cattggcggc aagcaagcgc tcgaaacggt gcagcggctg    3420
ttgccggtgc tgtgccagga ccatggcctg accccggacc aagtggtggc tatcgccagc    3480
aacattggcg gcaagcaagc gctcgaaacg gtgcagcggc tgttgccggt gctgtgccag    3540
gaccatggcc tgaccccgga ccaagtggtg gctatcgcca gccacgatgg cggcaagcaa    3600
gcgctcgaaa gcattgtggc ccagctgagc cggcctgatc cggcgttggc gcgttgacc    3660
aacgaccatc tggtggcgtt ggcatgtctt ggtggacgac ccgcgctcga tgcagtcaaa    3720
aagggtctgc ctcatgctcc cgcattgatc aaaagaacca accggcggat tcccgagaga    3780
```

```
acttcccatc gagtcgcggg atcccagctg gtgaagagcg agctggagga gaagaagtcc    3840
gagctgcggc acaagctgaa gtacgtgccc cacgagtaca tcgagctgat cgagatcgcc    3900
aggaacagca cccaggaccg catcctggag atgaaggtga tggagttctt catgaaggtg    3960
tacggctaca ggggaaagca cctgggcgga agcagaaagc ctgacggcgc catctataca    4020
gtgggcagcc ccatcgatta cggcgtgatc gtggacacaa aggcctacag cggcggctac    4080
aatctgccta tcggccaggc cgacgagatg cagagatacg tggaggagaa ccagacccgg    4140
aataagcaca tcaaccccaa cgagtggtgg aaggtgtacc ctagcagcgt gaccgagttc    4200
aagttcctgt tcgtgagcgg ccacttcaag ggcaactaca aggcccagct gaccaggctg    4260
aaccacatca ccaactgcaa tggcgccgtg ctgagcgtgg aggagctgct gatcggcggc    4320
gagatgatca aagccggcac cctgacactg gaggaggtgc ggcgcaagtt caacaacggc    4380
gagatcaact tctgataact taagtttaaa ccgctgatca gcctcgactg tgccttctag    4440
ttgccagcca tctgttgttt gcccctcccc cgtgccttcc ttgacccctgg aaggtgccac    4500
tcccactgtc ctttcctaat aaaatgagga aattgcatcg cattgtctga gtaggtgtca    4560
ttctattctg gggggtgggg tggggcagga cagcaagggg gaggattggg aagacaatag    4620
caggcatgct ggggatgcgg tgggctctat ggcttctgag gcggaaagaa ccagctgggg    4680
ctctaggggg tatccccacg cgccctgtag cggcgcatta agcgcggcgg gtgtggtggt    4740
tacgcgcagc gtgaccgcta cacttgccag cgccctagcg cccgctcctt tcgctttctt    4800
cccttccttt ctcgccacgt tcgccggctt tccccgtcaa gctctaaatc ggggctccc    4860
tttagggttc cgatttagtg ctttacggca cctcgacccc aaaaaacttg attagggtga    4920
tggttcacgt agtgggccat cgccctgata gacggttttt cgccctttga cgttggagtc    4980
cacgttcttt aatagtggac tcttgttcca aactggaaca cactcaacc ctatctcggt    5040
ctattctttt gatttataag ggattttgcc gatttcggcc tattggttaa aaaatgagct    5100
gatttaacaa aaatttaacg cgaattaatt ctgtggaatg tgtgtcagtt agggtgtgga    5160
aagtccccag gctccccagc aggcagaagt atgcaaagca tgcatctcaa ttagtcagca    5220
accaggtgtg gaaagtcccc aggctcccca gcaggcagaa gtatgcaaag catgcatctc    5280
aattagtcag caaccatagt cccgccccta actccgccca tcccgcccct aactccgccc    5340
agttccgccc attctccgcc ccatggctga ctaatttttt ttatttatgc agaggccgag    5400
gccgcctctg cctctgagct attccagaag tagtgaggag gcttttttgg aggcctaggc    5460
ttttgcaaaa agctcccggg agcttgtata tccattttcg gatctgatca agagacagga    5520
tgaggatcgt ttcgcatgat tgaacaagat ggattgcacg caggttctcc ggccgcttgg    5580
gtggagaggc tattcggcta tgactgggca acagacaa tcggctgctc tgatgccgcc    5640
gtgttccggc tgtcagcgca ggggcgcccg gttcttttg tcaagaccga cctgtccggt    5700
gccctgaatg aactgcagga cgaggcagcg cggctatcgt ggctggccac gacgggcgtt    5760
ccttgcgcag ctgtgctcga cgttgtcact gaagcgggaa gggactggct gctattgggc    5820
gaagtgccgg ggcaggatct cctgtcatct caccttgctc ctgccgagaa agtatccatc    5880
atggctgatg caatgcggcg gctgcatacg cttgatccgg ctacctgccc attcgaccac    5940
caagcgaaac atcgcatcga gcgagcacgt actcggatgg aagccggtct tgtcgatcag    6000
gatgatctgg acgaagagca tcaggggctc gcgccagccg aactgttcgc caggctcaag    6060
gcgcgcatgc ccgacggcga ggatctcgtc gtgacccatg gcgatgcctg cttgccgaat    6120
```

```
atcatggtgg aaaatggccg cttttctgga ttcatcgact gtggccggct gggtgtggcg   6180
gaccgctatc aggacatagc gttggctacc cgtgatattg ctgaagagct tggcggcgaa   6240
tgggctgacc gcttcctcgt gctttacggt atcgccgctc ccgattcgca gcgcatcgcc   6300
ttctatcgcc ttccttgacga gttcttctga gcgggactct ggggttcgaa atgaccgacc   6360
aagcgacgcc caacctgcca tcacgagatt tcgattccac cgccgccttc tatgaaaggt   6420
tgggcttcgg aatcgttttc cgggacgccg gctggatgat cctccagcgc ggggatctca   6480
tgctggagtt cttcgcccac cccaacttgt ttattgcagc ttataatggt tacaaataaa   6540
gcaatagcat cacaaatttc acaaataaag cattttttc actgcattct agttgtggtt    6600
tgtccaaact catcaatgta tcttatcatg tctgtatacc gtcgacctct agctagagct   6660
tggcgtaatc atggtcatag ctgtttcctg tgtgaaattg ttatccgctc acaattccac   6720
acaacatacg agccggaagc ataaagtgta agcctggggg tgcctaatga gtgagctaac   6780
tcacattaat tgcgttgcgc tcactgcccg ctttccagtc gggaaacctg tcgtgccagc   6840
tgcattaatg aatcggccaa cgcgcgggga gaggcggttt gcgtattggg cgctcttccg   6900
cttcctcgct cactgactcg ctgcgctcgg tcgttcggct gcggcgagcg gtatcagctc   6960
actcaaaggc ggtaatacgg ttatccacag aatcaggggg taacgcagga agaacatgt    7020 gagcaaaagg ccagcaaaag gccaggaacc gtaaaaaggc cgcgttgctg cgttttttcc   7080
ataggctccg ccccctgac gagcatcaca aaatcgacg ctcaagtcag aggtggcgaa     7140
acccgacagg actataaaga taccaggcgt ttccccctgg aagctccctc gtgcgctctc   7200
ctgttccgac cctgccgctt accggatacc tgtccgcctt tctcccttcg ggaagcgtgg   7260
cgctttctca tagctcacgc tgtaggtatc tcagttcggt gtaggtcgtt cgctccaagc   7320
tgggctgtgt gcacgaaccc cccgttcagc ccgaccgctg cgccttatcc ggtaactatc   7380
gtcttgagtc aacccggta agacacgact tatcgccact ggcagcagcc actggtaaca    7440
ggattagcag agcgaggtat gtaggcggtg ctacagagtt cttgaagtgg tggcctaact   7500
acggctacac tagaagaaca gtatttggta tctgcgctct gctgaagcca gttaccttcg   7560
gaaaaagagt tggtagctct tgatccggca aacaaaccac cgctggtagc ggttttttg    7620 tttgcaagca gcagattacg cgcagaaaaa aaggatctca agaagatcct ttgatctttt   7680
ctacggggtc tgacgctcag tggaacgaaa actcacgtta agggattttg gtcatgagat   7740
tatcaaaaag gatcttcacc tagatccttt taaattaaaa atgaagtttt aaatcaatct   7800
aaagtatata tgagtaaact tggtctgaca gttaccaatg cttaatcagt gaggcaccta   7860
tctcagcgat ctgtctattt cgttcatcca tagttgcctg actccccgtc gtgtagataa   7920
ctacgatacg ggagggctta ccatctggcc ccagtgctgc aatgataccg cgagacccac   7980
gctcaccggc tccagattta tcagcaataa accagccagc cggaagggcc gagcgcagaa   8040
gtggtcctgc aactttatcc gcctccatcc agtctattaa ttgttgccgg gaagctagag   8100
taagtagttc gccagttaat agtttgcgca acgttgttgc cattgctaca ggcatcgtgg   8160
tgtcacgctc gtcgtttggt atggcttcat tcagctccgg ttcccaacga tcaaggcgag   8220
ttacatgatc ccccatgttg tgcaaaaaag cggttagctc cttcggtcct ccgatcgttg   8280
tcagaagtaa gttggccgca gtgttatcac tcatggttat ggcagcactg cataattctc   8340
ttactgtcat gccatccgta agatgctttt ctgtgactgg tgagtactca accaagtcat   8400
tctgagaata gtgtatgcgg cgaccgagtt gctcttgccc ggcgtcaata cgggataata   8460
ccgcgccaca tagcagaact ttaaaagtgc tcatcattgg aaaacgttct cggggcgaa    8520
```

| | |
|---|---:|
| aactctcaag gatcttaccg ctgttgagat ccagttcgat gtaacccact cgtgcaccca | 8580 |
| actgatcttc agcatctttt actttcacca gcgtttctgg gtgagcaaaa acaggaaggc | 8640 |
| aaaatgccgc aaaaaaggga ataagggcga cacggaaatg ttgaatactc atactcttcc | 8700 |
| tttttcaata ttattgaagc atttatcagg gttattgtct catgagcgga tacatatttg | 8760 |
| aatgtattta gaaaaataaa caaatagggg ttccgcgcac atttccccga aaagtgccac | 8820 |
| ctgacgtcga cggatcggga gatctcccga tcccctatgg tgcactctca gtacaatctg | 8880 |
| ctctgatgcc gcatagttaa gccagtatct gctccctgct tgtgtgttgg aggtcgctga | 8940 |
| gtagtgcgcg agcaaaattt aagctacaac aaggcaaggc ttgaccgaca attgcatgaa | 9000 |
| gaatctgctt agggttaggc gttttgcgct gcttcgcgat gtacgggcca gatatacgc | 9059 |

<210> SEQ ID NO 23
<211> LENGTH: 8753
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

| | |
|---|---:|
| gttgacattg attattgact agttattaat agtaatcaat tacggggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atggtgatgc ggttttggca gtacatcaat gggcgtggat | 420 |
| agcggtttga ctcacgggga tttccaagtc tccaccccat tgacgtcaat gggagtttgt | 480 |
| tttggcacca aaatcaacgg gactttccaa aatgtcgtaa caactccgcc ccattgacgc | 540 |
| aaatgggcgg taggcgtgta cggtgggagg tctatataag cagagctctc tggctaacta | 600 |
| gagaacccac tgcttactgg cttatcgaaa ttaatacgac tcactatagg gagacccaag | 660 |
| ctggctagcg ccaccatgga ctacaaagac catgacggtg attataaaga tcatgacatc | 720 |
| gattacaagg atgacgatga caagatggcc cccaagaaga agaggaaggt gggcattcac | 780 |
| cgcggggtac ctatggtgga cttgaggaca ctcggttatt cgcaacagca acaggagaaa | 840 |
| atcaagccta aggtcaggag caccgtcgcg caacaccacg aggcgcttgt ggggcatggc | 900 |
| ttcactcatg cgcatattgt cgcgctttca cagcaccctg cggcgcttgg gacggtggct | 960 |
| gtcaaatacc aagatatgat tgcggccctg cccgaagcca cgcacgaggc aattgtaggg | 1020 |
| gtcggtaaac agtggtcggg agcgcgagca cttgaggcgc tgctgactgt ggcgggtgag | 1080 |
| cttaggggggc ctccgctcca gctcgacacc gggcagctgc tgaagatcgc gaagagaggg | 1140 |
| ggagtaacag cggtagaggc agtgcacgcc tggcgcaatg cgctcaccgg tgcccccctg | 1200 |
| aacctgaccc cggaccaagt ggtggctatc gccagcacg atggcggcaa gcaagcgctc | 1260 |
| gaaacggtgc agcggctgtt gccggtgctg tgccaggacc atggcctgac cccggaccaa | 1320 |
| gtggtggcta tcgccagcaa cattggcggc aagcaagcgc tcgaaacggt gcagcggctg | 1380 |
| ttgccggtgc tgtgccagga ccatggcctg actccggacc aagtggtggc tatcgccagc | 1440 |

-continued

| | |
|---|---|
| cacgatggcg gcaagcaagc gctcgaaacg gtgcagcggc tgttgccggt gctgtgccag | 1500 |
| gaccatggcc tgactccgga ccaagtggtg gctatcgcca gccacgatgg cggcaagcaa | 1560 |
| gcgctcgaaa cggtgcagcg gctgttgccg gtgctgtgcc aggaccatgg cctgaccccg | 1620 |
| gaccaagtgg tggctatcgc cagcaacggt ggcggcaagc aagcgctcga acggtgcag | 1680 |
| cggctgttgc cggtgctgtg ccaggaccat ggcctgaccc cggaccaagt ggtggctatc | 1740 |
| gccagcaacg gtggcggcaa gcaagcgctc gaaacggtgc agcggctgtt gccggtgctg | 1800 |
| tgccaggacc atggcctgac cccggaccaa gtggtggcta tcgccagcaa caatggcggc | 1860 |
| aagcaagcgc tcgaaacggt gcagcggctg ttgccggtgc tgtgccagga ccatggcctg | 1920 |
| actccggacc aagtggtggc tatcgccagc cacgatggcg gcaagcaagc gctcgaaacg | 1980 |
| gtgcagcggc tgttgccggt gctgtgccag gaccatggcc tgactccgga ccaagtggtg | 2040 |
| gctatcgcca gccacgatgg cggcaagcaa gcgctcgaaa cggtgcagcg gctgttgccg | 2100 |
| gtgctgtgcc aggaccatgg cctgactccg gaccaagtgg tggctatcgc cagccacgat | 2160 |
| ggcggcaagc aagcgctcga acggtgcag cggctgttgc cggtgctgtg ccaggaccat | 2220 |
| ggcctgaccc cggaccaagt ggtggctatc gccagccacg atggcggcaa gcaagcgctc | 2280 |
| gaaacggtgc agcggctgtt gccggtgctg tgccaggacc atggcctgac cccggaccaa | 2340 |
| gtggtggcta tcgccagcaa cattggcggc aagcaagcgc tcgaaacggt gcagcggctg | 2400 |
| ttgccggtgc tgtgccagga ccatggcctg actccggacc aagtggtggc tatcgccagc | 2460 |
| cacgatggcg gcaagcaagc gctcgaaacg gtgcagcggc tgttgccggt gctgtgccag | 2520 |
| gaccatggcc tgaccccgga ccaagtggtg gctatcgcca gcaacattgg cggcaagcaa | 2580 |
| gcgctcgaaa cggtgcagcg gctgttgccg gtgctgtgcc aggaccatgg cctgaccccg | 2640 |
| gaccaagtgg tggctatcgc cagcaacaat ggcggcaagc aagcgctcga acggtgcag | 2700 |
| cggctgttgc cggtgctgtg ccaggaccat ggcctgaccc cggaccaagt ggtggctatc | 2760 |
| gccagcaaca atggcggcaa gcaagcgctc gaaacggtgc agcggctgtt gccggtgctg | 2820 |
| tgccaggacc atggcctgac cccggaccaa gtggtggcta tcgccagcaa caatggcggc | 2880 |
| aagcaagcgc tcgaaacggt gcagcggctg ttgccggtgc tgtgccagga ccatggcctg | 2940 |
| actccggacc aagtggtggc tatcgccagc cacgatggcg gcaagcaagc gctcgaaacg | 3000 |
| gtgcagcggc tgttgccggt gctgtgccag gaccatggcc tgaccccgga ccaagtggtg | 3060 |
| gctatcgcca gcaacattgg cggcaagcaa gcgctcgaaa cggtgcagcg gctgttgccg | 3120 |
| gtgctgtgcc aggaccatgg cctgaccccg gaccaagtgg tggctatcgc cagcaacaat | 3180 |
| ggcggcaagc aagcgctcga acggtgcag cggctgttgc cggtgctgtg ccaggaccat | 3240 |
| ggcctgaccc cggaccaagt ggtggctatc gccagcaacg gtggcggcaa gcaagcgctc | 3300 |
| gaaagcattg tggcccagct gagccggcct gatccggcgt tggccgcgtt gaccaacgac | 3360 |
| catctggtgg cgttggcatg tcttggtgga cgacccgcgc tcgatgcagt caaaaagggt | 3420 |
| ctgcctcatg ctcccgcatt gatcaaaaga accaaccggc ggattcccga gagaacttcc | 3480 |
| catcgagtcg cgggatccca gctggtgaag agcgagctgg aggagaagaa gtccgagctg | 3540 |
| cggcacaagc tgaagtacgt gccccacgag tacatcgagc tgatcgagat cgccaggaac | 3600 |
| agcacccagg accgcatcct ggagatgaag gtgatggagt tcttcatgaa ggtgtacggc | 3660 |
| tacaggggaa agcacctggg cggaagcaga aagcctgacg gcgccatcta cagtgggc | 3720 |
| agccccatcg attacggcgt gatcgtggac acaaaggcct acagcggcgg ctacaatctg | 3780 |
| cctatcggcc aggccgacga gatgcagaga tacgtggagg agaaccagac ccggaataag | 3840 |

```
cacatcaacc ccaacgagtg gtggaaggtg taccctagca gcgtgaccga gttcaagttc    3900
ctgttcgtga gcggccactt caagggcaac tacaaggccc agctgaccag gctgaaccac    3960
atcaccaact gcaatggcgc cgtgctgagc gtggaggagc tgctgatcgg cggcgagatg    4020
atcaaagccg gcaccctgac actggaggag gtgcggcgca gttcaacaa cggcgagatc    4080 aacttctgat aacttaagtt taaaccgctg atcagcctcg actgtgcctt ctagttgcca    4140
gccatctgtt gtttgcccct ccccgtgcc ttccttgacc ctggaaggtg ccactcccac    4200
tgtcctttcc taataaaatg aggaaattgc atcgcattgt ctgagtaggt gtcattctat    4260
tctggggggt ggggtggggc aggacagcaa ggggaggat tgggaagaca atagcaggca    4320
tgctggggat gcggtgggct ctatggcttc tgaggcggaa agaaccagct ggggctctag    4380
ggggtatccc cacgcgccct gtagcggcgc attaagcgcg gcgggtgtgg tggttacgcg    4440
cagcgtgacc gctacacttg ccagcgccct agcgcccgct cctttcgctt tcttcccttc    4500
ctttctcgcc acgttcgccg ctttccccg tcaagctcta atcggggc tcccttagg    4560 gttccgattt agtgctttac ggcacctcga ccccaaaaaa cttgattagg gtgatggttc    4620
acgtagtggg ccatcgccct gatagacggt ttttcgccct ttgacgttgg agtccacgtt    4680
ctttaatagt ggactcttgt tccaaactgg aacaacactc aaccctatct cggtctattc    4740
ttttgattta taaggatttt gccgatttc ggcctattgg ttaaaaaatg agctgattta    4800
acaaaaattt aacgcgaatt aattctgtgg aatgtgtgtc agttagggtg tggaaagtcc    4860
ccaggctccc cagcaggcag aagtatgcaa agcatgcatc tcaattagtc agcaaccagg    4920
tgtggaaagt ccccaggctc cccagcaggc agaagtatgc aaagcatgca tctcaattag    4980
tcagcaacca tagtcccgcc cctaactccg cccatcccgc cctaactccg cccagttccg    5040
gcccattctc cgccccatgg ctgactaatt tttttatt atgcagaggc cgaggccgcc    5100
tctgcctctg agctattcca gaagtagtga ggaggctttt ttggaggcct aggcttttgc    5160
aaaaagctcc cgggagcttg tatatccatt ttcggatctg atcaagagac aggatgagga    5220
tcgtttcgca tgattgaaca agatggattg cacgcaggtt ctccggccgc ttgggtggag    5280
aggctattcg gctatgactg ggcacaacag acaatcggct gctctgatgc cgccgtgttc    5340
cggctgtcag cgcaggggcg cccggttctt tttgtcaaga ccgacctgtc cggtgccctg    5400
aatgaactgc aggacgaggc agcgcggcta tcgtggctgg ccacgacggg cgttccttgc    5460
gcagctgtgc tcgacgttgt cactgaagcg ggaagggact ggctgctatt gggcgaagtg    5520
ccggggcagg atctcctgtc atctcacctt gctcctgccg agaaagtatc catcatggct    5580
gatgcaatgc ggcggctgca tacgcttgat ccggctacct gcccattcga ccaccaagcg    5640
aaacatcgca tcgagcgagc acgtactcgg atggaagccg gtcttgtcga tcaggatgat    5700
ctggacgaag agcatcaggg gctcgcgcca gccgaactgt tcgccaggct caaggcgcgc    5760
atgcccgacg gcgaggatct cgtcgtgacc catggcgatg cctgcttgcc gaatatcatg    5820
gtggaaaatg gccgcttttc tggattcatc gactgtggcc ggctgggtgt ggcggaccgc    5880
tatcaggaca tagcgttggc tacccgtgat attgctgaag agcttggcgg cgaatgggct    5940
gaccgcttcc tcgtgcttta cggtatcgcc gctcccgatt cgcagcgcat cgccttctat    6000
cgccttcttg acgagttctt ctgagcggga ctctggggtt cgaaatgacc gaccaagcga    6060
cgcccaacct gccatcacga gatttcgatt ccaccgccgc cttctatgaa aggttgggct    6120
tcggaatcgt tttccgggac gccggctgga tgatcctcca gcgcgggat ctcatgctgg    6180
```

```
agttcttcgc ccaccccaac ttgtttattg cagcttataa tggttacaaa taaagcaata      6240
gcatcacaaa tttcacaaat aaagcatttt tttcactgca ttctagttgt ggtttgtcca      6300
aactcatcaa tgtatcttat catgtctgta taccgtcgac ctctagctag agcttggcgt      6360
aatcatggtc atagctgttt cctgtgtgaa attgttatcc gctcacaatt ccacacaaca      6420
tacgagccgg aagcataaag tgtaaagcct ggggtgccta atgagtgagc taactcacat      6480
taattgcgtt gcgctcactg cccgctttcc agtcgggaaa cctgtcgtgc cagctgcatt      6540
aatgaatcgg ccaacgcgcg gggagaggcg gtttgcgtat gggcgctct tccgcttcct      6600 cgctcactga ctcgctgcgc tcggtcgttc ggctgcggcg agcggtatca gctcactcaa      6660
aggcggtaat acggttatcc acagaatcag gggataacgc aggaaagaac atgtgagcaa      6720
aaggccagca aaaggccagg aaccgtaaaa aggccgcgtt gctggcgttt ttccataggc      6780
tccgcccccc tgacgagcat cacaaaaatc gacgctcaag tcagaggtgg cgaaacccga      6840
caggactata aagataccag gcgtttcccc ctggaagctc cctcgtgcgc tctcctgttc      6900
cgaccctgcc gcttaccgga tacctgtccg cctttctccc ttcgggaagc gtggcgcttt      6960
ctcatagctc acgctgtagg tatctcagtt cggtgtaggt cgttcgctcc aagctgggct      7020
gtgtgcacga accccccgtt cagcccgacc gctgcgcctt atccggtaac tatcgtcttg      7080
agtccaaccc ggtaagacac gacttatcgc cactggcagc agccactggt aacaggatta      7140
gcagagcgag gtatgtaggc ggtgctacag agttcttgaa gtggtggcct aactacggct      7200
acactagaag aacagtattt ggtatctgcg ctctgctgaa gccagttacc ttcggaaaaa      7260
gagttggtag ctcttgatcc ggcaaacaaa ccaccgctgg tagcggtttt tttgtttgca      7320
agcagcagat tacgcgcaga aaaaaaggat ctcaagaaga tcctttgatc ttttctacgg      7380
ggtctgacgc tcagtggaac gaaaactcac gttaagggat tttggtcatg agattatcaa      7440
aaaggatctt cacctagatc cttttaaatt aaaaatgaag ttttaaatca atctaaagta      7500
tatatgagta aacttggtct gacagttacc aatgcttaat cagtgaggca cctatctcag      7560
cgatctgtct atttcgttca tccatagttg cctgactccc cgtcgtgtag ataactacga      7620
tacgggaggg cttaccatct ggccccagtg ctgcaatgat accgcgagac ccacgctcac      7680
cggctccaga tttatcagca ataaaccagc cagccggaag ggccgagcgc agaagtggtc      7740
ctgcaacttt atccgcctcc atccagtcta ttaattgttg ccgggaagct agagtaagta      7800
gttcgccagt taatagtttg cgcaacgttg ttgccattgc tacaggcatc gtggtgtcac      7860
gctcgtcgtt tggtatggct tcattcagct ccggttccca acgatcaagg cgagttacat      7920 gatccccat gttgtgcaaa aaagcggtta gctccttcgg tcctccgatc gttgtcagaa      7980
gtaagttggc cgcagtgtta tcactcatgg ttatggcagc actgcataat tctcttactg      8040
tcatgccatc cgtaagatgc ttttctgtga ctggtgagta ctcaaccaag tcattctgag      8100
aatagtgtat gcggcgaccg agttgctctt gcccggcgtc aatacgggat aataccgcgc      8160
cacatagcag aactttaaaa gtgctcatca ttggaaaacg ttcttcgggg cgaaaactct      8220
caaggatctt accgctgttg agatccagtt cgatgtaacc cactcgtgca cccaactgat      8280
cttcagcatc ttttactttc accagcgttt ctgggtgagc aaaaacagga aggcaaaatg      8340
ccgcaaaaaa gggaataagg gcgacacgga aatgttgaat actcatactc ttcctttttc      8400
aatattattg aagcatttat cagggttatt gtctcatgag cggatacata tttgaatgta      8460
tttagaaaaa taaacaaata ggggttccgc gcacatttcc ccgaaaagtg ccacctgacg      8520
tcgacggatc gggagatctc ccgatcccct atggtgcact ctcagtacaa tctgctctga      8580
```

```
tgccgcatag ttaagccagt atctgctccc tgcttgtgtg ttggaggtcg ctgagtagtg      8640
cgcgagcaaa atttaagcta caacaaggca aggcttgacc gacaattgca tgaagaatct      8700
gcttagggtt aggcgttttg cgctgcttcg cgatgtacgg gccagatata cgc             8753
```

<210> SEQ ID NO 24
<211> LENGTH: 9059
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24

```
gttgacattg attattgact agttattaat agtaatcaat tacggggtca ttagttcata        60
gcccatatat ggagttccgc gttacataac ttacggtaaa tggcccgcct ggctgaccgc       120
ccaacgaccc ccgcccattg acgtcaataa tgacgtatgt tcccatagta acgccaatag       180
ggactttcca ttgacgtcaa tgggtggagt atttacggta aactgcccac ttggcagtac       240
atcaagtgta tcatatgcca gtacgcccc ctattgacgt caatgacggt aaatggcccg        300
cctggcatta tgcccagtac atgaccttat gggactttcc tacttggcag tacatctacg       360
tattagtcat cgctattacc atggtgatgc ggttttggca gtacatcaat gggcgtggat       420
agcggtttga ctcacgggga tttccaagtc tccaccccat tgacgtcaat gggagtttgt       480
tttggcacca aaatcaacgg gactttccaa aatgtcgtaa caactccgcc ccattgacgc       540
aaatgggcgg taggcgtgta cggtgggagg tctatataag cagagctctc tggctaacta       600
gagaacccac tgcttactgg cttatcgaaa ttaatacgac tcactatagg gagacccaag       660
ctggctagcg ccaccatgga ctacaaagac catgacggtg attataaaga tcatgacatc       720
gattacaagg atgacgatga caagatggcc cccaagaaga agaggaaggt gggcattcac       780
cgcggggtac ctatggtgga cttgaggaca ctcggttatt cgcaacagca acaggagaaa       840
atcaagccta aggtcaggag caccgtcgcg caacaccacg aggcgcttgt ggggcatggc       900
ttcactcatg cgcatattgt cgcgctttca cagcaccctg cggcgcttgg gacggtggct       960
gtcaaatacc aagatatgat tgcggccctg cccgaagcca gcacgaggc aattgtaggg      1020 gtcggtaaac agtggtcggg agcgcagca cttgaggcgc tgctgactgt ggcgggtgag      1080 cttaggggc ctccgctcca gctcgacacc gggcagctgc tgaagatcgc gaagagaggg      1140
ggagtaacag cggtagaggc agtgcacgcc tggcgcaatg cgctcaccgg tgccccctg       1200 aacctgaccc cggaccaagt ggtggctatc gccagccacg atggcggcaa gcaagcgctc      1260
gaaacggtgc agcggctgtt gccggtgctg tgccaggacc atggcctgac cccggaccaa      1320
gtggtggcta tcgccagcaa cattggcggc aagcaagcgc tcgaaacggt gcagcggctg      1380
ttgccggtgc tgtgccagga ccatggcctg actccggacc aagtggtggc tatcgccagc      1440
cacgatggcg gcaagcaagc gctcgaaacg gtgcagcggc tgttgccggt gctgtgccag      1500
gaccatggcc tgactccgga ccaagtggtg gctatcgcca gccacgatgg cggcaagcaa      1560
gcgctcgaaa cggtgcagcg gctgttgccg gtgctgtgcc aggaccatgg cctgaccccg      1620
gaccaagtgg tggctatcgc cagcaacggt ggcggcaagc aagcgctcga aacggtgcag      1680
cggctgttgc cggtgctgtg ccaggaccat ggcctgaccc cggaccaagt ggtggctatc      1740
gccagcaacg gtggcggcaa gcaagcgctc gaaacggtgc agcggctgtt gccggtgctg      1800
```

```
tgccaggacc atggcctgac cccggaccaa gtggtggcta tcgccagcaa caatggcggc    1860
aagcaagcgc tcgaaacggt gcagcggctg ttgccggtgc tgtgccagga ccatggcctg    1920
actccggacc aagtggtggc tatcgccagc cacgatggcg gcaagcaagc gctcgaaacg    1980
gtgcagcggc tgttgccggt gctgtgccag gaccatggcc tgactccgga ccaagtggtg    2040
gctatcgcca gccacgatgg cggcaagcaa gcgctcgaaa cggtgcagcg gctgttgccg    2100
gtgctgtgcc aggaccatgg cctgactccg gaccaagtgg tggctatcgc cagccacgat    2160
ggcggcaagc aagcgctcga aacggtgcag cggctgttgc cggtgctgtg ccaggaccat    2220
ggcctgaccc cggaccaagt ggtggctatc gccagccacg atggcggcaa gcaagcgctc    2280
gaaacggtgc agcggctgtt gccggtgctg tgccaggacc atggcctgac cccggaccaa    2340
gtggtggcta tcgccagcaa cattggcggc aagcaagcgc tcgaaacggt gcagcggctg    2400
ttgccggtgc tgtgccagga ccatggcctg actccggacc aagtggtggc tatcgccagc    2460
cacgatggcg gcaagcaagc gctcgaaacg gtgcagcggc tgttgccggt gctgtgccag    2520
gaccatggcc tgaccccgga ccaagtggtg gctatcgcca gcaacattgg cggcaagcaa    2580
gcgctcgaaa cggtgcagcg gctgttgccg gtgctgtgcc aggaccatgg cctgaccccg    2640
gaccaagtgg tggctatcgc cagcaacaat ggcggcaagc aagcgctcga acggtgcag    2700 cggctgttgc cggtgctgtg ccaggaccat ggcctgaccc cggaccaagt ggtggctatc    2760
gccagcaaca atggcggcaa gcaagcgctc gaaacggtgc agcggctgtt gccggtgctg    2820
tgccaggacc atggcctgac cccggaccaa gtggtggcta tcgccagcaa caatggcggc    2880
aagcaagcgc tcgaaacggt gcagcggctg ttgccggtgc tgtgccagga ccatggcctg    2940
actccggacc aagtggtggc tatcgccagc cacgatggcg gcaagcaagc gctcgaaacg    3000
gtgcagcggc tgttgccggt gctgtgccag gaccatggcc tgaccccgga ccaagtggtg    3060
gctatcgcca gcaacattgg cggcaagcaa gcgctcgaaa cggtgcagcg gctgttgccg    3120
gtgctgtgcc aggaccatgg cctgaccccg gaccaagtgg tggctatcgc cagcaacaat    3180
ggcggcaagc aagcgctcga aacggtgcag cggctgttgc cggtgctgtg ccaggaccat    3240
ggcctgaccc cggaccaagt ggtggctatc gccagcaacg tggcggcaa gcaagcgctc    3300 gaaacggtgc agcggctgtt gccggtgctg tgccaggacc atggcctgac cccggaccaa    3360
gtggtggcta tcgccagcaa cattggcggc aagcaagcgc tcgaaacggt gcagcggctg    3420
ttgccggtgc tgtgccagga ccatggcctg accccggacc aagtggtggc tatcgccagc    3480
aacattggcg gcaagcaagc gctcgaaacg gtgcagcggc tgttgccggt gctgtgccag    3540
gaccatggcc tgaccccgga ccaagtggtg gctatcgcca gccacgatgg cggcaagcaa    3600
gcgctcgaaa gcattgtggc ccagctgagc cggcctgatc cggcgttggc cgcgttgacc    3660
aacgaccatc tggtggcgtt ggcatgtctt ggtggacgac ccgcgctcga tgcagtcaaa    3720
aagggtctgc ctcatgctcc cgcattgatc aaaagaacca accggcggat tcccgagaga    3780
acttcccatc gagtcgcggg atcccagctg gtgaagagcg agctggagga agaagtcc    3840 gagctgcggc acaagctgaa gtacgtgccc cacgagtaca tcgagctgat cgagatcgcc    3900
aggaacagca cccaggaccg catcctggag atgaaggtga tggagttctt catgaaggtg    3960
tacggctaca ggggaaagca cctgggcgga agcagaaagc ctgacggcgc catctataca    4020
gtgggcagcc ccatcgatta cggcgtgatc gtggacacaa aggcctacag cggcggctac    4080
aatctgccta tcgccaggc cgacgagatg cagagatacg tggaggagaa ccagacccgg    4140
aataagcaca tcaacccca cgagtggtgg aaggtgtacc ctagcagcgt gaccgagttc    4200
```

-continued

```
aagttcctgt tcgtgagcgg ccacttcaag ggcaactaca aggcccagct gaccaggctg    4260
aaccacatca ccaactgcaa tggcgccgtg ctgagcgtgg aggagctgct gatcggcggc    4320
gagatgatca aagccggcac cctgacactg gaggaggtgc ggcgcaagtt caacaacggc    4380
gagatcaact tctgataact taagtttaaa ccgctgatca gcctcgactg tgccttctag    4440
ttgccagcca tctgttgttt gcccctcccc cgtgccttcc ttgaccctgg aaggtgccac    4500
tcccactgtc ctttcctaat aaaatgagga aattgcatcg cattgtctga gtaggtgtca    4560
ttctattctg ggggtgggg tggggcagga cagcaagggg gaggattggg aagacaatag    4620
caggcatgct ggggatgcgg tgggctctat ggcttctgag gcggaaagaa ccagctgggg    4680
ctctaggggg tatccccacg cgccctgtag cggcgcatta agcgcggcgg gtgtggtggt    4740
tacgcgcagc gtgaccgcta cacttgccag cgccctagcg cccgctcctt tcgctttctt    4800
cccttccttt ctcgccacgt tcgccggctt tccccgtcaa gctctaaatc ggggctccc    4860
tttagggttc cgatttagtg ctttacggca cctcgacccc aaaaaacttg attagggtga    4920
tggttcacgt agtgggccat cgccctgata cggttttt cgccctttga cgttggagtc    4980
cacgttcttt aatagtggac tcttgttcca aactggaaca acactcaacc ctatctcggt    5040
ctattctttt gatttataag ggattttgcc gatttcggcc tattggttaa aaaatgagct    5100
gatttaacaa aaatttaacg cgaattaatt ctgtggaatg tgtgtcagtt agggtgtgga    5160
aagtccccag gctccccagc aggcagaagt atgcaaagca tgcatctcaa ttagtcagca    5220
accaggtgtg gaaagtcccc aggctcccca gcaggcagaa gtatgcaaag catgcatctc    5280
aattagtcag caaccatagt cccgccccta actccgccca tcccgcccct aactccgccc    5340
agttccgccc attctccgcc ccatggctga ctaattttt ttatttatgc agaggccgag    5400
gccgcctctg cctctgagct attccagaag tagtgaggag gcttttttgg aggcctaggc    5460
ttttgcaaaa agctcccggg agcttgtata tccattttcg gatctgatca agagacagga    5520
tgaggatcgt ttcgcatgat tgaacaagat ggattgcacg caggttctcc ggccgcttgg    5580
gtggagaggc tattcggcta tgactgggca caacagacaa tcggctgctc tgatgccgcc    5640
gtgttccggc tgtcagcgca ggggcgcccg gttcttttg tcaagaccga cctgtccggt    5700
gccctgaatg aactgcagga cgaggcagcg cggctatcgt ggctggccac gacgggcgtt    5760
ccttgcgcag ctgtgctcga cgttgtcact gaagcgggaa gggactggct gctattgggc    5820
gaagtgccgg ggcaggatct cctgtcatct caccttgctc ctgccgagaa agtatccatc    5880
atggctgatg caatgcggcg gctgcatacg cttgatccgg ctacctgccc attcgaccac    5940
caagcgaaac atcgcatcga gcgagcacgt actcggatgg aagccggtct tgtcgatcag    6000
gatgatctgg acgaagagca tcaggggctc gcgccagccg aactgttcgc caggctcaag    6060
gcgcgcatgc ccgacggcga ggatctcgtc gtgacccatg gcgatgcctg cttgccgaat    6120
atcatggtgg aaaatggccg cttttctgga ttcatcgact gtggccggct gggtgtggcg    6180
gaccgctatc aggacatagc gttggctacc cgtgatattg ctgaagagct tggcggcgaa    6240
tgggctgacc gcttcctcgt gctttacggt atcgccgctc ccgattcgca gcgcatcgcc    6300
ttctatcgcc ttcttgacga gttcttctga gcgggactct ggggttcgaa atgaccgacc    6360
aagcgacgcc caacctgcca tcacgagatt tcgattccac cgccgccttc tatgaaaggt    6420
tgggcttcgg aatcgttttc cgggacgccg gctggatgat cctccagcgc ggggatctca    6480
tgctggagtt cttcgcccac cccaacttgt ttattgcagc ttataatggt tacaaataaa    6540
```

```
gcaatagcat cacaaatttc acaaataaag cattttttc actgcattct agttgtggtt      6600
tgtccaaact catcaatgta tcttatcatg tctgtatacc gtcgacctct agctagagct     6660
tggcgtaatc atggtcatag ctgtttcctg tgtgaaattg ttatccgctc acaattccac     6720
acaacatacg agccggaagc ataaagtgta aagcctgggg tgcctaatga gtgagctaac     6780
tcacattaat tgcgttgcgc tcactgcccg ctttccagtc gggaaacctg tcgtgccagc     6840
tgcattaatg aatcggccaa cgcgcgggga ggcggttt gcgtattggg cgctcttccg      6900
cttcctcgct cactgactcg ctgcgctcgg tcgttcggct gcggcgagcg gtatcagctc     6960
actcaaaggc ggtaatacgg ttatccacag aatcagggga taacgcagga aagaacatgt     7020
gagcaaaagg ccagcaaaag gccaggaacc gtaaaaaggc cgcgttgctg gcgtttttcc     7080
ataggctccg cccccctgac gagcatcaca aaaatcgacg ctcaagtcag aggtggcgaa     7140
acccgacagg actataaaga taccaggcgt ttccccctgg aagctccctc gtgcgctctc     7200
ctgttccgac cctgccgctt accggatacc tgtccgcctt tctcccttcg ggaagcgtgg     7260
cgctttctca tagctcacgc tgtaggtatc tcagttcggt gtaggtcgtt cgctccaagc     7320
tgggctgtgt gcacgaaccc cccgttcagc ccgaccgctg cgccttatcc ggtaactatc     7380
gtcttgagtc caacccggta agacacgact tatcgccact ggcagcagcc actggtaaca     7440
ggattagcag agcgaggtat gtaggcggtg ctacagagtt cttgaagtgg tggcctaact     7500
acggctacac tagaagaaca gtatttggta tctgcgctct gctgaagcca gttaccttcg     7560
gaaaaagagt tggtagctct tgatccggca acaaaccac cgctggtagc ggttttttg      7620
tttgcaagca gcagattacg cgcagaaaaa aaggatctca agaagatcct ttgatctttt    7680
ctacggggtc tgacgctcag tggaacgaaa actcacgtta agggattttg gtcatgagat     7740
tatcaaaaag gatcttcacc tagatccttt taaattaaaa atgaagtttt aaatcaatct     7800
aaagtatata tgagtaaact tggtctgaca gttaccaatg cttaatcagt gaggcaccta     7860
tctcagcgat ctgtctattt cgttcatcca tagttgcctg actccccgtc gtgtagataa     7920
ctacgatacg ggagggctta ccatctggcc ccagtgctgc aatgataccg cgagacccac     7980
gctcaccggc tccagattta tcagcaataa accagccagc cggaagggcc gagcgcagaa     8040
gtggtcctgc aactttatcc gcctccatcc agtctattaa ttgttgccgg gaagctagag     8100
taagtagttc gccagttaat agtttgcgca acgttgttgc cattgctaca ggcatcgtgg     8160
tgtcacgctc gtcgtttggt atggcttcat tcagctccgg ttcccaacga tcaaggcgag     8220
ttacatgatc ccccatgttg tgcaaaaaag cggttagctc cttcggtcct ccgatcgttg     8280
tcagaagtaa gttggccgca gtgttatcac tcatggttat ggcagcactg cataattctc     8340
ttactgtcat gccatccgta agatgctttt ctgtgactgg tgagtactca accaagtcat     8400
tctgagaata gtgtatgcgg cgaccgagtt gctcttgccc ggcgtcaata cgggataata     8460
ccgcgccaca tagcagaact ttaaaagtgc tcatcattgg aaaacgttct tcggggcgaa     8520
aactctcaag gatcttaccg ctgttgagat ccagttcgat gtaacccact cgtgcaccca     8580
actgatcttc agcatctttt actttcacca gcgtttctgg gtgagcaaaa acaggaaggc     8640
aaaatgccgc aaaaaaggga ataagggcga cacggaaatg ttgaatactc atactcttcc     8700
tttttcaata ttattgaagc atttatcagg gttattgtct catgagcgga tacatatttg     8760
aatgtattta gaaaaataaa caaatagggg ttccgcgcac atttccccga aaagtgccac     8820
ctgacgtcga cggatcggga gatctcccga tcccctatgg tgcactctca gtacaatctg     8880
ctctgatgcc gcatagttaa gccagtatct gctccctgct tgtgtgttgg aggtcgctga    8940
```

<210> SEQ ID NO 25
<211> LENGTH: 7053
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25

```
gtagtgcgcg agcaaaattt aagctacaac aaggcaaggc ttgaccgaca attgcatgaa    9000
gaatctgctt agggttaggc gttttgcgct gcttcgcgat gtacgggcca gatatacgc     9059 gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gccaccatgg actacaaaga ccatgacggt gattataaag atcatgacat cgattacaag    960
gatgacgatg acaagatggc ccccaagaag aagaggaagg tgggcattca ccgcggggta   1020
cctatggtgg acttgaggac actcggttat tcgcaacagc aacaggagaa aatcaagcct   1080
aaggtcagga gcaccgtcgc gcaacaccac gaggcgcttg ggggcatgg cttcactcat   1140
gcgcatattg tcgcgctttc acagcaccct gcggcgcttg gacggtggc tgtcaaatac   1200
caagatatga ttgcggccct gcccgaagcc acgcacgagg caattgtagg ggtcggtaaa   1260
cagtggtcgg gagcgcgagc acttgaggcg ctgctgactg tggcgggtga gcttagggg    1320
cctccgctcc agctcgacac cgggcagctg ctgaagatcg cgaagagagg gggagtaaca   1380
gcggtagagg cagtgcacgc ctggcgcaat gcgctcaccg gtgcccccct ggagacgggc   1440
gccgctacag ggcgcgtccc attcgccatt caggctgcgc aactgttggg aagggcgatc   1500
ggtgcgggcc tcttcgctat tacgccagct ggcgaaaggg ggatgtgctg caaggcgatt   1560
aagttgggta acgccagggt tttcccagtc acgacgttgt aaaacgacgg ccagtgagcg   1620
cgcgtaatac gactcactat agggcgaatt gggtaccggg cccccctcg aggtcctcca   1680
gcttttgttc cctttagtga gggttaattg cgcgcttggc gtaatcatgg tcatagctgt   1740
ttcctgtgtg aaattgttat ccgctcacaa ttccacacaa catacgagcc ggaagcataa   1800
agtgtaaagc ctggggtgcc taatgagtga gctaactcac attaattgcg ttgcgctcac   1860
```

-continued

| | | | | | |
|---|---|---|---|---|---|
| tgcccgcttt | ccaccggtcg | tctccaacga | ccatctggtg | gcgttggcat | gtcttggtgg | 1920 |
| acgacccgcg | ctcgatgcag | tcaaaaaggg | tctgcctcat | gctcccgcat | tgatcaaaag | 1980 |
| aaccaaccgg | cggattcccg | agagaacttc | ccatcgagtc | gcgggatccc | agctggtgaa | 2040 |
| gagcgagctg | gaggagaaga | agtccgagct | gcggcacaag | ctgaagtacg | tgccccacga | 2100 |
| gtacatcgag | ctgatcgaga | tcgccaggaa | cagcacccag | gaccgcatcc | tggagatgaa | 2160 |
| ggtgatggag | ttcttcatga | aggtgtacgg | ctacagggga | aagcacctgg | gcggaagcag | 2220 |
| aaagcctgac | ggcgccatct | atacagtggg | cagccccatc | gattacggcg | tgatcgtgga | 2280 |
| cacaaaggcc | tacagcggcg | gctacaatct | gcctatcggc | caggccgacg | agatgcagag | 2340 |
| atacgtggag | gagaaccaga | cccggaataa | gcacatcaac | cccaacgagt | ggtggaaggt | 2400 |
| gtaccctagc | agcgtgaccg | agttcaagtt | cctgttcgtg | agcggccact | tcaagggcaa | 2460 |
| ctacaaggcc | cagctgacca | ggctgaacca | catcaccaac | tgcaatggcg | ccgtgctgag | 2520 |
| cgtggaggag | ctgctgatcg | gcggcgagat | gatcaaagcc | ggcacccctga | cactggagga | 2580 |
| ggtgcggcgc | aagttcaaca | acggcgagat | caacttctga | taacttaagt | ttaaaccgct | 2640 |
| gatcagcctc | gactgtgcct | tctagttgcc | agccatctgt | tgtttgcccc | tcccccgtgc | 2700 |
| cttccttgac | cctggaaggt | gccactccca | ctgtcctttc | ctaataaaat | gaggaaattg | 2760 |
| catcgcattg | tctgagtagg | tgtcattcta | ttctgggggg | tggggtgggg | caggacagca | 2820 |
| agggggagga | ttgggaagac | aatagcaggc | atgctgggga | tgcggtgggc | tctatggctt | 2880 |
| ctgaggcgga | aagaaccagc | tggggctcta | gggggtatcc | ccacgcgccc | tgtagcggcg | 2940 |
| cattaagcgc | ggcgggtgtg | gtggttacgc | gcagcgtgac | cgctacactt | gccagcgccc | 3000 |
| tagcgcccgc | tcctttcgct | ttcttccctt | cctttctcgc | cacgttcgcc | ggctttcccc | 3060 |
| gtcaagctct | aaatcggggg | ctccctttag | ggttccgatt | tagtgcttta | cggcacctcg | 3120 |
| acccccaaaa | acttgattag | ggtgatggtt | cacgtagtgg | gccatcgccc | tgatagacgg | 3180 |
| tttttcgccc | tttgacgttg | gagtccacgt | tctttaatag | tggactcttg | ttccaaactg | 3240 |
| gaacaacact | caaccctatc | tcggtctatt | cttttgattt | ataagggatt | ttgccgattt | 3300 |
| cggcctattg | gttaaaaaat | gagctgattt | aacaaaaatt | taacgcgaat | taattctgtg | 3360 |
| gaatgtgtgt | cagttagggt | gtggaaagtc | cccaggctcc | ccagcaggca | gaagtatgca | 3420 |
| aagcatgcat | ctcaattagt | cagcaaccag | gtgtggaaag | tccccaggct | ccccagcagg | 3480 |
| cagaagtatg | caaagcatgc | atctcaatta | gtcagcaacc | atagtcccgc | ccctaactcc | 3540 |
| gcccatcccg | cccctaactc | cgcccagttc | cgcccattct | ccgccccatg | gctgactaat | 3600 |
| tttttttatt | tatgcagagg | ccgaggccgc | ctctgcctct | gagctattcc | agaagtagtg | 3660 |
| aggaggcttt | tttggaggcc | taggcttttg | caaaaagctc | ccgggagctt | gtatatccat | 3720 |
| tttcggatct | gatcaagaga | caggatgagg | atcgtttcgc | atgattgaac | aagatggatt | 3780 |
| gcacgcaggt | tctccggccg | cttgggtgga | gaggctattc | ggctatgact | gggcacaaca | 3840 |
| gacaatcggc | tgctctgatg | ccgccgtgtt | ccggctgtca | gcgcagggc | gcccggttct | 3900 |
| ttttgtcaag | accgacctgt | ccggtgccct | gaatgaactg | caggacgagg | cagcgcggct | 3960 |
| atcgtggctg | gccacgacgg | gcgttccttg | cgcagctgtg | ctcgacgttg | tcactgaagc | 4020 |
| gggaagggac | tggctgctat | tgggcgaagt | gccggggcag | gatctcctgt | catctcacct | 4080 |
| tgctcctgcc | gagaaagtat | ccatcatggc | tgatgcaatg | cggcggctgc | atacgcttga | 4140 |
| tccggctacc | tgcccattcg | accaccaagc | gaaacatcgc | atcgagcgag | cacgtactcg | 4200 |
| gatggaagcc | ggtcttgtcg | atcaggatga | tctggacgaa | gagcatcagg | ggctcgcgcc | 4260 |

```
agccgaactg ttcgccaggc tcaaggcgcg catgcccgac ggcgaggatc tcgtcgtgac    4320
ccatggcgat gcctgcttgc cgaatatcat ggtggaaaat ggccgctttt ctggattcat    4380
cgactgtggc cggctgggtg tggcggaccg ctatcaggac atagcgttgg ctacccgtga    4440
tattgctgaa gagcttggcg gcgaatgggc tgaccgcttc ctcgtgcttt acggtatcgc    4500
cgctcccgat tcgcagcgca tcgccttcta tcgccttctt gacgagttct tctgagcggg    4560
actctggggt tcgaaatgac cgaccaagcg acgcccaacc tgccatcacg agatttcgat    4620
tccaccgccg ccttctatga aaggttgggc ttcggaatcg ttttccggga cgccggctgg    4680
atgatcctcc agcgcgggga tctcatgctg gagttcttcg cccacecca cttgtttatt    4740 gcagcttata atggttacaa ataaagcaat agcatcacaa atttcacaaa taaagcattt    4800
ttttcactgc attctagttg tggttttgtcc aaactcatca atgtatctta tcatgtctgt    4860
ataccgtcga cctctagcta gagcttggcg taatcatggt catagctgtt tcctgtgtga    4920
aattgttatc cgctcacaat tccacacaac atacgagccg gaagcataaa gtgtaaagcc    4980
tggggtgcct aatgagtgag ctaactcaca ttaattgcgt tgcgctcact gcccgctttc    5040
cagtcgggaa acctgtcgtg ccagctgcat taatgaatcg gccaacgcgc ggggagaggc    5100
ggtttgcgta ttgggcgctc ttccgcttcc tcgctcactg actcgctgcg ctcggtcgtt    5160
cggctgcggc gagcggtatc agctcactca aaggcggtaa tacggttatc cacagaatca    5220
ggggataacg caggaaagaa catgtgagca aaaggccagc aaaaggccag gaaccgtaaa    5280
aaggccgcgt tgctggcgtt tttccatagg ctccgccccc ctgacgagca tcacaaaaat    5340
cgacgctcaa gtcagaggtg gcgaaacccg acaggactat aaagatacca ggcgtttccc    5400
cctggaagct ccctcgtgcg ctctcctgtt ccgaccctgc cgcttaccgg atacctgtcc    5460
gcctttctcc cttcgggaag cgtggcgctt tctcatagct cacgctgtag gtatctcagt    5520
tcggtgtagg tcgttcgctc caagctgggc tgtgtgcacg aaccccccgt tcagcccgac    5580
cgctgcgcct tatccggtaa ctatcgtctt gagtccaacc cggtaagaca cgacttatcg    5640
ccactggcag cagccactgg taacaggatt agcagagcga gtatgtaggc ggtgctaca    5700 gagttcttga agtggtggcc taactacggc tacactagaa gaacagtatt tggtatctgc    5760
gctctgctga agccagttac cttcggaaaa agagttggta gctcttgatc cggcaaacaa    5820
accaccgctg gtagcggttt ttttgtttgc aagcagcaga ttacgcgcag aaaaaaagga    5880
tctcaagaag atcctttgat cttttctacg gggtctgacg ctcagtggaa cgaaaactca    5940
cgttaaggga ttttggtcat gagattatca aaaaggatct tcacctagat ccttttaaat    6000
taaaaatgaa gttttaaatc aatctaaagt atatatgagt aaacttggtc tgacagttac    6060
caatgcttaa tcagtgaggc acctatctca gcgatctgtc tatttcgttc atccatagtt    6120
gcctgactcc ccgtcgtgta gataactacg atacgggagg gcttaccatc tggccccagt    6180
gctgcaatga taccgcgaga cccacgctca ccggctccag atttatcagc aataaaccag    6240
ccagccggaa gggccgagcg cagaagtggt cctgcaactt tatccgcctc catccagtct    6300
attaattgtt gccgggaagc tagagtaagt agttcgccag ttaatagttt gcgcaacgtt    6360
gttgccattg ctacaggcat cgtggtgtca cgctcgtcgt ttggtatggc ttcattcagc    6420
tccggttccc aacgatcaag gcgagttaca tgatccccca tgttgtgcaa aaaagcggtt    6480
agctccttcg gtcctccgat cgttgtcaga agtaagttgg ccgcagtgtt atcactcatg    6540
gttatggcag cactgcataa ttctcttact gtcatgccat ccgtaagatg cttttctgtg    6600
```

```
actggtgagt actcaaccaa gtcattctga aatagtgta tgcggcgacc gagttgctct    6660
tgcccggcgt caatacggga taataccgcg ccacatagca aactttaaa agtgctcatc    6720 attggaaaac gttcttcggg gcgaaaactc tcaaggatct taccgctgtt gagatccagt    6780
tcgatgtaac ccactcgtgc acccaactga tcttcagcat cttttacttt caccagcgtt    6840
tctgggtgag caaaaacagg aaggcaaaat gccgcaaaaa agggaataag ggcgacacgg    6900
aaatgttgaa tactcatact cttcctttt caatattatt gaagcattta tcagggttat    6960
tgtctcatga gcggatacat atttgaatgt atttagaaaa ataaacaaat aggggttccg    7020
cgcacatttc cccgaaaagt gccacctgac gtc                                7053
```

<210> SEQ ID NO 26
<211> LENGTH: 5952
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (1597)..(1597)
<223> OTHER INFORMATION: a, c, t, g, unknown or other

<400> SEQUENCE: 26

```
gacggatcgg gagatctccc gatccctat ggtcgactct cagtacaatc tgctctgatg    60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat cgatatctgc ggccgcacca tggtgagcaa gggcgaggag ctgttcaccg    960
gggtggtgcc catcctggtc gagctggacg gcgacgtaaa cggccacaag ttcagcgtgt    1020
ccggcgaggg cgagggcgat gccacctacg gcaagctgac cctgaagttc atctgcacca    1080
ccggcaagct gcccgtgccc tggcccaccc tcgtgaccac cctgacctac ggcgtgcagt    1140
gcttcagccg ctaccccgac cacatgaagc agcacgactt cttcaagtcc gccatgcccg    1200
aaggctacgt ccaggagcgc acaatttttt tcaaggatga tggaaactac aagtaaggcg    1260
cgaccatctt cttcaaggac gacggcgcgc tgggatcct gcaggcagga gcgcacaatt    1320
tttttcaagg atgatggaaa ctacaagacc cgcgccgagg tgaagttcga gggcgacacc    1380
ctggtgaacc gcatcgagct gaagggcatc gacttcaagg aggacggcaa catcctgggg    1440
```

-continued

```
cacaagctgg agtacaacta caacagccac aacgtctata tcatggccga caagcagaag    1500
aacggcatca aggtgaactt caagatccgc cacaacatcg aggacggcag cgtgcagctc    1560
gccgaccact accagcagaa cacccccatc ggcgacngcc ccgtgctgct gcccgacaac    1620
cactacctga gcacccagtc cgccctgagc aaagacccca acgagaagcg cgatcacatg    1680
gtcctgctgg agttcgtgac cgccgccggg atcactctcg gcatggacga gctgtacaag    1740
taaggatcca ctagtaacgg ccgccagtgt gctggaatta ttcgctgtc tgcgagggcc    1800 agctgttggg gtgagtactc cctctcaaaa gcgggcatga cttctgcgct aagattgtca    1860
gtttccaaaa acgaggagga tttgatattc acctggcccg cggtgatgcc tttgagggtg    1920
gccgcgtcca tctggtcaga aaagacaatc tttttgttgt caagcttgag gtgtggcagg    1980
cttgagatct ggccatacac ttgagtgaca atgacatcca ctttgccttt ctctccacag    2040
gtgtccactc ccaggtccaa ctgcaggtcg agcatgcatc tagggcggcc aattccgccc    2100
ctctccctcc ccccccccta acgttactgg ccgaagccgc ttggaataag gccggtgtgc    2160
gtttgtctat atgtgatttt ccaccatatt gccgtctttt ggcaatgtga gggcccggaa    2220
acctggccct gtcttcttga cgagcattcc tagggggtctt tcccctctcg ccaaaggaat    2280
gcaaggtctg ttgaatgtcg tgaaggaagc agttcctctg gaagcttctt gaagacaaac    2340
aacgtctgta cgacccttt gcaggcagcg gaaccccca cctggcgaca ggtgcctctg    2400
cggccaaaag ccacgtgtat aagatacacc tgcaaaggcg gcacaacccc agtgccacgt    2460
tgtgagttgg atagttgtgg aaagagtcaa atggctctcc tcaagcgtat tcaacaaggg    2520
gctgaaggat gcccagaagg taccccattg tatgggatct gatctggggc ctcggtgcac    2580
atgctttaca tgtgtttagt cgaggttaaa aaaacgtcta ggccccccga accacgggga    2640
cgtggttttc ctttgaaaaa cacgatgata agcttgccac aacccacaag gagacgacct    2700
tccatgaccg agtacaagcc cacggtgcgc ctcgccaccc gcgacgacgt ccccggggcc    2760
gtacgcaccc tcgccgccgc gttcgccgac taccccgcca cgcgccacac cgtcgacccg    2820
gaccgccaca tcgagcgggt caccgagctg caagaactct tcctcacgcg cgtcgggctc    2880
gacatcggca aggtgtgggt cgcggacgac ggcgccgcgg tggcggtctg gaccacgccg    2940
gagagcgtcg aagcggggc ggtgttcgcc gagatcggcc cgcgcatggc cgagttgagc    3000
ggttcccggc tggccgcgca gcaacagatg gaaggcctcc tggcgccgca ccggcccaag    3060
gagcccgcgt ggttcctggc caccgtcggc gtctcgcccg accaccaggg caagggtctg    3120
ggcagcgccg tcgtgctccc cggagtggag gcggccgagc gcgccggggt gcccgccttc    3180
ctggagacct ccgcgccccg caacctcccc ttctacgagc ggctcggctt caccgtcacc    3240
gccgacgtcg agtgcccgaa ggaccgcgcg acctggtgca tgacccgcaa gcccggtgcc    3300
tgacgcccgc cccacgaccc gcagcgcccg accgaaagga gcgcacgacc ccatggctcc    3360
gaccgaagcc gacccgggcg gccccgccga ccccgcaccc gccccgagg cccaccgact    3420 ctagagctcg ctgatcagcc tcgactgtgc cttctagttg ccagccatct gttgtttgcc    3480 cctccccgt gccttccttg accctggaag gtgccactcc cactgtcctt tcctaataaa    3540
atgaggaaat tgcatcgcat tgtctgagta ggtgtcattc tattctgggg ggtggggtgg    3600
ggcaggacag caaggggag gattgggaag acaatagcag gcatgctggg gatgcggtgg    3660
gctctatggc ttctgaggcg gaaagaacca gctgggctc gagtgcattc tagttgtggt    3720
ttgtccaaac tcatcaatgt atcttatcat gtctgtatac cgtcgacctc tagctagagc    3780
```

| | |
|---|---|
| ttggcgtaat catggtcata gctgtttcct gtgtgaaatt gttatccgct cacaattcca | 3840 |
| cacaacatac gagccggaag cataaagtgt aaagcctggg gtgcctaatg agtgagctaa | 3900 |
| ctcacattaa ttgcgttgcg ctcactgccc gctttccagt cgggaaacct gtcgtgccag | 3960 |
| ctgcattaat gaatcggcca acgcgcgggg agaggcggtt tgcgtattgg gcgctcttcc | 4020 |
| gcttcctcgc tcactgactc gctgcgctcg gtcgttcggc tgcggcgagc ggtatcagct | 4080 |
| cactcaaagg cggtaatacg gttatccaca gaatcagggg ataacgcagg aaagaacatg | 4140 |
| tgagcaaaag gccagcaaaa ggccaggaac cgtaaaaagg ccgcgttgct ggcgtttttc | 4200 |
| cataggctcc gcccccctga cgagcatcac aaaaatcgac gctcaagtca gaggtggcga | 4260 |
| aacccgacag gactataaag ataccaggcg tttccccctg gaagctccct cgtgcgctct | 4320 |
| cctgttccga ccctgccgct taccggatac ctgtccgcct ttctcccttc gggaagcgtg | 4380 |
| gcgctttctc aatgctcacg ctgtaggtat ctcagttcgg tgtaggtcgt tcgctccaag | 4440 |
| ctgggctgtg tgcacgaacc ccccgttcag cccgaccgct gcgccttatc cggtaactat | 4500 |
| cgtcttgagt ccaacccggt aagacacgac ttatcgccac tggcagcagc cactggtaac | 4560 |
| aggattagca gagcgaggta tgtaggcggt gctacagagt tcttgaagtg gtggcctaac | 4620 |
| tacggctaca ctagaaggac agtatttggt atctgcgctc tgctgaagcc agttaccttc | 4680 |
| ggaaaaagag ttggtagctc ttgatccggc aaacaaacca ccgctggtag cggtggtttt | 4740 |
| tttgtttgca agcagcagat tacgcgcaga aaaaaaggat ctcaagaaga tcctttgatc | 4800 |
| ttttctacgg ggtctgacgc tcagtggaac gaaaactcac gttaagggat tttggtcatg | 4860 |
| agattatcaa aaaggatctt cacctagatc cttttaaatt aaaaatgaag ttttaaatca | 4920 |
| atctaaagta tatatgagta aacttggtct gacagttacc aatgcttaat cagtgaggca | 4980 |
| cctatctcag cgatctgtct atttcgttca tccatagttg cctgactccc cgtcgtgtag | 5040 |
| ataactacga tacgggaggg cttaccatct ggccccagtg ctgcaatgat accgcgagac | 5100 |
| ccacgctcac cggctccaga tttatcagca ataaaccagc cagccggaag ggccgagcgc | 5160 |
| agaagtggtc ctgcaacttt atccgcctcc atccagtcta ttaattgttg ccgggaagct | 5220 |
| agagtaagta gttcgccagt taatagtttg cgcaacgttg ttgccattgc tacaggcatc | 5280 |
| gtggtgtcac gctcgtcgtt tggtatggct tcattcagct ccggttccca acgatcaagg | 5340 |
| cgagttacat gatcccccat gttgtgcaaa aaagcggtta gctccttcgg tcctccgatc | 5400 |
| gttgtcagaa gtaagttggc cgcagtgtta tcactcatgg ttatggcagc actgcataat | 5460 |
| tctcttactg tcatgccatc cgtaagatgc ttttctgtga ctggtgagta ctcaaccaag | 5520 |
| tcattctgag aatagtgtat gcggcgaccg agttgctctt gcccggcgtc aatacgggat | 5580 |
| aataccgcgc cacatagcag aactttaaaa gtgctcatca ttggaaaacg ttcttcgggg | 5640 |
| cgaaaactct caaggatctt accgctgttg agatccagtt cgatgtaacc cactcgtgca | 5700 |
| cccaactgat cttcagcatc ttttactttc accagcgttt ctgggtgagc aaaaacagga | 5760 |
| aggcaaaatg ccgcaaaaaa gggaataagg gcgacacgga aatgttgaat actcatactc | 5820 |
| ttcctttttc aatattattg aagcatttat cagggttatt gtctcatgag cggatacata | 5880 |
| tttgaatgta tttagaaaaa taaacaaata ggggttccgc gcacatttcc ccgaaaagtg | 5940 |
| ccacctgacg tc | 5952 |

<210> SEQ ID NO 27
<211> LENGTH: 187
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 27

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser
            180                 185

<210> SEQ ID NO 28
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Gly Gly Lys Gln Ala Leu Glu Thr Val Gln Arg Leu Leu Pro Val Leu
1               5                   10                  15

Cys Gln Asp His Gly Leu Thr Pro Asp Gln Val Val Ala Ile Ala Ser
            20                  25                  30

<210> SEQ ID NO 29
<211> LENGTH: 268
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gly Gly Lys Gln Ala Leu Glu Ser Ile Val Ala Gln Leu Ser Arg Pro
1               5                   10                  15

Asp Pro Ala Leu Ala Ala Leu Thr Asn Asp His Leu Val Ala Leu Ala
            20                  25                  30
```

Cys Leu Gly Gly Arg Pro Ala Leu Asp Ala Val Lys Lys Gly Leu Pro
         35                  40                  45

His Ala Pro Ala Leu Ile Lys Arg Thr Asn Arg Ile Pro Glu Arg
 50                  55                  60

Thr Ser His Arg Val Ala Gly Ser Gln Leu Val Lys Ser Glu Leu Glu
 65                  70                  75                  80

Glu Lys Lys Ser Glu Leu Arg His Lys Leu Lys Tyr Val Pro His Glu
                 85                  90                  95

Tyr Ile Glu Leu Ile Glu Ile Ala Arg Asn Ser Thr Gln Asp Arg Ile
            100                 105                 110

Leu Glu Met Lys Val Met Glu Phe Phe Met Lys Val Tyr Gly Tyr Arg
        115                 120                 125

Gly Lys His Leu Gly Gly Ser Arg Lys Pro Asp Gly Ala Ile Tyr Thr
    130                 135                 140

Val Gly Ser Pro Ile Asp Tyr Gly Val Ile Val Asp Thr Lys Ala Tyr
145                 150                 155                 160

Ser Gly Gly Tyr Asn Leu Pro Ile Gly Gln Ala Asp Glu Met Gln Arg
                165                 170                 175

Tyr Val Glu Glu Asn Gln Thr Arg Asn Lys His Ile Asn Pro Asn Glu
            180                 185                 190

Trp Trp Lys Val Tyr Pro Ser Ser Val Thr Glu Phe Lys Phe Leu Phe
        195                 200                 205

Val Ser Gly His Phe Lys Gly Asn Tyr Lys Ala Gln Leu Thr Arg Leu
    210                 215                 220

Asn His Ile Thr Asn Cys Asn Gly Ala Val Leu Ser Val Glu Glu Leu
225                 230                 235                 240

Leu Ile Gly Gly Glu Met Ile Lys Ala Gly Thr Leu Thr Leu Glu Glu
                245                 250                 255

Val Arg Arg Lys Phe Asn Asn Gly Glu Ile Asn Phe
            260                 265

<210> SEQ ID NO 30
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
acattgaggc actacttg                                                 18

<210> SEQ ID NO 31
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
acattgaggc acta                                                     14

<210> SEQ ID NO 32
<211> LENGTH: 24
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Tyr"
<220> FEATURE:
<221> NAME/KEY: MOD_RES
<222> LOCATION: (3)..(6)
<223> OTHER INFORMATION: Any amino acid
<220> FEATURE:
<221> NAME/KEY: misc_feature
<222> LOCATION: (3)..(6)
<223> OTHER INFORMATION: /note="This region may encompass 2-4 residues"
<220> FEATURE:
<221> NAME/KEY: VARIANT
<222> LOCATION: (5)..(6)
<223> OTHER INFORMATION: /replace=" "
<220> FEATURE:
<221> NAME/KEY: MOD_RES
<222> LOCATION: (8)..(10)
<223> OTHER INFORMATION: Any amino acid
<220> FEATURE:
<221> NAME/KEY: VARIANT
<222> LOCATION: (11)..(11)
<223> OTHER INFORMATION: /replace="Tyr"
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(23)
<223> OTHER INFORMATION: Any amino acid
<220> FEATURE:
<221> NAME/KEY: misc_feature
<222> LOCATION: (1)..(24)
<223> OTHER INFORMATION: /note="Variant residues given in the sequence
      have no preference with respect to those in the annotations for
      variant positions"

<400> SEQUENCE: 32

Phe Cys Xaa Xaa Xaa Xaa Cys Xaa Xaa Xaa Phe Xaa Xaa Xaa Xaa Xaa
1               5                   10                  15

Leu Xaa Xaa His Xaa Xaa Xaa His
            20

<210> SEQ ID NO 33
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(17)
<223> OTHER INFORMATION: Any amino acid
<220> FEATURE:
<221> NAME/KEY: MOD_RES
<222> LOCATION: (19)..(20)
<223> OTHER INFORMATION: Any amino acid

<400> SEQUENCE: 33

Cys Xaa Xaa Cys Xaa Xaa Xaa Xaa Xaa Xaa Xaa Xaa Xaa Xaa Xaa Xaa
```

```
1               5                  10                 15
Xaa Cys Xaa Xaa Cys
            20
```

<210> SEQ ID NO 34
<211> LENGTH: 28
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (13)..(16)
<223> OTHER INFORMATION: a, c, t, g, unknown or other

<400> SEQUENCE: 34
gtcatcctca tcnnnnaaac tgcaaaag                                         28

<210> SEQ ID NO 35
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 35
gtcatcctca tcctgataaa ctgcaaaag                                        29

<210> SEQ ID NO 36
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 36
gtcgtcctca tcttaataaa ctgcaaaaa                                        29

<210> SEQ ID NO 37
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 37
gtcatcttca tcagcataaa ctgtaaagt                                        29

<210> SEQ ID NO 38
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 38
ctgttccagt tttagtttgc tgaggataac                                       30

```
<210> SEQ ID NO 39
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 39
atgttcctca tctcccgaaa ctgcaaatg                                              29

<210> SEQ ID NO 40
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 40
gttttcctca tcaaagcaaa ctgcaaaat                                              29

<210> SEQ ID NO 41
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 41
cttttgcagt ctgtaggtgt tgaggttgac                                             30

<210> SEQ ID NO 42
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 42
gttttgcagt tcctttgat gaagatgac                                               29

<210> SEQ ID NO 43
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 43
gtcctgctca gcaaaagaaa ctgaaaaag                                              29

<210> SEQ ID NO 44
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"
```

<400> SEQUENCE: 44
cttttccagt tggtagcat caggaagac				29

<210> SEQ ID NO 45
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 45
attagccagt tttctctgat gaggatgac				29

<210> SEQ ID NO 46
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 46
cttttgcatt tttatagaga tgaggattta				30

<210> SEQ ID NO 47
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 47
gtcatcccaa tcgaagaaaa actgaaaaag				30

<210> SEQ ID NO 48
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 48
ctcatcctca tccatgcaca atgcaaaag				29

<210> SEQ ID NO 49
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 49
cttctgctgt ttcccatgct gaggatgac				29

<210> SEQ ID NO 50
<211> LENGTH: 29
<212> TYPE: DNA

```
<213> ORGANISM: Unknown
<220> FEATURE:
<221> NAME/KEY: source
<223> OTHER INFORMATION: /note="Description of Unknown: Target
      oligonucleotide"

<400> SEQUENCE: 50
cctttgttct tttattggat gaggatgac                                    29

<210> SEQ ID NO 51
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 51
gtcatcctca tacataaaaa ctgccttag                                    29

<210> SEQ ID NO 52
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 52
atcatcctca tccatccaat gttcaaaag                                    29

<210> SEQ ID NO 53
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 53
tttttgcagt ttttcatgat gtggatgtt                                    29

<210> SEQ ID NO 54
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 54
atcttcctca ttacaggaaa atgtaatag                                    29

<210> SEQ ID NO 55
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 55
ggcttcctga cccacggaaa ctgtaaatg                                    29
```

<210> SEQ ID NO 56
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 56
gttttgcaca tttcaattaa ctgcaaaag                              29

<210> SEQ ID NO 57
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 57
ctttagcaat tggagttgga ggaggatgac                             30

<210> SEQ ID NO 58
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 58
gtcttcctcc tctgcacatc actgcaaaag                             30

<210> SEQ ID NO 59
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 59
cttatgcaga ttgctgatga tgagtatcac                             30

<210> SEQ ID NO 60
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 60
attttgcagt taacaaatga tgagcatgag                             30

<210> SEQ ID NO 61
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target -continued oligonucleotide"

<400> SEQUENCE: 61
gccagtctca gcatggtgaa actgcaaaag        30

<210> SEQ ID NO 62
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 62
ctcattctgt tcatgaaaaa actgcaaaag        30

<210> SEQ ID NO 63
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 63
gaagtcctca tcccgaagaa actgaaagag        30

<210> SEQ ID NO 64
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 64
catttgcggt tttatgtgaa agaggaagac        30

<210> SEQ ID NO 65
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 65
ataatccttt tctgtttaaa acagcaaaag        30

<210> SEQ ID NO 66
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 66
ctttttcagt ttccatgtaa tttggatgtc        30

<210> SEQ ID NO 67
<211> LENGTH: 30

```
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 67
gtcttgctgt tgcacctcaa actgcaaaag                                       30

<210> SEQ ID NO 68
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 68
gtcatccgca tcgccctgga actggaaaaa                                       30

<210> SEQ ID NO 69
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 69
cttttcctgt tttagtttgt tgaggatgat                                       30

<210> SEQ ID NO 70
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 70
ggaatgccca tcaccacaaa actgcaaaag                                       30

<210> SEQ ID NO 71
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 71
gttttgctcc tgtacttcaa actgcaaaag                                       30

<210> SEQ ID NO 72
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 72
```
gtcatcctca tcctgataaa ctgcaaaag                                29

<210> SEQ ID NO 73
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 73
gtcgtcctca tcttaataaa ctgcaaaaa                                29

<210> SEQ ID NO 74
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 74
catttccagt ttaaagagat gaggaggcc                                29

<210> SEQ ID NO 75
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 75
ctattacagt tttaagagat gaggtctca                                29

<210> SEQ ID NO 76
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 76
ctgttacagt ttaaagagag gaggcctct                                29

<210> SEQ ID NO 77
<211> LENGTH: 22
<212> TYPE: DNA
<213> ORGANISM: Unknown
<220> FEATURE:
<221> NAME/KEY: source
<223> OTHER INFORMATION: /note="Description of Unknown: Target oligonucleotide"
<220> FEATURE:
<221> NAME/KEY: modified_base
<222> LOCATION: (10)..(13)
<223> OTHER INFORMATION: a, c, t, g, unknown or other

<400> SEQUENCE: 77
agcagcgtcn nnngagtgag ga                                       22

<210> SEQ ID NO 78
<211> LENGTH: 23

```
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 78
agcagcgtct tcgagagtga gga                                             23

<210> SEQ ID NO 79
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 79
agcagtgtca ggctggtgtg agga                                            24

<210> SEQ ID NO 80
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 80
tcctcacacc agcctgacac tgct                                            24

<210> SEQ ID NO 81
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 81
ccctcactca gtacagactt tgct                                            24

<210> SEQ ID NO 82
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 82
acctcactcc caggcgtcgc tgct                                            24

<210> SEQ ID NO 83
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 83
```
agcatcgtct gaagtgagtg aggc                                           24

<210> SEQ ID NO 84
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 84
ttctcacaca ctatggacgt tgct                                           24

<210> SEQ ID NO 85
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 85
agcattgtct catgtgagtg aggt                                           24

<210> SEQ ID NO 86
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 86
ccctccctcc ccctagacgc tgct                                           24

<210> SEQ ID NO 87
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 87
ccctcactca tgtgatacgc tgct                                           24

<210> SEQ ID NO 88
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 88
tcctcacacc agcctgacac tgct                                           24

<210> SEQ ID NO 89
<211> LENGTH: 24
<212> TYPE: DNA
<213> ORGANISM: Unknown
<220> FEATURE:
<221> NAME/KEY: source

```
<223> OTHER INFORMATION: /note="Description of Unknown: Target
      oligonucleotide"

<400> SEQUENCE: 89
ccctcactcc caggagaagc tgct                                              24

<210> SEQ ID NO 90
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 90
gcctcactgc agccgccgct gct                                               23

<210> SEQ ID NO 91
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 91
agcaccgtcc ccctcagtga ggc                                               23

<210> SEQ ID NO 92
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 92
gcctcactca gccctgaccc tgct                                              24

<210> SEQ ID NO 93
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 93
ccctcactcc ttgggaccat gct                                               23

<210> SEQ ID NO 94
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 94
agcagtgtca ggctggtgtg agga                                              24

<210> SEQ ID NO 95
```

```
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 95
gcctcactct ttttgacatt gct                                             23

<210> SEQ ID NO 96
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 96
tcctcacccc cttaggacac tgct                                            24

<210> SEQ ID NO 97
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 97
tcctcacacc agcctgacac tgct                                            24

<210> SEQ ID NO 98
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 98
agcagagtca gacttgagtg aggt                                            24

<210> SEQ ID NO 99
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 99
agcagagtct ctgagagtga ggc                                             23

<210> SEQ ID NO 100
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 100
```

-continued ttttcactct ttcagacgct gct                    23

<210> SEQ ID NO 101
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 101
tgcagcggcg tagggagtg agga                    24

<210> SEQ ID NO 102
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 102
agcatcgtct tctgtgagtg agta                    24

<210> SEQ ID NO 103
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 103
agcatagtct aggccgagtg aggc                    24

<210> SEQ ID NO 104
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 104
agcattgtct cctggagtga ggg                    23

<210> SEQ ID NO 105
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 105
tcctcactga atatgacgtt gct                    23

<210> SEQ ID NO 106
<211> LENGTH: 24
<212> TYPE: DNA
<213> ORGANISM: Unknown
<220> FEATURE:

```
<221> NAME/KEY: source
<223> OTHER INFORMATION: /note="Description of Unknown: Target
      oligonucleotide"

<400> SEQUENCE: 106
agaaacgtcg tggaggagtg aggg                                          24

<210> SEQ ID NO 107
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 107
agcacggtca tgatgagtga ggc                                           23

<210> SEQ ID NO 108
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 108
agcagcgtct cccttgagtg atgg                                          24

<210> SEQ ID NO 109
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 109
ttctcactca ctcaggacac ttct                                          24

<210> SEQ ID NO 110
<211> LENGTH: 22
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (10)..(13)
<223> OTHER INFORMATION: a, c, t, g, unknown or other

<400> SEQUENCE: 110
tcccaccaan nnngaaggtg tg                                            22

<210> SEQ ID NO 111
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 111
```

-continued

```
tcccaccaac atgctgaagg tgtg                                              24

<210> SEQ ID NO 112
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 112
cacacctgca ggactcgggt ggga                                              24

<210> SEQ ID NO 113
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 113
cacaccatcc tacctttggt gggt                                              24

<210> SEQ ID NO 114
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 114 tcccccacg tctgtgaagg tgtg                                               24

<210> SEQ ID NO 115
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 115
cccgaccaga ttgtgaaggt gtg                                               23

<210> SEQ ID NO 116
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 116
acccaccgag atacgcgggt gtg                                               23

<210> SEQ ID NO 117
<211> LENGTH: 24
<212> TYPE: DNA
<213> ORGANISM: Unknown
<220> FEATURE:
```

```
<221> NAME/KEY: source
<223> OTHER INFORMATION: /note="Description of Unknown: Target
      oligonucleotide"

<400> SEQUENCE: 117
tccctccaac atcacgaggg tggg                                            24

<210> SEQ ID NO 118
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 118
cacaccggca gactgcggcg gga                                             23

<210> SEQ ID NO 119
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 119
cacacccaca aaagatggtg ggt                                             23

<210> SEQ ID NO 120
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 120
ctcaccatca cttcctgggt ggga                                            24

<210> SEQ ID NO 121
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 121
ttcaccatca ccgctccggt ggga                                            24

<210> SEQ ID NO 122
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 122
tcccgccaac aaatgacgga gtg                                             23
```

```
<210> SEQ ID NO 123
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 123
cgcaccgcca gacatatggt ggga                                              24

<210> SEQ ID NO 124
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 124
tcccccctgc catgaggagg tgtg                                              24

<210> SEQ ID NO 125
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 125
acccacccac tactgagggt gag                                               23

<210> SEQ ID NO 126
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 126
cacacctcca attagaggcg gga                                               23

<210> SEQ ID NO 127
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 127
tccctcccta agggtgatgg ggtg                                              24

<210> SEQ ID NO 128
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"
```

```
<400> SEQUENCE: 128
acccaccaaa atgcagctgg tgtg                                            24

<210> SEQ ID NO 129
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 129
ttccaccaag tatcagaagg tgta                                            24

<210> SEQ ID NO 130
<211> LENGTH: 32
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 130
tcccaccagg atatccgggt tacgcaggtg tg                                   32

<210> SEQ ID NO 131
<211> LENGTH: 36
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (17)..(20)
<223> OTHER INFORMATION: a, c, t, g, unknown or other

<400> SEQUENCE: 131
tcctgcccag ctccatnnnn accagaacaa cactga                               36

<210> SEQ ID NO 132
<211> LENGTH: 49
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (17)..(33)
<223> OTHER INFORMATION: a, c, t, g, unknown or other

<400> SEQUENCE: 132
tcagtgttgt tctggtnnnn nnnnnnnnnn nnnatggagc tgggcagga                 49

<210> SEQ ID NO 133
<211> LENGTH: 44
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
```

```
<222> LOCATION: (17)..(28)
<223> OTHER INFORMATION: a, c, t, g, unknown or other

<400> SEQUENCE: 133
tcaattttct actgttnnnn nnnnnnnttt ggagctggtc agga        44

<210> SEQ ID NO 134
<211> LENGTH: 49
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (17)..(33)
<223> OTHER INFORMATION: a, c, t, g, unknown or other

<400> SEQUENCE: 134
tcctgcccag atccttnnnn nnnnnnnnn nnntccagca caatattga        49

<210> SEQ ID NO 135
<211> LENGTH: 51
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (17)..(35)
<223> OTHER INFORMATION: a, c, t, g, unknown or other

<400> SEQUENCE: 135
ccctccccag ctccctnnnn nnnnnnnnn nnnnnacatg atcaacattc a        51

<210> SEQ ID NO 136
<211> LENGTH: 48
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (17)..(32)
<223> OTHER INFORMATION: a, c, t, g, unknown or other

<400> SEQUENCE: 136
gcagacttgt tctggtnnnn nnnnnnnnn nnagggatct ggggagga        48

<210> SEQ ID NO 137
<211> LENGTH: 46
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (17)..(30)
<223> OTHER INFORMATION: a, c, t, g, unknown or other

<400> SEQUENCE: 137
tcaatgttgg ttaactnnnn nnnnnnnnn atggatttgg gcagga        46
```

```
<210> SEQ ID NO 138
<211> LENGTH: 46
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (17)..(30)
<223> OTHER INFORMATION: a, c, t, g, unknown or other

<400> SEQUENCE: 138
tcctgcccat ctccatnnnn nnnnnnnnnn gcaataacat aaatga                      46

<210> SEQ ID NO 139
<211> LENGTH: 56
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (17)..(40)
<223> OTHER INFORMATION: a, c, t, g, unknown or other

<400> SEQUENCE: 139
gcattgatgt actgttnnnn nnnnnnnnnn nnnnnnnnnn agcgagttgg ggagga           56

<210> SEQ ID NO 140
<211> LENGTH: 48
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (17)..(32)
<223> OTHER INFORMATION: a, c, t, g, unknown or other

<400> SEQUENCE: 140
gcagtgttgt tctgttnnnn nnnnnnnnnn nnagagagtt gggatgga                    48

<210> SEQ ID NO 141
<211> LENGTH: 55
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (17)..(39)
<223> OTHER INFORMATION: a, c, t, g, unknown or other

<400> SEQUENCE: 141
tcactgttca tcttatnnnn nnnnnnnnnn nnnnnnnna cggagctggg caggg             55

<210> SEQ ID NO 142
<211> LENGTH: 44
<212> TYPE: DNA
<213> ORGANISM: Unknown
<220> FEATURE:
<221> NAME/KEY: source
```

```
<223> OTHER INFORMATION: /note="Description of Unknown: Target
      oligonucleotide"
<220> FEATURE:
<221> NAME/KEY: modified_base
<222> LOCATION: (17)..(28)
<223> OTHER INFORMATION: a, c, t, g, unknown or other

<400> SEQUENCE: 142
tcctgccccg caccatnnnn nnnnnnnnca cagaacactg atgt                     44

<210> SEQ ID NO 143
<211> LENGTH: 40
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(22)
<223> OTHER INFORMATION: a, c, t, g, unknown or other

<400> SEQUENCE: 143
ttttctgtca ccaatcctnn nnactgtggg gtggagggga                          40

<210> SEQ ID NO 144
<211> LENGTH: 51
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(33)
<223> OTHER INFORMATION: a, c, t, g, unknown or other

<400> SEQUENCE: 144
ttttctgtca ccaatcctnn nnnnnnnnn nnnactgtgg ggtggagggg a              51

<210> SEQ ID NO 145
<211> LENGTH: 49
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(31)
<223> OTHER INFORMATION: a, c, t, g, unknown or other

<400> SEQUENCE: 145
ttccacccag ccctcagtnn nnnnnnnnn naggatgggt ggctggaaa                 49

<210> SEQ ID NO 146
<211> LENGTH: 60
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(42)
<223> OTHER INFORMATION: a, c, t, g, unknown or other
```

```
<400> SEQUENCE: 146
ttttctataa ctcatattnn nnnnnnnnnn nnnnnnnnnn nnttttTggg gtggaggggg        60

<210> SEQ ID NO 147
<211> LENGTH: 62
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(44)
<223> OTHER INFORMATION: a, c, t, g, unknown or other

<400> SEQUENCE: 147
gggtaagtca ctcaacctnn nnnnnnnnnn nnnnnnnnnn nnnnattgtg gggtgggggg        60
ga                                                                     62

<210> SEQ ID NO 148
<211> LENGTH: 59
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(41)
<223> OTHER INFORMATION: a, c, t, g, unknown or other

<400> SEQUENCE: 148
tcttccatca ctaattctnn nnnnnnnnnn nnnnnnnnnn natggtaggg tggagggta         59

<210> SEQ ID NO 149
<211> LENGTH: 47
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(29)
<223> OTHER INFORMATION: a, c, t, g, unknown or other

<400> SEQUENCE: 149
tccccaccac accacaatnn nnnnnnnna gaaactgtga cagaata                      47

<210> SEQ ID NO 150
<211> LENGTH: 53
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(35)
<223> OTHER INFORMATION: a, c, t, g, unknown or other

<400> SEQUENCE: 150
tattctgtca ctattcctnn nnnnnnnnnn nnnnnacgat ggggcgtggg ggg              53
```

-continued

```
<210> SEQ ID NO 151
<211> LENGTH: 47
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(29)
<223> OTHER INFORMATION: a, c, t, g, unknown or other

<400> SEQUENCE: 151
tccctcccac cccacctann nnnnnnnnna ggattggggg caggact                47

<210> SEQ ID NO 152
<211> LENGTH: 50
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(32)
<223> OTHER INFORMATION: a, c, t, g, unknown or other

<400> SEQUENCE: 152
ccgtcagtca cccctcctnn nnnnnnnnnn nnacagtggg gtggagtggg             50

<210> SEQ ID NO 153
<211> LENGTH: 54
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(36)
<223> OTHER INFORMATION: a, c, t, g, unknown or other

<400> SEQUENCE: 153
tcccttccac ctcaccaann nnnnnnnnnn nnnnnnaggg ttgggtacag aaca         54

<210> SEQ ID NO 154
<211> LENGTH: 53
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(35)
<223> OTHER INFORMATION: a, c, t, g, unknown or other

<400> SEQUENCE: 154
tatccagaca cccaccctnn nnnnnnnnnn nnnntgtgt ggggtggatg ggg           53

<210> SEQ ID NO 155
<211> LENGTH: 54
<212> TYPE: DNA
<213> ORGANISM: Unknown
<220> FEATURE:
<221> NAME/KEY: source
<223> OTHER INFORMATION: /note="Description of Unknown: Target
```

```
      oligonucleotide"
<220> FEATURE:
<221> NAME/KEY: modified_base
<222> LOCATION: (19)..(36)
<223> OTHER INFORMATION: a, c, t, g, unknown or other

<400> SEQUENCE: 155 ctcccccccac ccccccaaann nnnnnnnnnn nnnnnntgga gtggggacag aaaa         54

<210> SEQ ID NO 156
<211> LENGTH: 53
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(35)
<223> OTHER INFORMATION: a, c, t, g, unknown or other

<400> SEQUENCE: 156
ttcccaccac cccacaacnn nnnnnnnnnn nnnnnatgac agatgacagt aaa            53

<210> SEQ ID NO 157
<211> LENGTH: 56
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(38)
<223> OTHER INFORMATION: a, c, t, g, unknown or other

<400> SEQUENCE: 157 tgcccccccac cccagagtnn nnnnnnnnnn nnnnnnnnat tataagagac agaaaa       56

<210> SEQ ID NO 158
<211> LENGTH: 51
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(33)
<223> OTHER INFORMATION: a, c, t, g, unknown or other

<400> SEQUENCE: 158
agtactgtca cctgtgctnn nnnnnnnnnn nnnatgttgg ggtggaaggg a              51

<210> SEQ ID NO 159
<211> LENGTH: 52
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(34)
<223> OTHER INFORMATION: a, c, t, g, unknown or other

<400> SEQUENCE: 159
```
tggtcagcca ccccacctnn nnnnnnnnnn nnnnaccacg gggtggaggg ga            52

<210> SEQ ID NO 160
<211> LENGTH: 52
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(34)
<223> OTHER INFORMATION: a, c, t, g, unknown or other

<400> SEQUENCE: 160 tccccctccac cccgtggtnn nnnnnnnnnn nnnnaggtgg ggtggctgac ca           52

<210> SEQ ID NO 161
<211> LENGTH: 52
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(34)
<223> OTHER INFORMATION: a, c, t, g, unknown or other

<400> SEQUENCE: 161
tgttccatcg ccactgctnn nnnnnnnnnn nnnntttggg gggtgggggg tg            52

<210> SEQ ID NO 162
<211> LENGTH: 61
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(43)
<223> OTHER INFORMATION: a, c, t, g, unknown or other

<400> SEQUENCE: 162
catcccatca cccatcctnn nnnnnnnnnn nnnnnnnnnn nnntttttttt ggtggggggg   60 a                                                                    61

<210> SEQ ID NO 163
<211> LENGTH: 52
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(34)
<223> OTHER INFORMATION: a, c, t, g, unknown or other

<400> SEQUENCE: 163
aggactgtcc ctgctcctnn nnnnnnnnnn nnnactgtg gggtgttggg gg             52

<210> SEQ ID NO 164

```
<211> LENGTH: 51
<212> TYPE: DNA
<213> ORGANISM: Unknown
<220> FEATURE:
<221> NAME/KEY: source
<223> OTHER INFORMATION: /note="Description of Unknown: Target
      oligonucleotide"
<220> FEATURE:
<221> NAME/KEY: modified_base
<222> LOCATION: (19)..(33)
<223> OTHER INFORMATION: a, c, t, g, unknown or other

<400> SEQUENCE: 164
caccccccac cccccacann nnnnnnnnnn nnntggagtg ttgatagtat a           51

<210> SEQ ID NO 165
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
tcaccttgcc ccacagggca gt                                          22

<210> SEQ ID NO 166
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
tgcccctgac tcctta                                                 16

<210> SEQ ID NO 167
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
tcactttgcc ccacagggca tt                                          22

<210> SEQ ID NO 168
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
tccacctggc tcctgt                                                 16

<210> SEQ ID NO 169
<211> LENGTH: 25
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 169
tcaccttgcc ccacagggca gtaac                                               25

<210> SEQ ID NO 170
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
tggagcacct gacccca                                                        17

<210> SEQ ID NO 171
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
tcactttgcc ccacagggca ttgac                                               25

<210> SEQ ID NO 172
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
ctgtgcccct gactcct                                                        17

<210> SEQ ID NO 173
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
tcaccttgcc cc                                                             12

<210> SEQ ID NO 174
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
tcaggagtca ggtgca                                                         16

<210> SEQ ID NO 175
```

```
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
aaatgaggca ggtgca                                                  16

<210> SEQ ID NO 176
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
tcaggagtca gatgca                                                  16

<210> SEQ ID NO 177
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
gcaggagtta agggta                                                  16

<210> SEQ ID NO 178
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
aggagtcagg tgcacca                                                 17

<210> SEQ ID NO 179
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
aggagaaaag ggcacct                                                 17

<210> SEQ ID NO 180
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
```

-continued

```
aggagtcaga tgcacca                                                17

<210> SEQ ID NO 181
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
atgaggcagg tgcattt                                                17

<210> SEQ ID NO 182
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
gcagtaacgg ca                                                     12

<210> SEQ ID NO 183
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 183
tcgtgaccac cctgacctac gg                                          22

<210> SEQ ID NO 184
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 184
tgccgtcctc gatgttgtgg cg                                          22

<210> SEQ ID NO 185
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 185
ggtgcacctg actcct                                                 16

<210> SEQ ID NO 186
<211> LENGTH: 15
<212> TYPE: DNA
<213> ORGANISM: Unknown
<220> FEATURE:
```

```
<221> NAME/KEY: source
<223> OTHER INFORMATION: /note="Description of Unknown: Target
      oligonucleotide"

<400> SEQUENCE: 186
gcacctgact cctgt                                                    15

<210> SEQ ID NO 187
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 187
caaacagaca ccatggtgca cct                                           23

<210> SEQ ID NO 188
<211> LENGTH: 25
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 188
caaacagaca ccatggtgca cctga                                         25

<210> SEQ ID NO 189
<211> LENGTH: 21
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 189
caccttgccc cacagggcag t                                             21

<210> SEQ ID NO 190
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 190
caccttgccc cacagggcag taa                                           23

<210> SEQ ID NO 191
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 191
caccttgccc cacagggcag taac                                          24
```

```
<210> SEQ ID NO 192
<211> LENGTH: 22
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 192
caccttgccc cacagggcag ta                                             22

<210> SEQ ID NO 193
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 193
gccccacagg gcagtaacgg caga                                           24

<210> SEQ ID NO 194
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 194
gcttacattt gcttctgaca caactgtgtt                                     30

<210> SEQ ID NO 195
<211> LENGTH: 25
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 195
acaagacagg tttaaggaga ccaat                                          25

<210> SEQ ID NO 196
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 196
tgccccacag ggcagt                                                    16

<210> SEQ ID NO 197
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"
```

```
<400> SEQUENCE: 197
cttgggtttc tgataggcac tgactctct                                    29

<210> SEQ ID NO 198
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 198
cctgtggaga agtct                                                   15

<210> SEQ ID NO 199
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 199
cctgtggaga agtctgccgt                                              20

<210> SEQ ID NO 200
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 200
ctgataggca ctgactct                                                18

<210> SEQ ID NO 201
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 201
ctgataggca ctgactctct                                              20

<210> SEQ ID NO 202
<211> LENGTH: 22
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 202
ctgataggca ctgactctct ct                                           22

<210> SEQ ID NO 203
<211> LENGTH: 26
<212> TYPE: DNA
<213> ORGANISM: Unknown
```

```
<220> FEATURE:
<221> NAME/KEY: source
<223> OTHER INFORMATION: /note="Description of Unknown: Target
      oligonucleotide"

<400> SEQUENCE: 203
ctgataggca ctgactctct ctgcct                                          26

<210> SEQ ID NO 204
<211> LENGTH: 28
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 204
ctgataggca ctgactctct ctgcctat                                        28

<210> SEQ ID NO 205
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 205
ctgataggca ctgactctct ctgcctatt                                       29

<210> SEQ ID NO 206
<211> LENGTH: 28
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 206
ccacgttcac cttgccccac agggcagt                                        28

<210> SEQ ID NO 207
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 207
agaccaccag cagcct                                                     16

<210> SEQ ID NO 208
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 208
ccaagggtag accaccagca gcct                                            24
```

```
<210> SEQ ID NO 209
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 209
ctccacagga gtcaggtgca ccat                                            24

<210> SEQ ID NO 210
<211> LENGTH: 26
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 210
atcagaaacc caagagtctt ctctgt                                          26

<210> SEQ ID NO 211
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 211
gcctatcaga aacccaagag tcttctctgt                                      30

<210> SEQ ID NO 212
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 212
atcagaaacc caagagtctt ctct                                            24

<210> SEQ ID NO 213
<211> LENGTH: 28
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 213
gcctatcaga aacccaagag tcttctct                                        28

<210> SEQ ID NO 214
<211> LENGTH: 22
<212> TYPE: DNA
<213> ORGANISM: Unknown
<220> FEATURE:
<221> NAME/KEY: source
<223> OTHER INFORMATION: /note="Description of Unknown: Target
      oligonucleotide"
```

```
<400> SEQUENCE: 214
atcagaaacc caagagtctt ct                                              22

<210> SEQ ID NO 215
<211> LENGTH: 26
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 215
gcctatcaga aacccaagag tcttct                                          26

<210> SEQ ID NO 216
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 216
atcagaaacc caagagtctt                                                 20

<210> SEQ ID NO 217
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 217
gcctatcaga aacccaagag tctt                                            24

<210> SEQ ID NO 218
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 218
atcagaaacc caagagtct                                                  19

<210> SEQ ID NO 219
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 219
gcctatcaga aacccaagag tct                                             23

<210> SEQ ID NO 220
<211> LENGTH: 17
<212> TYPE: DNA
```

```
<213> ORGANISM: Unknown
<220> FEATURE:
<221> NAME/KEY: source
<223> OTHER INFORMATION: /note="Description of Unknown: Target
      oligonucleotide"

<400> SEQUENCE: 220
atcagaaacc caagagt                                                    17

<210> SEQ ID NO 221
<211> LENGTH: 21
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 221
gcctatcaga aacccaagag t                                               21

<210> SEQ ID NO 222
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 222
ctattgctta catttgcttc tgacacaact                                      30

<210> SEQ ID NO 223
<211> LENGTH: 28
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 223
gggtttctga taggcactga ctctctct                                        28

<210> SEQ ID NO 224
<211> LENGTH: 28
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 224
attgcttaca tttgcttctg acacaact                                        28

<210> SEQ ID NO 225
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 225
attgcttaca tttgcttctg acacaactgt                                      30
```

-continued

```
<210> SEQ ID NO 226
<211> LENGTH: 25
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 226
gcttacattt gcttctgaca caact                                           25

<210> SEQ ID NO 227
<211> LENGTH: 27
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 227
gcttacattt gcttctgaca caactgt                                         27

<210> SEQ ID NO 228
<211> LENGTH: 29
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 228
gcttacattt gcttctgaca caactgtgt                                       29

<210> SEQ ID NO 229
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 229
aaggagacca atagaaact                                                  19

<210> SEQ ID NO 230
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 230
taaggagacc aatagaaact                                                 20

<210> SEQ ID NO 231
<211> LENGTH: 21
<212> TYPE: DNA
<213> ORGANISM: Unknown
<220> FEATURE:
<221> NAME/KEY: source
<223> OTHER INFORMATION: /note="Description of Unknown: Target
```

```
            oligonucleotide"

<400> SEQUENCE: 231
ttaaggagac caatagaaac t                                      21

<210> SEQ ID NO 232
<211> LENGTH: 17
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 232
tgccccacag ggcagta                                           17

<210> SEQ ID NO 233
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 233
caaacagaca ccatg                                             15

<210> SEQ ID NO 234
<211> LENGTH: 17
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 234
caaacagaca ccatggt                                           17

<210> SEQ ID NO 235
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 235
agacaccatg gtgcac                                            16

<210> SEQ ID NO 236
<211> LENGTH: 22
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 236
caaacagaca ccatggtgca cc                                     22

<210> SEQ ID NO 237
<211> LENGTH: 17
```

```
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 237
aacggcagac ttctcca                                                    17

<210> SEQ ID NO 238
<211> LENGTH: 14
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 238
aacggcagac ttct                                                       14

<210> SEQ ID NO 239
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 239
gcagtaacgg cagact                                                     16

<210> SEQ ID NO 240
<211> LENGTH: 30
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 240
ccttgcccca cagggcagta acggcagact                                      30

<210> SEQ ID NO 241
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 241
gcacctgact cctgg                                                      15

<210> SEQ ID NO 242
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 242
```

```
ctgataggca ctgactcg                                                    18

<210> SEQ ID NO 243
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 243
atcagaaacc caagagtctt ctcg                                             24

<210> SEQ ID NO 244
<211> LENGTH: 21
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 244
caccttgccc cacagggcag g                                                21

<210> SEQ ID NO 245
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 245
ggtgcacctg actccg                                                      16

<210> SEQ ID NO 246
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 246
gccccacagg gcagtaacgg cagg                                             24

<210> SEQ ID NO 247
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 247
gcacctgact cctga                                                       15

<210> SEQ ID NO 248
<211> LENGTH: 18
<212> TYPE: DNA
<213> ORGANISM: Unknown
<220> FEATURE:
<221> NAME/KEY: source
```

```
-continued

<223> OTHER INFORMATION: /note="Description of Unknown: Target
      oligonucleotide"

<400> SEQUENCE: 248
ctgataggca ctgactca                                                 18

<210> SEQ ID NO 249
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 249
atcagaaacc caagagtctt ctca                                          24

<210> SEQ ID NO 250
<211> LENGTH: 21
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 250
caccttgccc cacagggcag a                                             21

<210> SEQ ID NO 251
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 251
ggtgcacctg actcca                                                   16

<210> SEQ ID NO 252
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 252
gccccacagg gcagtaacgg cagt                                          24

<210> SEQ ID NO 253
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 253
gcacctgact cctgc                                                    15

<210> SEQ ID NO 254
```

```
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 254
ctgataggca ctgactcc                                                     18

<210> SEQ ID NO 255
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 255
atcagaaacc caagagtctt ctcc                                              24

<210> SEQ ID NO 256
<211> LENGTH: 21
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 256
caccttgccc cacagggcag c                                                 21

<210> SEQ ID NO 257
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 257
ggtgcacctg actccc                                                       16

<210> SEQ ID NO 258
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 258
gccccacagg gcagtaacgg cagc                                              24

<210> SEQ ID NO 259
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 259
```
tcacctgact cctgt								15

<210> SEQ ID NO 260
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 260
ttgataggca ctgactct							18

<210> SEQ ID NO 261
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 261
ttcagaaacc caagagtctt ctct						24

<210> SEQ ID NO 262
<211> LENGTH: 21
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 262
taccttgccc cacagggcag t							21

<210> SEQ ID NO 263
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 263
tgtgcacctg actcct							16

<210> SEQ ID NO 264
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 264
tccccacagg gcagtaacgg caga						24

<210> SEQ ID NO 265
<211> LENGTH: 15
<212> TYPE: DNA
<213> ORGANISM: Unknown
<220> FEATURE:

<221> NAME/KEY: source
<223> OTHER INFORMATION: /note="Description of Unknown: Target
      oligonucleotide"

<400> SEQUENCE: 265
gaacctgact cctgt                                                    15

<210> SEQ ID NO 266
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 266
cagataggca ctgactct                                                 18

<210> SEQ ID NO 267
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 267
aacagaaacc caagagtctt ctct                                          24

<210> SEQ ID NO 268
<211> LENGTH: 21
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 268
ctccttgccc cacagggcag t                                             21

<210> SEQ ID NO 269
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 269
gatgcacctg actcct                                                   16

<210> SEQ ID NO 270
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 270
gacccacagg gcagtaacgg caga                                          24

```
<210> SEQ ID NO 271
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 271
tcccaccctt aggct                                                    15

<210> SEQ ID NO 272
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 272
cactagcaac ctcaaaca                                                 18

<210> SEQ ID NO 273
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 273
ctgccgttac tgccctgt                                                 18

<210> SEQ ID NO 274
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 274
caaagaacct ctgggtccaa                                               20

<210> SEQ ID NO 275
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 275
tcaccttgcc ccaca                                                    15

<210> SEQ ID NO 276
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"
```

```
<400> SEQUENCE: 276
tctccacagg agtca                                                    15

<210> SEQ ID NO 277
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 277
caccaccaac ttcat                                                    15

<210> SEQ ID NO 278
<211> LENGTH: 22
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 278
agcaacctca aacagacacc at                                            22

<210> SEQ ID NO 279
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 279
aacggcagac ttctccaca                                                19

<210> SEQ ID NO 280
<211> LENGTH: 14
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 280
tatgcctggc acca                                                     14

<210> SEQ ID NO 281
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 281
catcatagga aacaccaat                                                19

<210> SEQ ID NO 282
<211> LENGTH: 17
<212> TYPE: DNA
<213> ORGANISM: Unknown
```

```
<220> FEATURE:
<221> NAME/KEY: source
<223> OTHER INFORMATION: /note="Description of Unknown: Target
      oligonucleotide"

<400> SEQUENCE: 282
ctctctgcct attggtc                                                    17

<210> SEQ ID NO 283
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 283
ccaagggtag accaccagc                                                  19

<210> SEQ ID NO 284
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 284
ggtgcacctg actcc                                                      15

<210> SEQ ID NO 285
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 285
tgccccacag ggcagtaac                                                  19

<210> SEQ ID NO 286
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 286
gcctattggt ctattttcc                                                  19

<210> SEQ ID NO 287
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 287
ccaagggtag accacc                                                     16
```

```
<210> SEQ ID NO 288
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 288
gtgttcacta gcaacctc                                                    18

<210> SEQ ID NO 289
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 289
tctccacagg agtcaggtgc                                                  20

<210> SEQ ID NO 290
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 290
tcttttcccc ttttatgc                                                    18

<210> SEQ ID NO 291
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 291
gaggcatgac aacgc                                                       15

<210> SEQ ID NO 292
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 292
tttatttcca gacttc                                                      16

<210> SEQ ID NO 293
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"
```

-continued

```
<400> SEQUENCE: 293
ctgaaggctc cagttctcc                                               19

<210> SEQ ID NO 294
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 294
ttccagactt cacttc                                                  16

<210> SEQ ID NO 295
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 295
ctgaaggctc cagttctc                                                18

<210> SEQ ID NO 296
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 296
gaaggctcca gttctccc                                                18

<210> SEQ ID NO 297
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 297
tttcgaattc gtcctattt                                               19

<210> SEQ ID NO 298
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 298
ctgtttcttc aatagtggag cat                                          23

<210> SEQ ID NO 299
<211> LENGTH: 24
<212> TYPE: DNA
```

<213> ORGANISM: Unknown
<220> FEATURE:
<221> NAME/KEY: source
<223> OTHER INFORMATION: /note="Description of Unknown: Target oligonucleotide"

<400> SEQUENCE: 299
cggctctgca aactcttatt tttt                                          24

<210> SEQ ID NO 300
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 300
ccccatcaaa cacaaa                                                   16

<210> SEQ ID NO 301
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 301 ctctttttt cttttttgt                                                 18

<210> SEQ ID NO 302
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 302
gtaattccat cagtc                                                    15

<210> SEQ ID NO 303
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 303
gaacccttca cactaccca                                                19

<210> SEQ ID NO 304
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target oligonucleotide"

<400> SEQUENCE: 304
agactaaccg attgaatat                                                19

<210> SEQ ID NO 305
<211> LENGTH: 21
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 305
ttatttccag acttcacttc t                                          21

<210> SEQ ID NO 306
<211> LENGTH: 22
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 306
accctctgaa ggctccagtt ct                                         22

<210> SEQ ID NO 307
<211> LENGTH: 17
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 307
tcacttctaa tggtgat                                               17

<210> SEQ ID NO 308
<211> LENGTH: 22
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 308
gtgcttaatt ttaccctctg aa                                         22

<210> SEQ ID NO 309
<211> LENGTH: 17
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 309
ctgcctaaca ggaggtg                                               17

<210> SEQ ID NO 310
<211> LENGTH: 21
<212> TYPE: DNA
<213> ORGANISM: Unknown
<220> FEATURE:
<221> NAME/KEY: source
<223> OTHER INFORMATION: /note="Description of Unknown: Target -continued oligonucleotide"

<400> SEQUENCE: 310
cctccttcct agtctcctga t                                                    21

<210> SEQ ID NO 311
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 311
gtccctagtg gccccact                                                        18

<210> SEQ ID NO 312
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 312
ctggttctgg gtactttat                                                       20

<210> SEQ ID NO 313
<211> LENGTH: 21
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 313
ctcggcgctg ctgctgctgc t                                                    21

<210> SEQ ID NO 314
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 314
gcgtccctcg caagtcag                                                        18

<210> SEQ ID NO 315
<211> LENGTH: 14
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 315
ttctctccgc gcct                                                            14

<210> SEQ ID NO 316
<211> LENGTH: 25

```
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 316
gccgccgccg ccgcccgccc cgaat                                        25

<210> SEQ ID NO 317
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 317
cggcgctgct gctgctgct                                               19

<210> SEQ ID NO 318
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 318
gcgtccctcg caagtcaggg                                              20

<210> SEQ ID NO 319
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 319
gcgctcaagt catcgccgca                                              20

<210> SEQ ID NO 320
<211> LENGTH: 17
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 320
gtacttctcc acgggaa                                                 17

<210> SEQ ID NO 321
<211> LENGTH: 17
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 321
```
cgcttgctcg aggccct                                                   17

<210> SEQ ID NO 322
<211> LENGTH: 17
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 322
caggcccctg cacgacc                                                   17

<210> SEQ ID NO 323
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 323
gggattttct ctgcgttct                                                 19

<210> SEQ ID NO 324
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 324
gtcccacctg tctggacg                                                  18

<210> SEQ ID NO 325
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 325
cgtcctgtgg acgcgtat                                                  18

<210> SEQ ID NO 326
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 326
cacccgactt ctgaacgtgc ggt                                            23

<210> SEQ ID NO 327
<211> LENGTH: 16
<212> TYPE: DNA
<213> ORGANISM: Unknown
<220> FEATURE:
<221> NAME/KEY: source

```
<223> OTHER INFORMATION: /note="Description of Unknown: Target
      oligonucleotide"

<400> SEQUENCE: 327
cttcccctgg cactgg                                                    16

<210> SEQ ID NO 328
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 328
cccggacccc agcagcagct tccg                                           24

<210> SEQ ID NO 329
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 329
ggcctgcggc atccct                                                    16

<210> SEQ ID NO 330
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 330
tccctacctc gtcccacgg                                                 19

<210> SEQ ID NO 331
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 331
acccagcagc tcggcccag                                                 19

<210> SEQ ID NO 332
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 332
ccgcctcggg ccaggaccc                                                 19

<210> SEQ ID NO 333
```

-continued

```
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 333
tcgccgcgct caccgtcca                                                  19

<210> SEQ ID NO 334
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 334
gcctgcgact gtggct                                                     16

<210> SEQ ID NO 335
<211> LENGTH: 15
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 335
ccacttcagc ccagg                                                      15

<210> SEQ ID NO 336
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 336
cctctcttct gaggcg                                                     16

<210> SEQ ID NO 337
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 337
gtcccccttc gaccag                                                     16

<210> SEQ ID NO 338
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 338
```

-continued

```
ctaagagacc taggctttct                                               20

<210> SEQ ID NO 339
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 339
cctccgaatg gctggctgtg gat                                           23

<210> SEQ ID NO 340
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 340
ggcccactca cccttgctgt tgtt                                          24

<210> SEQ ID NO 341
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 341
ccgatccctc accgtcat                                                 18

<210> SEQ ID NO 342
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 342
cgactttccc gccgaggg                                                 18

<210> SEQ ID NO 343
<211> LENGTH: 25
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 343
gctccagcaa agaaaccagc aagag                                         25

<210> SEQ ID NO 344
<211> LENGTH: 23
<212> TYPE: DNA
<213> ORGANISM: Unknown
<220> FEATURE:
```

```
<221> NAME/KEY: source
<223> OTHER INFORMATION: /note="Description of Unknown: Target
      oligonucleotide"

<400> SEQUENCE: 344
acaacagcca accttccctt ttg                                              23

<210> SEQ ID NO 345
<211> LENGTH: 22
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 345
ccctgcttct gacggtatgt at                                               22

<210> SEQ ID NO 346
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 346
ctttcagcag gtttct                                                      16

<210> SEQ ID NO 347
<211> LENGTH: 24
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 347
actactccct gcttctgacg gtat                                             24

<210> SEQ ID NO 348
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 348
ctttcagcag gtttcttcat                                                  20

<210> SEQ ID NO 349
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 349
cacctcggcc gcagccacg                                                   19
```

```
<210> SEQ ID NO 350
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 350
gctcccacct cagcgacgcg                                                   20

<210> SEQ ID NO 351
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 351
cccacatcca aatcccact                                                    19

<210> SEQ ID NO 352
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 352
gctgccttgg atcctgaa                                                     18

<210> SEQ ID NO 353
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 353
ctacggcgcg gacttccaag                                                   20

<210> SEQ ID NO 354
<211> LENGTH: 16
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 354
cctaccggtc cgcaag                                                       16

<210> SEQ ID NO 355
<211> LENGTH: 17
<212> TYPE: DNA
<213> ORGANISM: Unknown
<220> FEATURE:
<221> NAME/KEY: source
<223> OTHER INFORMATION: /note="Description of Unknown: Target
      oligonucleotide"
```

```
<400> SEQUENCE: 355
ttgcccatcc acgtcag                                                  17

<210> SEQ ID NO 356
<211> LENGTH: 18
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 356
cacagaccat ttctttct                                                 18

<210> SEQ ID NO 357
<211> LENGTH: 22
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 357
gtccaagacc tcaatccttt gg                                            22

<210> SEQ ID NO 358
<211> LENGTH: 17
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 358
acctcggccc ttctcag                                                  17

<210> SEQ ID NO 359
<211> LENGTH: 53
<212> TYPE: DNA
<213> ORGANISM: Homo sapiens

<400> SEQUENCE: 359
cttcctctgc ctgcacctag gcccttctt ggggcaaggg cagcaatagt ccc           53

<210> SEQ ID NO 360
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 360
cttcctctgc ctgcacctag gcccttctt cttggggcaa gggcagcaat agt           53

<210> SEQ ID NO 361
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 361
cttcctctgc ctgcacctag gccccttctt tcttggggca agggcagcaa tag         53

<210> SEQ ID NO 362
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 362
cttcctctgc ctgcacctag gccccttctt ttcttggggc aagggcagca ata         53

<210> SEQ ID NO 363
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 363
cttcctctgc ctgcacctag gcccctgggg caagggcagc aatagtccc              49

<210> SEQ ID NO 364
<211> LENGTH: 308
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 364
catctattgc ttacatttgc ttctgacaca actgtgttca ctagcaacct caaacagaca    60
ccatggtgca cctgactcct gtggagaagt ctgccgttac tgccctgtgg ggcaaggtga   120
acgtggatga agttggtggt gaggccctgg gcaggttggt atcaaggtta caagacaggt   180
ttaaggagac caatagaaac tgggcatgtg gagacagaga agactcttgg gtttctgata   240
ggcactgact ctctctgcct attggtctat tttcccaccc ttaggctgct ggtggtctac   300
ccttggac                                                          308

<210> SEQ ID NO 365
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 365
tgcacctgac tcctgtggag                                              20

<210> SEQ ID NO 366
<211> LENGTH: 20
<212> TYPE: DNA
<213> ORGANISM: Unknown
<220> FEATURE:
<221> NAME/KEY: source
<223> OTHER INFORMATION: /note="Description of Unknown: Target

```
oligonucleotide"

<400> SEQUENCE: 366
tttgcttctg acacaactgt                                              20

<210> SEQ ID NO 367
<211> LENGTH: 17
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 367
tctgcctatt ggtctat                                                 17

<210> SEQ ID NO 368
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 368
tccacgttca ccttgcccca cag                                          23

<210> SEQ ID NO 369
<211> LENGTH: 19
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 369
tgcaccatgg tgtctgttt                                               19

<210> SEQ ID NO 370
<211> LENGTH: 23
<212> TYPE: DNA
<213> ORGANISM: Unknown
<220> FEATURE:
<221> NAME/KEY: source
<223> OTHER INFORMATION: /note="Description of Unknown: Target
      oligonucleotide"

<400> SEQUENCE: 370
tgggtccaag ggtagaccac cag                                          23
```